United States Patent
Holtzman et al.

(10) Patent No.: US 9,834,596 B2
(45) Date of Patent: Dec. 5, 2017

(54) ANTIBODIES TO TAU

(71) Applicant: Washington University, St. Louis, MO (US)

(72) Inventors: David Holtzman, St. Louis, MO (US); Hong Jiang, St. Louis, MO (US); Marc Diamond, St. Louis, MO (US); Najla Kfoury, St. Louis, MO (US); Brandon Holmes, St. Louis, MO (US)

(73) Assignee: Washington University, St. Louis, MO (US)

( * ) Notice: Subject to any disclaimer, the term of this patent is extended or adjusted under 35 U.S.C. 154(b) by 74 days.

(21) Appl. No.: 14/412,309

(22) PCT Filed: Jul. 3, 2013

(86) PCT No.: PCT/US2013/049333
§ 371 (c)(1),
(2) Date: Dec. 31, 2014

(87) PCT Pub. No.: WO2014/008404
PCT Pub. Date: Jan. 9, 2014

(65) Prior Publication Data
US 2015/0183855 A1    Jul. 2, 2015

Related U.S. Application Data

(60) Provisional application No. 61/667,515, filed on Jul. 3, 2012, provisional application No. 61/694,989, filed on Aug. 30, 2012.

(51) Int. Cl.
C07K 16/18 (2006.01)
G01N 33/68 (2006.01)
A61K 39/00 (2006.01)

(52) U.S. Cl.
CPC ......... *C07K 16/18* (2013.01); *G01N 33/6896* (2013.01); *A61K 2039/505* (2013.01); *C07K 2317/34* (2013.01); *C07K 2317/565* (2013.01); *C07K 2317/76* (2013.01); *C07K 2317/92* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 5,492,812 A | 2/1996 | Vooheis | |
| 5,601,985 A | 2/1997 | Trojanowski et al. | |
| 6,121,003 A | 9/2000 | Vanmechelen et al. | |
| 6,589,746 B1 | 7/2003 | Zemlan | |
| 6,797,478 B1 | 9/2004 | Zemlan et al. | |
| 6,900,293 B2 | 5/2005 | Mercken et al. | |
| 7,238,788 B2 | 7/2007 | Lee | |
| 7,348,157 B2 | 3/2008 | Eriksson et al. | |
| 7,442,516 B2 | 10/2008 | Ohno et al. | |
| 7,446,180 B2 | 11/2008 | Novak | |
| 7,728,109 B2 | 6/2010 | Kikly | |
| 8,012,936 B2 | 9/2011 | Sigurdsson et al. | |
| 8,084,584 B2 | 12/2011 | Sugo et al. | |
| 8,318,917 B2 | 11/2012 | Taylor et al. | |
| 8,673,949 B2 | 3/2014 | Albright et al. | |
| 8,697,076 B2 | 4/2014 | Binder et al. | |
| 8,703,137 B2 | 4/2014 | Chain | |
| 8,748,386 B2 | 6/2014 | Sigurdsson | |
| 8,778,343 B2 | 7/2014 | Kayed | |
| 8,895,714 B2 | 11/2014 | Tickle et al. | |
| 8,926,974 B2 | 1/2015 | Griswold-Prenner et al. | |
| 8,980,270 B2 | 3/2015 | Griswold-Prenner et al. | |
| 8,980,271 B2 | 3/2015 | Griswold-Prenner et al. | |
| 9,051,367 B2 | 6/2015 | Griswold-Prenner et al. | |
| 9,161,520 B2 | 10/2015 | Kontsekova et al. | |
| 9,351,986 B2 | 5/2016 | Kunz et al. | |
| 2002/0086009 A1 | 7/2002 | Ishiguro et al. | |
| 2002/0182660 A1 | 12/2002 | Fong | |
| 2002/0188106 A1 | 12/2002 | Mandelkow et al. | |
| 2006/0167227 A1 | 7/2006 | Kontsekova et al. | |
| 2007/0134724 A1 | 6/2007 | Davis et al. | |
| 2008/0220449 A1 | 9/2008 | Vasan et al. | |
| 2010/0009388 A1 | 1/2010 | An et al. | |
| 2010/0284909 A1 | 11/2010 | Wisniewski et al. | |
| 2010/0316564 A1 | 12/2010 | Sigurdsson | |
| 2011/0177109 A1* | 7/2011 | Smith, III et al. .. | C07K 14/4711 424/185.1 |
| 2011/0305706 A1 | 12/2011 | Brady et al. | |
| 2011/0318358 A1 | 12/2011 | Sigurdsson et al. | |
| 2012/0087861 A1 | 4/2012 | Nitsch et al. | |
| 2012/0142602 A1 | 6/2012 | Brady et al. | |
| 2012/0183599 A1 | 7/2012 | Pfeifer et al. | |
| 2012/0276009 A1 | 11/2012 | Pfeifer et al. | |

(Continued)

FOREIGN PATENT DOCUMENTS

| | | |
|---|---|---|
| AU | 2013205313 A1 | 5/2013 |
| CN | 101307108 I | 11/2008 |

(Continued)

OTHER PUBLICATIONS

Chen 1995 "enhancement and destruction of antibody function by somatic mutation: unequal occurrence is controlled by V gene combinatorial associations" embo 14(12):2784-2794.*
Kussie 1994 "single engineered amino acid substitution changes antibody fine specificity" J immunol 152(1):146-52.*
Yanamandra et al., "Anti-tau antibodies that block tau aggregate seeding in vitro markedly decrease pathology and improve cognition in vivo", Neuron, 2013, pp. 402-414, vol. 80, No. 2.
Office Action for Chinese Application No. 201380045706.3, dated Dec. 21, 2016.
Frost et al., "Prion-like Mechanisms in Neurodegenerative Diseases", Nat Rev Neurosci., 2010, pp. 155-159, vol. 11, No. 3.
Holtzman et al., "Nerve Growth Factor Protects the Neonatal Brain Against Hypoxic-Ischemic Injury", Annals of Neurology, 1996, pp. 114-122, vol. 39, No. 1.

(Continued)

*Primary Examiner* — Adam M Weidner

(57) ABSTRACT

This invention relates to antibodies to tau and methods of use thereof.

14 Claims, 98 Drawing Sheets
(51 of 98 Drawing Sheet(s) Filed in Color)

(56) References Cited

U.S. PATENT DOCUMENTS

| | | | |
|---|---|---|---|
| 2012/0302595 | A1 | 11/2012 | Baulieu et al. |
| 2012/0321594 | A1 | 12/2012 | Hong et al. |
| 2013/0022544 | A1 | 1/2013 | Wisniewski |
| 2013/0028914 | A1 | 1/2013 | Kayed |
| 2013/0095492 | A1 | 4/2013 | DeBernardis et al. |
| 2014/0056901 | A1 | 2/2014 | Agadjanyan et al. |
| 2014/0159244 | A1 | 6/2014 | Lu et al. |
| 2014/0161875 | A1 | 6/2014 | Winderickx et al. |
| 2014/0171373 | A1 | 6/2014 | Ashe et al. |
| 2014/0286954 | A1 | 9/2014 | Moe et al. |
| 2014/0294724 | A1 | 10/2014 | Chain |
| 2014/0294731 | A1 | 10/2014 | Pfeifer et al. |
| 2014/0302046 | A1 | 10/2014 | Sigurdsson |
| 2015/0050215 | A1 | 2/2015 | Novak et al. |
| 2015/0064726 | A1 | 3/2015 | Michaelsen et al. |
| 2015/0175682 | A1 | 6/2015 | Pfeifer et al. |
| 2015/0183854 | A1 | 7/2015 | Mori et al. |
| 2015/0183855 | A1 | 7/2015 | Diamond et al. |
| 2015/0232524 | A1 | 8/2015 | Agadjanyan et al. |
| 2015/0232544 | A1 | 8/2015 | Griswold-Prenner et al. |
| 2015/0259406 | A1 | 9/2015 | Pfeifer et al. |
| 2015/0266947 | A1 | 9/2015 | Sierks et al. |
| 2015/0307600 | A1 | 10/2015 | Alderfer et al. |
| 2015/0309054 | A1 | 10/2015 | Diamond et al. |
| 2015/0344553 | A1 | 12/2015 | Weinreb et al. |
| 2016/0024193 | A1 | 1/2016 | Ayalon et al. |
| 2016/0031976 | A1 | 2/2016 | Seubert et al. |
| 2016/0031977 | A1 | 2/2016 | Lu et al. |

FOREIGN PATENT DOCUMENTS

| | | | |
|---|---|---|---|
| EP | 0310132 | A2 | 4/1989 |
| ES | 2321996 | L | 6/2009 |
| WO | 9311231 | A1 | 6/1993 |
| WO | 9418560 | A1 | 8/1994 |
| WO | 9822120 | A1 | 5/1998 |
| WO | 0014546 | A1 | 3/2000 |
| WO | WO2011032155 | * | 3/2011 |
| WO | 2012045882 | A2 | 4/2012 |
| WO | 2012106363 | A2 | 8/2012 |
| WO | 2013177104 | A2 | 11/2013 |
| WO | 2014008404 | A1 | 1/2014 |
| WO | 201496321 | A1 | 6/2014 |
| WO | 2014159244 | A2 | 10/2014 |
| WO | 2015200806 | A2 | 12/2015 |

OTHER PUBLICATIONS

International Search Report and Written Opinion from related International Application No. PCT/US2013/049333, dated Oct. 14, 2013; 17 pgs.

Kfoury et al., "Trans-cellular Propagation of Tau Aggregation by Fibrillar Species", Journal of Biological Chemistry, 2012, pp. 19440-19451, vol. 287, No. 23.

Khuchua et al., "Deletion of the N-Terminus of Murine MAP2 by Gene Targeting Disrupts Hippocampal CA1 Neuron Architecture and Alters Contextual Memory", Neuroscience, 2003, pp. 101-111, vol. 119, No. 1.

LoPresti et al., "Functional implications for the microtubule-associated protein tau: Localization in oligodendrocytes", Proc. Natl. Acad. Sci. USA, 1995, pp. 10369-10373, vol. 92, No. 22.

Porzig et al., "Epitope mapping of mAbs AT8 and Tau5 directed against hyperphosphorylated regions of the human tau protein", Biochemical and Biophysical Research Communications, 2007, pp. 644-649, vol. 358, No. 2.

Troquier et al., "Targeting Phospho-Ser422 by Active Tau Immunotherapy in the THY-Tau22 Mouse Model: A Suitable Therapeutic Approach", Current Alzheimer Research, 2012, pp. 397-405, vol. 9.

Wozniak et al., "Apoptotic neurodegeneration induced by ethanol in neonatal mice is associated with profound learning/memory deficits in juveniles followed by progressive functional recovery in adults", Neurobiology of Disease, 2004, pp. 403-414, vol. 17, No. 3.

Yamada et al., "In Vivo Microdialysis Reveals Age-Dependent Decrease of Brain Interstitial Fluid Tau Levels in P301S Human Tau Transgenic Mice", The Journal of Neuroscience, 2011, pp. 13110-13117, vol. 31, No. 37.

Yanamandra et al., "Anti-tau antibodies that block tau aggregate seeding in vitro markedly decrease pathology and Improve cognition in vivo", NIH Public Access, 2013, pp. 402-414, vol. 80, No. 2.

Supplemental European Search Report for Application No. 13813988.6 dated May 6, 2016.

Written Opinion of Intellectual Property Office of Singapore for Application No. 11201408626Y dated Feb. 25, 2016.

Search Report of Intellectual Property Office of Singapore for Application No. 11201408626Y dated Jan. 13, 2016.

Supplemental European Search Report for Application No. 13813988.6 dated Aug. 29, 2016.

* cited by examiner

A

Htau N-terminal

Met A E P R Q E F E V Met E D H A G T Y G L G D R K D Q G G Y T Met H Q D Q E G
D T D A G L K E S P L Q T P T E D G S E E P G S E T S D A K S T P T A E D V T A P L V D E G
A P G K Q A A A Q P H T E I P E G T T A E E A G I G D T P S L E D E A A G H V T Q A R
Met V S K S K D G

B

Htau C-terminal

Met P D L K N V K S K I G S T E N L K H Q P G G G K V Q I I N K K L D L S N V Q S K C
G S K D N I K H V P G G G S V Q I V Y K P V D L S K V T S K C G S L G N I H H K P G G G Q
V E V K S E K L D F K D R V Q S K I G S L D N I T H V P G G G N K K I E T H K L T F R E N A
K A K T D H G A E I V Y K S P V V S G D T S P R H L S N V S S T G S I D Met V D S P Q L A
T L A D E V S A S L G Q A G L

FIG. 1

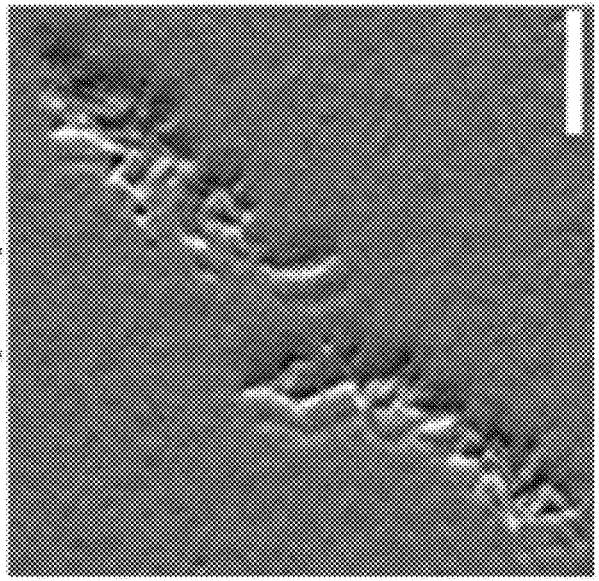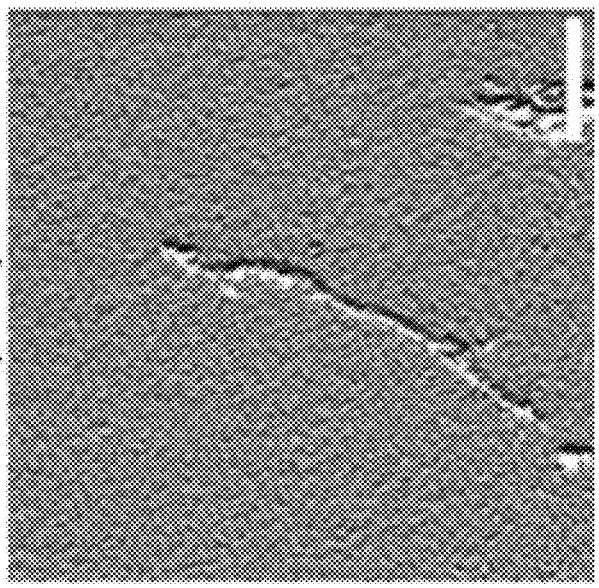
FIG. 15B

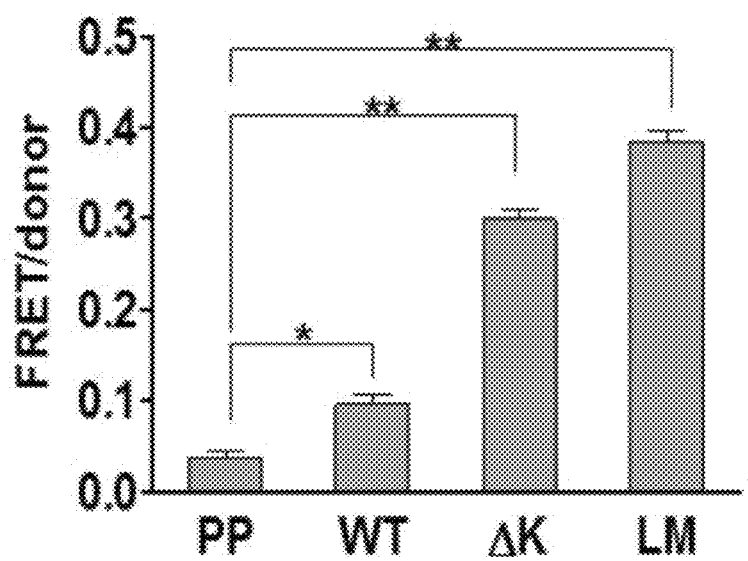
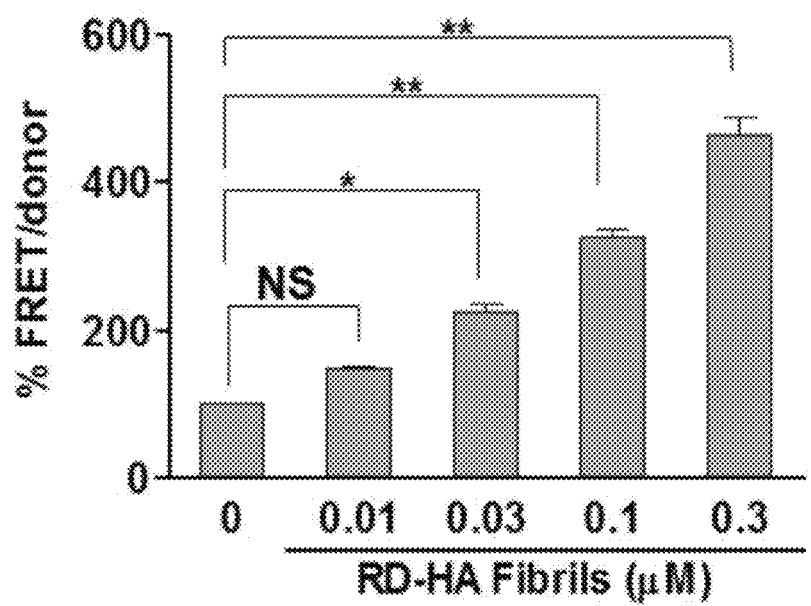
FIG. 16

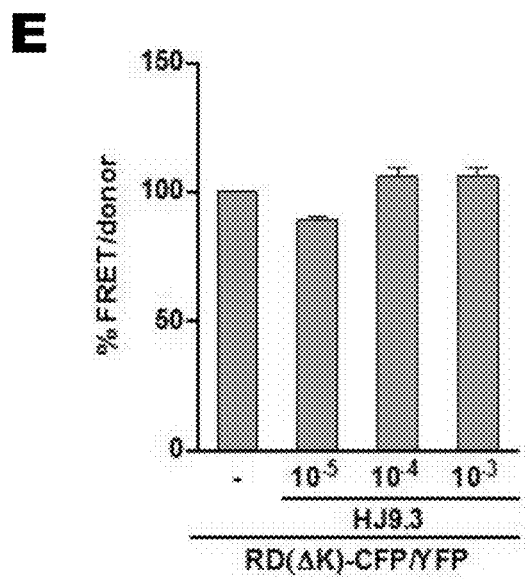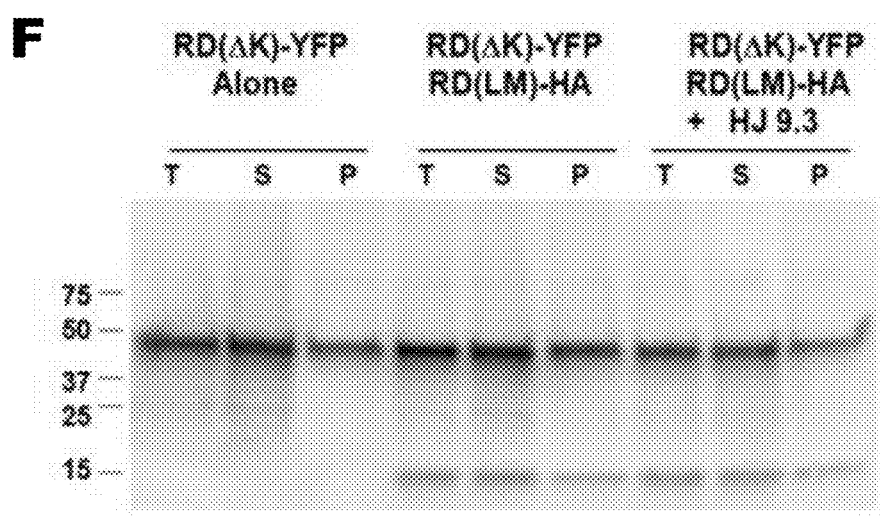
FIG. 19

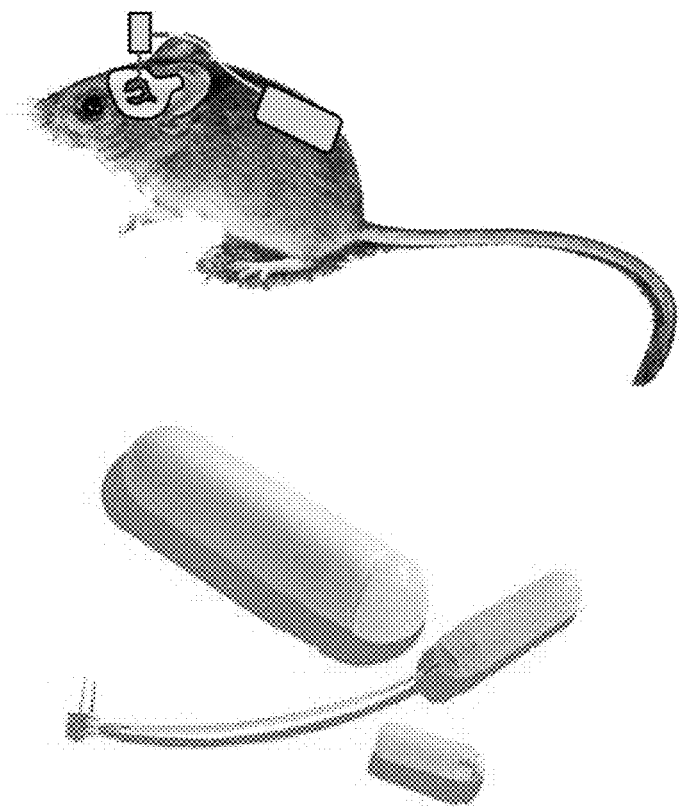
Alzet osmotic pump
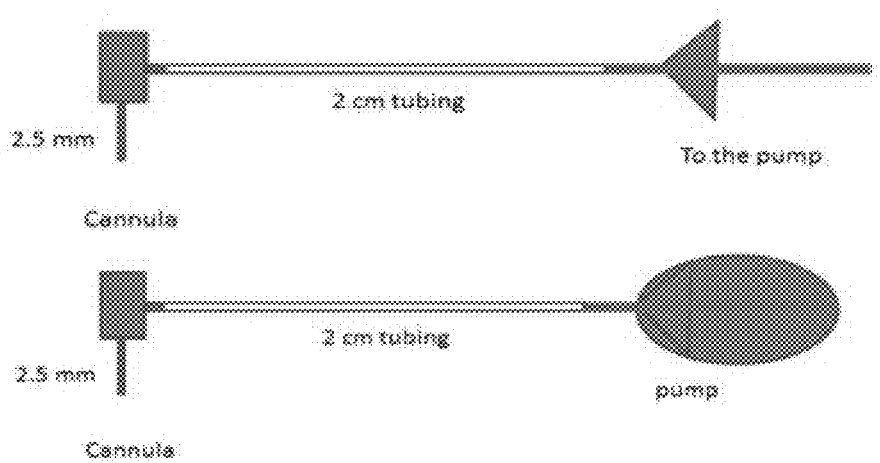
FIG. 23B

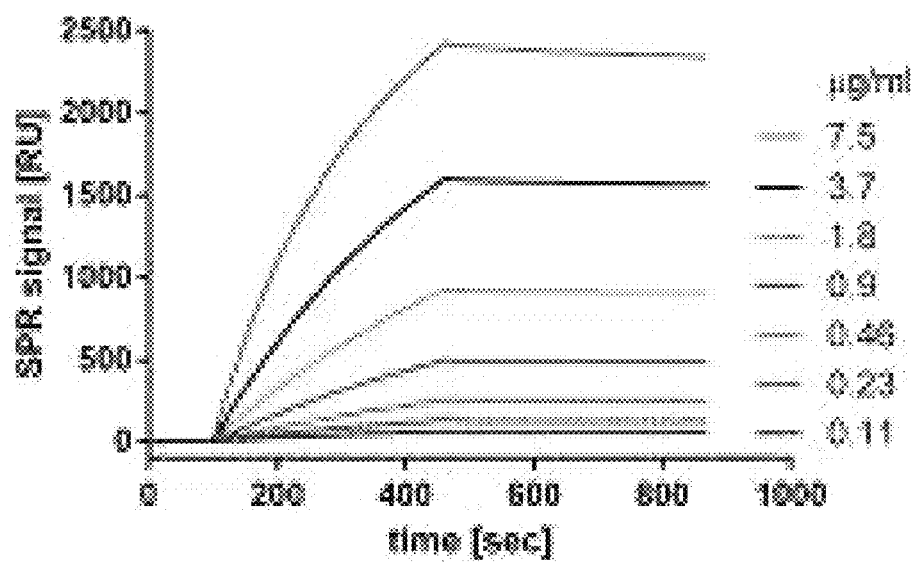
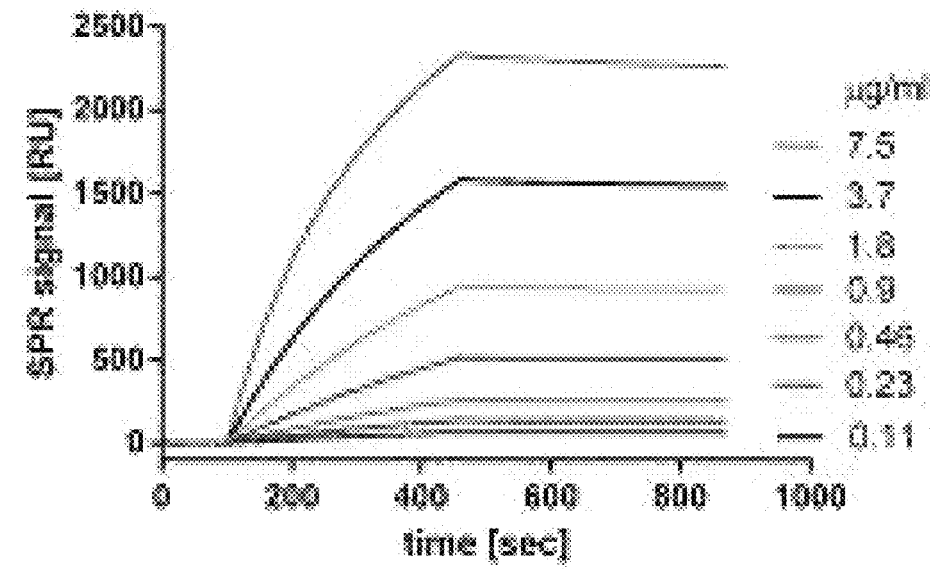
FIG. 30

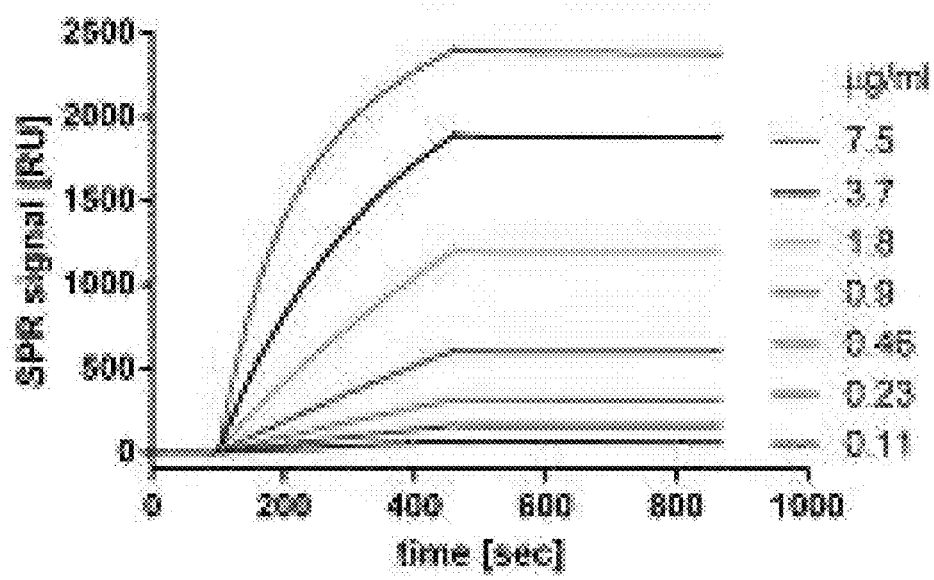
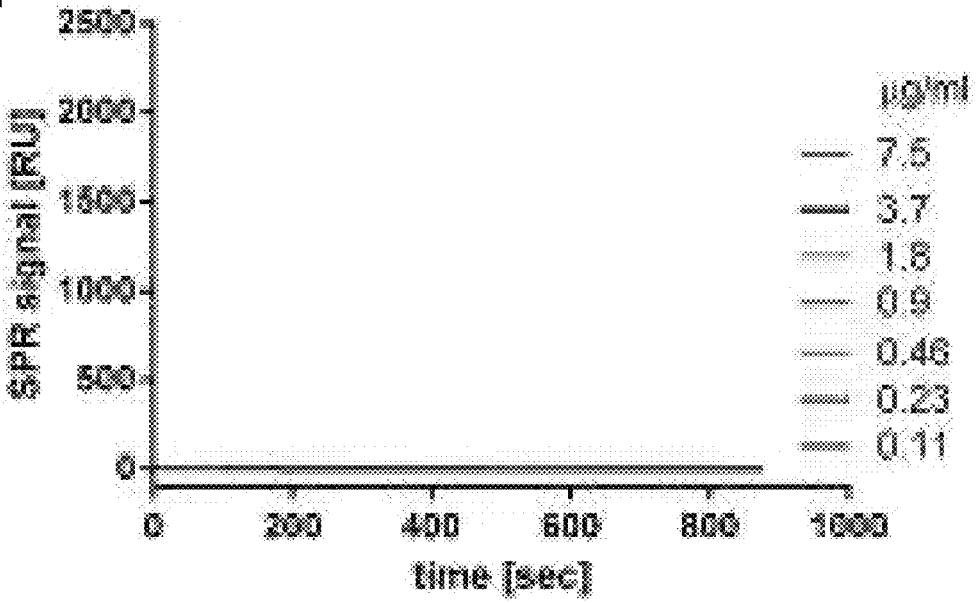
FIG. 30

FIG. 34

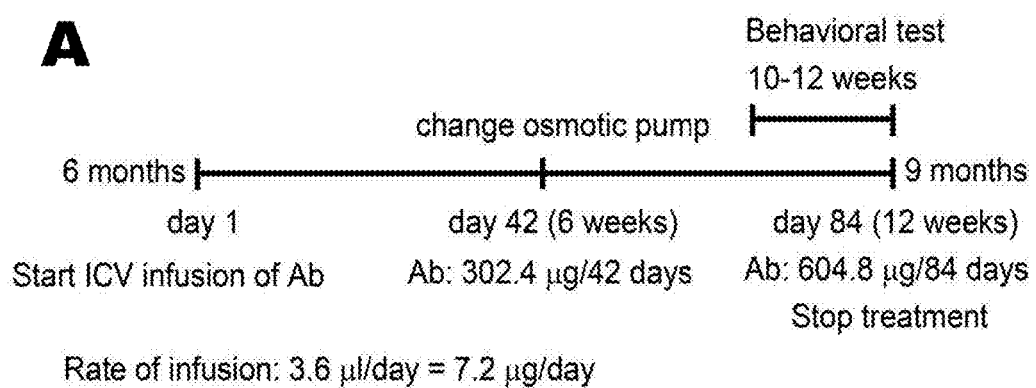
FIG. 35

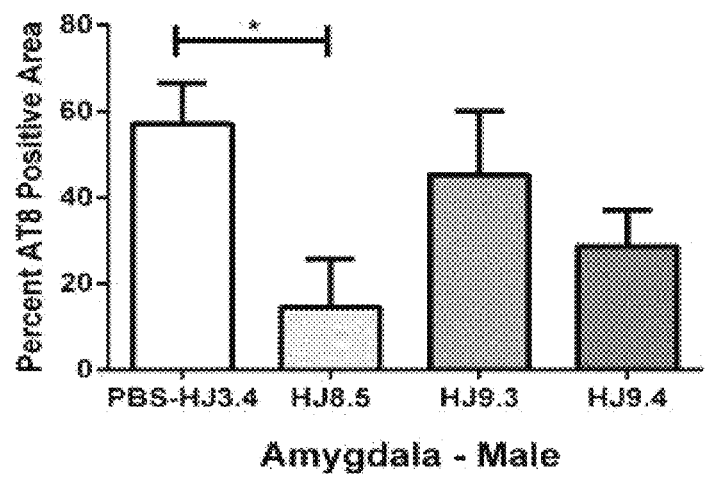
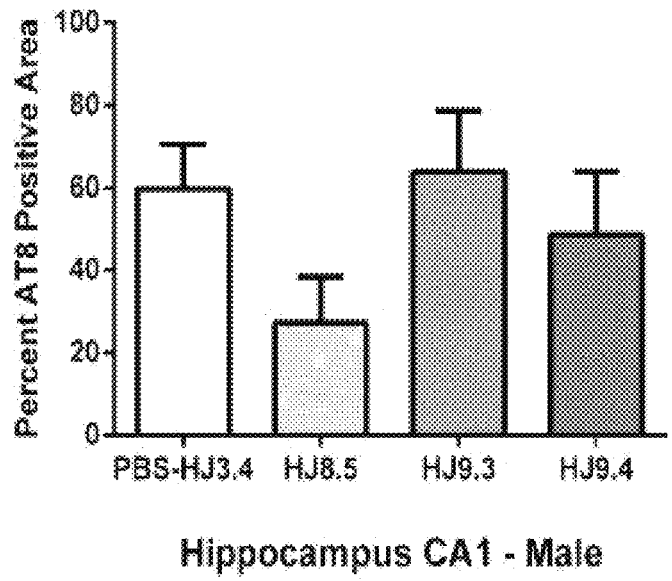
FIG. 38

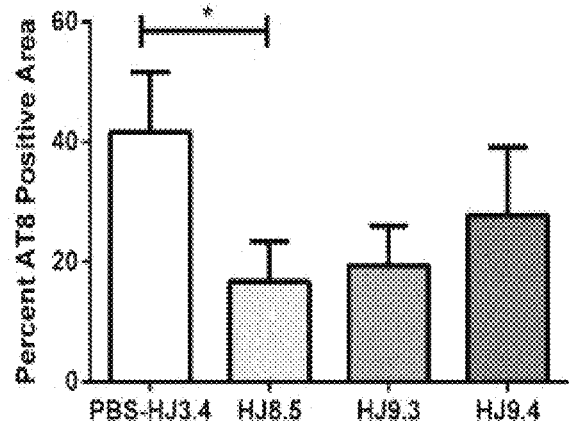
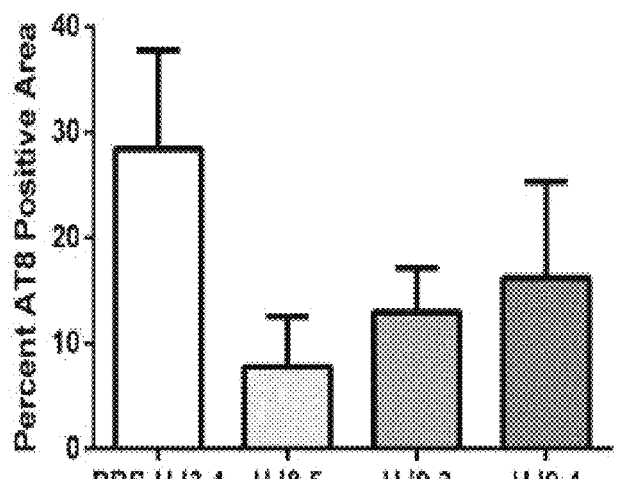
FIG. 38

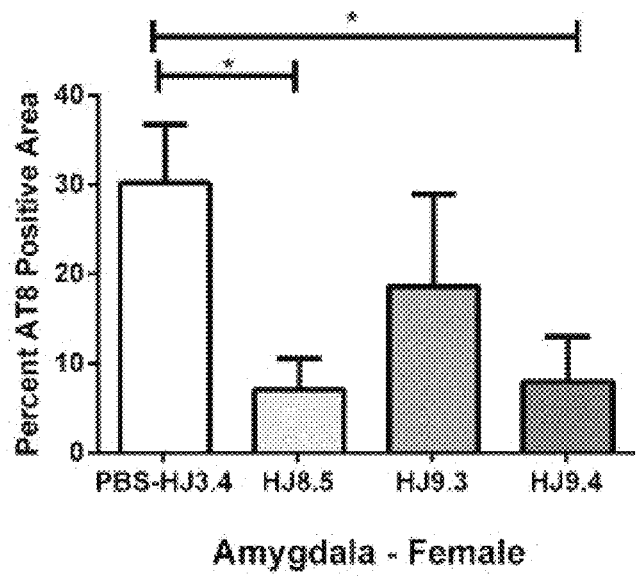
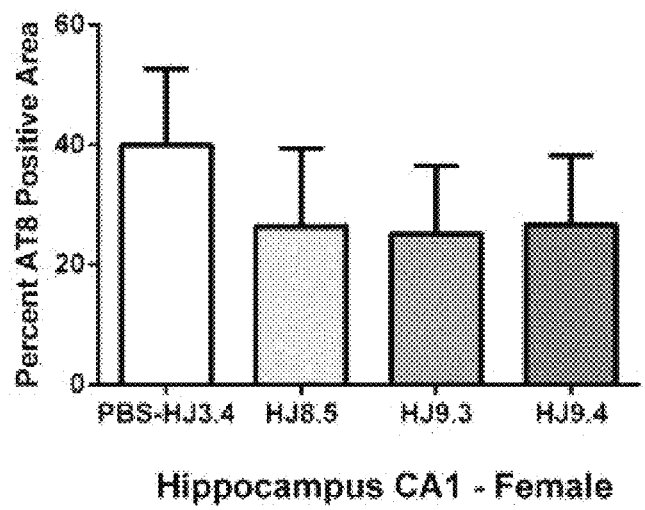
FIG. 38

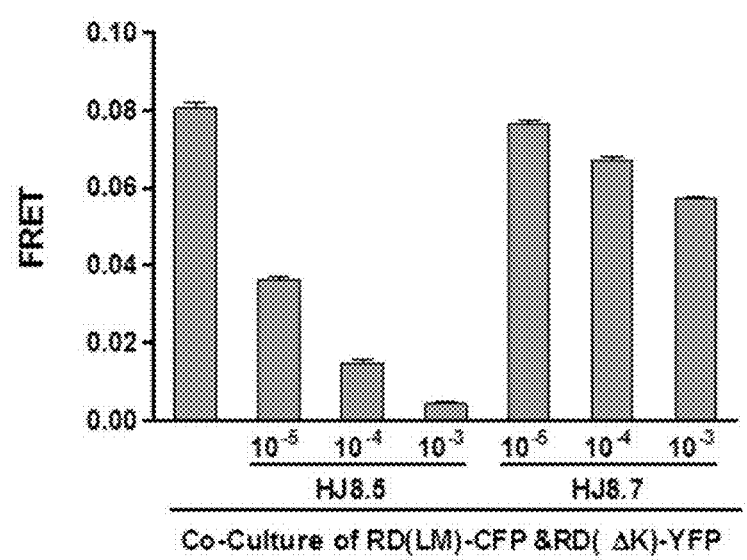
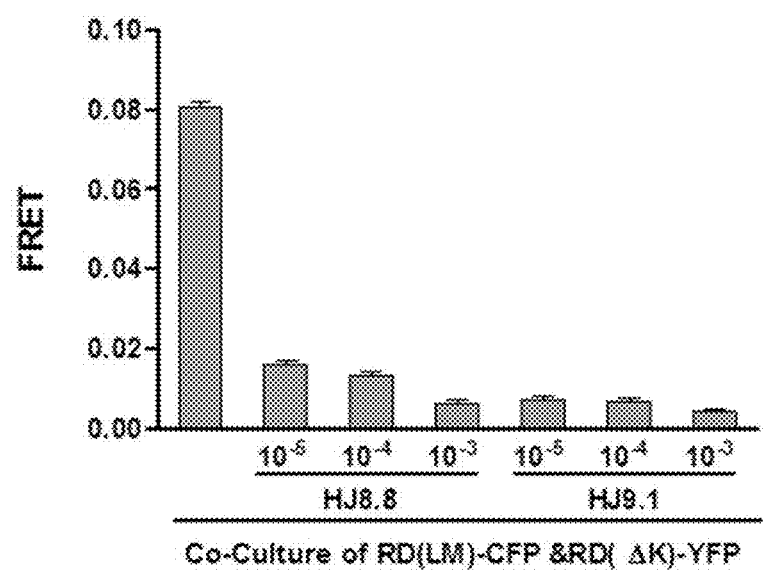
FIG. 47

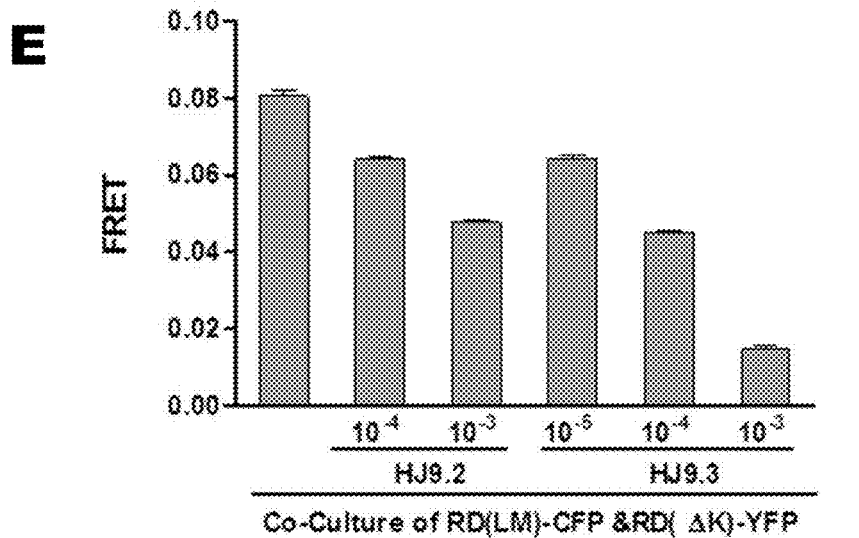
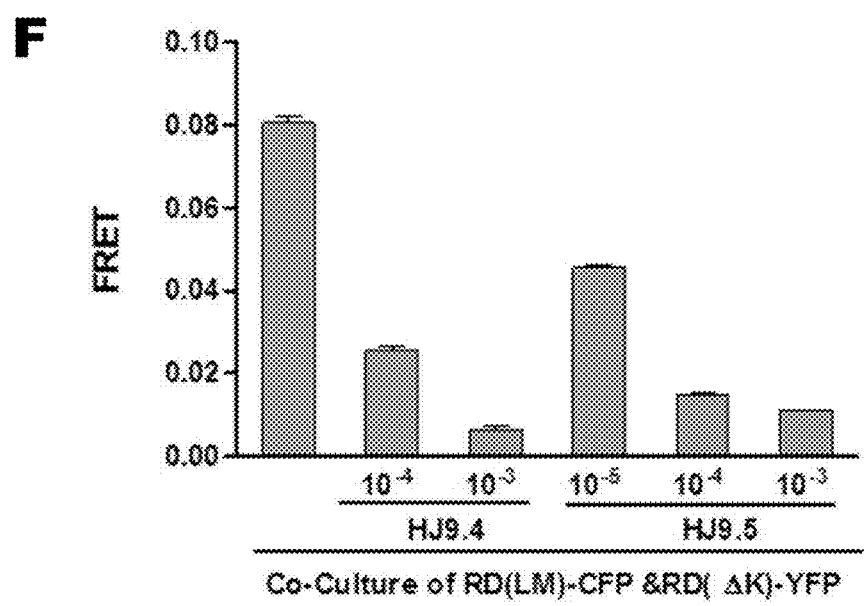
FIG. 47

ANTIBODIES TO TAU

GOVERNMENT SUPPORT

This invention was made with government support under 1R01NS071835 awarded by the National Institutes of Health. The government has certain rights in the invention.

FIELD OF THE INVENTION

This invention relates to antibodies to tau and methods of use thereof.

BACKGROUND OF THE INVENTION

Aggregation of the microtubule associated protein tau is associated with several neurodegenerative disorders, including Alzheimer's disease (AD) and frontotemporal dementia. In AD, pathological tau aggregation spreads progressively throughout the brain, possibly along existing neural networks. AD is the most common cause of dementia and is an increasing public health problem. It is currently estimated to afflict 5 million people in the United States, with an expected increase to 13 million by the year 2050. Alzheimer's Disease leads to loss of memory, cognitive function, and ultimately loss of independence. It takes a heavy personal and financial toll on the patient and the family. Because of the severity and increasing prevalence of the AD and other neurodegenerative diseases associated with aggregation of tau in the population, it is urgent that better treatments and detection methods be developed.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 1 depicts the amino acid sequence for N-terminal (A) and C-terminal (B) human tau (htau).

FIG. 34. No detected cellular uptake of tau antibodies bound to P301S Tau aggregates. P301S brain lysates were added to HEK293 cells for 3 hrs. For detection of tau, all 3 different anti-tau or control (HJ3.4, A$\beta$ antibody) antibodies were used followed by Alexa-fluor546 anti-mouse IgG staining. In addition, P301S brain lysates were pre-incubated with and without 3 different anti-tau antibodies and HJ3.4 antibody, then added to HEK293 cells, fixed and permeabilized. Alexa-fluor546 anti-mouse IgG were used to identify the internalized antibodies. 4',6'-diamidino-2-phenylindole (DAPI; shown in blue) was used for nuclear stain.

FIG. 35. Experimental outline of ICV infusion of antibodies and efficacy of antibody by different treatment method. (A) Experimental plan for infusion of antibodies or vehicle (PBS) by intracerebroventricular injection into the left lateral ventricle of the brain. (B) Representative cresyl violet staining of the coronally sectioned brain region to verify the surgically implanted probe placement into the left lateral ventricle. In this study, we included the mice which had correct probe placements into the left lateral ventricle.

DETAILED DESCRIPTION

Figure 2A:
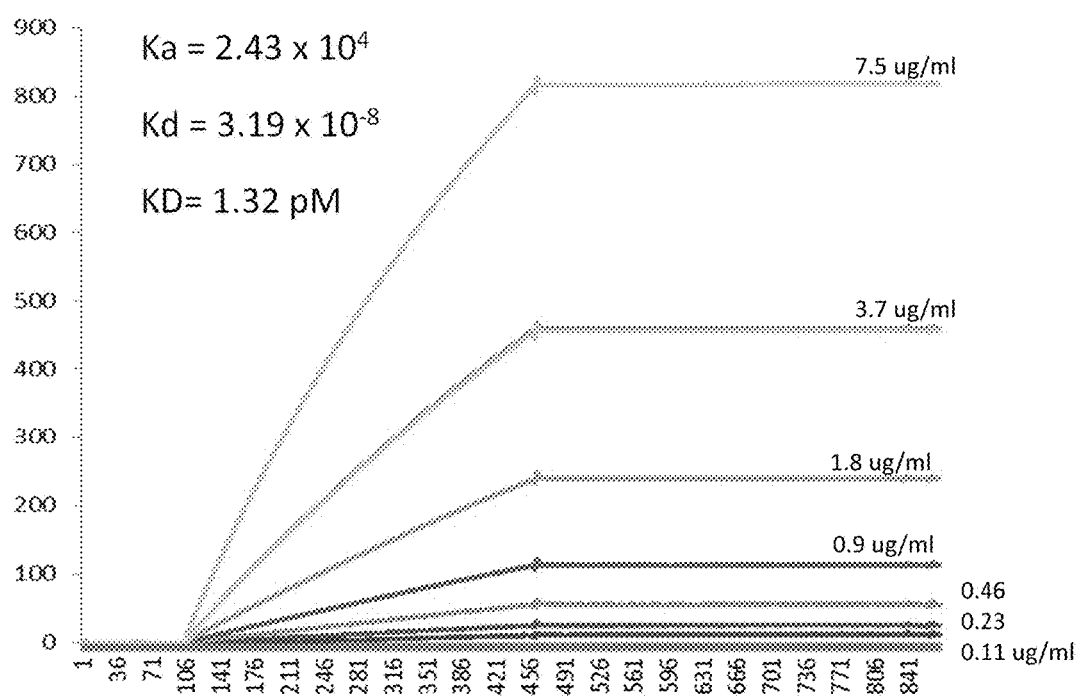
FIG. 2 depicts graphs showing the KD for HJ8.1 towards Human Tau (A) and Mouse Tau (B).
Figure 2B:
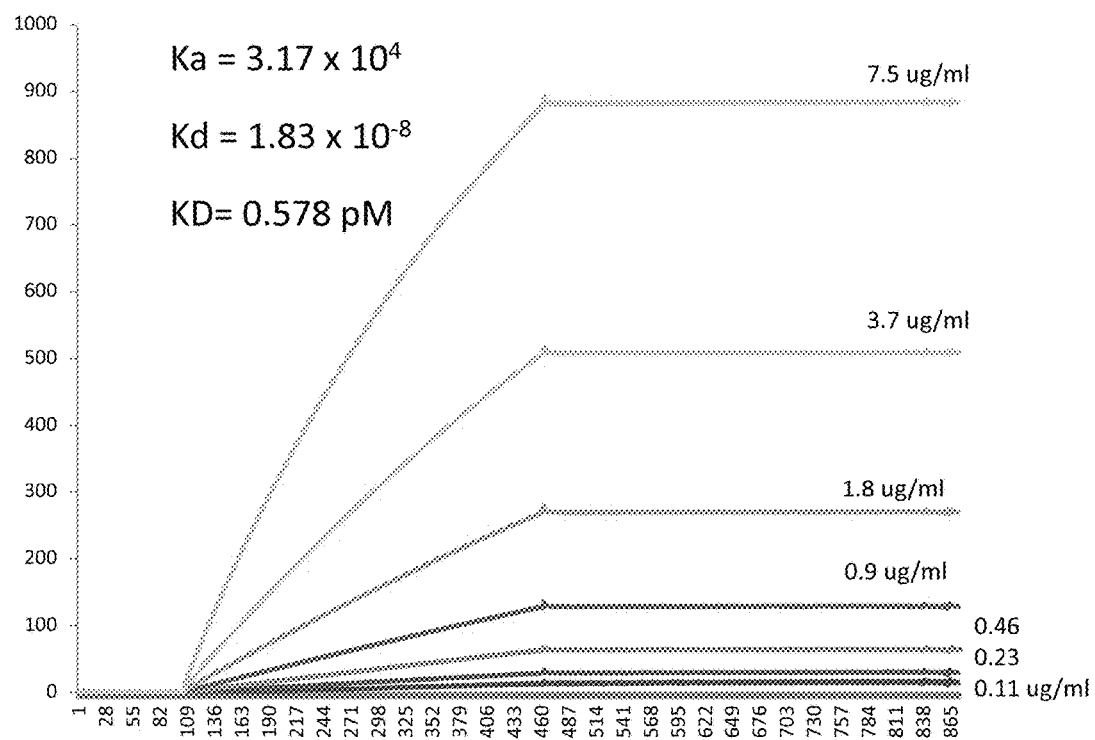
Figure 3A:
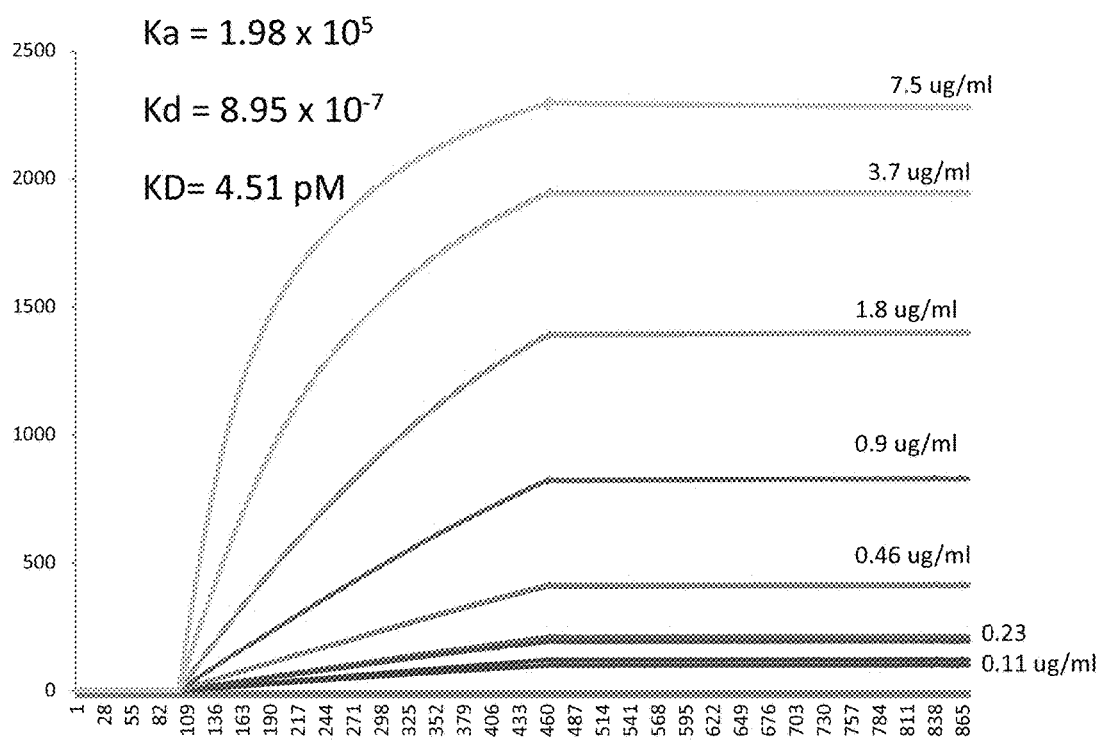
FIG. 3 depicts graphs showing the KD for HJ8.2 towards Human Tau (A) and Mouse Tau (B).
Figure 3B:
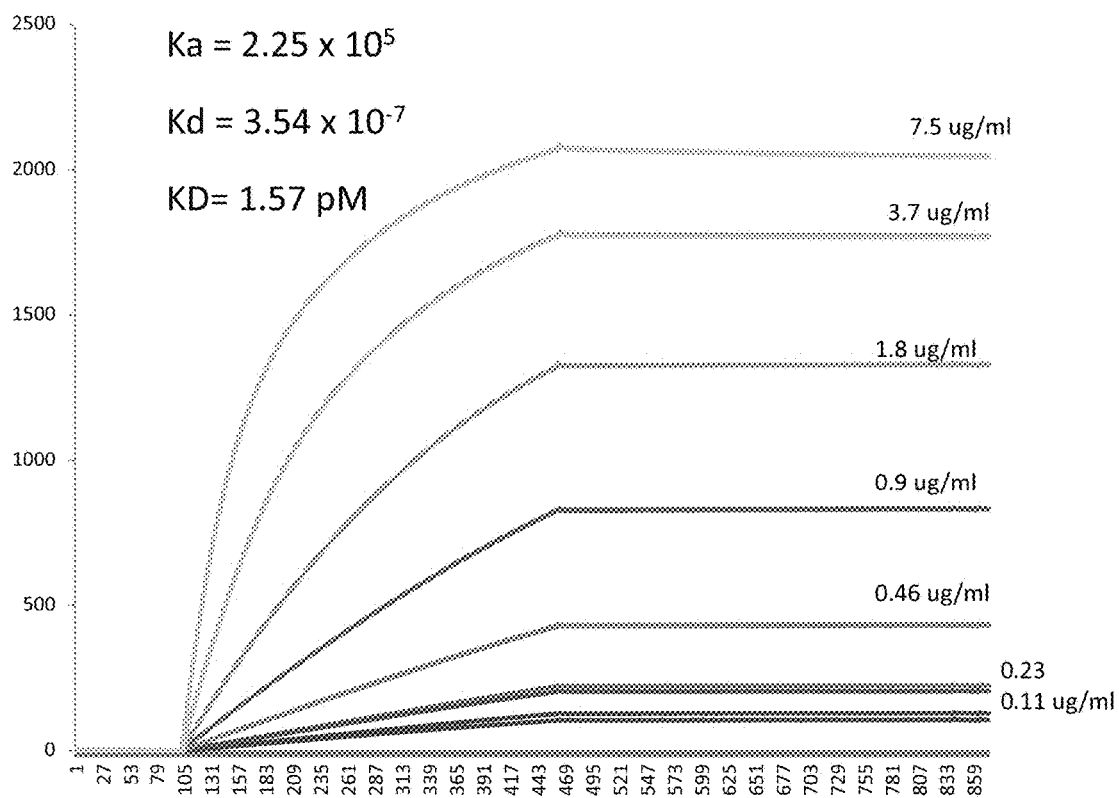
Figure 4A:
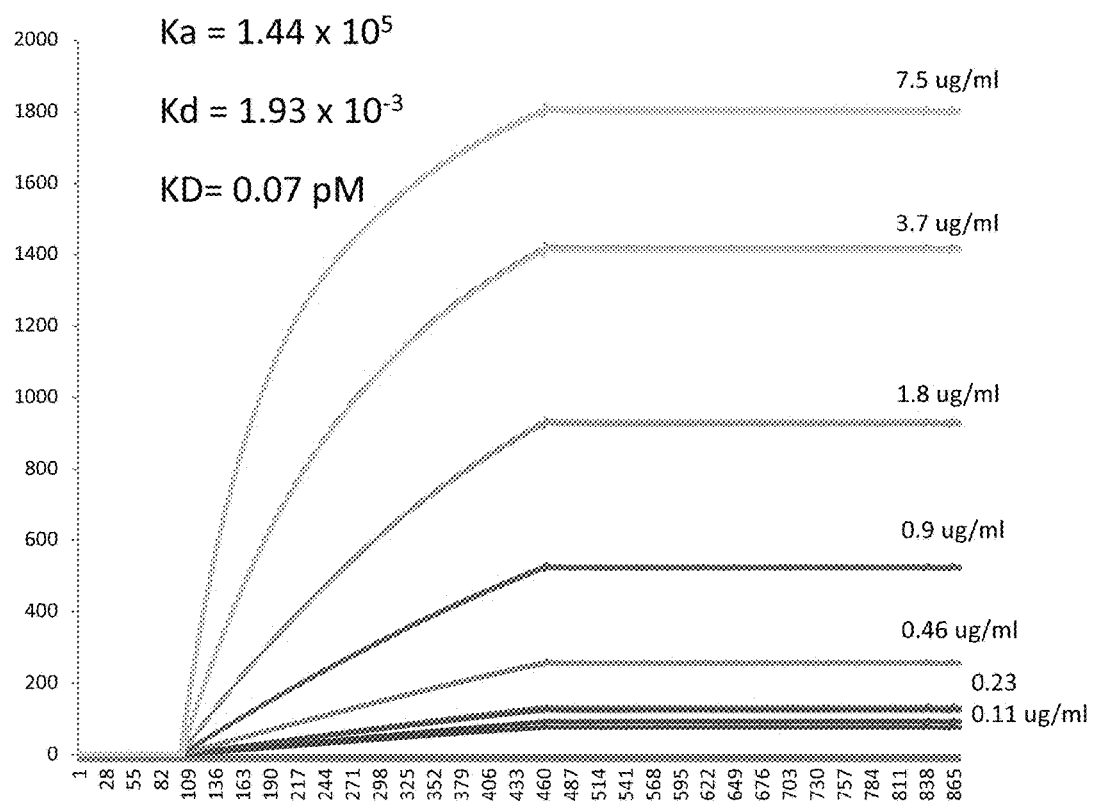
FIG. 4 depicts graphs showing the KD for HJ8.3 towards Human Tau (A) and Mouse Tau (B).
Figure 4B:
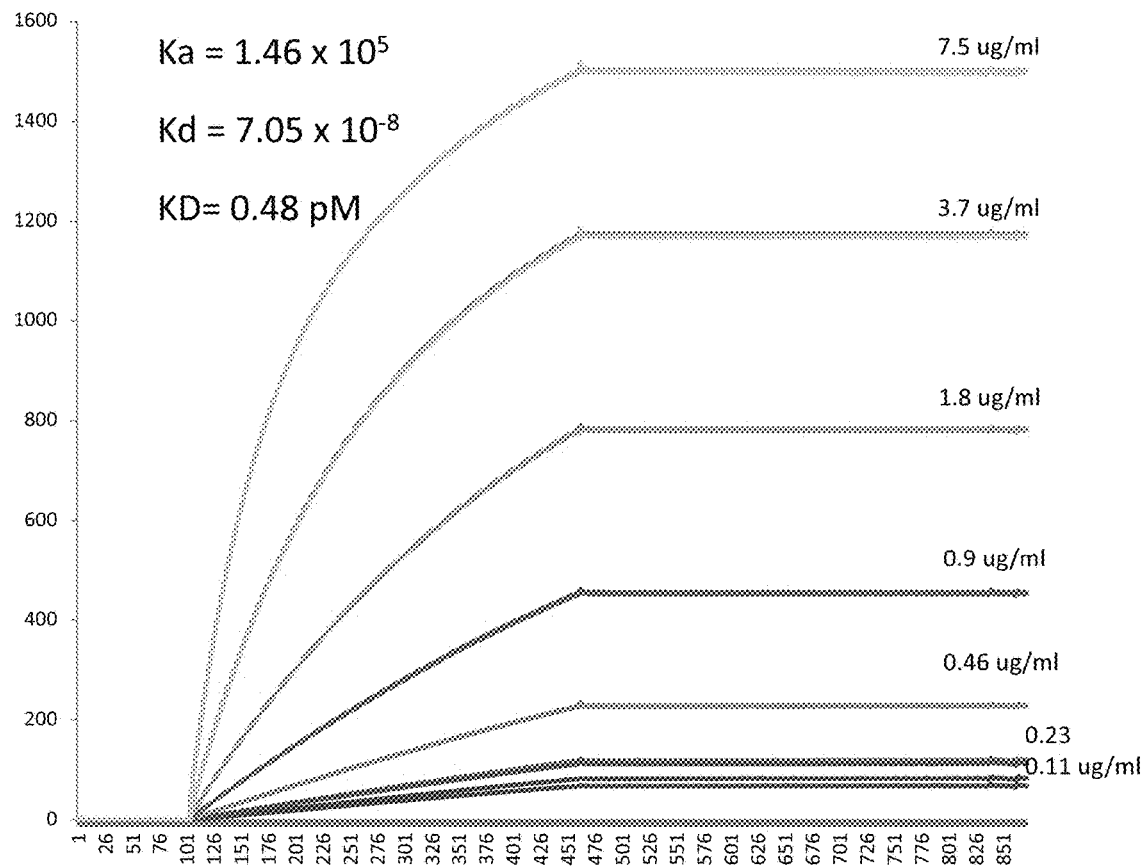
Figure 5A:
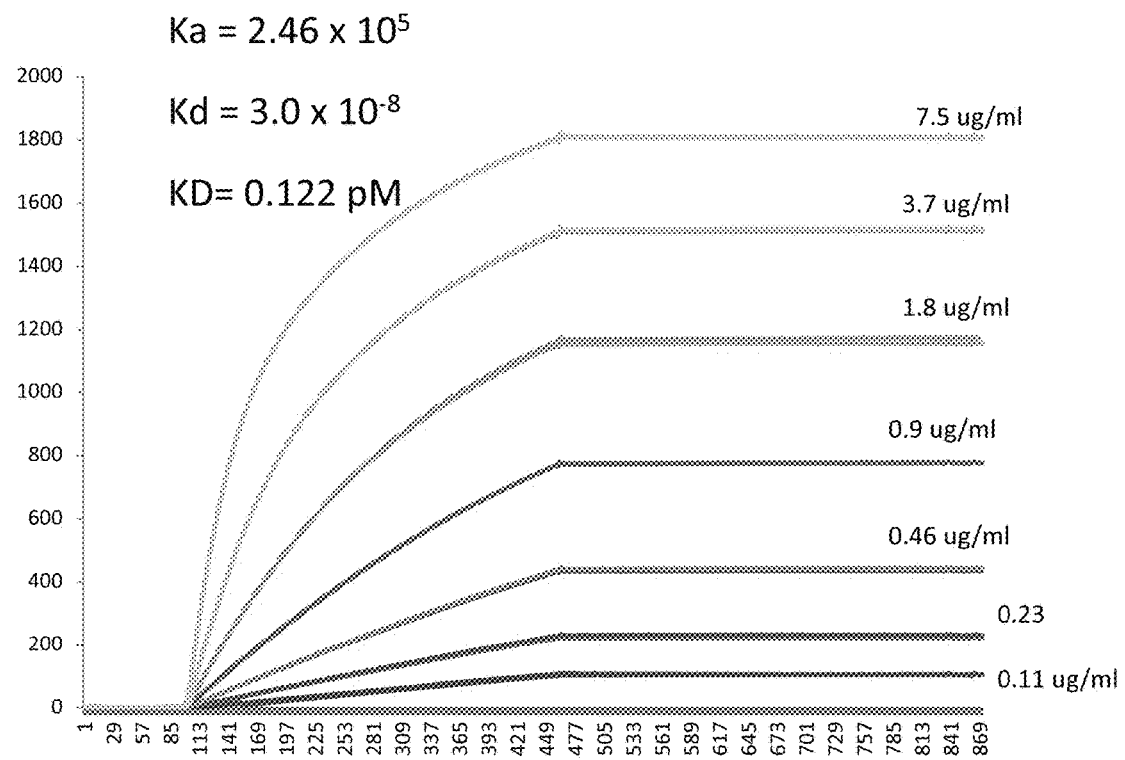
FIG. 5 depicts graphs showing the KD for HJ8.4 towards Human Tau (A) and Mouse Tau (B).
Figure 5B:
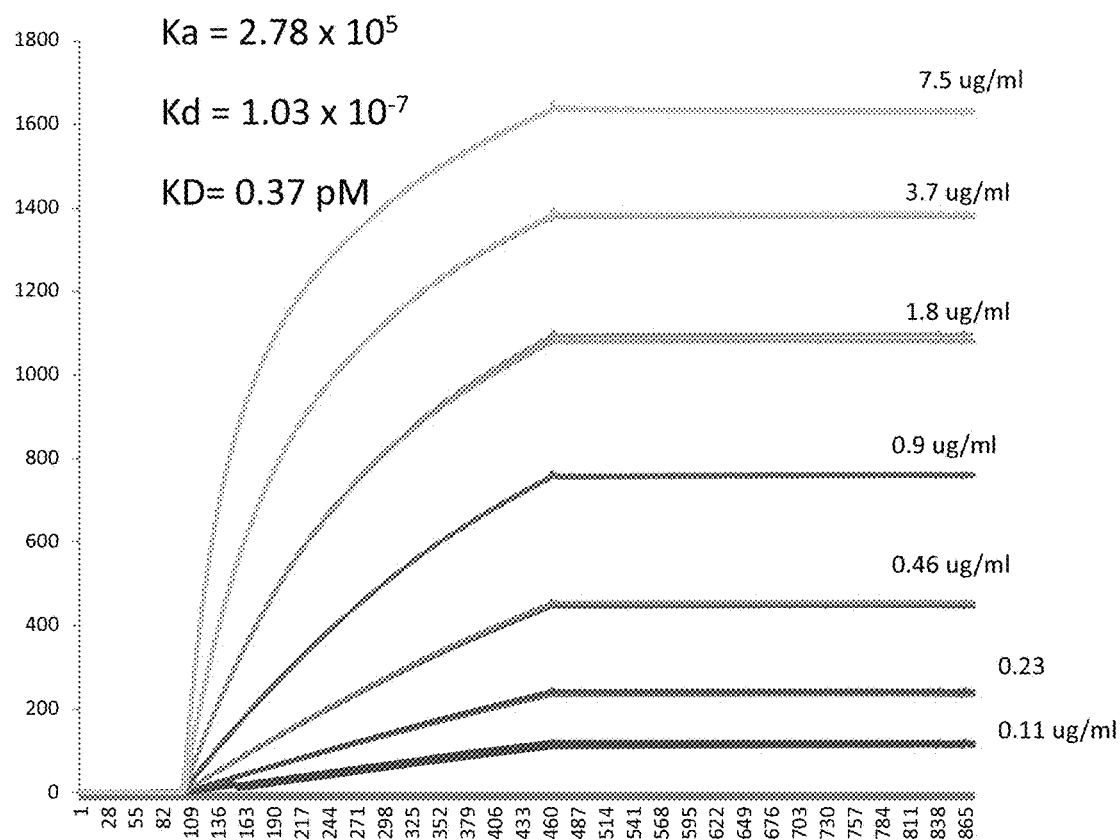
Figure 6A:
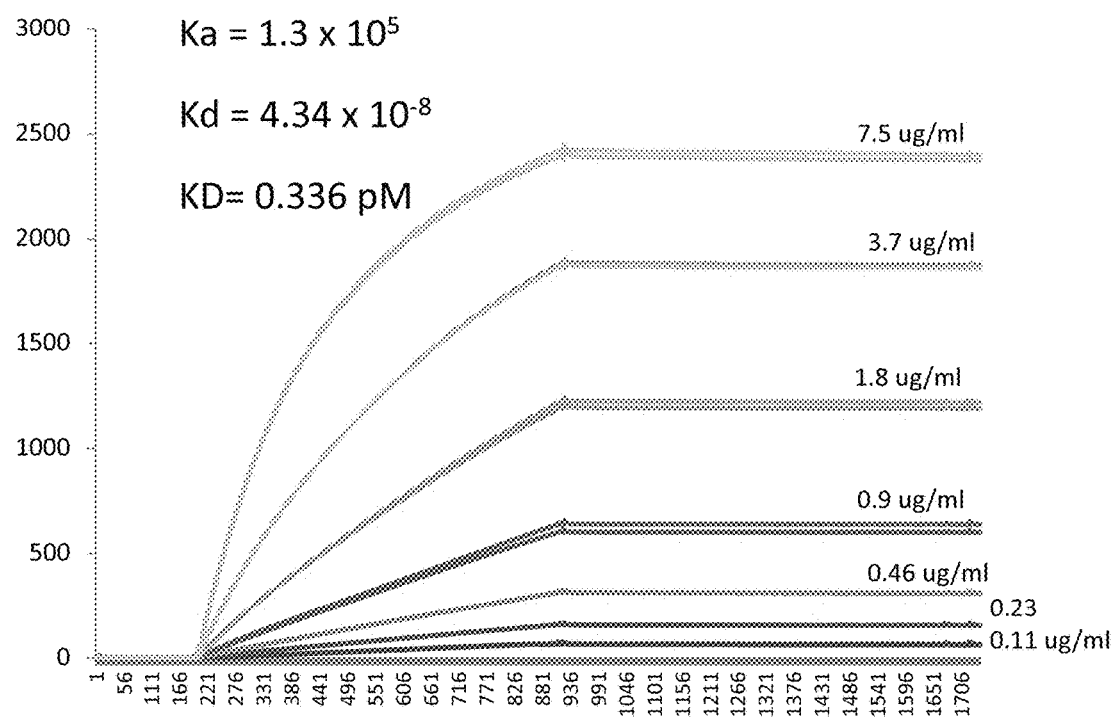
FIG. 6 depicts graphs showing the KD for HJ8.5 towards Human Tau (A) and Mouse Tau (B).
Figure 6B:
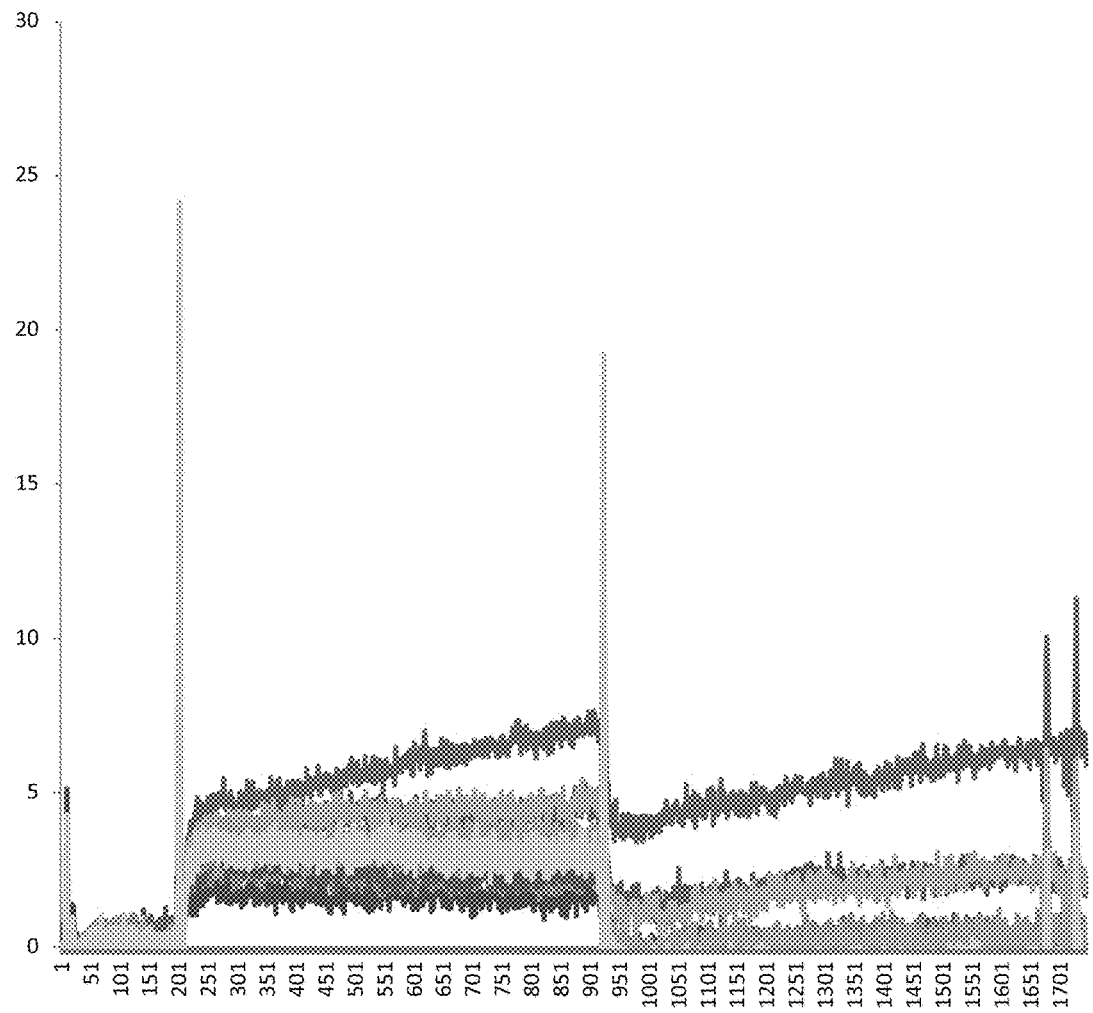
Figure 7A:
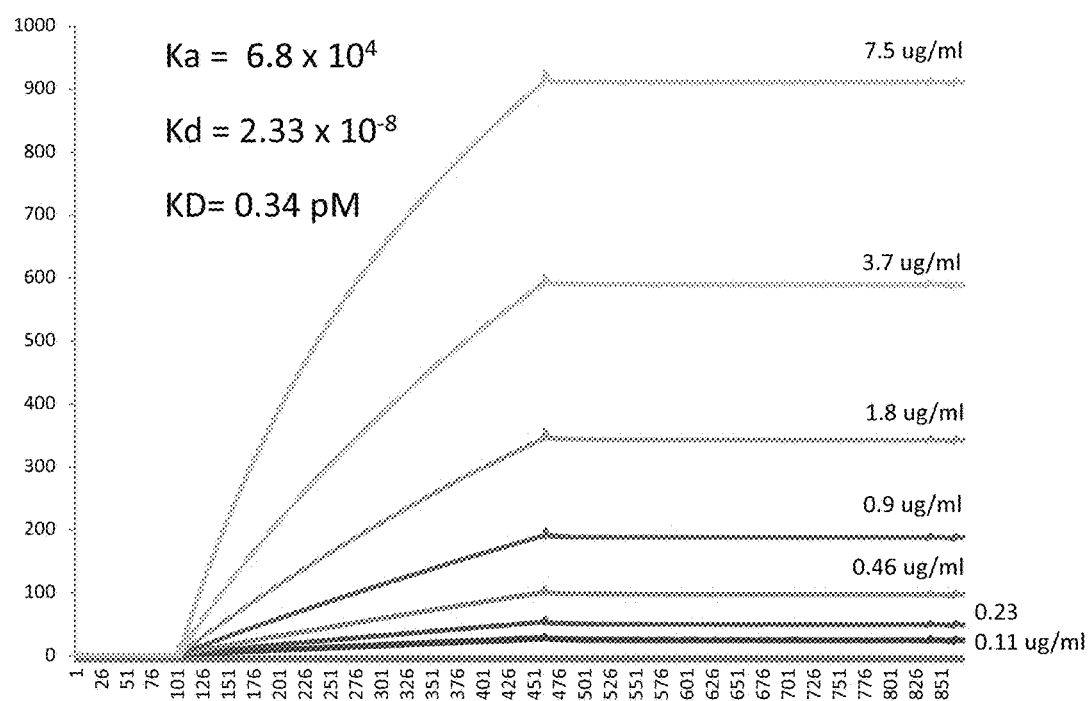
FIG. 7 depicts graphs showing the KD for HJ8.7 towards Human Tau (A) and Mouse Tau (B).
Figure 7B:
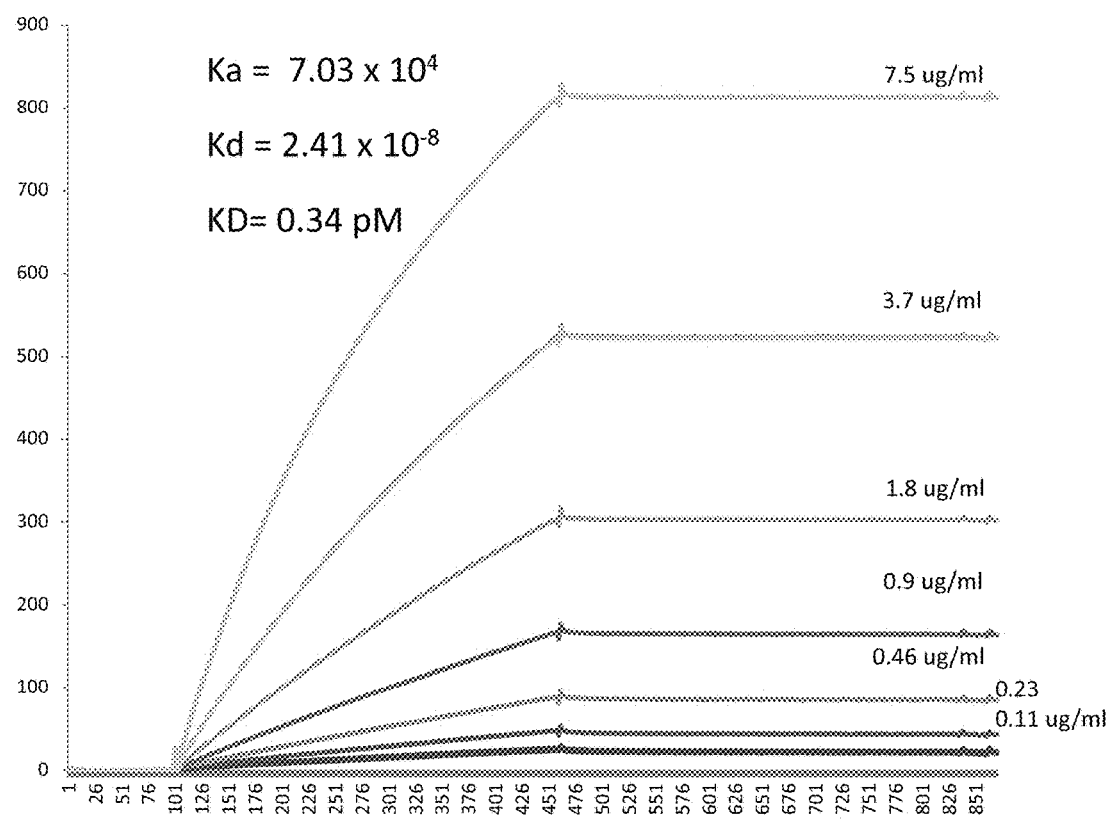
Figure 8A:
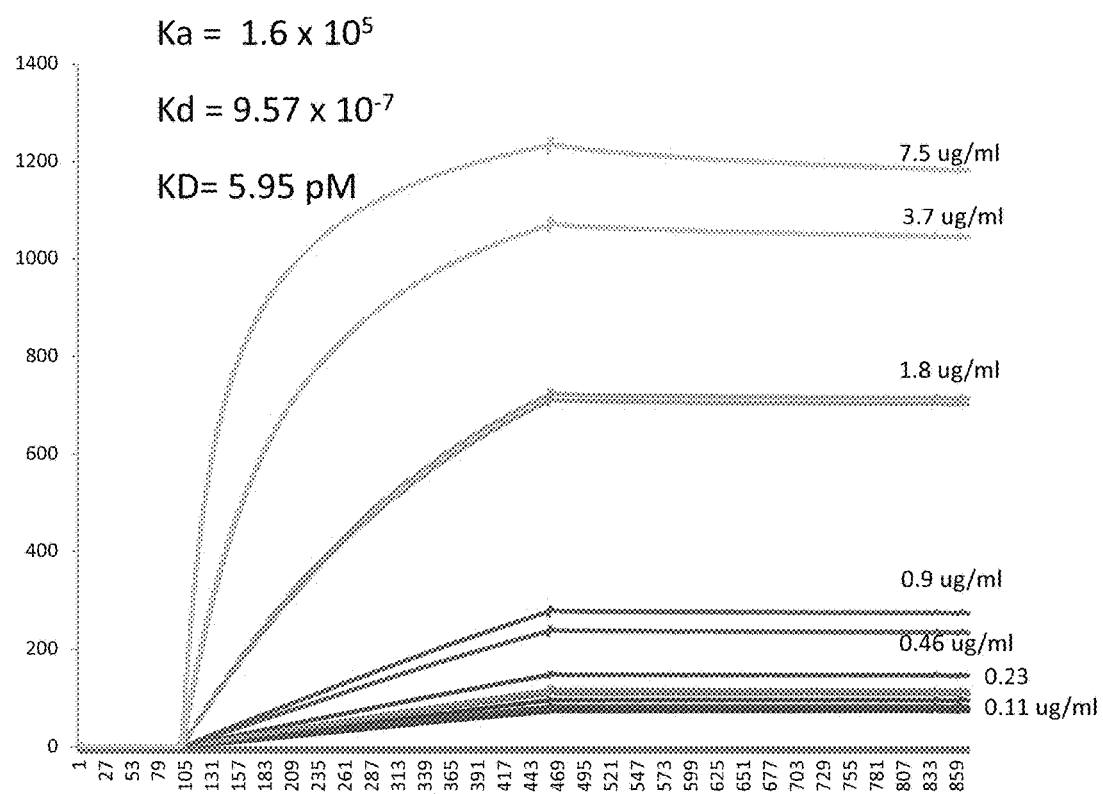
FIG. 8 depicts graphs showing the KD for HJ8.8 towards Human Tau (A) and Mouse Tau (B).
Figure 8B:
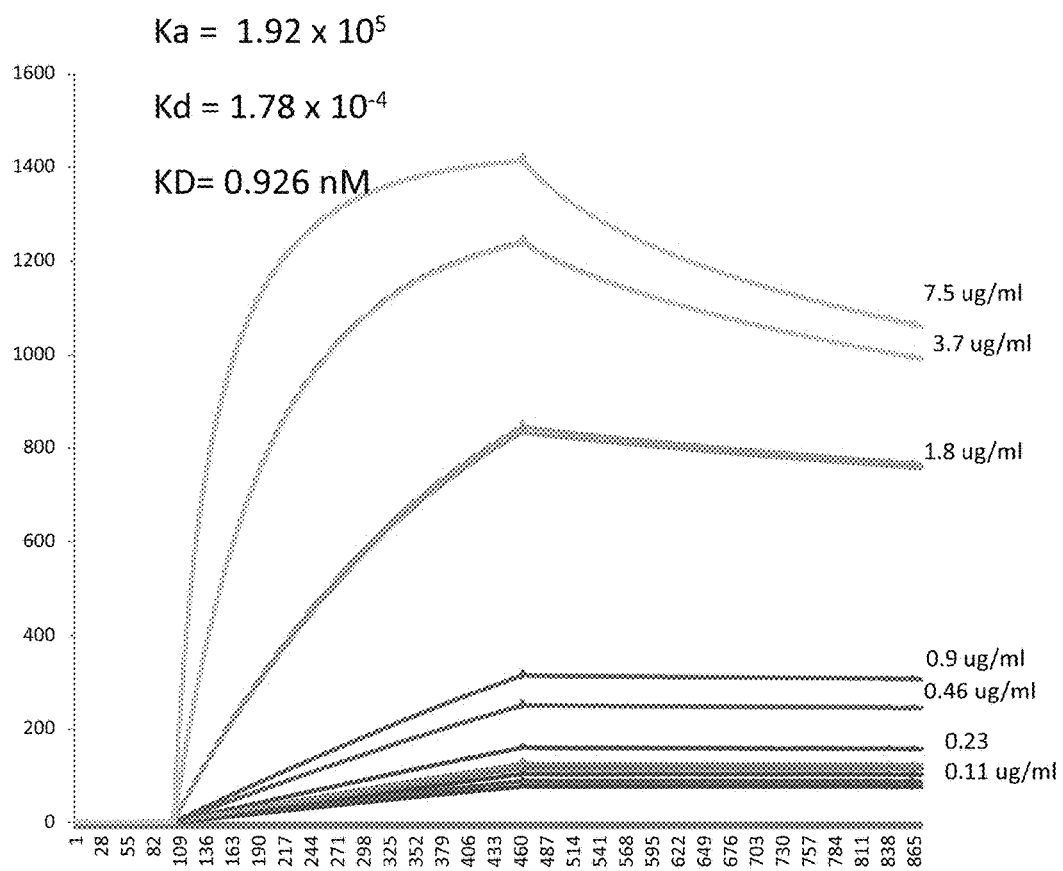
Figure 9A:
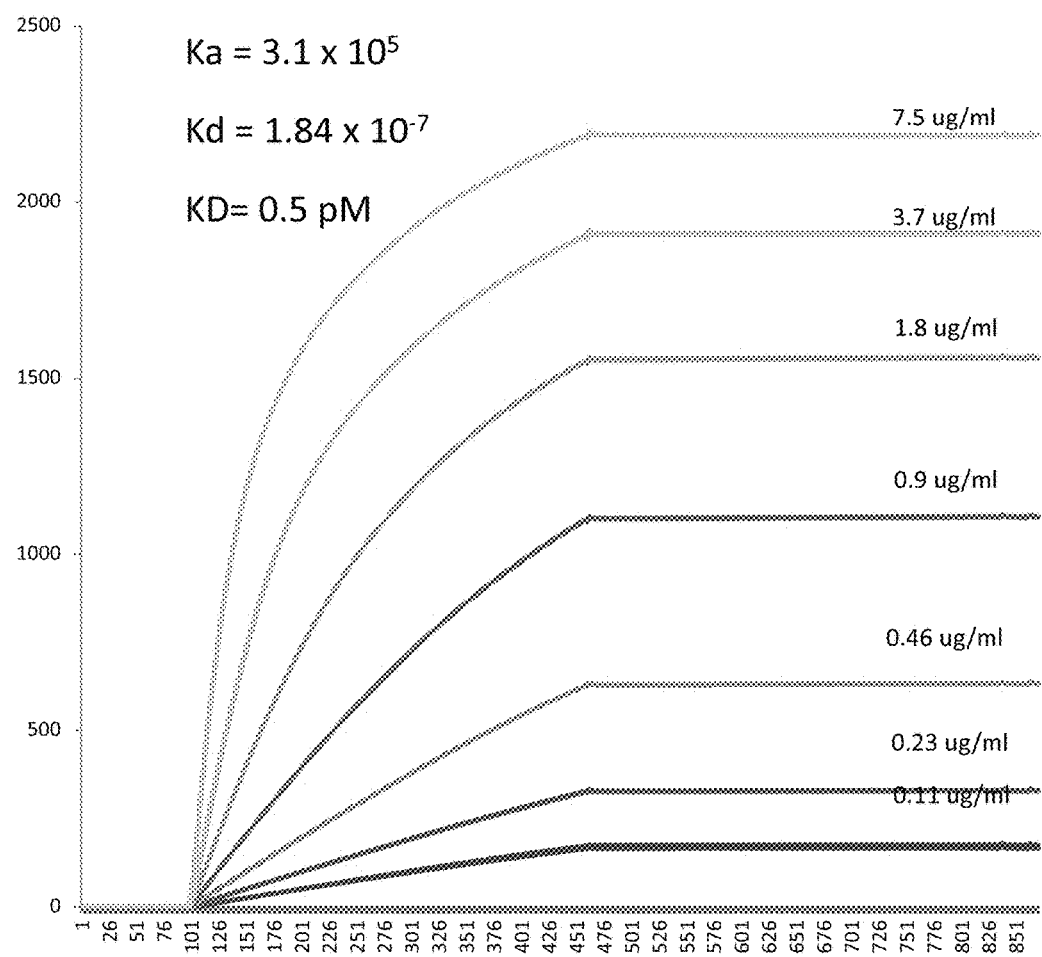
FIG. 9 depicts graphs showing the KD for HJ9.1 towards Human Tau (A) and Mouse Tau (B).
Figure 9B:
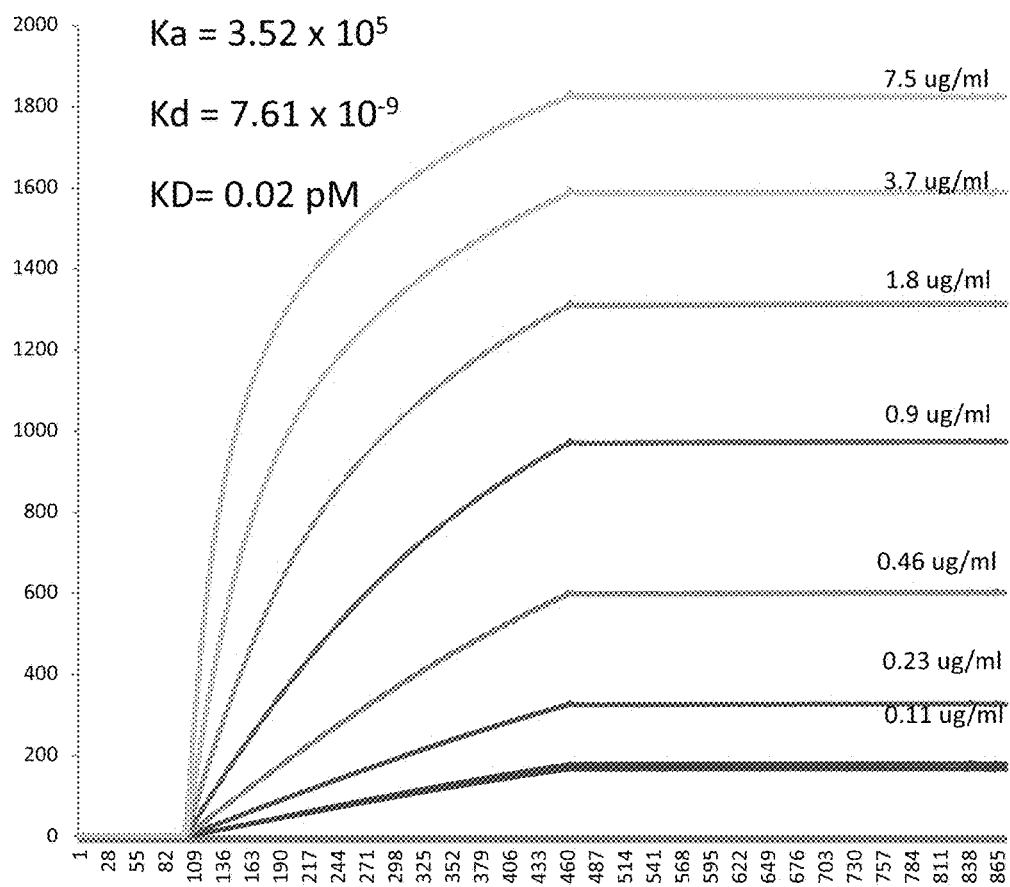
Figure 10A:
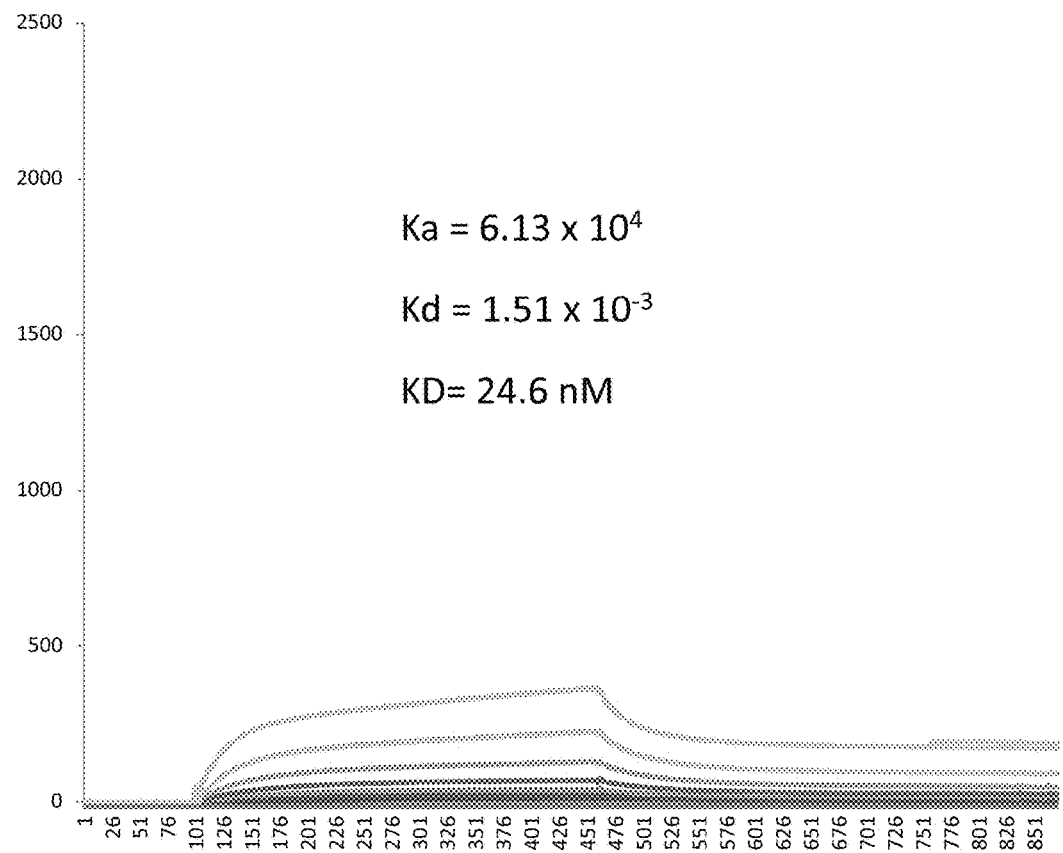
FIG. 10 depicts graphs showing the KD for HJ9.2 towards Human Tau (A) and Mouse Tau (B).
Figure 10B:
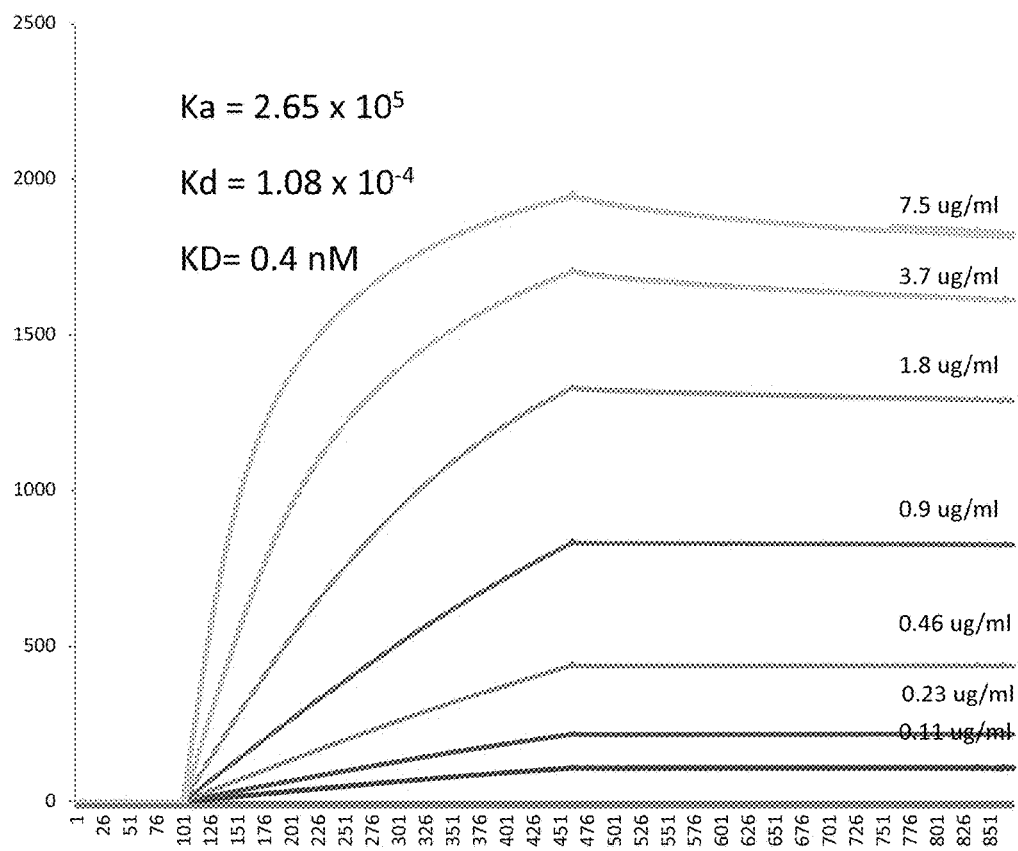
Figure 11A:
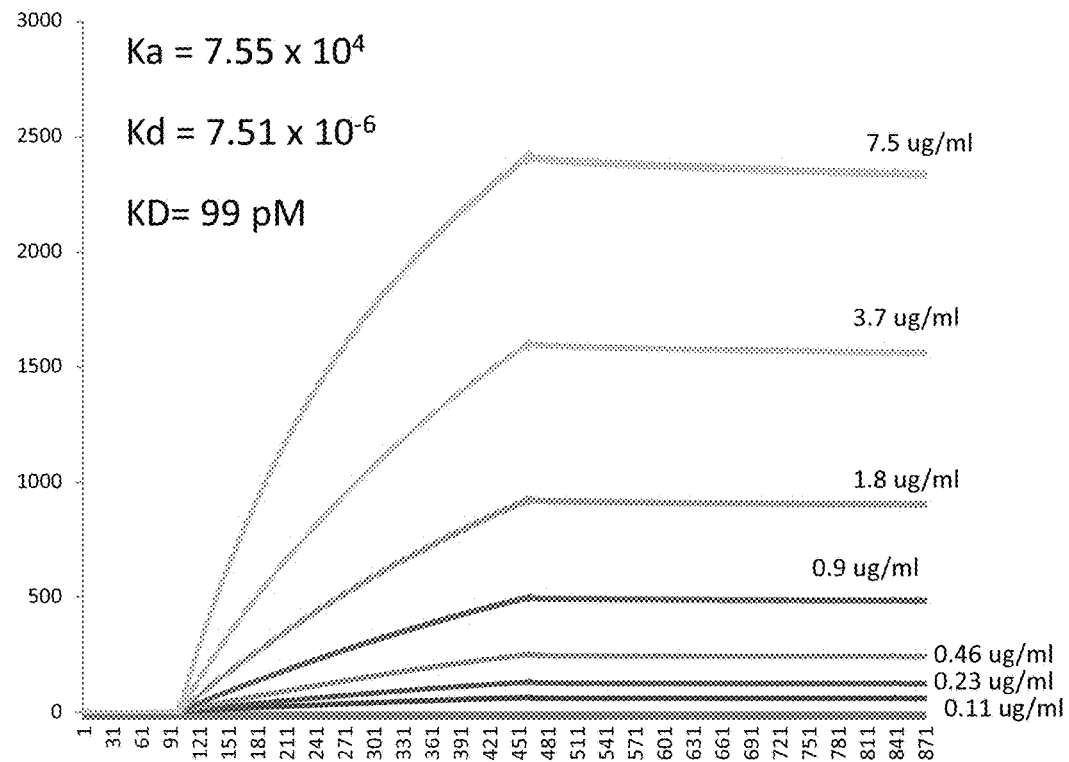
FIG. 11 depicts graphs showing the KD for HJ9.3 towards Human Tau (A) and Mouse Tau (B).
Figure 11B:
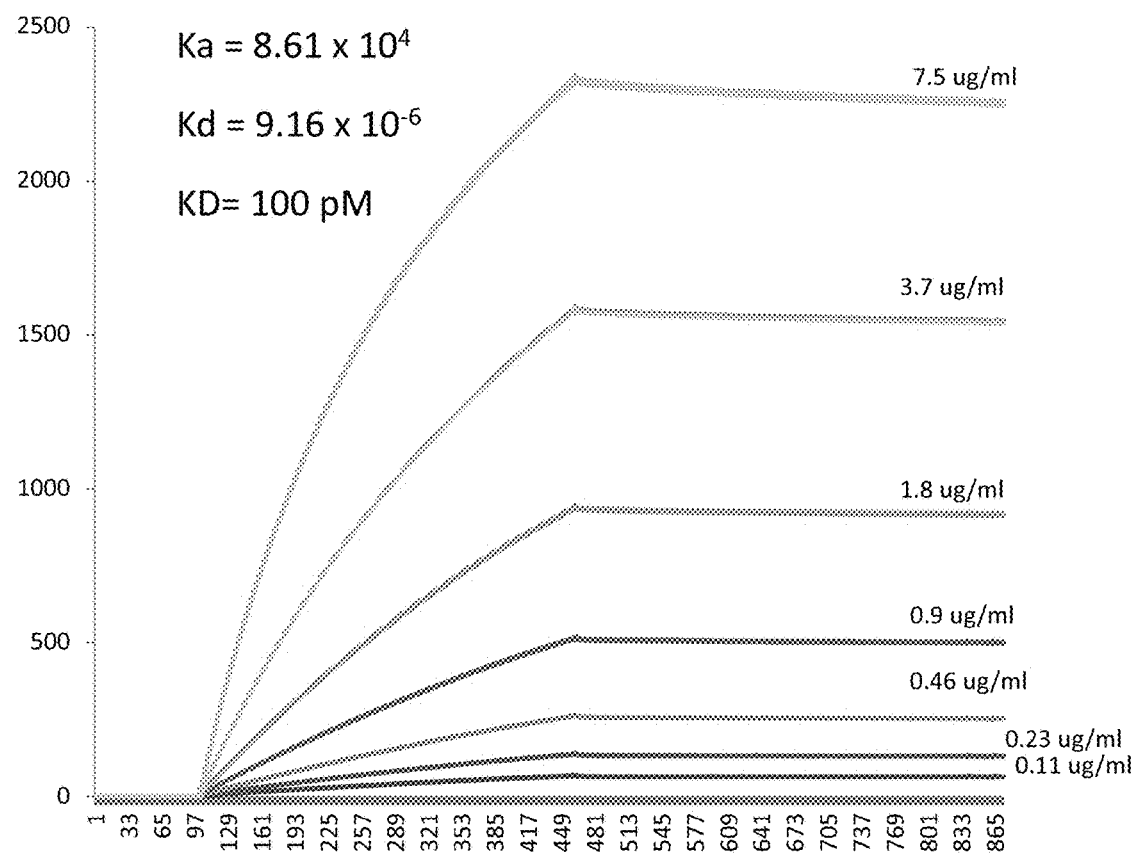
Figure 12A:
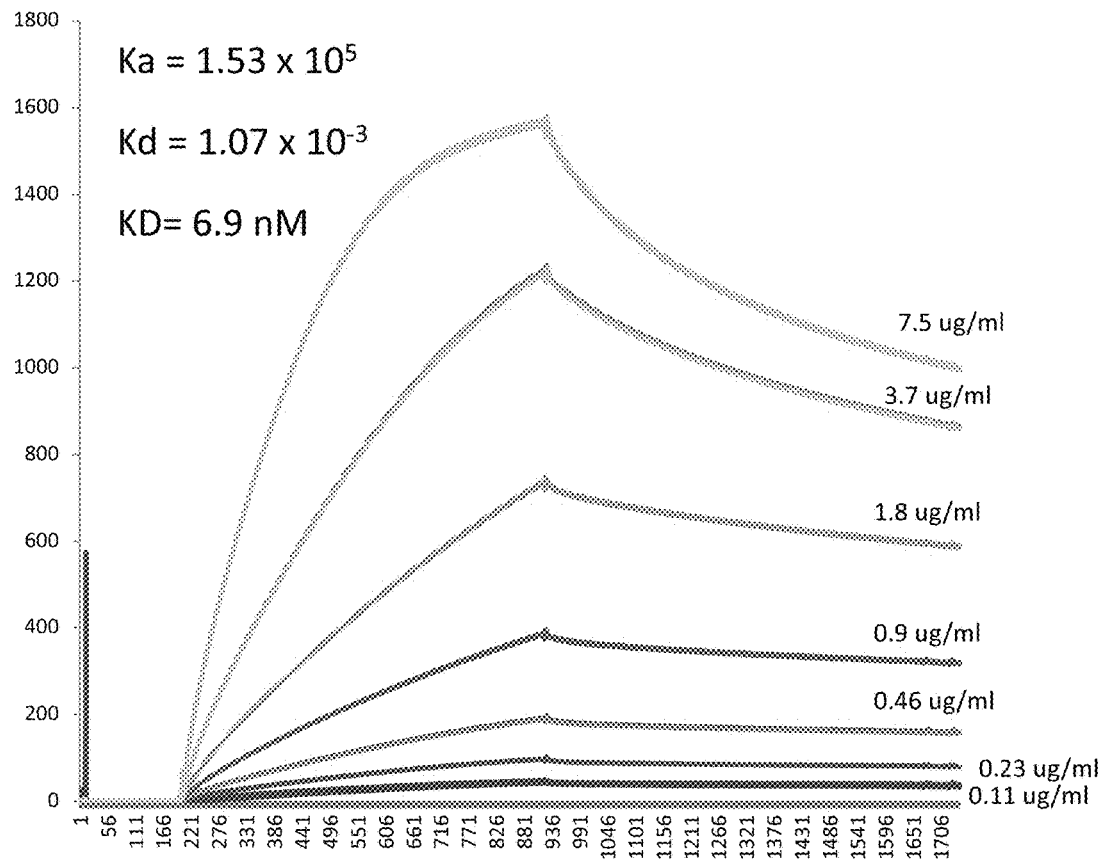
FIG. 12 depicts graphs showing the KD for HJ9.4 towards Human Tau (A) and Mouse Tau (B).
Figure 12B:
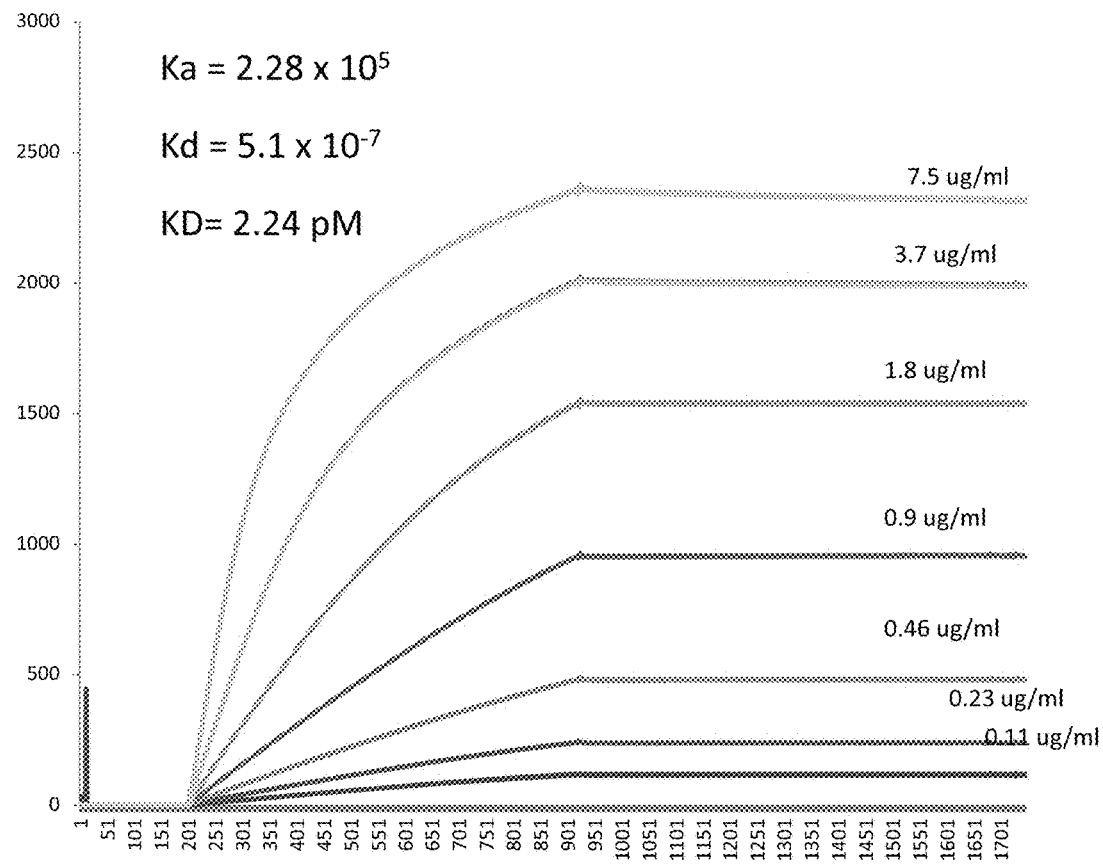
Figure 13A:
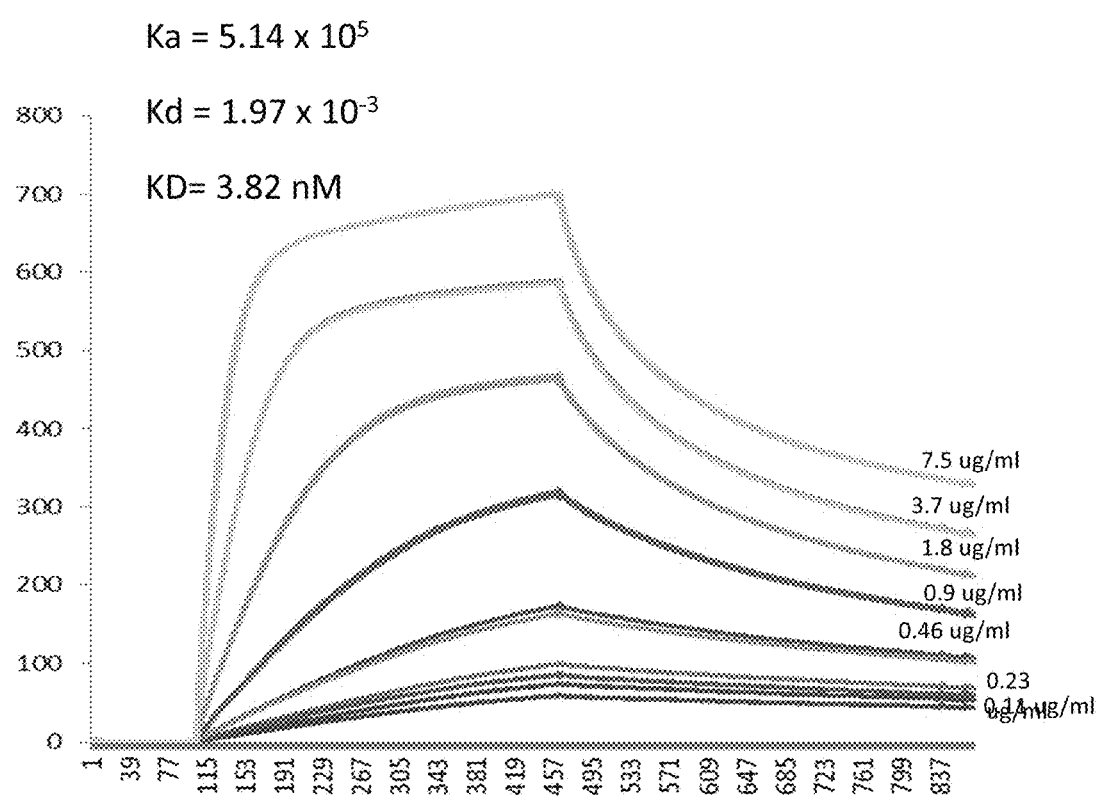
FIG. 13 depicts graphs showing the KD for HJ9.5 towards Human Tau (A) and Mouse Tau (B).
Figure 13B:
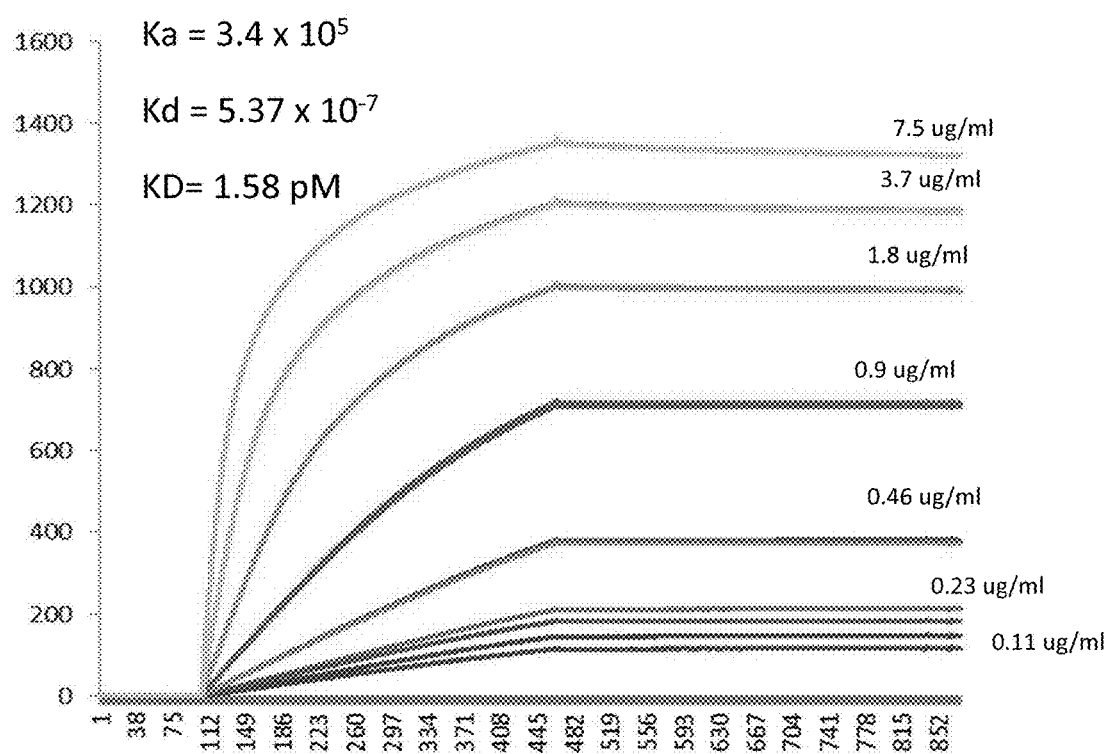

The common minimal connection between Alzheimer's Disease and all the tauopathies is the aggregation state of tau. Under all these diseased conditions, monomeric tau is known to be converted into polymeric ordered fibrils. Neurofibrillary tangles (NFTs), which are comprised of fibrillar tau aggregates, are a neuropathological hallmark of tauopathies. Applicants have discovered that spreading of tau pathology in the brain may be caused by a form of tau aggregate released from a "donor" cell entering a second "recipient" cell, and inducing further misfolding and aggregation of tau in the recipient cell via direct protein-protein contact. The specific form of tau aggregate which facilitates this cell-to-cell spread of tau aggregates is referred to as "tau seeds" and the activity may be referred to herein as "seeding activity", since this form of tau aggregate seeds or nucleates tau aggregation in the cell it enters (i.e. the "recipient cell").

Tau can exist in both a monomeric form and in different aggregated forms. As used herein, the term "tau aggregate" refers to a molecular complex that comprises two or more tau monomers. Without wishing to be bound by theory, a tau aggregate may comprise a nearly unlimited number of monomers bound together. For example, a tau aggregate may comprise 2, 3, 4, 5, 6, 7, 8, 9, 10 or more tau monomers. Alternatively, a tau aggregate may comprise 20, 30, 40, 50, 60, 70, 80, 90, 100 or more tau monomers. A tau aggregate may also comprise 500, 1000, 1500, 2000, 2500, 3000, 3500, 4000, 4500, 5000 or more tau monomers. The terms "fibrillar tau aggregate" and "tau fibril" refer to forms of tau aggregates, and these terms are used interchangeably herein. A fibrillar tau aggregate is a polymeric, ordered fiber comprising tau. Tau fibrils are generally not soluble, but shorter assemblies, or oligomers, can be soluble. Tau aggregate also refers to soluble tau oligomers and protofibrils, which may act as intermediates during tau aggregation. Also included in the definition of tau aggregate is the term "tau seed", which refers to a tau aggregate that is capable of nucleating or "seeding" intracellular tau aggregation when internalized by a cell, or when exposed to monomeric tau in vitro. Tau seeding activity may be assessed in a cellular tau aggregation assay as described herein.

In addition, applicants have discovered antibodies that specifically bind to tau and methods of use thereof. In an aspect, the present invention provides antibodies that specifically bind tau. In another aspect, the present invention provides means for effectively slowing and/or reducing cell-to-cell propagation of tau aggregation. Antibodies of the invention may slow and/or reduce the propagation of tau aggregation by promoting the disaggregation of protein fibrils, blockading the conversion of monomeric tau into aggregated tau in the cell, promoting intracellular degradation of tau aggregates, preventing entry of the tau aggregates into neighboring cells, or a combination thereof. In another aspect, the present invention provides means to detect tau aggregate in a sample of biological fluid obtained from a subject. In another aspect, the present invention provides means to measure the amount of tau aggregate in a sample of biological fluid obtained from a subject. In another aspect, the present invention provides means to classify a subject based on the amount of tau aggregate measured in a sample of biological fluid obtained from a subject. Classifying a subject based on the amount of tau aggregate measured in a sample of biological fluid obtained from the subject may be used to identify subjects that will develop a symptom and/or disease associated with tau aggregation in the subject's lifetime.

The present invention encompasses the discovery that anti-tau antibodies may slow the propagation of fibrillar tau aggregates by binding extracellular tau released from cells, thereby preventing entry of the tau aggregates into neighboring cells and slowing spread of tau aggregation. In an aspect, the present invention provides means for preventing entry of a tau aggregate into a cell. In another aspect, the present invention provides means for reducing intracellular tau aggregation. In another aspect, the present invention provides means for decreasing tau seeding activity. Antibodies of the invention useful in preventing entry of the tau aggregates into neighboring cells include those which bind an epitope within tau.

I. Antibodies that Bind to Tau

In humans, there are six isoforms of tau that are generated by alternative splicing of exons 2, 3, and 10. The isoforms ranging from 352 to 441 amino acids. Exons 2 and 3 encode 29-amino acid inserts each in the N-terminus (called N, and hence, tau isoforms may be 2N (both inserts), 1N (exon 2 only), or 0N (neither). All tau isoforms have three repeats of the microtubule binding domain. Inclusion of exon 10 at the C-terminus leads to inclusion of a fourth microtubule binding domain encoded by exon 10. Hence, tau isoforms may be comprised of four repeats of the microtubule binding domain (exon 10 included) or three repeats of the microtubule binding domain (exon 10 excluded). Anti-tau antibodies of the invention may include antibodies that bind any of the isoforms of tau. In an exemplary embodiment, anti-tau antibodies of the invention may include antibodies that bind to an isoform of tau that comprises exon 10.

As noted above, tau can be found in soluble and insoluble compartments, in monomeric and aggregated forms, in ordered or disordered structures, intracellularly and extracellularly, and may be complexed with other proteins or molecules. Anti-tau antibodies of the invention may include antibodies that bind to one or more forms of tau as described. In some embodiments, an anti-tau antibody binds a tau monomer. In other embodiments, an anti-tau antibody binds a tau aggregate. In still other embodiments, an anti-tau antibody binds a tau fibril. In different embodiments, an anti-tau antibody binds a tau monomer and a tau aggregate. In alternative embodiments, an anti-tau antibody binds to a tau aggregate and a tau fibril. In different embodiments, an anti-tau antibody binds to a tau fibril and a tau monomer.

Anti-tau antibodies useful herein also include all antibodies that specifically bind tau aggregates present in a biological sample. Anti-tau antibodies useful herein also include all antibodies that reduce cell-to-cell propagation of tau aggregation. In other words, useful antibodies slow and/or decrease the amount of tau that enters recipient cells, compared to the amount that would enter a recipient cell in the absence of an antibody of the invention. Hence, useful antibodies decrease the amount of tau aggregation that occurs in the recipient cells.

In an aspect, antibodies useful herein include those antibodies which have been isolated, characterized, purified, are functional and have been recovered (obtained) for use in a functional therapeutic composition which is administered to a living subject. In another aspect, antibodies useful herein include those antibodies which have been isolated, characterized, purified, are functional and have been recovered (obtained) for use in an assay to detect tau aggregates in a biological sample obtained from a living subject and predict the development of symptoms associated with tau aggregation over the lifetime of the subject. In another aspect, antibodies useful herein include those antibodies which have been isolated, characterized, purified, are functional and have been recovered (obtained) or for use in an assay to detect tau aggregates in a biological sample obtained from a living subject and classify the subject as having an increased risk of developing symptoms associated with tau aggregation over the subject's lifetime. In another aspect, antibodies useful herein include those antibodies which have been isolated, characterized, purified, are functional and have been recovered (obtained) for use and are listed in Table A, as well as variants thereof (e.g. humanized forms, chimeric forms, and immunological fragments).

TABLE A

Antibodies of the invention

| Antibody Name | Tau epitope |
|---|---|
| HJ8.1.1 | DRKDQGGYTMHQD (SEQ ID NO: 1) |
| HJ8.1.2 | TDHGAE (SEQ ID NO: 10) |
| HJ8.2 | PRHLSNV (SEQ ID NO: 3) |
| HJ8.3 | PRHLSNV (SEQ ID NO: 3) |
| HJ8.4 | KTDHGA (SEQ ID NO: 11) |
| HJ8.5 | DRKDQGGYTMHQD (SEQ ID NO: 1) |
| HJ8.7 | AAGHV (SEQ ID NO: 5) |
| HJ8.8 | EPRQ (SEQ ID NO: 4) |
| HJ9.1 | TDHGAEIVYKSPVVSG (SEQ ID NO: 6) |
| HJ9.2 | EFEVMED (SEQ ID NO: 7) |
| HJ9.3 | GGKVQIINKK (SEQ ID NO: 8) |
| HJ9.4 | EFEVMED (SEQ ID NO: 7) |
| HJ9.5 | EFEVMED (SEQ ID NO: 7) |

The term "antibody" includes the term "monoclonal antibody". "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" for example are single chain forms, generally designated Fv regions, of antibodies with this specificity. Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated. Antibodies are properly cross-linked via disulfide bonds, as is known.

The basic antibody unit of an antibody useful herein comprises a tetramer. Each tetramer is composed of two identical pairs of polypeptide chains, each pair having one "light' (about 25 kDa) and one "heavy" chain (about 50-70 kDa). The amino-terminal portion of each chain includes a variable region of about 100 to 110 or more amino acids primarily responsible for antigen recognition. The carboxyterminal portion of each chain defines a constant region primarily responsible for effector function.

Anti-tau antibodies useful herein include those which are isolated, characterized, purified, function and have been recovered (obtained) from a process for their preparation and thus available for use herein in a useful form in a therapeutically, medicinally, or diagnostically sufficient amount.

Light chains are classified as gamma, mu, alpha, and lambda. Heavy chains are classified as gamma, mu, alpha, delta, or epsilon, and define the antibody's isotype as IgO, IgM, IgA, IgD and IgE, respectively. Within light and heavy chains, the variable and constant regions are joined by a "J" region of about 12 or more amino acids, with the heavy chain also including a "D" region of about 10 more amino acids.

The variable regions of each light/heavy chain pair form the antibody binding site. Thus, an intact antibody has two binding sites. The chains exhibit the same general structure of relatively conserved framework regions (FR) joined by three hypervariable regions, also called complementarily determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acids to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-tau antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing a region of the tau protein coding sequence or an appropriate subregion thereof. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-tau antibody that is composed partially or fully of amino acid sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for tau is maintained or enhanced in the context of fully human germline framework regions or framework regions that are substantially human. Substantially human frameworks have at least 90%, 95%, or 99% sequence identity with a known human framework sequence. Fully useful human antibodies may also be produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-tau antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid falls under the following category, the framework amino acid of a human immunoglobulin to be used (acceptor immunoglobulin) is replaced by a framework amino acid from a CDR-providing nonhuman immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model (Queen, et al., op. cit., and Co, et al., Proc. Natl. Acad. Sci. USA (1991) 88:2869). When each of the amino acids in the human framework region of the acceptor immunoglobulin and a corresponding amino acid in the donor immunoglobulin is unusual for human immunoglobulin at that position, such an amino acid is replaced by an amino acid typical for human immunoglobulin at that position.

In all instances, an antibody of the invention specifically binds tau. In exemplary embodiments, an antibody of the invention specifically binds human tau. The phrase "specifically binds" herein means antibodies bind to the protein with an affinity constant or Affinity of interaction (KD) in the range of 0.1 pM to 10 nM, with a preferred range being 0.1 pM to 1 nM. The sequence of tau from a variety of species is known in the art, and methods of determining whether an antibody binds to tau are known in the art. For instance, see the Examples.

The antibodies of the present invention may also be used as fusion proteins known as single chain variable fragments (scFv). These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

In a preferred embodiment, the scFvs of the present invention are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

An isolated antibody of the present invention that binds to tau preferably recognizes one of several epitopes. In one embodiment, the isolated antibody of the present invention that binds to tau recognizes an epitope listed in Table A. In another embodiment, the isolated antibody of the present invention that binds to tau recognizes an epitope within the amino acid sequences of SEQ ID NO: 1 (DRKDQGGYT-MHQD). Preferably, the isolated antibody recognizes an epitope within at least three contiguous amino acids of SEQ ID NO: 1, including within at least 6 contiguous amino acids of SEQ ID NO: 1, within at least 7 contiguous amino acids of SEQ ID NO: 1, within at least 8 contiguous amino acids of SEQ ID NO: 1, within at least 9 contiguous amino acids of SEQ ID NO: 1, within at least 10 contiguous amino acids of SEQ ID NO: 1, within at least 11 contiguous amino acids of SEQ ID NO: 1, within at least 12 contiguous amino acids of SEQ ID NO: 1, and within at least 13 contiguous amino acids of SEQ ID NO: 1. In an exemplary embodiment, an isolated antibody of the present invention that recognizes an epitope within SEQ ID NO: 1 is the antibody HJ8.5. In another exemplary embodiment, an isolated antibody of the present invention that recognizes an epitope within SEQ ID NO: 1 is the antibody HJ8.1.1.

In another embodiment, the isolated antibody of the present invention that binds to tau recognizes an epitope within the amino acid sequence of SEQ ID NO: 2 (KTD-HGAE). Preferably, the isolated antibody recognizes an epitope within at least three contiguous amino acids of SEQ ID NO: 2, including within at least 4 contiguous amino acids of SEQ ID NO: 2 within at least 5 contiguous amino acids of SEQ ID NO: 2 within at least 6 contiguous amino acids of SEQ ID NO: 2, and within at least 7 contiguous amino acids of SEQ ID NO: 2. In an exemplary embodiment, an isolated antibody of the present invention that recognizes an epitope within SEQ ID NO: 2 is the antibody HJ8.1.2. In another exemplary embodiment, an isolated antibody of the present invention that recognizes an epitope within SEQ ID NO: 2 is the antibody HJ8.4.

In another embodiment, the isolated antibody of the present invention that binds to tau recognizes an epitope within the amino acid sequence of SEQ ID NO: 3 (PRHL-SNV). Preferably, the isolated antibody recognizes an epitope within at least three contiguous amino acids of SEQ ID NO: 3, including within at least 4 contiguous amino acids of SEQ ID NO: 3, within at least 5 contiguous amino acids of SEQ ID NO: 3, within at least 6 contiguous amino acids of SEQ ID NO: 3, and within at least 7 contiguous amino acids of SEQ ID NO: 3. In an exemplary embodiment, an isolated antibody of the present invention that recognizes an epitope within SEQ ID NO: 3 is the antibody HJ8.2. In another exemplary embodiment, an isolated antibody of the present invention that recognizes an epitope within SEQ ID NO: 3 is the antibody HJ8.3.

In still another embodiment, the isolated antibody of the present invention that binds to tau recognizes an epitope within the amino acid sequences of SEQ ID NO: 4 (EPRQ). Preferably, the isolated antibody recognizes an epitope within at least three contiguous amino acids of SEQ ID NO: 4, including within at least 4 contiguous amino acids of SEQ ID NO: 4. In an exemplary embodiment, an isolated antibody of the present invention that recognizes an epitope within SEQ ID NO: 4 is the antibody HJ8.8.

In yet a further embodiment, the isolated antibody of the present invention that binds to tau recognizes an epitope within the amino acid sequence of SEQ ID NO: 5 (AAGHV). Preferably, the isolated antibody recognizes an epitope within at least three contiguous amino acids of SEQ ID NO: 5, including within at least 4 contiguous amino acids of SEQ ID NO: 5, and within at least 5 contiguous amino acids of SEQ ID NO: 5. In an exemplary embodiment, an isolated antibody of the present invention that recognizes an epitope within SEQ ID NO: 5 is the antibody HJ8.7.

In an additional embodiment, the isolated antibody of the present invention that binds to tau recognizes an epitope within the amino acid sequence of SEQ ID NO: 6 (TDH-GAEIVYKSPVVSG). Preferably, the isolated antibody recognizes an epitope within at least five contiguous amino acids of SEQ ID NO: 6, including within at least 6 contiguous amino acids of SEQ ID NO: 6, within at least 7 contiguous amino acids of SEQ ID NO: 6, within at least 8 contiguous amino acids of SEQ ID NO: 6, within at least 9 contiguous amino acids of SEQ ID NO: 5, within at least 9 contiguous amino acids of SEQ ID NO: 6, within at least 10 contiguous amino acids of SEQ ID NO: 6, within at least 11 contiguous amino acids of SEQ ID NO: 6, within at least 12 contiguous amino acids of SEQ ID NO: 6, within at least 13 contiguous amino acids of SEQ ID NO: 6, within at least 14 contiguous amino acids of SEQ ID NO: 6, within at least 15 contiguous amino acids of SEQ ID NO: 6, and within at least 16 contiguous amino acids of SEQ ID NO: 6. In an exemplary embodiment, an isolated antibody of the present invention that recognizes an epitope within SEQ ID NO: 6 is the antibody HJ9.1.

In another embodiment, the isolated antibody of the present invention that binds to tau recognizes an epitope within the amino acid sequence of SEQ ID NO: 7 (EFE-VMED). Preferably, the isolated antibody recognizes an epitope within at least three contiguous amino acids of SEQ ID NO: 7, including within at least 4 contiguous amino acids of SEQ ID NO: 6, within at least 5 contiguous amino acids of SEQ ID NO: 7, within at least 6 contiguous amino acids of SEQ ID NO: 7, and within at least 7 contiguous amino acids of SEQ ID NO: 7. In an exemplary embodiment, an isolated antibody of the present invention that recognizes an epitope within SEQ ID NO: 7 is the antibody HJ9.2. In an exemplary embodiment, an isolated antibody of the present invention that recognizes an epitope within SEQ ID NO: 7 is the antibody HJ9.4. In an exemplary embodiment, an isolated antibody of the present invention that recognizes an epitope within SEQ ID NO: 7 is the antibody HJ9.5.

In yet another embodiment, the isolated antibody of the present invention that binds to tau recognizes an epitope within the amino acid sequence of SEQ ID NO: 8 (GGK-VQIINKK). Preferably, the isolated antibody recognizes an epitope within at least three contiguous amino acids of SEQ ID NO: 8, including within at least 4 contiguous amino acids of SEQ ID NO: 8, within at least 5 contiguous amino acids of SEQ ID NO: 8, within at least 6 contiguous amino acids of SEQ ID NO: 8, within at least 7 contiguous amino acids of SEQ ID NO: 8, within at least 8 contiguous amino acids of SEQ ID NO: 8, within at least 9 contiguous amino acids of SEQ ID NO: 8, and within at least 10 contiguous amino acids of SEQ ID NO: 8. In an exemplary embodiment, an isolated antibody of the present invention that recognizes an epitope within SEQ ID NO: 8 is the antibody HJ9.3.

A preferred antibody is a humanized form of mouse antibody derived from a hybridoma designated HJ8.5. As used herein, the term "derived from" means that the "derived" antibody comprises at least one CDR region from the antibody produced hybridoma HJ8.5. Stated another way, the "derived antibody" comprises at least one CDR region comprised of the amino acid sequence selected from the group consisting of SEQ ID NO: 16, 17, 18, 19, 20 and 21.

In one embodiment, an antibody of the invention may be derived from the hybridoma HJ8.5, and may be encoded by a nucleic acid sequence comprising 90, 91, 92, 93, 94, 95, 96, 97, 98, or 99% identity to the light chain variable region of SEQ ID NO:12, or may be encoded by a nucleic acid sequence comprising 90, 91, 92, 93, 94, 95, 96, 97, 98, or 99% identity to the heavy chain variable region of SEQ ID NO:13. In another embodiment, an antibody of the invention may be derived from the hybridoma HJ8.5, and may comprise an amino acid sequence with 90, 91, 92, 93, 94, 95, 96, 97, 98, or 99% identity to the light chain variable region of SEQ ID NO:14, or may comprise an amino acid sequence with 90, 91, 92, 93, 94, 95, 96, 97, 98, or 99% identity to the heavy chain variable region of SEQ ID NO:15. In each of the above embodiments, the antibody may be humanized.

In an exemplary embodiment of an antibody of the invention that binds to tau, the antibody comprises the light chain nucleic acid sequence of SEQ ID NO:12 and the heavy chain nucleic acid sequence of SEQ ID NO:13 [i.e. the monoclonal antibody referred to herein as HJ8.5]. In another exemplary embodiment of an antibody of the invention that binds to tau, the antibody comprises the light chain amino acid sequence of SEQ ID NO:14 and the heavy chain amino acid sequence of SEQ ID NO:15 [i.e. the monoclonal antibody referred to herein as HJ8.5].

In one embodiment, an antibody of the invention may comprise a light chain CDR1, such as antibody 1 of Table B. In another embodiment, an antibody of the invention may comprise a light chain CDR2, such as antibody 4 of Table B. In yet another embodiment, an antibody of the invention may comprise a light chain CDR3, such as antibody 6 of Table B. In an alternative embodiment, an antibody of the invention may comprise a combination of two or three light chain CDRs, such as the antibodies 2, 3, and 5 of Table B.

Similarly, in one embodiment, an antibody of the invention may comprise a heavy chain CDR1, such as antibody 7 of Table B. In another embodiment, an antibody of the invention may comprise a heavy chain CDR2, such as antibody 10 of Table B. In yet another embodiment, an antibody of the invention may comprise a heavy chain CDR3, such as antibody 12 of Table B. In an alternative embodiment, an antibody of the invention may comprise a combination of two or three heavy chain CDRs, such as the antibodies 8, 9, 11 of Table B.

Alternatively, an antibody of the invention may comprise one or more light chain CDRs and one or more heavy chain CDRs, such as the antibodies 13-48 of Table B.

TABLE B

| Antibody | Light Chain CDR1 | Light Chain CDR2 | Light Chain CDR3 | Heavy Chain CDR1 | Heavy Chain CDR2 | Heavy Chain CDR3 |
|---|---|---|---|---|---|---|
| 1 | SEQ ID NO: 16 | | | | | |
| 2 | SEQ ID NO: 16 | SEQ ID NO: 17 | | | | |
| 3 | SEQ ID NO: 16 | SEQ ID NO: 17 | SEQ ID NO: 18 | | | |
| 4 | | SEQ ID NO: 17 | | | | |
| 5 | | SEQ ID NO: 17 | SEQ ID NO: 18 | | | |
| 6 | | | SEQ ID NO: 18 | | | |
| 7 | | | | SEQ ID NO: 19 | | |
| 8 | | | | SEQ ID NO: 19 | SEQ ID NO: 20 | |
| 9 | | | | SEQ ID NO: 19 | SEQ ID NO: 20 | SEQ ID NO: 21 |
| 10 | | | | | SEQ ID NO: 20 | |
| 11 | | | | | SEQ ID NO: 20 | SEQ ID NO: 21 |
| 12 | | | | | | SEQ ID NO: 21 |
| 13 | SEQ ID NO: 16 | | | SEQ ID NO: 19 | | |
| 14 | SEQ ID NO: 16 | | | SEQ ID NO: 19 | SEQ ID NO: 20 | |
| 15 | SEQ ID NO: 16 | | | SEQ ID NO: 19 | SEQ ID NO: 20 | SEQ ID NO: 21 |
| 16 | SEQ ID NO: 16 | | | | SEQ ID NO: 20 | |
| 16 | SEQ ID NO: 16 | | | | SEQ ID NO: 20 | SEQ ID NO: 21 |
| 17 | SEQ ID NO: 16 | | | | | SEQ ID NO: 21 |
| 19 | SEQ ID NO: 16 | SEQ ID NO: 17 | | SEQ ID NO: 19 | | |
| 20 | SEQ ID NO: 16 | SEQ ID NO: 17 | | SEQ ID NO: 19 | SEQ ID NO: 20 | |
| 21 | SEQ ID NO: 16 | SEQ ID NO: 17 | | SEQ ID NO: 19 | SEQ ID NO: 20 | SEQ ID NO: 21 |
| 22 | SEQ ID NO: 16 | SEQ ID NO: 17 | | | SEQ ID NO: 20 | |
| 23 | SEQ ID NO: 16 | SEQ ID NO: 17 | | | SEQ ID NO: 20 | SEQ ID NO: 21 |
| 24 | SEQ ID NO: 16 | SEQ ID NO: 17 | | | | SEQ ID NO: 21 |
| 25 | SEQ ID NO: 16 | SEQ ID NO: 17 | SEQ ID NO: 18 | SEQ ID NO: 19 | | |
| 26 | SEQ ID NO: 16 | SEQ ID NO: 17 | SEQ ID NO: 18 | SEQ ID NO: 19 | SEQ ID NO: 20 | |
| 27 | SEQ ID NO: 16 | SEQ ID NO: 17 | SEQ ID NO: 18 | SEQ ID NO: 19 | SEQ ID NO: 20 | SEQ ID NO: 21 |
| 28 | SEQ ID NO: 16 | SEQ ID NO: 17 | SEQ ID NO: 18 | | SEQ ID NO: 20 | |
| 29 | SEQ ID NO: 16 | SEQ ID NO: 17 | SEQ ID NO: 18 | | SEQ ID NO: 20 | SEQ ID NO: 21 |
| 30 | SEQ ID NO: 16 | SEQ ID NO: 17 | SEQ ID NO: 18 | | | SEQ ID NO: 21 |
| 31 | | SEQ ID NO: 17 | | SEQ ID NO: 19 | | |
| 32 | | SEQ ID NO: 17 | | SEQ ID NO: 19 | SEQ ID NO: 20 | |
| 33 | | SEQ ID NO: 17 | | SEQ ID NO: 19 | SEQ ID NO: 20 | SEQ ID NO: 21 |
| 34 | | SEQ ID NO: 17 | | | SEQ ID NO: 20 | |
| 35 | | SEQ ID NO: 17 | | | SEQ ID NO: 20 | SEQ ID NO: 21 |
| 36 | | SEQ ID NO: 17 | | | | SEQ ID NO: 21 |
| 37 | | SEQ ID NO: 17 | SEQ ID NO: 18 | SEQ ID NO: 19 | | |
| 38 | | SEQ ID NO: 17 | SEQ ID NO: 18 | SEQ ID NO: 19 | SEQ ID NO: 20 | |
| 39 | | SEQ ID NO: 17 | SEQ ID NO: 18 | SEQ ID NO: 19 | SEQ ID NO: 20 | SEQ ID NO: 21 |
| 40 | | SEQ ID NO: 17 | SEQ ID NO: 18 | | SEQ ID NO: 20 | |
| 41 | | SEQ ID NO: 17 | SEQ ID NO: 18 | | SEQ ID NO: 20 | SEQ ID NO: 21 |
| 42 | | SEQ ID NO: 17 | SEQ ID NO: 18 | | | SEQ ID NO: 21 |
| 43 | | | SEQ ID NO: 18 | SEQ ID NO: 19 | | |
| 44 | | | SEQ ID NO: 18 | SEQ ID NO: 19 | SEQ ID NO: 20 | |

TABLE B-continued

| Anti- | Light Chain | | | Heavy Chain | | |
|---|---|---|---|---|---|---|
| body | CDR1 | CDR2 | CDR3 | CDR1 | CDR2 | CDR3 |
| 45 | | SEQ ID NO: 18 | SEQ ID NO: 19 | | SEQ ID NO: 20 | SEQ ID NO: 21 |
| 46 | | | SEQ ID NO: 18 | | | SEQ ID NO: 20 |
| 47 | | | SEQ ID NO: 18 | | SEQ ID NO: 20 | SEQ ID NO: 21 |
| 48 | | | SEQ ID NO: 18 | | | SEQ ID NO: 21 |

In various embodiments, an antibody of the invention is humanized. For instance, in one embodiment, a humanized antibody of the invention may comprise a light chain variable region comprising a CDR1 of amino acid sequence SEQ ID NO: 16 with zero to two amino acid substitutions, a CDR2 of amino acid sequence SEQ ID NO: 17 with zero to two amino acid substitutions, and a CDR3 of amino acid sequence SEQ ID NO: 18 with zero to two amino acid substitutions, or may comprise a heavy chain variable region comprising a CDR1 of amino acid sequence SEQ ID NO: 19 with zero to two amino acid substitutions, a CDR2 of amino acid sequence SEQ ID NO: 20 with zero to two amino acid substitutions, and a CDR3 of amino acid sequence SEQ ID NO: 21 with zero to two amino acid substitutions. In a preferred embodiment, a humanized antibody of the invention may comprise a light chain variable region comprising a CDR1 of amino acid sequence SEQ ID NO: 16 with zero to two amino acid substitutions, a CDR2 of amino acid sequence SEQ ID NO: 17 with zero to two amino acid substitutions, a CDR3 of amino acid SEQ ID NO: 18 with zero to two amino acid substitutions, a heavy chain variable region comprising a CDR1 of amino acid sequence SEQ ID NO: 19 with zero to two amino acid substitutions, a CDR2 of amino acid sequence SEQ ID NO: 20 with zero to two amino acid substitutions, and a CDR3 of amino acid sequence SEQ ID NO: 21 with zero to two amino acid substitutions. In an exemplary embodiment, a humanized antibody of the invention may comprise a light chain variable region comprising a CDR1 of amino acid sequence SEQ ID NO: 16, a CDR2 of amino acid sequence SEQ ID NO: 17, a CDR3 of amino acid sequence SEQ ID NO: 18, a heavy chain variable region comprising a CDR1 of amino acid sequence SEQ ID NO: 19, a CDR2 of amino acid sequence SEQ ID NO: 20, and a CDR3 of amino acid sequence SEQ ID NO: 21. The invention also encompasses the corresponding nucleic acid sequences of SEQ ID NO: 16, 17, 18, 19, 20, and 21, which can readily be determined by one of skill in the art, and may be incorporated into a vector or other large DNA molecule, such as a chromosome, in order to express an antibody of the invention.

II. Method of Use

In an aspect, the present invention provides antibodies for use in a functional therapeutic composition which is administered to a living subject. In another aspect, the present invention provides antibodies for use in an immunoassay to detect tau aggregates in a sample of biological fluid obtained from a living subject. In another aspect, the present invention provides antibodies for use in an immunoassay to measure the amount of tau aggregate in a sample of biological fluid obtained from a living subject. The amount of tau aggregate in a sample of biological fluid obtained from a subject can be used to classify a subject as having high or low amounts of tau aggregate, and may be further used to predict the risk of developing symptoms and/or disease associated with tau aggregation over the lifetime of the subject.

Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In embodiments where the animal is a mouse, the mouse may be a C57BL/6 mouse, a Balb/c mouse, a 129sv, or any other laboratory strain. In an exemplary embodiment, the subject is a C57BL/6J mouse. In a preferred embodiment, the subject is human.

A. Method of Treatment

In an aspect, the present invention comprises a method of reducing the spread of tau aggregation in the brain of a subject. In another aspect the present invention comprises a method for reducing intracellular aggregation of tau induced by tau seeds. In each aspect, the method comprises administering a pharmacologically effective amount of anti-tau antibody to a subject. Suitable antibodies are described above in Section I. In a preferred embodiment, an antibody is selected from the group consisting of an antibody from Table 1 and an antibody from Table 2, including a humanized antibody, a chimeric antibody or an immunological fragment thereof.

A subject may or may not be having a symptom associated with tau aggregation prior to administration of a pharmacologically effective amount of anti-tau antibody. Stated another way, a subject may or may not be experiencing a symptom associated with tau aggregation. A skilled artisan will appreciate that pathological tau aggregation likely commences prior to diagnosis or the onset of symptoms associated with tau aggregation. In some embodiments, a subject is having a symptom associated with tau aggregation. In other embodiments, a subject is not having a symptom associated with tau aggregation. In still other embodiments, a subject has detectable tau pathology but is not having any other symptom associated with tau aggregation. Reducing the spread of tau aggregation in the brain of a subject may reduce the development and/or progression of symptoms associated with the pathological aggregation of tau.

Preventing propagation of fibrillar tau aggregates may treat pathologies associated with generation and spread of tau aggregates. As used herein, the terms "treating" or "treatment" include prevention, attenuation, reversal, or improvement in at least one symptom or sign of symptoms associated with tau aggregation. One definition of symptoms associated with tau aggregation refers to any symptom caused by the formation of tau aggregates being composed of, in part, tau fibrils. Exemplary disorders that have symptoms associated with tau aggregation include, but are not limited to, progressive supranuclear palsy, dementia pugilistica (chronic traumatic encephalopathy), frontotemporal dementia and parkinsonism linked to chromosome 17, Lytico-Bodig disease (Parkinson-dementia complex of Guam), tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, argyrophilic grain disease (AGD), Frontotemporal lobar degeneration, Alzheimer's Disease, and frontotemporal dementia. Methods for diagnosing these disorders are known in the art.

Exemplary symptoms associated with tau aggregation may include impaired cognitive function, altered behavior, emotional dysregulation, seizures, and impaired nervous system structure or function. Impaired cognitive function includes but is not limited to difficulties with memory, attention, concentration, language, abstract thought, creativity, executive function, planning, and organization. Altered behavior includes but is not limited to physical or verbal aggression, impulsivity, decreased inhibition, apathy, decreased initiation, changes in personality, abuse of alcohol, tobacco or drugs, and other addiction-related behaviors. Emotional dysregulation includes but is not limited to depression, anxiety, mania, irritability, and emotional incontinence. Seizures include but are not limited to generalized tonic-clonic seizures, complex partial seizures, and non-epileptic, psychogenic seizures. Impaired nervous system structure or function includes but is not limited to hydrocephalus, Parkinsonism, sleep disorders, psychosis, impairment of balance and coordination. This includes motor impairments such as monoparesis, hemiparesis, tetraparesis, ataxia, ballismus and tremor. This also includes sensory loss or dysfunction including olfactory, tactile, gustatory, visual and auditory sensation. Furthermore, this includes autonomic nervous system impairments such as bowel and bladder dysfunction, sexual dysfunction, blood pressure and temperature dysregulation. Finally, this includes hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators. Methods for detecting and evaluating symptoms associated with tau aggregation are known in the art.

In some embodiments, a symptom associated with tau aggregation refers to dementia. Dementia is not itself a specific disease, but is an overall term that describes a wide range of symptoms associated with a decline in memory or other thinking skills severe enough to reduce a person's ability to perform everyday activities. Dementia is also a shared clinical feature of many diseases associated with tau aggregation. A skilled practitioner will be familiar with the numerous methods available to diagnose the severity of dementia. For example, several cognitive tests and screening questionnaires for dementia are known in the art, all with varying degrees of sensitivity and specificity. Non-limiting examples include the mini mental state examination (MMSE), the abbreviated mental test may score (AMTS), the modified mini mental state exam (3MS), the cognitive abilities screening instrument (CASI), the Trail-making test, the clock drawing test, the Informant Questionnaire on cognitive decline in the elderly, the General practitioner assessment of cognition, the Clinical Dementia Rating (CDR), Eight-item informant interview to differentiate aging and dementia (AD8).

In some embodiments, the severity of the symptoms of dementia are quantified using the CDR. Using the CDR, a score of 0 indicates no symptoms, a score of 0.5 indicates very mild symptoms, a score of 1 indicates mild symptoms, a score of 2 indicates moderate symptoms and a score of 3 indicates severe symptoms. Thus, any increase in a CDR score for a subject indicates a worsening in cognition and an increase in dementia. Moreover, change in CDR from 0 to greater than 0, indicates the development or onset of dementia.

In some embodiments, a symptom associated with tau aggregation refers to tau pathology. The term "tau pathology" refers to the pathological aggregation of tau. In some embodiments, tau pathology refers to neurofibrially tangles. In other embodiments, tau pathology refers to hyperphosphorylated tau. In still other embodiments, tau pathology refers to a high level of tau aggregates detectable in blood, plasma, serum, CSF, or ISF, anywhere from 1.2 to approximately 40-fold higher than that detected in individuals without disease. Methods for detecting pathological aggregation of tau are in known in the art and further detailed in the Examples.

In an exemplary embodiment, a method of reducing the spread of tau aggregation in the brain of a subject comprises administering a pharmacologically effective amount of anti-tau antibody to the subject, wherein the antibody is selected from the group consisting of an isolated antibody comprising a light chain variable region comprising a CDR1 of amino acid sequence SEQ ID NO: 16 with zero to two amino acid substitutions, an isolated antibody comprising a light chain variable region comprising a CDR2 of amino acid sequence SEQ ID NO: 17 with zero to two amino acid substitutions, an isolated antibody comprising a light chain variable region comprising a CDR3 of amino acid sequence SEQ ID NO: 18 with zero to two amino acid substitutions, an isolated antibody comprising a heavy chain variable region comprising a CDR1 of amino acid sequence SEQ ID NO: 19 with zero to two amino acid substitutions, an isolated antibody comprising a heavy chain variable region comprising a CDR2 of amino acid sequence SEQ ID NO: 20 with zero to two amino acid substitutions, and an isolated antibody comprising a heavy chain variable region comprising a CDR3 of amino acid sequence SEQ ID NO: 21 with zero to two amino acid substitutions.

In another exemplary embodiment, a method of reducing the spread of tau aggregation in the brain of a subject comprises administering a pharmacologically effective amount of anti-tau antibody to the subject, wherein the antibody specifically binds tau and recognizes an epitope comprising SEQ ID NO: 1 (DRKDQGGYTMHQD).

In another exemplary embodiment, a method of reducing the spread of tau aggregation in the brain of a subject comprises administering a pharmacologically effective amount of anti-tau antibody to the subject, wherein the antibody specifically binds tau and recognizes an epitope consisting of SEQ ID NO: 1 (DRKDQGGYTMHQD).

The antibodies in a pharmacologically effective amount preferred in pharmaceutical grade, including immunologically reactive fragments, may be administered to a subject. Administration is performed using standard effective techniques, include peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes, but is not limited to, via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

The concentration of humanized antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living patient could be made up to contain from 1-5 mL sterile buffered water of phosphate buffered saline and about 1-5000 mg of any one of or a combination of the humanized antibody of the present discovery. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-tau antibody concentration. Therapeutic agents of the discovery can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies). Dosages administered are effective dosages and may have to be adjusted to compensate. The pH of the formulations that are generally of pharmaceutical grade quality will be selected to balance antibody stability (chemical and physical) and comfort to the patient when administered. Generally, a pH between 4 and 8 is tolerated. Doses will vary from individual to individual based on size, weight, and other physio-biological characteristics of the individual receiving the successful administration.

As used herein, the term "effective amount" means an amount of a substance such as a compound that leads to measurable and beneficial effects for the patient administered the substance, i.e., significant efficacy. The effective amount or dose of compound administered according to this discovery will be determined by the circumstances surrounding the case, including the compound administered, the route of administration, the status of the symptoms being treated and similar patient and administration situation considerations among other considerations. In an aspect, a typical dose contains from about 0.01 mg/kg to about 100 mg/kg of an anti-tau antibody described herein. Doses can range from about 0.05 mg/kg to about 100 mg/kg, more preferably from about 0.1 mg/kg to about 50 mg/kg, or from 0.5 mg/kg to about 50 mg/kg. The frequency of dosing may be daily or once, twice, three times or more per week or per month, as needed as to effectively treat the symptoms. Alternatively, the frequency of dosing may be at least once every three months, as needed as to effectively treat the symptoms. For example, dosing may be about every 5 weeks, about every 6 weeks, about every 7 weeks, about every 8 weeks, about every 9 weeks, about every 10 weeks, about every 11 weeks, or about every 12 weeks.

The timing of administration of the treatment relative to the disease itself and duration of treatment will be determined by the circumstances surrounding the case. Treatment could begin after diagnosis of a disease associated with tau aggregation. Alternatively, treatment could begin after clinical confirmation of a symptom associated with tau aggregation. Further still, treatment could begin after detection of tau pathology. Treatment could begin immediately in a hospital or clinic, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as humanized antibodies, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

B. Method of Detecting Tau Aggregates in Biological Fluid

In an aspect, the invention provides means to detect tau aggregate in a sample of biological fluid obtained from a subject. In another aspect, the invention provides means to measure the amount of tau aggregate in a sample of biological fluid obtained from a subject. The method generally comprises (i) obtaining a sample of a biological fluid from a subject, and (ii) measuring the amount of tau aggregate in the sample using an antibody that specifically binds tau. Suitable antibodies are described above in Section I. Suitable subjects are described above.

As used herein, the term "biological fluid" refers to a fluid obtained from a subject. Any biological fluid comprising a tau aggregate is suitable. Non-limiting examples include blood, plasma, serum, urine, CSF and ISF. The fluid may be used "as is", the cellular components may be isolated from the fluid, or a protein fraction may be isolated from the fluid using standard techniques.

As will be appreciated by a skilled artisan, the method of collecting a sample of biological fluid can and will vary depending upon the nature of the biological fluid and the type of analysis to be performed. Any of a variety of methods generally known in the art may be utilized to collect a sample of biological fluid. Generally speaking, the method preferably maintains the integrity of the sample such that tau aggregate can be accurately detected and the amount measured according to the invention.

Once a sample is obtained, it is processed in vitro in order to detect and measure the amount of tau aggregate using an anti-tau antibody. In some embodiments, the concentration of tau aggregate in the sample is increased prior to detection and measurement. In some embodiments, tau aggregate is immunoprecipitated from a sample prior to detection and measurement using at least one isolated anti-tau antibody. In other embodiments, tau aggregate is immunoprecipitated from a sample prior to detection and measurement using at least two isolated anti-tau antibodies. In embodiments where at least two antibodies are used to immunoprecipitate tau aggregates, preferably a first antibody binds a first epitope of tau and a second antibody binds a second, non-overlapping epitope of tau. The use of two antibodies that bind two distinct epitopes of tau may be more efficient at capturing all possible tau aggregate conformers. Non-limiting examples of suitable antibody pairs for immunoprecipitation are listed in Table C. In a preferred embodiment, tau aggregate is immunoprecipitated from a sample prior to detection and measurement using at least two isolated anti-tau antibodies, wherein at least a first antibody recognizes an epitope within SEQ ID NO: 1 and at least a second antibody recognizes an epitope within SEQ ID NO: 8. A skilled artisan will be able to determine with routine experimentation whether or not tau aggregate in a sample needs to be concentrated or immunoprecipitated prior to detection and measurement, and will be able to do so using methods known in the art.

method may occur in solution, or the antibody or tau aggregate may be immobilized on a solid surface. Non-limiting examples of suitable surfaces include microtitre plates, test tubes, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An anti-tau antibody may also be attached to the substrate non-covalently. For example, a biotinylated anti-tau antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-tau antibody composition to the sample (or to the immunoprecipitated or concentrated tau aggregate) and incubating the mixture for a period of time long enough for the anti-tau antibody to bind to any antigen present. After this time, the complex may be washed and then the complex is detected and the amount measured by any method well known in the art. Methods of detecting and measuring an amount of an antibody-polypeptide complex are generally based on the detection of a label or marker. The term "label", as used herein, refers to any

TABLE C

|  |  | Second Antibody | | | | | | | | | | | | |
|---|---|---|---|---|---|---|---|---|---|---|---|---|---|
|  |  | HJ8.1.1 | HJ8.1.2 | HJ8.2 | HJ8.3 | HJ8.4 | HJ8.5 | HJ8.7 | HJ8.8 | HJ9.1 | HJ9.2 | HJ9.3 | HJ9.4 | HJ9.5 |
| First Antibody | HJ8.1.1 |  | X | X | X | X |  | X | X | X | X | X | X | X |
|  | HJ8.1.2 | X |  | X | X |  | X | X | X | X | X | X | X | X |
|  | HJ8.2 | X | X |  |  | X | X | X | X | X | X | X | X | X |
|  | HJ8.3 | X | X |  |  | X | X | X | X | X | X | X | X | X |
|  | HJ8.4 | X |  | X | X |  | X | X | X | X | X | X | X | X |
|  | HJ8.5 |  | X | X | X | X |  | X | X | X | X | X | X | X |
|  | HJ8.7 | X | X | X | X | X | X |  | X | X | X | X | X | X |
|  | HJ8.8 | X | X | X | X | X | X | X |  | X | X | X | X | X |
|  | HJ9.1 | X | X | X | X | X | X | X | X |  | X | X | X | X |
|  | HJ9.2 | X | X | X | X | X | X | X | X | X |  | X |  |  |
|  | HJ9.3 | X | X | X | X | X | X | X | X | X | X |  | X | X |
|  | HJ9.4 | X | X | X | X | X | X | X | X | X |  | X |  |  |
|  | HJ9.5 | X | X | X | X | X | X | X | X | X |  | X |  |  |

Methods for detecting and measuring an amount of protein using an antibody are well known in the art. All suitable methods for detecting and measuring an amount of protein using an antibody known to one of skill in the art are contemplated within the scope of the invention. Non-limiting examples include an ELISA, a sandwich immunoassay, a radioimmunoassay, an immunoblot or Western blot, flow cytometry, immunohistochemistry, and an array.

In general, an antibody-based method of detecting and measuring an amount of tau aggregate comprises contacting some or all of the sample comprising tau aggregate with an anti-tau antibody under conditions effective to allow for formation of a complex between the antibody and the tau aggregate. Typically, the entire sample is not needed, allowing one skilled in the art to repeatedly detect and measure the amount of tau aggregate in the sample over time. The substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, and luciferase). Methods of detecting and measuring an amount of an antibody-polypeptide complex based on the detection of a label or marker are well known in the art.

In a preferred embodiment, a method for measuring the amount of tau aggregate in a sample is an immunoassay comprising two captures antibodies and a detection antibody, wherein each capture antibody is an isolated anti-tau antibody that recognizes a tau epitope distinct from the other, and the detection antibody is an isolated anti-tau antibody attached to a label. The detection antibody may be the same antibody as one of the two capture antibodies or, alternatively, the detection antibody may recognize a tau epitope not recognized by either capture antibody. Typically, the first capture antibody and the second capture antibody are used in an amount from about 10:1 to about 1:10, from about 5:1 to about 1:5, from about 3:1 to about 1:3, or from about 2:1 to about 1:2. In some embodiments, the first capture antibody and the second capture antibody are used at about equivalent concentrations. Non-limiting examples of suitable pairs of capture antibodies include the antibodies disclosed in Table D and Table E. Non-limiting examples of suitable detection antibodies include the antibodies listed in Table A, as well as antibodies that specifically bind tau and recognize an epitope within an amino acid sequence selected from the group consisting of SEQ ID NOs: 1-11. In an exemplary embodiment, a first capture antibody is an isolated antibody that specifically binds tau and recognizes an epitope within SEQ ID NO: 7, a second capture antibody is an isolated antibody that specifically binds tau and recognizes an epitope within SEQ ID NO: 8, and a detection antibody is an isolated antibody that specifically binds tau and recognizes an epitope within SEQ ID NO: 8.

TABLE D

First and Second Capture Antibodies

| | | Second Capture Antibody | | | | | | | | | | | | |
|---|---|---|---|---|---|---|---|---|---|---|---|---|---|---|
| | | HJ8.1.1 | HJ8.1.2 | HJ8.2 | HJ8.3 | HJ8.4 | HJ8.5 | HJ8.7 | HJ8.8 | HJ9.1 | HJ9.2 | HJ9.3 | HJ9.4 | HJ9.5 |
| First Capture Antibody | HJ8.1.1 | | X | X | X | X | | X | X | X | X | X | X | X |
| | HJ8.1.2 | X | | X | X | | X | X | X | X | X | X | X | X |
| | HJ8.2 | X | X | | | X | X | X | X | X | X | X | X | X |
| | HJ8.3 | X | X | | | X | X | X | X | X | X | X | X | X |
| | HJ8.4 | X | | X | X | | X | X | X | X | X | X | X | X |
| | HJ8.5 | | X | X | X | X | | X | X | X | X | X | X | X |
| | HJ8.7 | X | X | X | X | X | X | | X | X | X | X | X | X |
| | HJ8.8 | X | X | X | X | X | X | X | | X | X | X | X | X |
| | HJ9.1 | X | X | X | X | X | X | X | X | | X | X | X | X |
| | HJ9.2 | X | X | X | X | X | X | X | X | X | | X | | |
| | HJ9.3 | X | X | X | X | X | X | X | X | X | X | | X | X |
| | HJ9.4 | X | X | X | X | X | X | X | X | X | | X | | |
| | HJ9.5 | X | X | X | X | X | X | X | X | X | | X | | |

TABLE E

First and Second Capture Antibodies: each antibody specifically binds tau and recognizes an epitope within the amino acid sequence indicated by the SEQ ID NO shown.

| | | Second Capture Antibody | | | | | | | |
|---|---|---|---|---|---|---|---|---|---|
| | | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| First Capture Antibody | SEQ ID NO: 1 | | X | X | X | X | X | X | X |
| | SEQ ID NO: 2 | X | | X | X | X | X | X | X |
| | SEQ ID NO: 3 | X | X | | X | X | X | X | X |
| | SEQ ID NO: 4 | X | X | X | | X | X | X | X |
| | SEQ ID NO: 5 | X | X | X | X | | X | X | X |
| | SEQ ID NO: 6 | X | X | X | X | X | | X | X |
| | SEQ ID NO: 7 | X | X | X | X | X | X | | X |
| | SEQ ID NO: 8 | X | X | X | X | X | X | X | |

In another aspect, the invention provides means to classify a subject based on the amount of tau aggregate measured in a sample of biological fluid obtained from the subject. The method generally comprises (i) obtaining a sample of a biological fluid from a subject and measuring the amount of tau aggregate in the sample using an antibody that specifically binds tau, (ii) comparing the amount of tau aggregate in the sample to a reference value, and (iii) classifying the subject as having a high or low amount of tau aggregate based on the amount of tau aggregate measured in the sample. Methods for obtaining a sample of a biological fluid from a subject and measuring the amount of tau aggregate in the sample using an antibody that specifically binds tau are detailed above and further described in the Examples.

Any suitable reference value known in the art may be used. For example, a suitable reference value may be the amount of tau aggregate in a sample of biological fluid obtained from a subject, or group of subjects, of the same species that has no clinically detectable symptom of tau aggregation. In another example, a suitable reference value may be the amount of tau aggregate in a biological fluid sample obtained from a subject, or group of subjects, of the same species that has no detectable tau pathology. In another example, a suitable reference value may be the amount of tau aggregate in a biological fluid sample obtained from a subject, or group of subjects, of the same species that has a Clinical Dementia Rating score of zero (CDR=0). In another example, a suitable reference value may be the background signal of the assay as determined by methods known in the art. In another example, a suitable reference value may be a measurement of the amount of tau aggregate in a reference sample obtained from the same subject. The reference sample comprises the same type of biological fluid as the test sample, and may be obtained from a subject when the subject had no clinically detectable symptom of tau aggregation. A skilled artisan will appreciate that it is not always possible or desirable to obtain a reference sample from a subject when the subject is otherwise healthy. For example, when monitoring the effectiveness of a therapy, a reference sample may be a sample obtained from a subject before therapy began. In such an example, a subject may have tau pathology but may not have other symptoms of tau aggregation (e.g. dementia, declined cognition, etc.) or the subject may have tau pathology and one or more other symptom of tau aggregation. In an additional example, a suitable reference sample may be a biological fluid from an individual or group of individuals that has been shown not to have tau aggregates.

According to the invention, a subject may be classified based on the amount of tau aggregate measured in the sample. Classifying a subject based on the amount of tau aggregate measured in a sample of biological fluid obtained from the subject may be used to identify subjects that will develop a disease and/or symptom associated with tau aggregation in the subject's lifetime. Generally speaking, a subject may be classified as having a high or low amount of tau aggregate compared to a reference value, wherein a high amount of tau aggregate is an amount above the reference value and a low amount is an amount equal to or below the reference value. In preferred embodiments, to classify a subject as having a high amount of tau aggregate, the amount of tau aggregate in the sample of biological fluid compared to the reference value is increased at least 2-fold. For example, the amount of tau aggregate in the sample compared to the reference value is increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold. When the amount of tau aggregate in the sample of biological fluid obtained from a subject is increased at least 2-fold compared to a reference value, and the reference value is a sample of the same type of biological fluid obtained from one or more disease free individuals with no detectable symptom of tau aggregation (or a sample equivalent thereto), the subject is more likely to develop a disease and/or symptom associated with tau aggregation in the subject's lifetime.

DEFINITIONS

As used herein, "antibody" refers to an immunoglobulin derived molecule that specifically recognizes tau. An antibody of the invention may be a full length antibody (IgM, IgG, IgA, IgE) or may be an antibody fragment (Fab, F(ab')2, scFv). An antibody may be chimeric or may be humanized.

As used herein, "CDR" means "complementary determining region." CDRs may also be referred to as hypervariable regions.

As used herein, "light chain" is the small polypeptide subunit of the antibody. A typical antibody comprises two light chains and two heavy chains.

As used herein, the "heavy chain" is the large polypeptide subunit of the antibody. The heavy chain of an antibody contain a series of immunoglobulin domains, with at least one variable domain and at least one constant domain.

"Humanized", as used herein, refers to the process where monoclonal antibodies are produced using recombinant DNA to create constructs capable of expression in human cell culture. Any known techniques for producing these constructs will work for purposes of the present invention.

As used herein, "single chain variable fragments" or "scFv" or "scFvs", refer to fusion proteins of the variable regions of the heavy and light chains of immunoglobulins connected via a linker. In some embodiment, the linker is a peptide of about 10 to 25 amino acids.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples 1-8

Aggregation of the microtubule associated protein tau in neurons and glia is associated with over 20 neurodegenerative disorders including Alzheimer disease (AD), progressive supranuclear palsy, and frontotemporal dementia. Recent evidence from human studies suggests that tau pathology does not distribute randomly through the brain, but instead is linked to existing networks of neuronal connectivity. The fibrillar tau pathology of AD progresses along known anatomical connections, although the mechanisms by which networks degenerate are unknown. Importantly, recent pathological studies suggest that protein aggregates can move from one cell to another in human and mouse brain. Moreover, fibrillar forms of recombinant, human disease-associated proteins such as tau, SOD-1, α-synuclein and polygutamines are readily taken up from the extracellular space to trigger intracellular misfolding. These phenomena are reminiscent of prion propagation, for which exosomes and tunneling nanotubes have been proposed to mediate trans-cellular spread. It is an open question as to whether tau aggregates might spread protein misfolding from cell to cell via direct cell-cell contact or through extracellular space. Furthermore, it has not yet been determined whether pathological tau species can mediate true trans-cellular propagation of aggregation, whereby an aggregate is released from a "donor" cell, enters a second "recipient" cell, and induces further misfolding via direct protein-protein contact, as opposed to more indirect mechanisms. Here it is tested whether tau fibrils are released directly into the extracellular space and can propagate aggregation by this mechanism.

Example 1

Anti-Tau Antibodies

Two series of anti-tau antibodies were created using standard techniques: the HJ8 series (mouse monoclonal antibodies against recombinant human tau), and the HJ9 series (mouse monoclonal antibodies against recombinant mouse tau) (Table 1). Binding epitopes have been mapped for many of the antibodies (Table A).

TABLE 1

HJ8 series and HJ9 series against human and mouse tau

| Antibody | Isotype | Application |
|---|---|---|
| HJ 8.1 | IgG2b IgG1 | IP WB IHC(h&m) |
| HJ 8.2 | IgG2b | IP WB IHC(h&m) |
| HJ 8.3 | IgG2b | IP WB IHC(h&m) |
| HJ 8.4 | IgG1 | IP WB IHC(h&m) |
| HJ 8.5 | IgG2b | IP WB IHC(h) ELISA for coating staining 3 mon old mice |
| HJ 8.7 | IgG2b | IP WB IHC(h&m) HJ8.7B for ELISA detact staining |
| HJ 8.8 | IgG2b | IP WB IHC(h&m) staining |
| HJ 9.1 | IgG2b | IP WB IHC ELISA |
| HJ 9.2 | unknown | IP WB IHC ELISA for coating staining |
| HJ 9.3 | IgG2b | IP WB IHC ELISA for coating |
| HJ 9.4 | IgG2b | IP WB IHC |
| HJ 9.5 | IgG2b | IP WB IHC |

IP = Immunoprecipitation;
WB = Western] Blot;
ELISA = Enzyme-linked Immunosorbent Assay,
IHC = immunohistochemistry;
h = human;
m = mouse To characterize the binding affinity of the HJ8 and HJ9 series antibodies to mouse tau and human tau, Biacore's SPR technology was used. Biacore sensor chip CM-5 (Carboxymethylated dextran matrix) was activated by using EDC (1-ethyl-3-(3-dimethylaminopropyl)-carbodiimid) and NHS (N-hydroxysuccinimide) in 1:1 ratio. 2). Then ligand, either mouse tau or human Tau, were immobilized (20 ug/ml, in 10 mM sodium acetate pH 3.5) on Biacore CM-5 sensor chip at a flow rate of 5 μl/min. The remaining unbound area on the Biacore CM-5 sensor chip was deactivated by passage of 1 M ethanolamine pH 8.5.

Following preparation of the sensor chip surface, analytes (e.g. antibody) were injected with different concentrations (0.78 nM-400 nM) in filtered, degassed 0.01 M Hepes buffer, 0.15 M NaCl, 0.005% surfactant P20, pH 7.4 at a flow rate of 10 μl/min. All the samples were run in duplicates. After each cycle/run with single antibody concentration, the surface of the chip was regenerated by using 10 mM glycine pH 1.7, to remove the bound antibody/analyte, leaving the monomer/fibrils/ligand attached to the surface.

From the SPR sensorgram (FIG. 2-13), the rate of association or On rate ($K_a$), the rate of dissociation or Off rate ($K_d$) and the affinity constant or Affinity of interaction (KD, where $KD=K_d/K_a$) were obtained (Tables 2 and 3).

TABLE 2

Binding data of HJ8 series and HJ9 series to mouse tau

| Antibody | $K_a$ (1/Ms) | $K_d$ (1/s) | $K_D$ (M) |
|---|---|---|---|
| HJ 8.1 | $3.17 \times 10^4$ | $1.83 \times 10^{-8}$ | 0.578 pM |
| HJ 8.2 | $2.25 \times 10^5$ | $3.45 \times 10^{-7}$ | 1.57 pM |
| HJ 8.3 | $1.46 \times 10^5$ | $7.05 \times 10^{-8}$ | 0.48 pM |
| HJ 8.4 | $2.78 \times 10^5$ | $1.03 \times 10^{-7}$ | 0.37 pM |
| HJ 8.5 | No binding detected | | |
| HJ 8.7 | $7.03 \times 10^5$ | $2.41 \times 10^{-8}$ | 0.34 pM |
| HJ 8.8 | $1.92 \times 10^5$ | $1.78 \times 10^{-4}$ | 0.926 nM |
| HJ 9.1 | $3.52 \times 10^5$ | $7.61 \times 10^{-9}$ | 0.02 pM |
| HJ 9.2 | $2.65 \times 10^5$ | $1.08 \times 10^{-4}$ | 0.4 nM |
| HJ 9.3 | $8.61 \times 10^4$ | $9.16 \times 10^{-6}$ | 0.1 nM |
| HJ 9.4 | $2.28 \times 10^5$ | $5.1 \times 10^{-7}$ | 2.24 pM |
| HJ 9.5 | $3.4 \times 10^5$ | $5.37 \times 10^{-7}$ | 1.58 pM |

TABLE 3

Binding data of HJ8 series and HJ9 series to mouse tau

| Antibody | $K_a$ (1/Ms) | $K_d$ (1/s) | $K_D$ (M) |
|---|---|---|---|
| HJ 8.1 | $2.43 \times 104$ | $3.19 \times 10^{-8}$ | 1.32 pM |
| HJ 8.2 | $1.98 \times 10^5$ | $8.95 \times 10^{-7}$ | 4.51 pM |
| HJ 8.3 | $1.44 \times 10^5$ | $1.93 \times 10^{-3}$ | 0.07 pM |
| HJ 8.4 | $2.46 \times 10^5$ | $3 \times 10^{-8}$ | 0.122 pM |
| HJ 8.5 | $1.3 \times 10^5$ | $4.34 \times 10^{-8}$ | 0.336 pM |
| HJ 8.7 | $6.8 \times 10^4$ | $2.33 \times 10^{-8}$ | 0.34 pM |
| HJ 8.8 | $1.6 \times 10^5$ | $9.57 \times 10^{-7}$ | 5.95 pM |
| HJ 9.1 | $3.1 \times 10^5$ | $1.84 \times 10^{-3}$ | 0.5 pM |
| HJ 9.2 | $6.13 \times 10^4$ | $1.15 \times 10^{-3}$ | 24.6 nM |
| HJ 9.3 | $7.55 \times 10^4$ | $7.51 \times 10^{-6}$ | 99 pM |
| HJ 9.4 | $1.53 \times 10^5$ | $1.07 \times 10^{-3}$ | 6.9 nM |
| HJ 9.5 | $5.14 \times 10^5$ | $1.97 \times 10^{-3}$ | 3.82 nM |

Example 2

Full Length Tau is Present in ISF

Figure 14:
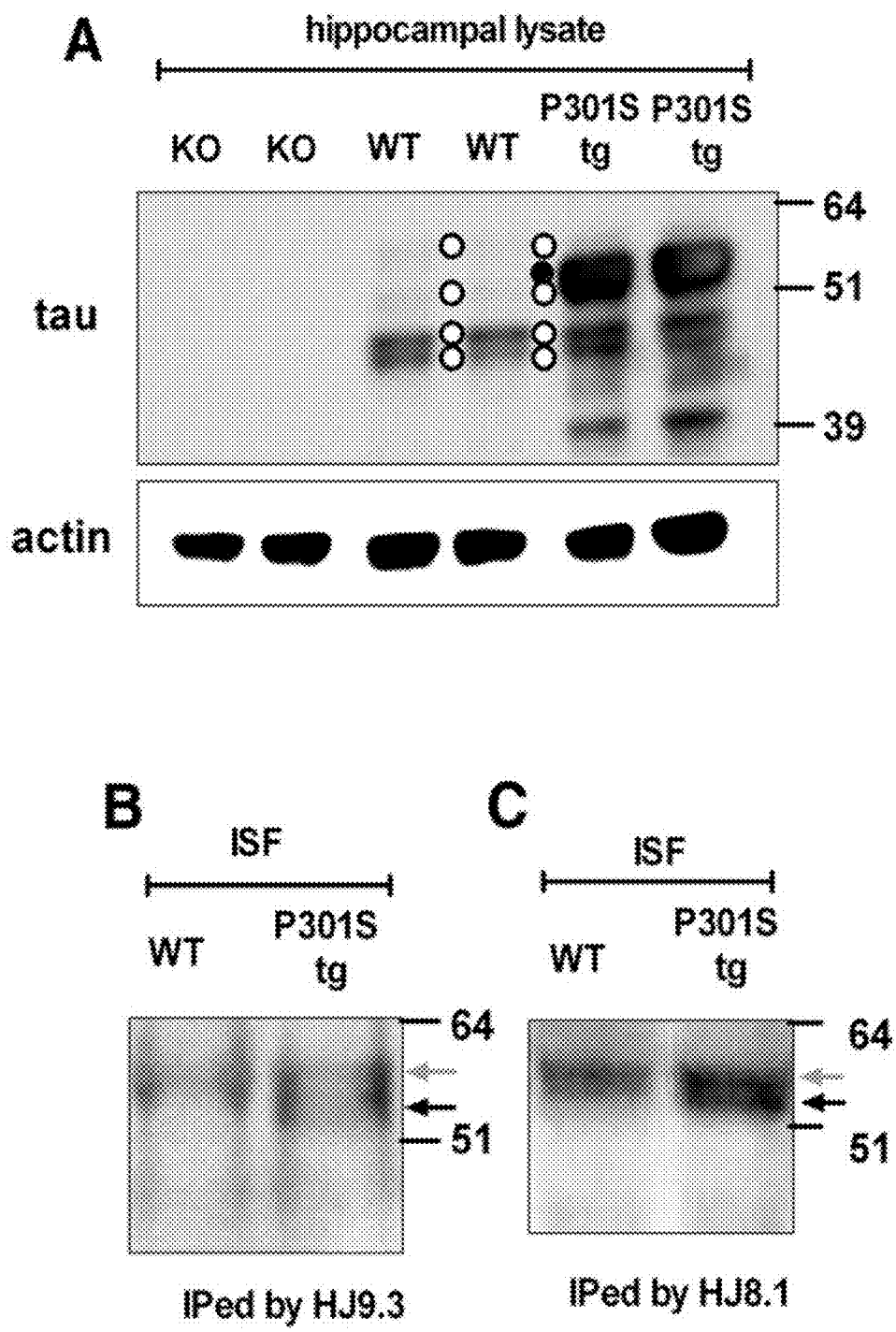
FIG. 14 depicts immunoblots showing the presence of full-length tau in ISF of wild-type and P301S tg mice. (A) Hippocampal lysates from Tau KO (KO), wild-type (WT), and P301S tg (P301S tg) mice were analyzed by immunoblot with the anti-tau antibody BT-2 or anti-actin antibody. Thirteen micrograms of protein were loaded per well. Four bands corresponding to endogenous murine tau and one band corresponding to human tau are indicated as white circles and a black circle, respectively. There is also a 39 kDa band representing a form of human tau in the P301S tg hippocampal lysate. This may represent a tau degradation product. ISF tau from wild-type (WT) and P301S tg (P301S tg) mice was immunoprecipitated by anti-tau monoclonal antibodies HJ9.3 (B) or HJ8.1 (C) and analyzed by immunoblot. The bands were visualized by biotinylated BT-2 antibody. The gray and black arrows indicate endogenous murine tau and human tau, respectively.

Tau was immunoprecipitated from ISF samples of both wild-type mice and P301S human tau transgenic mice (P301S tg mice, details in Methods) using tau antibodies recognizing both mouse and human tau. Two anti-tau monoclonal antibodies that worked well in immunoprecipitation assays were used, as the amount of monomeric tau in ISF is relatively low. Following immunoprecipitation, tau was analyzed by immunoblot. Endogenous murine tau isoforms migrate at 48-62 kDa. In wild-type brain lysate, tau appeared in four separate bands on SDS-PAGE (FIG. 14A). The most abundant species in wild-type mice migrated at 48 kDa. In P301S tg mice brain, in addition to the four endogenous murine tau bands, overexpressed human 1N4R tau was observed as an intense band migrating at 55 kDa as well as a 39 kDa band, which may represent a tau degradation product.

In contrast to total brain lysates, upon immunoprecipitation a single tau band was detected with antibody HJ9.3 recognizing the microtubule binding region (MTBR) of tau in ISF from wild-type mice (FIG. 14B). This band corresponded to the largest isoform 2N4R observed in mouse brain lysate. In ISF of P301S tg mice, a human-specific tau band was co-precipitated with the aforementioned mouse tau band and was slightly lower in molecular weight (FIG. 14B). These two bands were also precipitated by another mouse monoclonal antibody raised against tau HJ8.1 (FIG. 14C). These data suggested that the major species in ISF that is assessed by ELISA is likely full-length monomeric tau.

Example 3

Tau RD Proteins Form Fibrillar Aggregates in Transfected HEK293 Cells

Figure 15A:
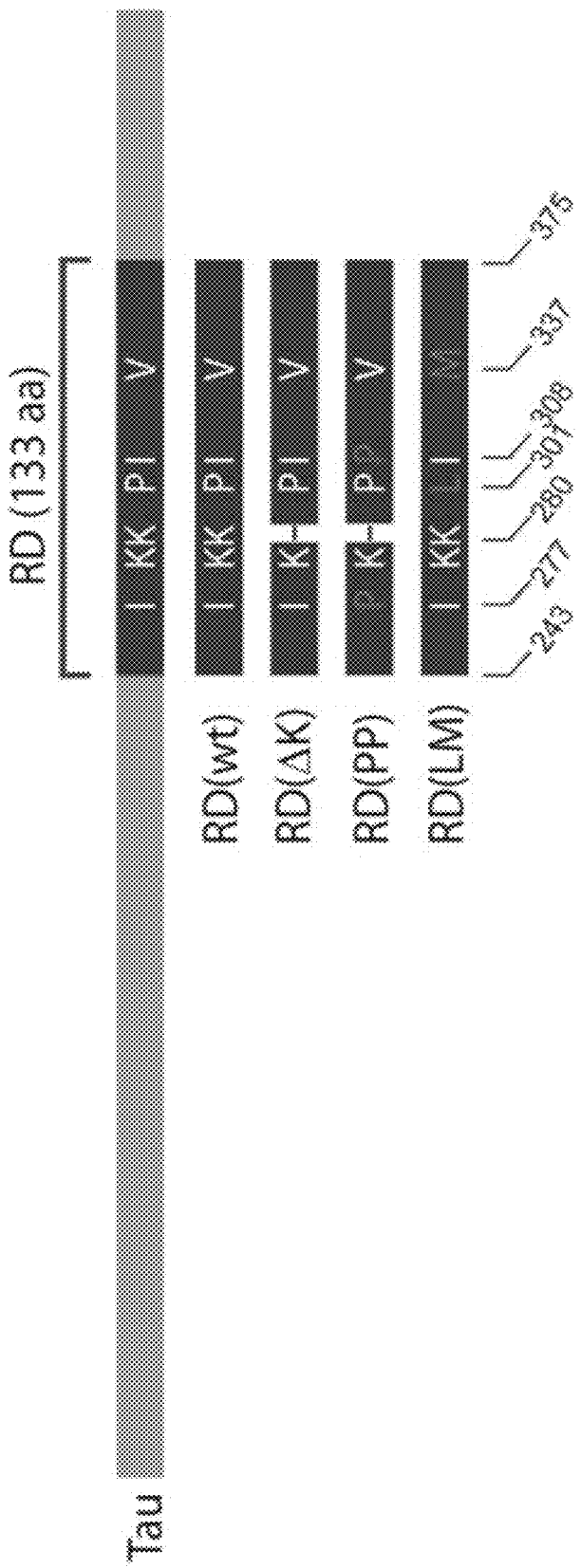
FIG. 15 (A) illustrates a schematic representation of the different mutant tau constructs used in this study, and (B-D) depict images showing Tau RD proteins form fibrillar aggregates in transfected HEK293 cells. (A) Depending on the experimental design, each form of mutant tau was either fused at the carboxyl terminus to cyan or yellow fluorescent protein (CFP or YFP), or to a hemagglutinin (HA) tag. (B) Atomic force microscopy (AFM) performed on SDS-insoluble material from HEK293 cells transiently transfected with the various forms of RD reveals that RD(ΔK)-HA and RD(LM)-HA produced obvious fibrillar species. No fibrils were detected in the aggregation-resistant RD(PP)-HA. (n=2), Scale bars, 1 μm. (C) HEK293 cells transiently transfected with the various forms of RD-YFP and YFP alone were stained with X-34, an amyloid-specific dye. Inclusions formed by RD(wt)-YFP, RD(ΔK)-YFP and RD(LM)-YFP, visualized by confocal microscopy, also stained positive for X-34. No X-34 positive cells were detected upon expression of YFP alone or RD(PP)-YFP. Arrows indicate inclusions stained with X-34. (n=3) (D) Non-Transfected cells (NT) and various forms of RD-YFP/CFP were transfected into HEK293 cells, followed by Triton/SDS extraction and Western blotting using an antibody against the RD region. Both monomer and higher order molecular weight species were detected. (S=Soluble protein and P=Pellet insoluble protein). This was repeated three times with identical results.

The tau gene encodes six protein isoforms, and multiple mutations cause dominantly inherited neurodegenerative disease. Depending on splicing, the tau protein has either three or four repeat regions that constitute the aggregation-prone core of the protein, which is termed the repeat domain (RD). Expression of the tau RD causes pathology in transgenic mice, and there is evidence for truncation of full-length tau to form fragments that comprise fibrils in patients. This construct was used rather than full-length tau because it reliably forms fibrils in cultured cells. Various mutations known to increase tau aggregation were engineered into a four-repeat RD protein: ΔK280 (termed ΔK), P301L, and V337M. The P301L and V337M mutants were combined in one protein (termed LM) to create a mutant form of RD with strongly increased aggregation potential, similar to what has been described previously. This "nonphysiologic" mutant facilitates assays of transfer events and trans-cellular propagation of misfolding that depend on efficient formation of intracellular aggregates, and complements similar, but less robust aggregation phenotypes of the "physiologic" ΔK mutant. Also engineered were two proline substitutions into the ΔK mutant, I277P and I308P (termed PP), which inhibit β-sheet formation and fibrillization, although they do not block formation of amorphous aggregates. Each form of mutant tau was fused either at the carboxyl terminus to cyan or yellow fluorescent protein (CFP or YFP), or to an HA tag. Constructs are diagrammed in FIG. 15A.

Figure 15C:
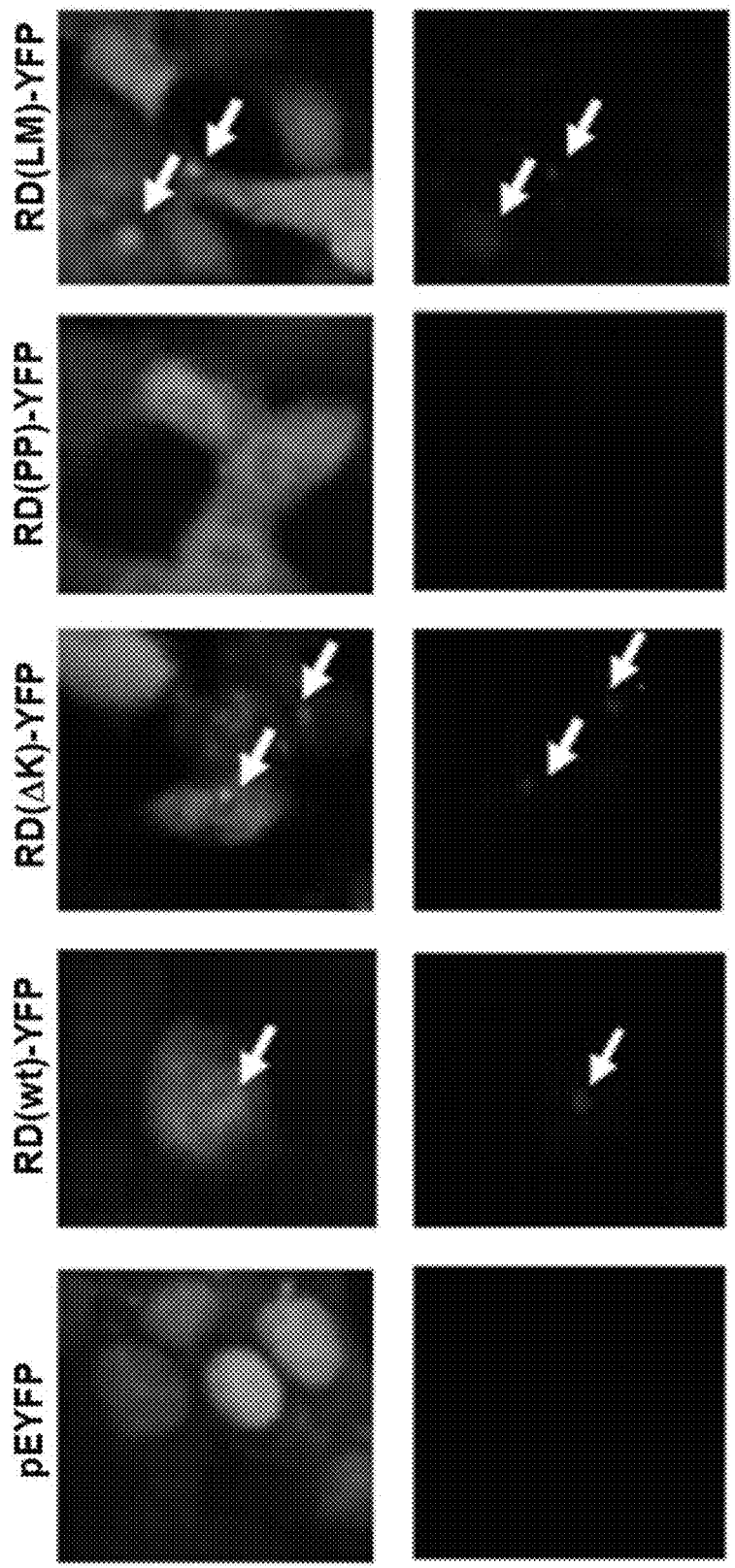
Figure 15D:
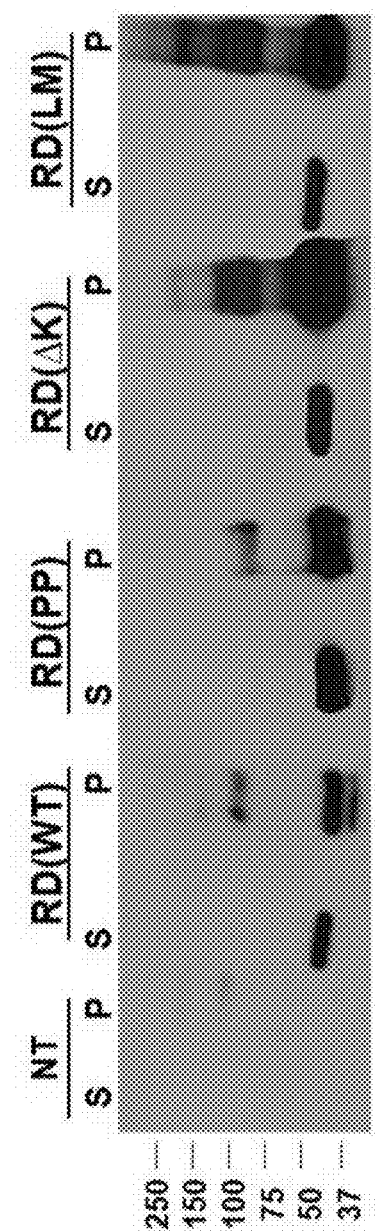

To evaluate the characteristics of tau RD intracellular aggregates, the various forms of RD were transiently transfected into HEK293 cells. Atomic force microscopy (AFM) was used to evaluate SDS-insoluble material. RD(ΔK)-HA and RD(LM)-HA produced evident fibrillar species (FIG. 15B). RD(ΔK)-HA and RD(LM)-HA aggregates within cells also stained positive for X-34, a thioflavin derivative that labels beta sheet fibrils and emits in the blue spectrum (FIG. 15C). Additionally, detergent fractionation was used to test whether the inclusions visible by light microscopy had a biochemical correlate. In SDS insoluble pellets (1% Triton X-100 in 1×PBS with protease inhibitors for isolation of soluble pellet followed by SDS/RIPA extraction of insoluble pellets), monomer and higher molecular weight species consistent with oligomers were detected (FIG. 15D).

Figure 16A:
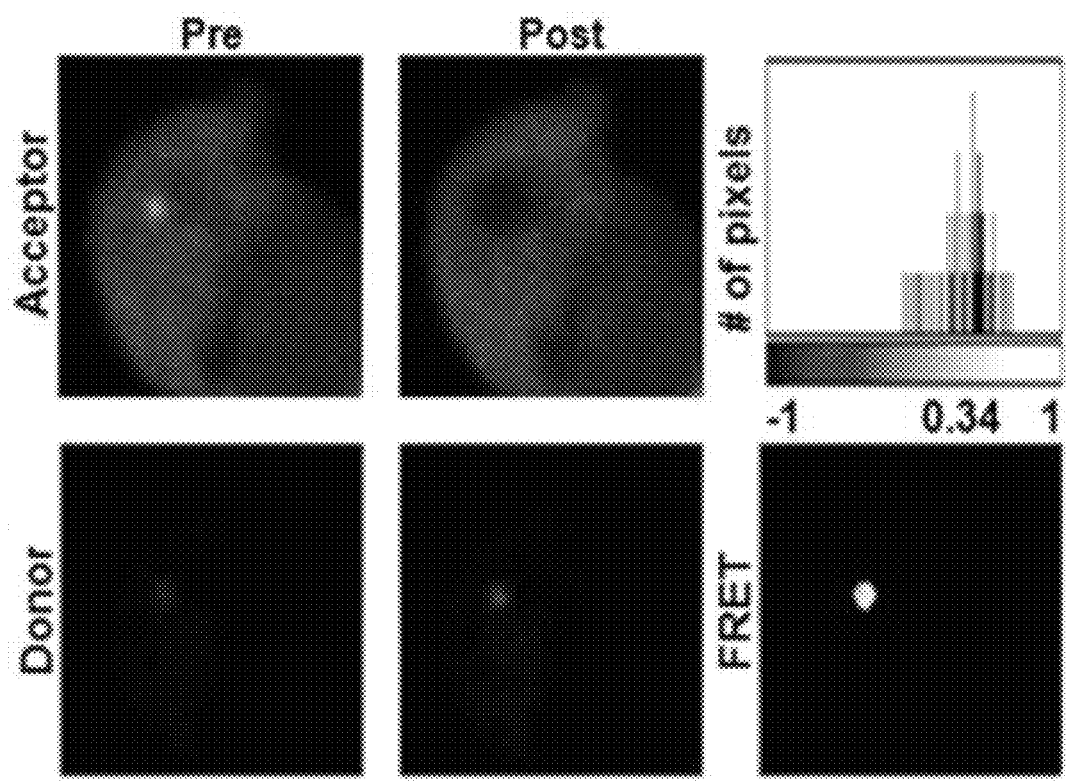
FIG. 16 shows Tau RD aggregates in HEK293 cells are detected by FRET. To quantitate intracellular RD protein aggregation by fluorescence resonance energy transfer (FRET), various RD mutants (wt, ΔK, PP, LM) fused to YFP and CFP were co-transfected into HEK293 cells. (A). HEK293 cells co-transfected with RD(LM)-CFP/YFP were imaged and intracellular aggregate formation was quantified using FRET acceptor photobleaching microscopy. Donor signal before (Pre) and after (Post) acceptor photobleaching confirmed that RD(LM)-CFP/YFP inclusions produced a mean FRET efficiency of 18.2%±0.058 SD (n=6). The upper and lower panels depict the acceptor and donor channels, respectively, before and after photobleaching. The top right image is a representative heat map of the calculated FRET efficiency. The scale bar of the histogram depicts the calculated FRET efficiency on a pixel-by-pixel basis. The FRET efficiency of Tau RD aggregate was ~34% in this cell. (B). Using a FPR, relative FRET from various constructs was determined. No significant FRET from RD(PP)-CFP/YFP was observed. However, RD(ΔK)-CFP/YFP and RD(LM)-CFP/YFP each produced a strong FRET signal (n=3). (C). HEK293 cells expressing RD(ΔK)-CFP/YFP were exposed to various concentrations of RD(wt)-HA fibrils (monomer equivalents of 0.01, 0.03, 0.1 and 0.3 µM) for 9 h. Extracellular RD(wt)-HA fibrils dose-dependently induced aggregation of RD(ΔK)-CFP/YFP (n=3). (* indicates a p-value<0.05, ** indicates a p-value<0.001, error bars represent the SEM).

The applicants previously used fluorescence resonance energy transfer (FRET) to quantitate intracellular huntingtin protein aggregation. To test whether this method could be used to track tau RD aggregation, the various RD mutants (wt, ΔK, PP, LM) were fused to yellow fluorescent protein (YFP: FRET acceptor) and cyan fluorescent protein (CFP: FRET donor). These constructs were co-transfected into HEK293 cells (denoted as RD-CFP/RD-YFP), and intracellular aggregate formation was quantified using FRET acceptor photobleaching confocal microscopy and spectral emission FRET using a fluorescence plate reader (FPR). For confocal microscopy, cells co-expressing RD(LM)-CFP/RD (LM) YFP were imaged and donor signal was measured before and after partial and complete acceptor photobleaching. The increase in donor signal after photobleaching resulted in a mean FRET efficiency of 18.2%±0.058 (n=6, data are ±standard deviation) confirming intermolecular interactions between the FRET-paired RD species (FIG. 16A). To measure RD-CFP/YFP aggregation by spectral FRET with a FPR, established methods were used. This was based on co-transfection of RD-YFP and RD-CFP in a 3:1 ratio, to maximize donor quenching within the limits of signal detection. Significant FRET from RD(PP)-CFP/YFP was not observed. However, RD(ΔK)-CFP/YFP and RD(LM)-CFP/YFP each produced a strong FRET signal (FIG. 16B), corroborating the microscopy findings.

It has been previously observed that a variety of cells will take up recombinant tau fibrils from the extracellular media. This triggers intracellular fibrillization of natively folded, full length tau protein fused to YFP. To confirm this phenomenon, FRET was used to monitor aggregation of RD(ΔK)-CFP/YFP induced by various amounts of recombinant RD fibrils. HEK293 cells were co-transfected with RD(ΔK)-CFP/YFP and cultured for 15 h. Various concentrations of RD-HA fibrils (monomer equivalents of 0.01, 0.03, 0.1 and 0.3 µM) were then added to the media for 9 h. Fibrils were then removed by changing the media, and the cells were allowed to recover for 4 h before being fixed and analyzed using FRET. A dose dependent increase in the FRET signal induced by recombinant fibrils relative to untreated RD(ΔK)-CFP/YFP cells was observed (FIG. 16C). In summary, a correlation between microscopic, molecular, biochemical, and biophysical measures of tau RD aggregation and fibril formation within cells was observed. Within certain limits, especially with controls for protein expression levels, the plate reader-based FRET assay provides a facile measure of this process.

Example 4

Trans-Cellular Induction of RD Aggregation

Figure 17A:
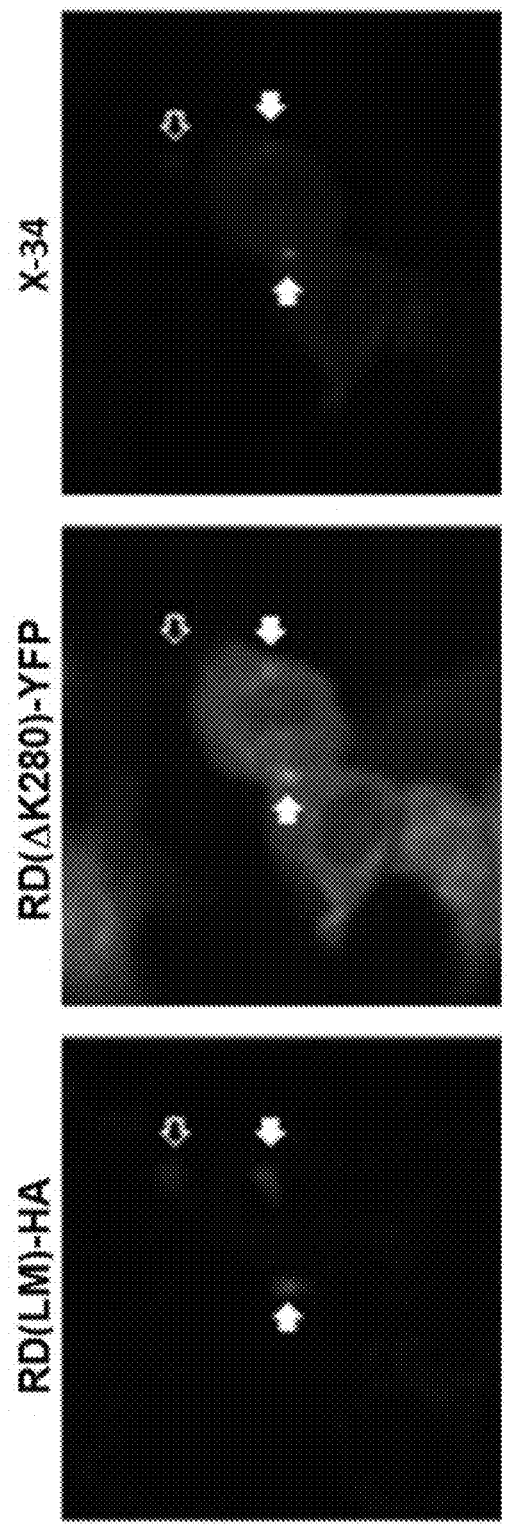
FIG. 17 depicts images and graphs showing Tau-RD aggregates transfer between cells and induce further aggregation. (A). HEK293 cells transfected with RD(ΔK)-YFP were co-cultured for 48 h with an equivalent number of cells expressing RD(LM)-HA. Cells were fixed with 4% paraformaldehyde and immunofluorescence/X-34 staining was performed. Multiple cells showed colocalization of RD(LM)-HA and RD(ΔK)-YFP within inclusions. These inclusions also stained positive for X-34, indicating beta sheet structure (solid arrows). In addition, some RD(LM)-HA inclusions stained positive for X-34 but did not colocalize with RD(ΔK)-YFP inclusions (open arrow). (B). Two populations of cells, one expressing RD(ΔK)-CFP/YFP, and the other expressing RD(LM)-HA, were co-cultured for 48 h. RD(PP)-HA or non-transfected cells, NT, were used as controls. FRET was increased by co-culture with RD(LM)-HA, but not with RD(PP)-HA, or mock-transfected cells (n=3). (C). To test for cell death induced by tau aggregates as a mechanism of tau release, HEK293 cells were transfected for 48 h with RD-HA (PP, ΔK, or LM), or were mock-transfected. Mock-transfected cells were treated with varying concentrations of staurosporine (1, 2, 4, 20 µM) for 30 minutes at 37° C. to induce cell death. Cells were then exposed to 5 µg/ml of propidium iodide and fluorescence was determined via plate reader. No evidence for cell death in the various transfected populations was observed. (** indicates a p-value<0.001, error bars represent the SEM).
Figure 17:
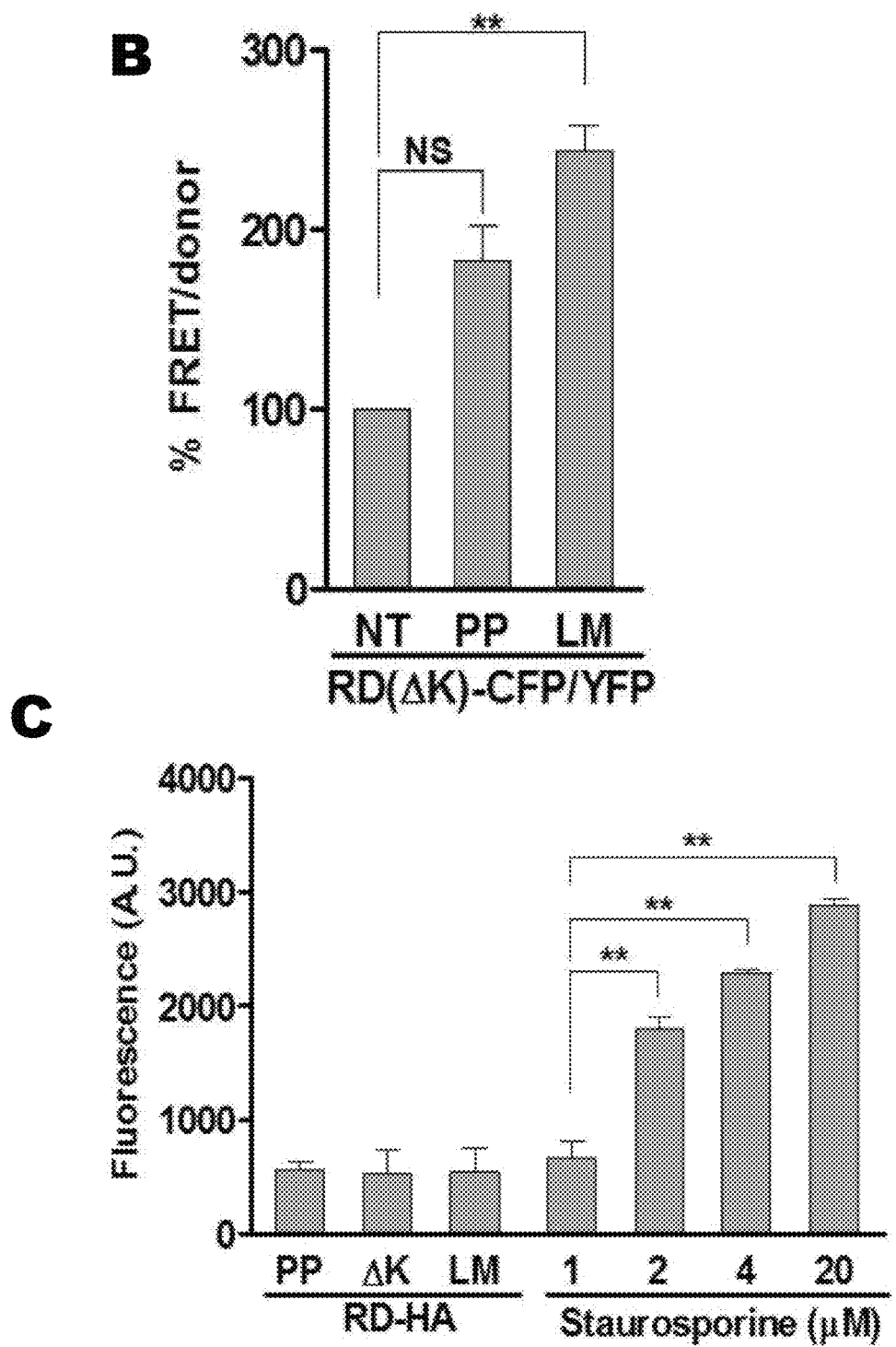

The applicants have previously determined that tau inclusions from one cell will transfer to naïve cells in co-culture. However it has not yet been demonstrated that these transferred aggregates can induce further aggregation in the recipient cells, nor whether induction of aggregation is based on direct protein-protein interaction. First tested was whether RD(LM)-HA aggregates derived from one donor cell population would form inclusions with RD(ΔK)-YFP in a different recipient population upon co-culture. One group of cells was transfected with aggregation-prone RD(LM)-HA, and a separate group transfected with RD(ΔK)-YFP. The next day, the cell populations were re-plated together and co-cultured for 48 h. After fixation, they were immunostained using an HA antibody, and counterstained with X-34. Many cells were observed with RD(LM)-HA and RD(ΔK)-YFP co-localized in inclusions (FIG. 17A). Frequently these inclusions also stained positive for X-34, indicating beta sheet structure. These studies were extended by using the FRET assay to monitor aggregation of RD(ΔK)-

CFP/YFP induced by co-culture with cells expressing RD(LM)-HA. In this case, two populations of cells were co-cultured. The donor population expressed RD(LM)-HA and the recipient population expressed RD(ΔK)-CFP/YFP. The β-sheet-resistant form of tau RD(PP)-HA or mock transfected cells were used as negative controls. After 48 h FRET was measured from the cell monolayers. A strong increase in FRET induced by co-culture with RD(LM)-HA versus RD(PP)-HA or mock transfected cells was observed (FIG. 17B). A small increase in FRET signal was observed following co-culture of RD(LM)-HA cells with RD(WT)-CFP/YFP recipient cells (data not shown). These results suggested movement of one aggregation-prone tau species from one cell to another to trigger co-localization in a beta-sheet rich inclusion. Aggregate release could potentially occur after cell death, however, no evidence for this was observed using propidium iodide staining of the various transfected populations (FIG. 17C).

Example 5

Propagation of Misfolding by Direct Protein Contact

Figure 18A:
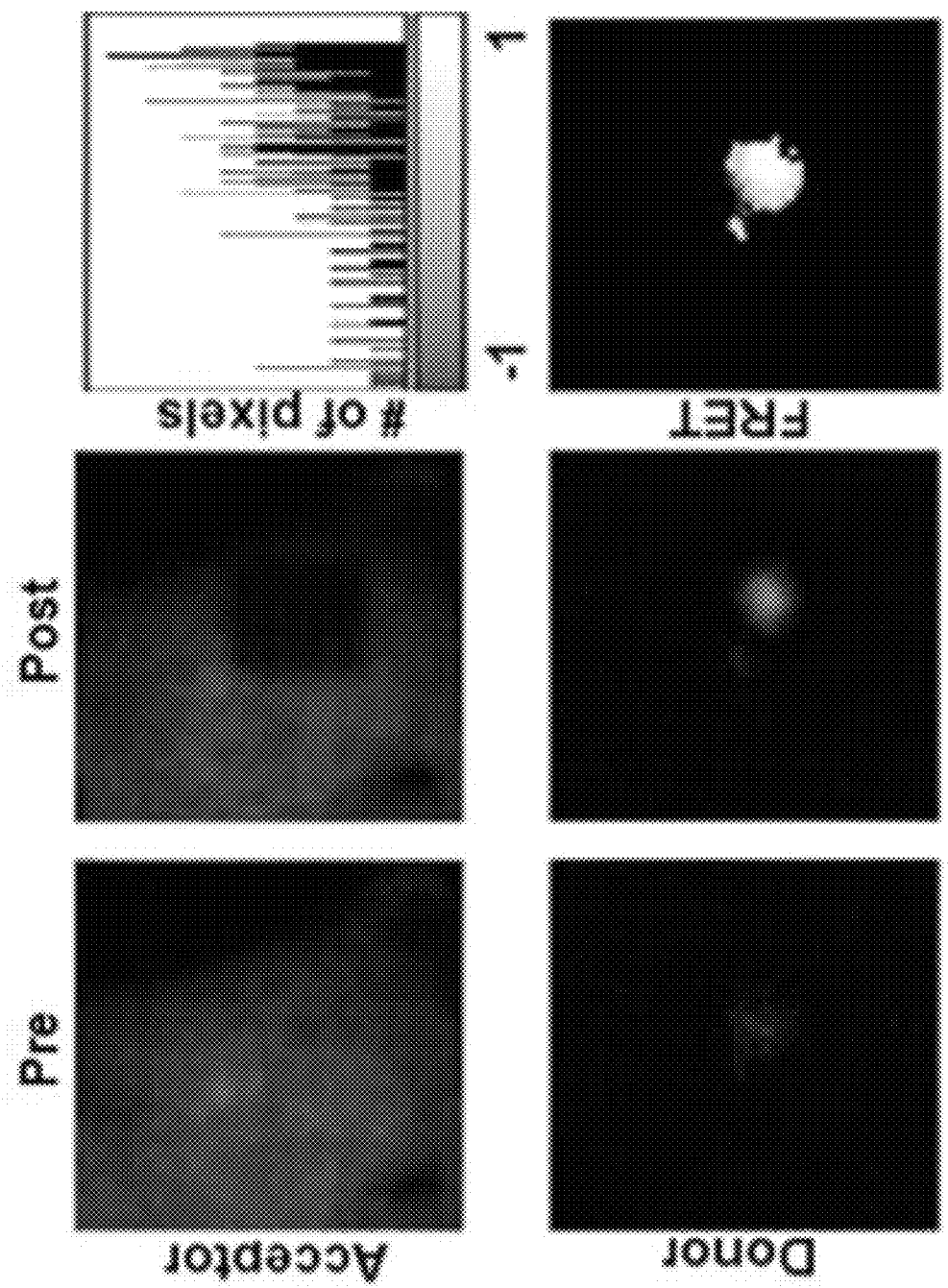
FIG. 18 depicts images and graphs showing RD aggregates propagate misfolding between cells. HEK293 cells were co-transfected with various RD-CFP and RD-HA constructs. 15 h later, these cells were co-cultured with cells expressing RD(ΔK)-YFP or RD(PP)-YFP for 48 h (A) FRET microscopy was performed to determine whether co-aggregation occurred via direct protein contact. CFP signal was measured before and after photobleaching of YFP. RD(LM)-CFP and RD(LM)-YFP aggregates had a mean FRET efficiency of 14.2%±0.053 SD (n=11) indicative of RD(LM)-CFP and RD(LM)-YFP in direct contact. The upper and lower panels depict the acceptor and donor channels, respectively, before (Pre) and after (Post) photobleaching. A representative heat map of the calculated FRET efficiency is shown at top right. The histogram depicts the calculated FRET efficiency on a pixel-by-pixel basis. The FRET efficiency of Tau RD aggregate was ~25% in this cell. Negative values are derived from unpaired CFP. (B) A FRET signal was observed when cells expressing RD(ΔK)-CFP/RD-HA were co-cultured with cells expressing RD(ΔK)-YFP. This signal increased when aggregation of RD(ΔK)-CFP was induced by co-expression of aggregation-prone forms of tau, either ΔK, or LM mutants. No significant signal was noted when either RD-CFP or RD-YFP contained the PP mutation that blocks β-sheet formation (n=3). (C) To test for amplification of misfolding, populations of cells expressing CFP alone or RD(LM)-CFP were preexposed for 48 h to cells expressing RD-HA with either PP, ΔK, or LM mutations to promote misfolding to varying degrees. These co-cultured populations were then split and co-cultured for 48 h with cells expressing RD(ΔK)-YFP to determine the degree of aggregation reported by cell-cell transfer and FRET. Prior exposure of RD(LM)-HA cells to the RD(ΔK)-CFP cell population increased FRET signal by 2.6 fold vs. prior exposure to RD(PP)-HA. Interposition of cells expressing pure CFP in the second population of cells completely blocked the effect of prior exposure to aggregation-prone RD-HA mutants (n=3). (* indicates a p-value<0.05, ** indicates a p-value<0.001, error bars represent the SEM).
Figure 18B:
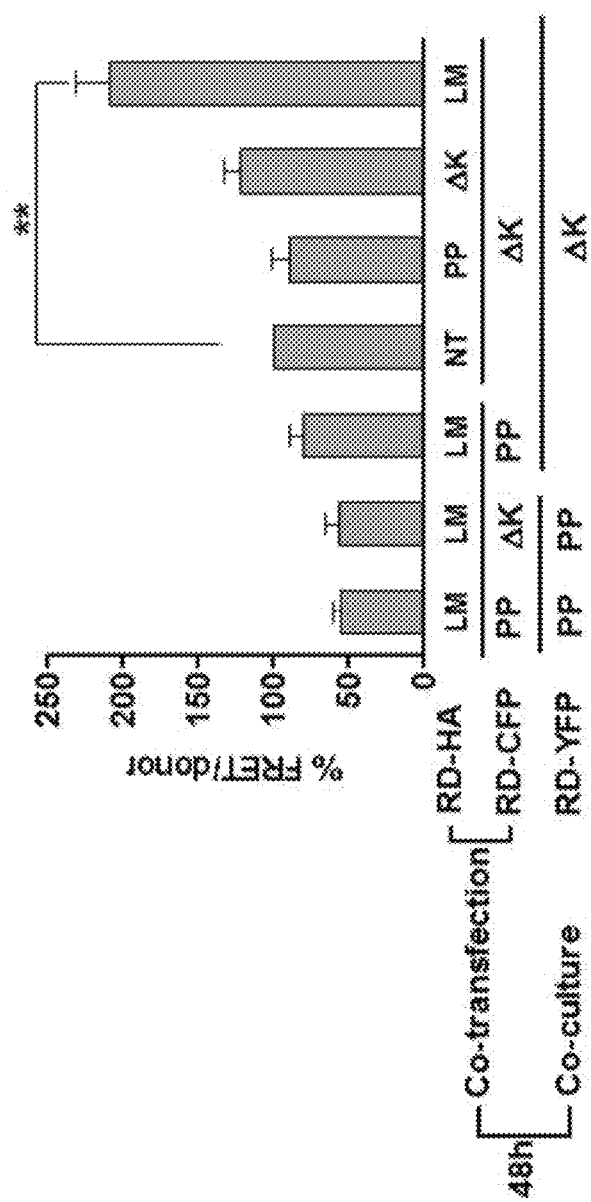
Figure 18C:
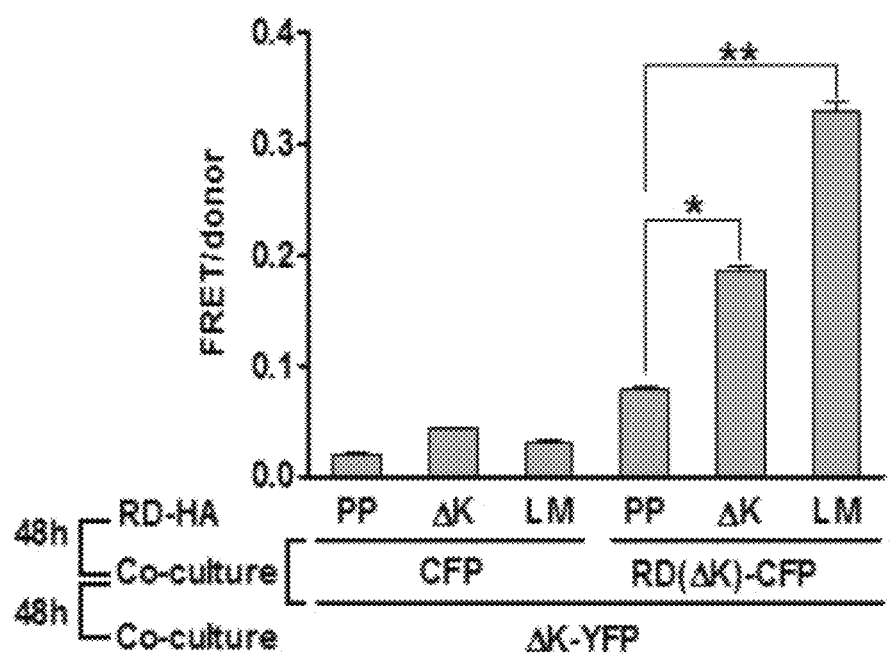

While strongly suggestive, these results could not formally address whether co-aggregation occurred via direct protein contact, with intermolecular association between tau RD derived from donor contacting the corresponding protein in recipient cells. FRET was used to address this question. First, RD(LM)-CFP was co-expressed within a donor cell population, and RD(LM)-YFP in a second recipient population. FRET from the cell monolayers was measured after 48 with both confocal microscopy and the FPR. Using confocal microscopy, CFP signal was measured before and after photobleaching of YFP. A mean FRET efficiency of ~14.2% was recorded, indicating that inclusions contained RD(LM)-CFP and RD(LM)-YFP in direct contact (FIG. 18A). Relative FRET signals were then compared via FPR, using different forms of unlabeled RD to induce aggregation of RD-CFP. First, RD(ΔK)-CFP and RD(LM)-HA were co-expressed within a donor cell population, and RD(ΔK)-YFP in a second recipient cell population. RD(LM)-HA serves as an enhancer of both RD(ΔK)-CFP aggregation and movement, prompting its subsequent transfer into the RD(ΔK)-YFP recipient cells. This led to a small but reproducible FRET signal increase in the co-cultured cells. This signal disappeared when either the CFP- or YFP-tagged RD constructs contained the PP mutation that blocks β-sheet formation (FIG. 18B), indicating that both members of the pair must have the capacity to form a beta sheet structure. Taken together with the prior experiments, these results suggested that propagation of misfolding by direct contact occurs, i.e. an aggregate from one cell exits to contact and trigger misfolding of natively folded protein in a second cell. This data implied that amplification of misfolding might also occur in serial cell co-cultures. It was predicted that pre-exposure of a "donor" cell population to aggregation seeds would increase final aggregation detected in a recipient cell population. This was tested by successively culturing three populations of cells. The first population expressed various forms of non-fluorescent RD-HA to form aggregation "seeds." The second group expressed CFP or RD(ΔK)-CFP, to be either non-permissive (CFP) or permissive RD(ΔK)-CFP) for aggregate maintenance. These two groups were co-cultured for 48 h to allow amplification of misfolding. Next, 50% of the combined first and second groups were then co-cultured for 48 h with a third group of cells expressing RD(ΔK)-YFP. This third recipient group served as a "reporter" to indicate the degree of RD(ΔK)-CFP intracellular aggregation and propagation. Prior exposure of RD(LM)-HA to the RD(ΔK)-CFP population increased final FRET by 2.6 fold vs. cells that had not been preexposed to aggregation-prone tau. As expected, interposition of cells expressing pure CFP in the second population of cells completely blocked the effect of prior exposure to tau RD "seeds" (FIG. 18C). Taken together these data indicate an amplification of tau aggregation within serially cultured cell populations.

Example 6

Figure 19:
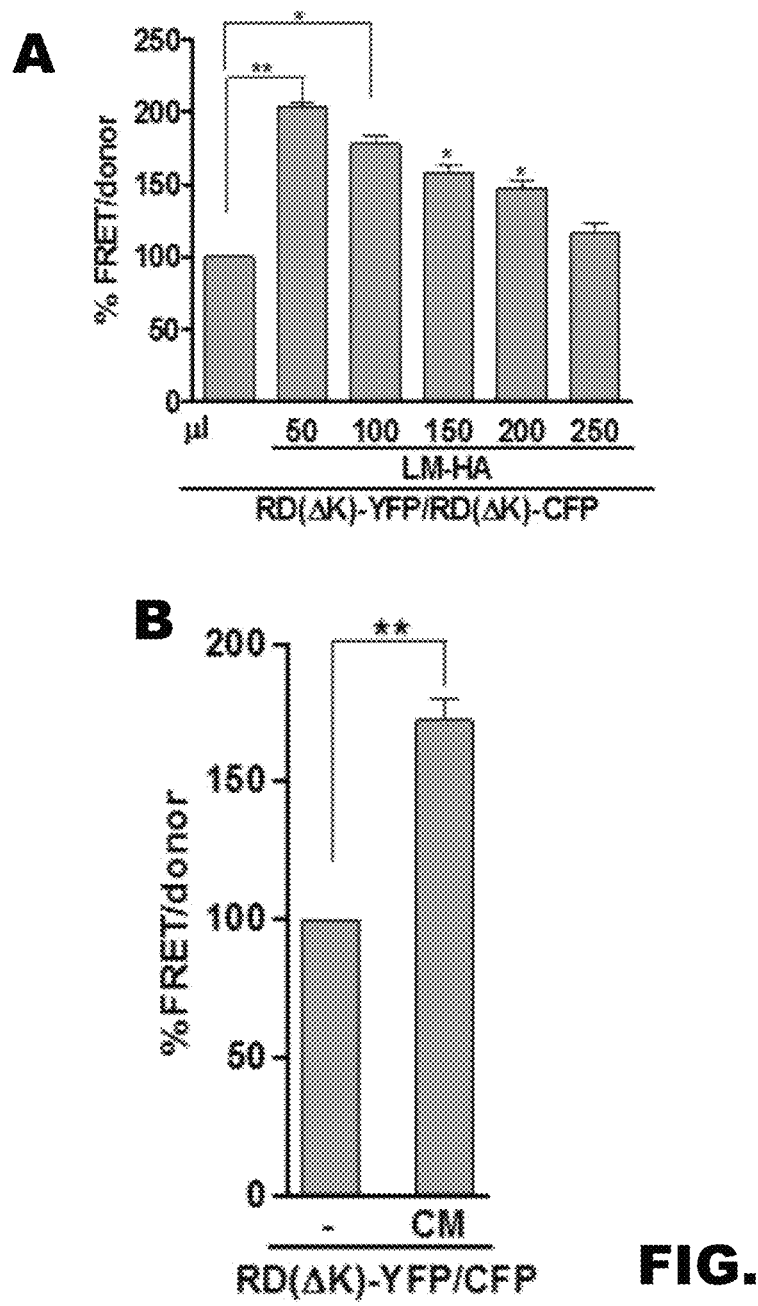
FIG. 19 depicts graphs and an immunoblot showing propagation of tau aggregates through the extracellular medium. (A) HEK293 cells transfected with RD(LM)-HA were co-cultured for 48 h with an equivalent number of RD(ΔK)-CFP/YFP cells prior to FRET analysis. Increasing the volume of cell culture medium reduced the efficiency of trans-cellular movement of aggregates. (B) Transfer of conditioned medium from cells expressing RD(LM)-HA to cells expressing RD(ΔK)-CFP/YFP was sufficient to induce aggregation by 60%. (C) HJ9.3 antibody added to the media reduced FRET, consistent with interference with propagation of aggregation. (D) Non-specific IgG had no effect on propagation. (E) HJ9.3 had no effect on intracellular aggregation of RD(ΔK)-CFP/YFP co-expressed within the same cell. (F) HJ9.3 blocked the effect of RD(LM)-HA to induce RD(ΔK)-YFP in co-cultured cells, as determined by detergent fractionation and western blot. (T=Total protein, S=Soluble protein and P=Pellet insoluble protein, (G) Quantitative analysis of three independent Western blots revealed a ~60% decrease in the pellet fraction, relative to the total fraction, after exposure to HJ9.3. (H) Cells expressing RD(LM)-YFP and mCherry were co-cultured and analyzed by flow cytometry. HJ9.3 decreased the percentage of dual positive cells from 2.07% to 1.31%. Cells mixed just prior to cytometry were a background control (* indicates a p-value<0.05, ** indicates a p-value<0.001, error bars represent the SEM).
Figure 19:
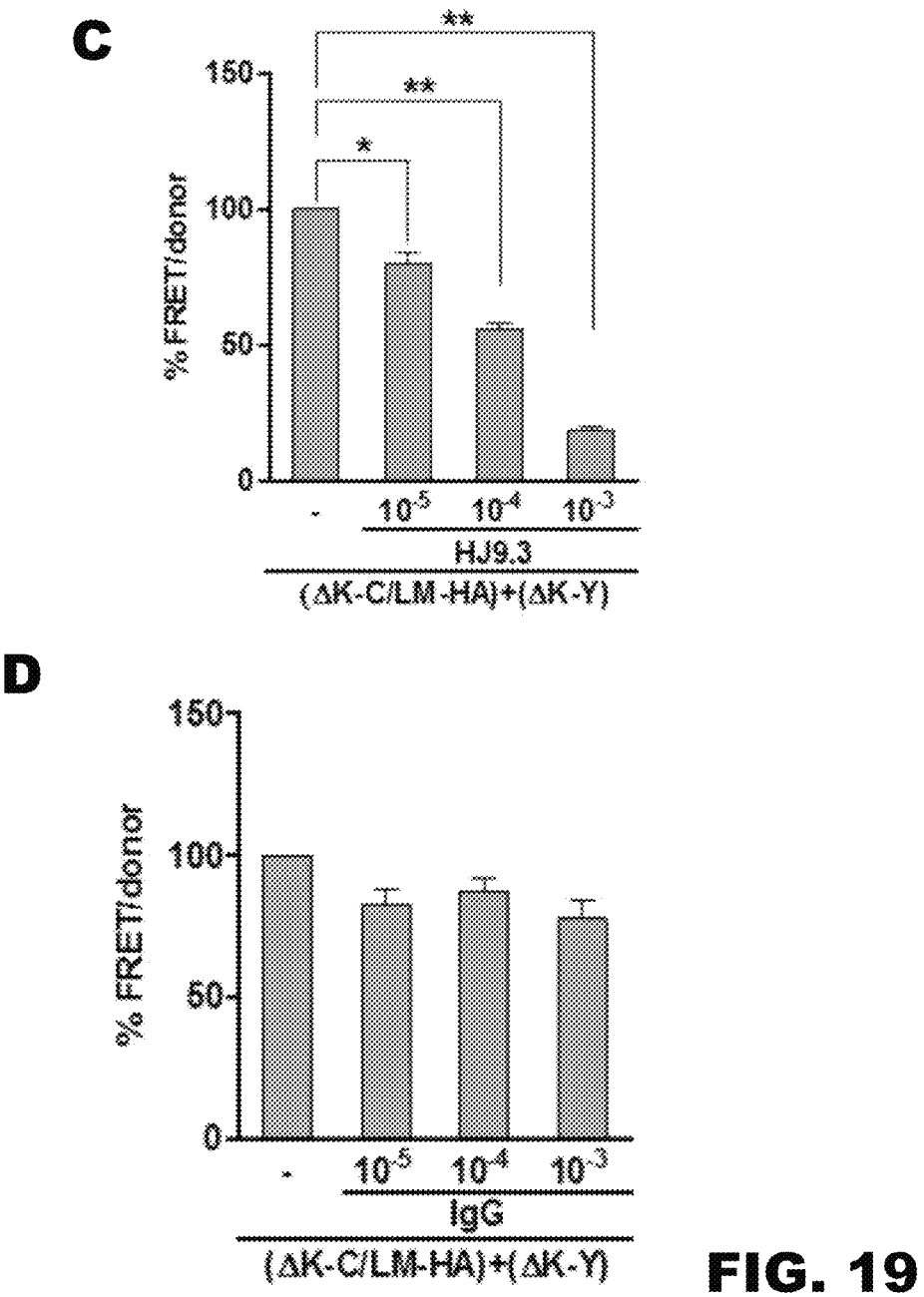
Figure 19:
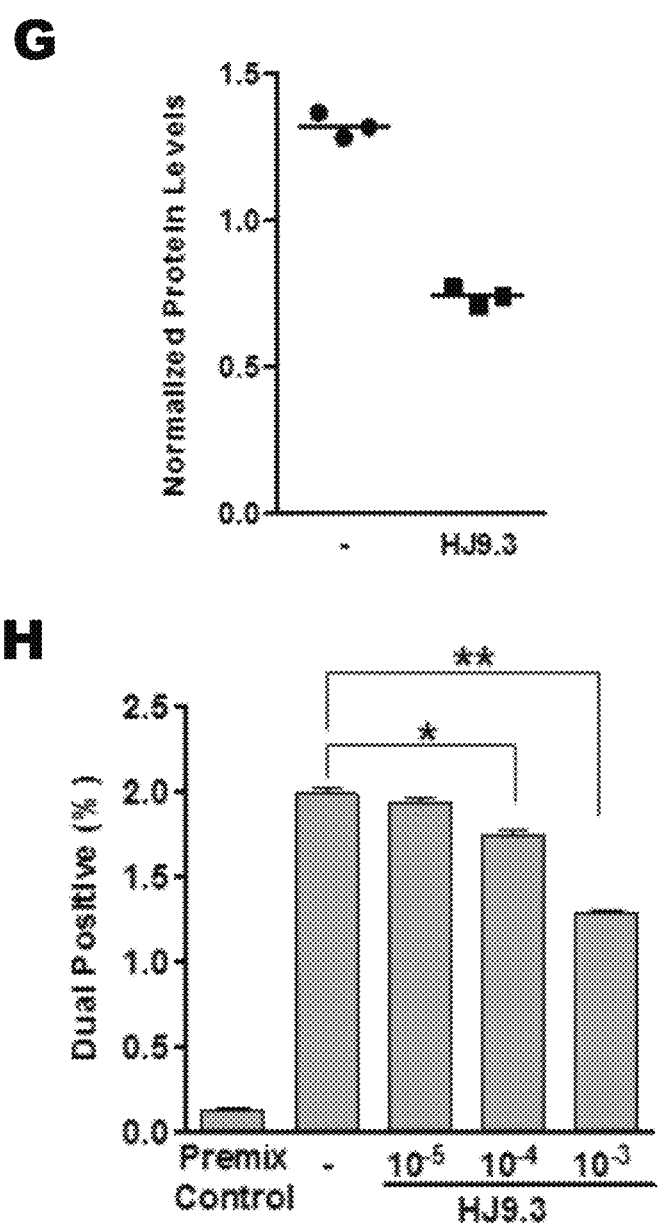

Cell-Cell Propagation Mediated by Release of Aggregates into the Extracellular Space The mechanism by which protein aggregates move between cells is unknown. For example, some have postulated prion protein propagation via tunneling nanotubes, while others have suggested exosomes. Since antibodies against tau protein have previously been reported to reduce pathology in vivo, it was hypothesized that tau aggregates might be released directly into the extracellular space. Whereas trans-cellular movement based on cell-cell contact should be independent of the volume of extracellular media, it was predicted that transcellular movement of tau might be sensitive to extracellular volume, as has been described for SOD1. To start, the effect of co-culture in the setting of various volumes of media was first tested. It was observed that increasing the cell culture medium volume reduced the efficiency of transcellular movement of aggregates (FIG. 19A). Further, transfer of conditioned medium from cells expressing RD(LM)-HA was sufficient to induce aggregation in cells expressing RD-CFP/YFP (FIG. 19B). These results were consistent with the movement of tau between cells through the extracellular space, but could not determine whether the protein was encapsulated in an endosome. It was reasoned that access to encapsulated tau would be blocked by the lipid membrane, whereas free tau would be accessible to an antibody. Thus, it was tested whether a mouse monoclonal antibody (HJ9.3) that can immunoprecipitate tau would block transcellular propagation. A modification of the cellular model of tau RD propagation described above was used, in which RD(LM)-HA and RD(ΔK)-CFP were co-expressed within one cell population, and co-cultured for 48 h with cells that express RD(ΔK)-YFP, prior to analysis by FRET. HJ9.3 versus pooled mouse IgG was tested for the 48 h co-culture period. A dose dependent reduction in trans-cellular propagation with HJ9.3 was observed, while non-specific IgG had no effect (FIGS. 19C and D). Importantly, HJ9.3 had no effect on intracellular aggregation of RD(ΔK)-CFP and RD(ΔK)-YFP when the two proteins were co-expressed within the same cell (FIG. 19E), indicating the antibody was not directly inhibiting intracellular aggregation. The role of free tau was further tested in transcellular propagation by evaluating induction of tau misfolding using biochemistry. The induction of aggregation by detergent fractionation and Western blot was confirmed, which revealed an increase in RD(ΔK)-YFP in the insoluble fraction induced by co-culture with RD(LM)-HA. HJ9.3 blocked the effect of RD(LM)-HA to induce insolubility of RD-YFP in co-cultured cells (FIGS. 19F and G).

The effectiveness of antibody addition suggested that free tau was directly transferring between cells, but left uncertain the mechanism of antibody inhibition. It was hypothesized that HJ9.3 was blocking uptake of tau fibrils into cells. To test this idea flow cytometry was used to monitor the effect of the antibody on trans-cellular movement of aggregates. The applicants have previously established a cytometry paradigm whereby one population of cells is labeled with mCherry, and the second contains tau-YFP fusions. After co-culture, it is possible to monitor trans-cellular movement based on the relative percentage of dual-positive (YFP/mCherry) cells. A population of HEK293 cells was transfected with tau RD(LM)-YFP, and a second population was transduced with lentivirus expressing mCherry. After washing and resuspending the two populations, the cells were then co-cultured for 48 h in the presence or absence of 10-fold dilutions of HJ9.3 in the medium. Cells were harvested and the relative number of dual positive cells measured using flow cytometry. Negative controls consisted of the same cell populations mixed prior to sorting. Each data point consisted of biological triplicates. Co-cultured cells had significantly more RD(LM)-YFP/mCherry dual positive cells (2.07%) compared to 0.142% of premixed cells (background). HJ9.3 decreased the percentage of dual positive cells from 2.07% to 1.31% (FIG. 19H). This parallels the effect of this antibody on transcellular propagation of aggregation as measured by FRET. The difference in the potency of this antibody in blocking propagation as measured by FRET and flow cytometry is most probably due to the differences between the two techniques used to measure this event.

Figure 20:
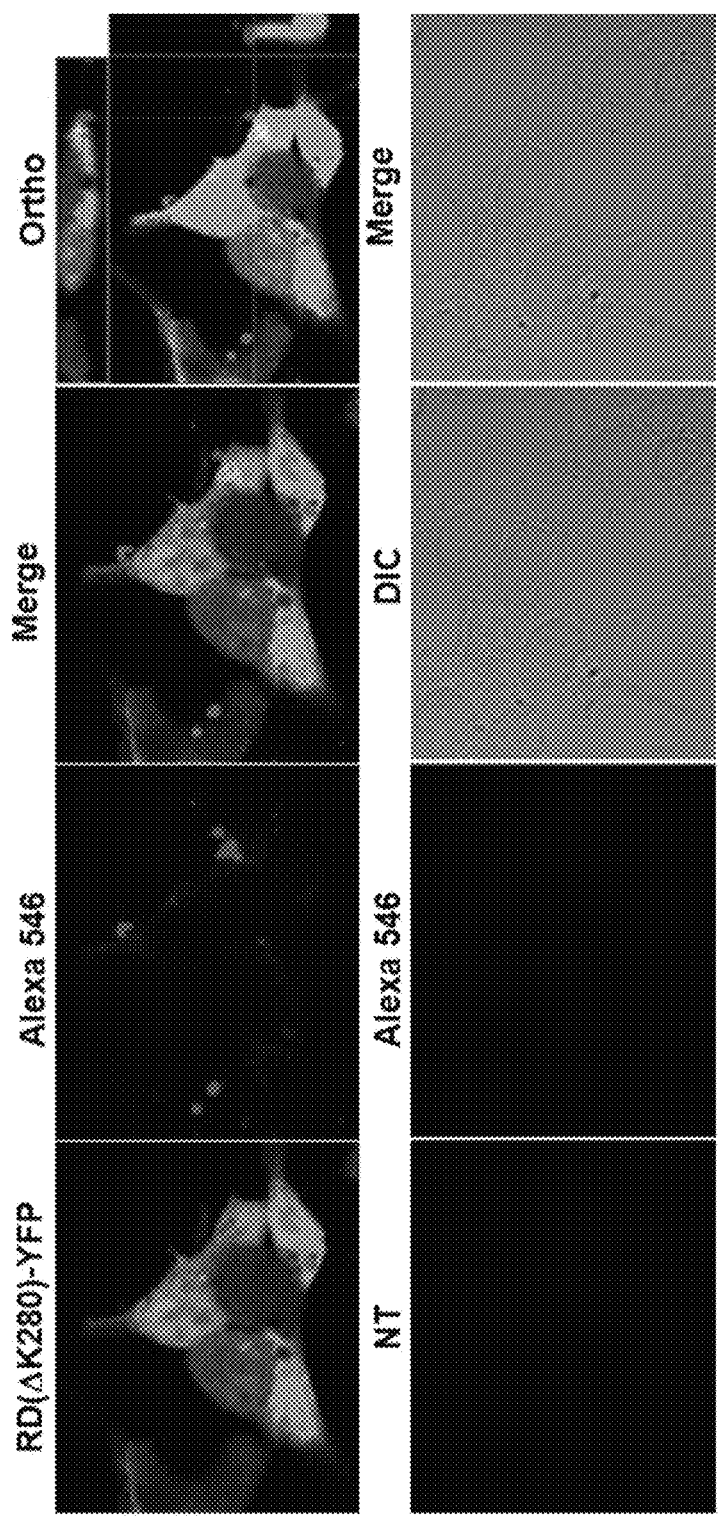
FIG. 20 depicts images of HEK293 cells transfected with RD(ΔK)-YFP (top panels) or mock-transfected (lower panels). HJ9.3 was added to the culture medium for the 48 h period. At the end of the experiment, the cells were fixed, permeabilized, and stained with an anti-mouse secondary antibody (labeled with Alexa 546). Confocal microscopy was used to analyze the localization of HJ9.3/tau complexes. The top panels show that many complexes are identified when RDΔ(K)-YFP is expressed, but none in its absence (lower panels). Orthogonal analyses (right panel) demonstrate that most complexes are present at the cell surface, although occasional intracellular complexes were observed.

To further monitor the effect of the HJ9.3 antibody on trans-cellular movement of aggregates, direct immunofluorescence was used in an attempt to define where the HJ9.3/antibody complexes deposited. RD(ΔK)-YFP cells or non-transfected cells were cultured in the presence of HJ9.3 for 48 hrs. Cells were fixed with 4% PFA, permeabilized with 0.25% TritonX-100 and then exposed to goat anti-mouse Alexa 546 labeled secondary antibody. A very small number of HJ9.3/tau complexes were present inside cells. However, most complexes were found outside of the cells, mainly bound to the cell membrane. This antibody decoration was not present in nontransfected cells indicating that the signal is specific to the HJ9.3/tau complexes (FIG. 20). Thus HJ9.3 blocks tau aggregate uptake, trapping aggregates outside the cell.

Example 7

Tau Fibrils Mediate Cell-Cell Propagation

Figure 21A:
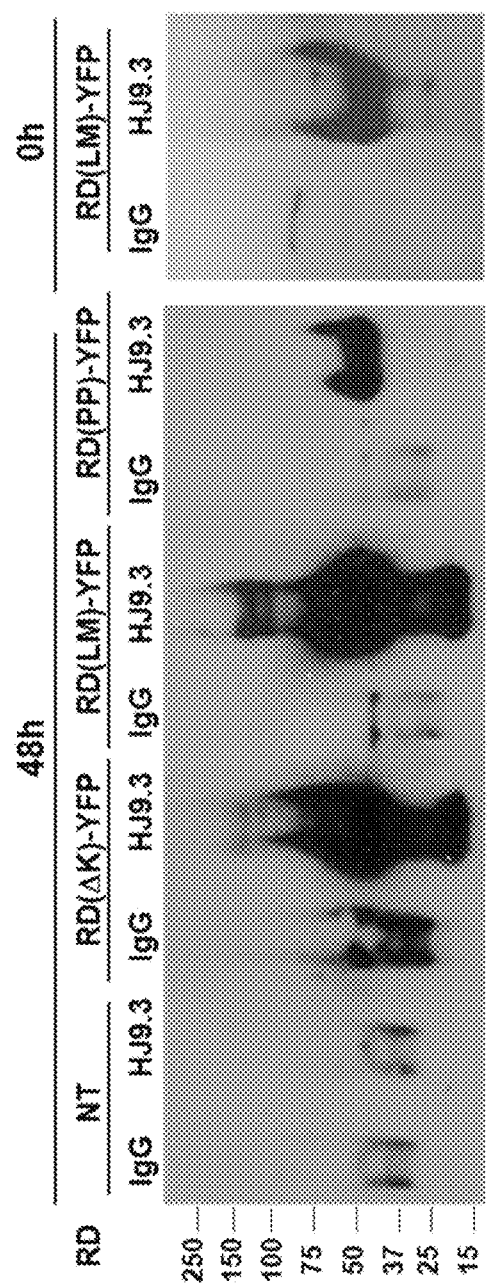
FIG. 21 depicts images and a graph showing Tau fibrils mediate cell-cell propagation. (A) Conditioned media was collected from transfected cell populations co-cultured for 0 h or 48 h with HJ9.3 or control IgG antibody (1:1000), followed by immunoprecipitation and Western blot. HJ9.3 specifically captured tau RD species from the cell media, while IgG did not. Higher-order aggregated species were present upon expression of RD(ΔK)-YFP or RD(LM)-YFP but not RD(PP)-YFP. (B) Quantitative analyses of three independent Western blots showed a ~10-fold increase in the tau after 48 h incubation. (C) Cells were exposed to HJ9.3 for various times. (D) Purified antibody/antigen complexes from media exposed for 48 h to HJ9.3 were deposited on AFM chips for imaging. Obvious fibrillar species in the media of cells expressing RD(ΔK)-HA and RD(LM)-HA were observed, while RD(PP)-HA produced only amorphous aggregates. Scale bar, 1 µm.
Figure 21:
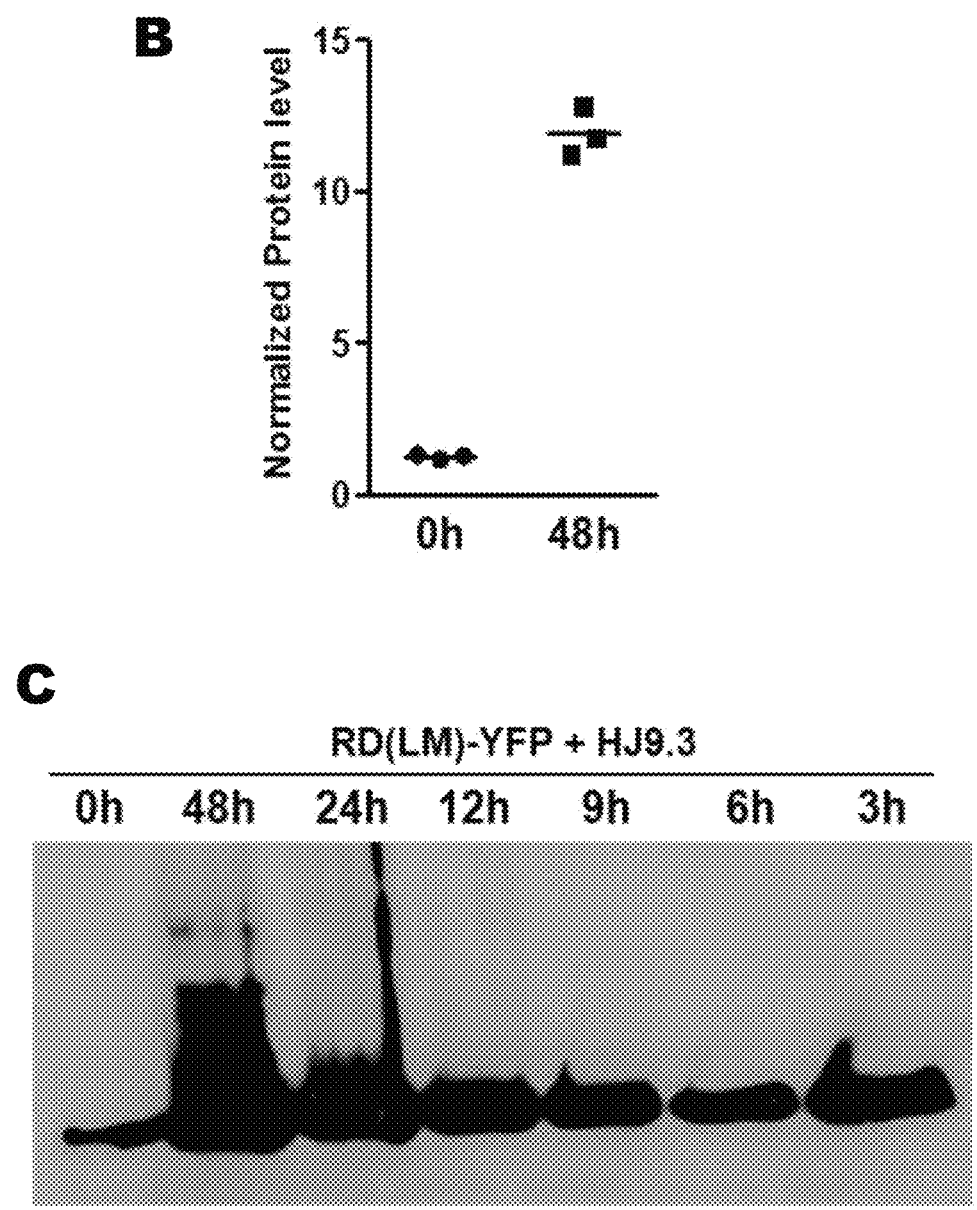

The activity of HJ9.3 in the propagation assay created an opportunity to define the tau species responsible. HJ9.3 was used to extract tau from the cell media. HJ9.3 or control IgG was added to the media of cells expressing a variety of RD constructs (wt, PP, ΔK, LM). Antibodies were added either at the beginning or the end of the 48 h culture period. Media were harvested for affinity purification of antibody/antigen complexes using protein-G-agarose beads. The complexes were washed, and then boiled in SDS loading buffer for analysis by Western blot. HJ9.3 specifically captured tau RD species from the cell media, while IgG had no appreciable effect (FIG. 21A). A ~10-fold increase in the tau protein present in the media was observed when HJ9.3 was present throughout the culture period, as opposed to addition at the end of this period (FIG. 21B). Higher-order molecular weight species were also noted in the media of RD(ΔK)-HA and RD(LM)-HA transfected cells, consistent with RD aggregates. RD(PP)-HA tau had the least protein present in the medium, and no higher-order species were observed on Western blot. A time course (0 h, 3 h, 6 h, 9 h, 12 h, 24 h and 48 h) of the previously described experiment showed a time-dependent increase in the levels of tau in the media, implying that HJ9.3 incubation was indeed increasing the steady-state level of tau protein present in the conditioned medium (FIG. 21C). Taken together, these data indicated that HJ9.3 blocks cell-to-cell propagation by interference with aggregate uptake into cells, and is consistent with a steady state flux of tau aggregates in and out of cells.

Figure 21D:
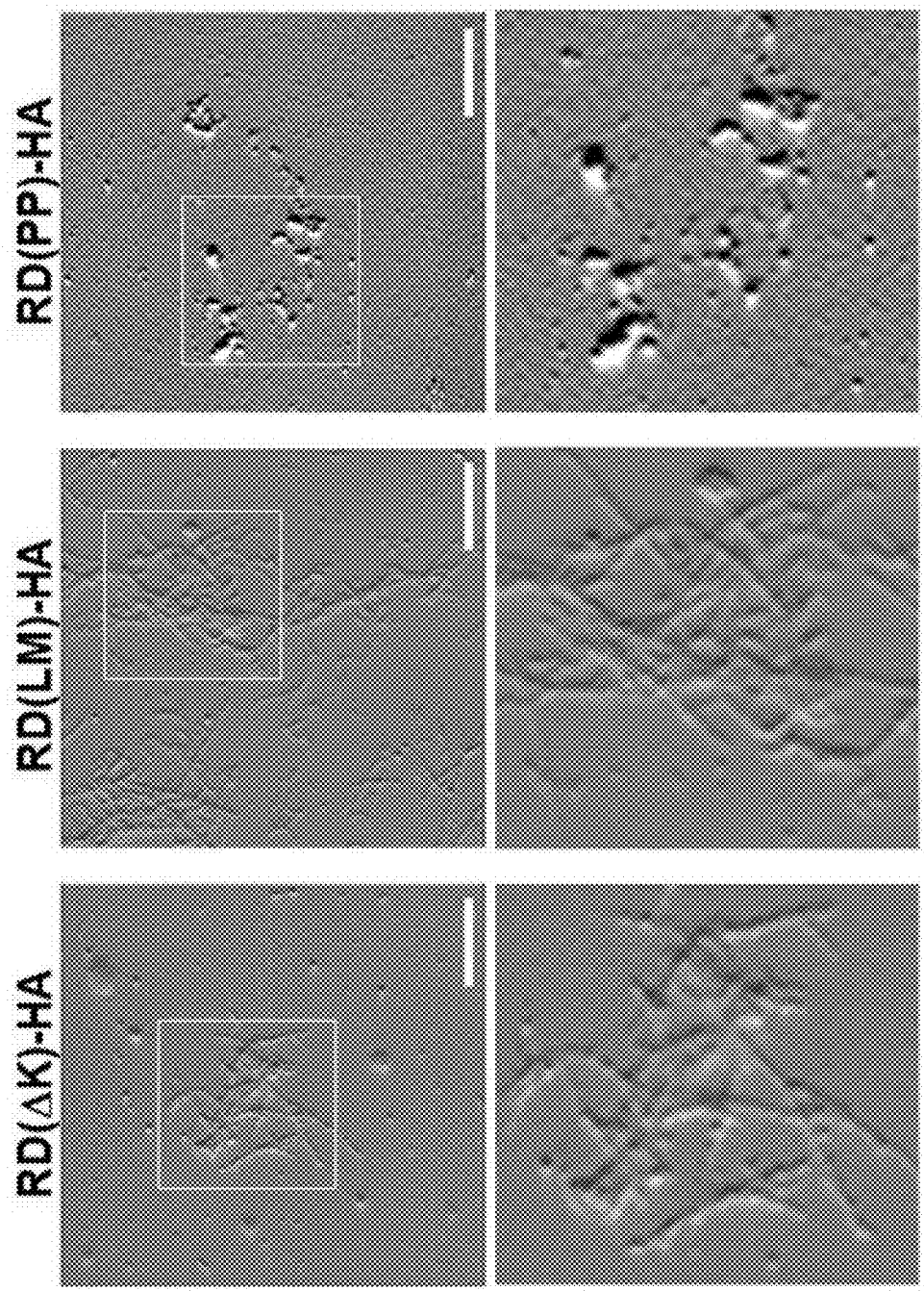

The precise nature of the tau species that mediate trans-cellular propagation is not known. Thus, HJ9.3 was used to trap these species for imaging via AFM. HEK293 cells that were transfected with the various tau mutants were cultured in the presence of HJ9.3. After 48 the antibody/antigen complexes were purified with protein-G agarose beads. The complexes were then eluted from the beads in high salt buffer, and deposited on AFM chips for imaging. Evident fibrillar species were detected in the media of cells expressing RD(ΔK)-HA and RD(LM)-HA, while RD(PP)-HA produced only amorphous aggregates, (FIG. 21D), and mock-transfected cells produced no signal (data not shown). These findings are consistent with free tau fibrils mediating trans-cellular propagation of tau aggregation by their release into the extracellular space.

Example 8

Effect of Anti-Tau Antibodies on Tau Pathology In Vivo

Figure 22:
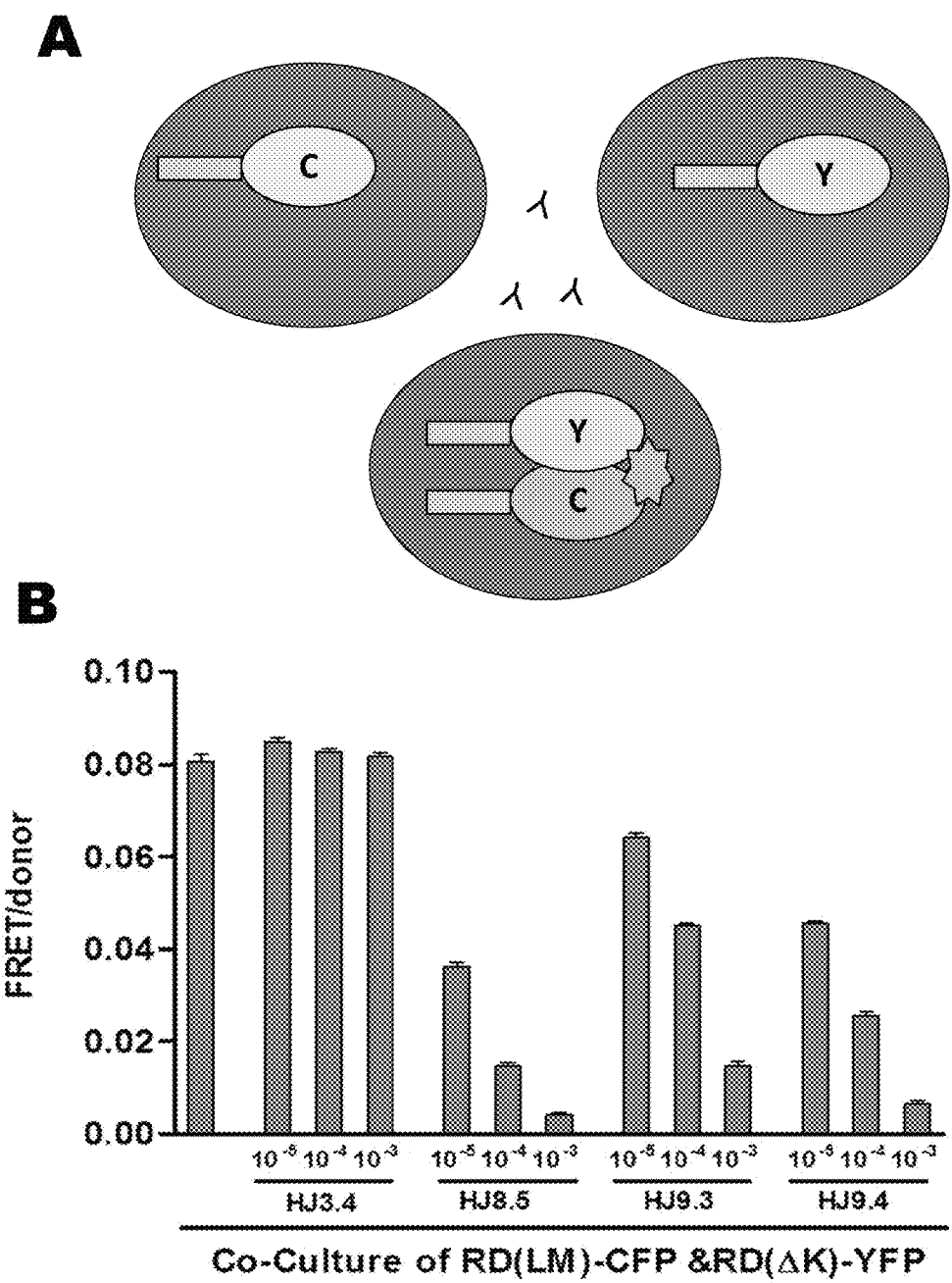
FIG. 22 depicts a schematic and graphs showing HJ8.5 and HJ9.4 activity against recombinant human tau. (A) depicts a schematic illustrating a co-culture of RD (LM)-CFP and RD(ΔK280)-YFP cells in presence and absence of different monoclonal full length tau antibodies. (B) depicts a graph showing HJ8.5, HJ9.3 and HJ9.4 were able to block tau propagation. (C) depicts a graph showing HJ8.5, HJ9.3 and HJ9.4 were able to detect RD-tau fibrils in an ELISA assay.
Figure 22C:
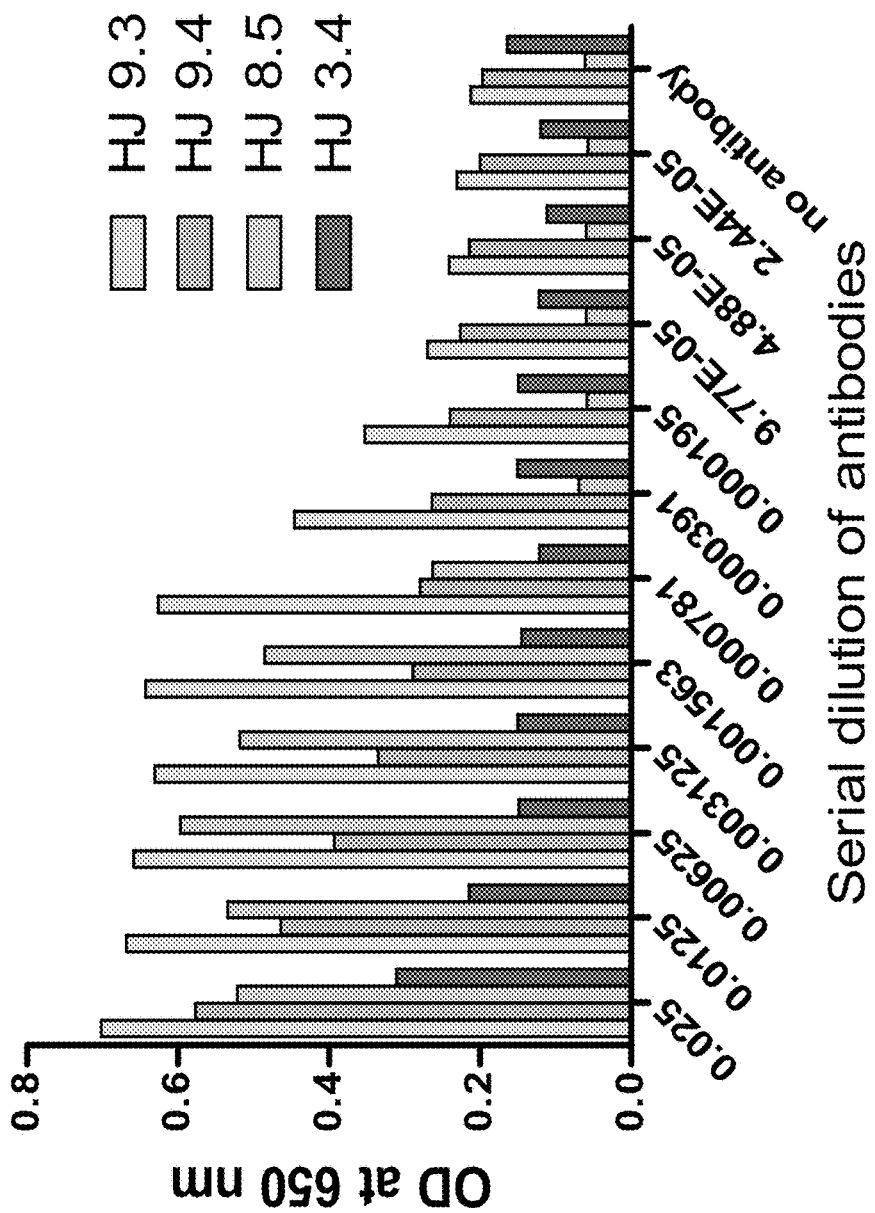

The activity of two additional antibodies against full length, recombinant human tau were tested in the propagation assay. RD(LM)-CFP and RD(ΔK)-YFP cells were co-cultured for 48 hrs in the presence and absence of different monoclonal antibodies that target different tau epitopes (HJ8.5, HJ9.3 and HJ9.4, FIG. 22A). HJ3.4 antibody against Aβ peptide was used as a negative control. All three anti-tau antibodies blocked the trans-cellular propagation of pro-aggregation mutants of RD-tau between cells (FIG. 22B). The negative control, HJ3.4, did not block trans-cellular propagation. HJ8.5, HJ9.3 and HJ9.4 also detected RD-tau fibrils by ELISA (FIG. 22C).

Figure 23A:
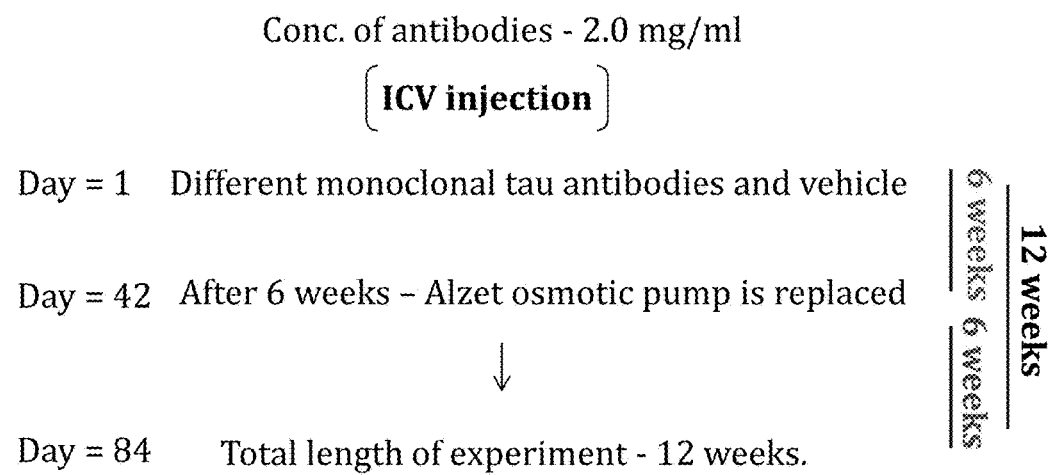
FIG. 23 depicts a schematic illustrating the experimental plan for (A) intracerebroventricular injection and (B) implantation of an osmotic pump in the lateral ventricle of each mouse. (C) shows an image verifying the placement of the cannula by cresyl violet staining.
Figure 23C:

To block the propagation of tau aggregates from cell to cell in vivo, a passive vaccination approach was used with antibodies targeting different epitopes on tau. Anti-tau antibodies, HJ8.5 and HJ9.3, or vehicle were each infused into the lateral ventricle of 6 month old, P301S tg mice by intracerebroventricular injection using Alzet osmotic pumps (2006 model, FIG. 23A). Brain cannula attached to an Alzet pump assembly were surgically implanted into the left lateral ventricle of each mouse at the position 0.4 mm anteroposterior to bregma, 1.0 mm lateral to midline and 2.5 mm dorsoventral (FIG. 23B). After treatment, placement of the cannula was verified by cresyl violet staining (FIG. 23C). The Alzet osmotic pumped was replaced after 6 weeks, and the experiment concluded on day 84.

Figure 24:
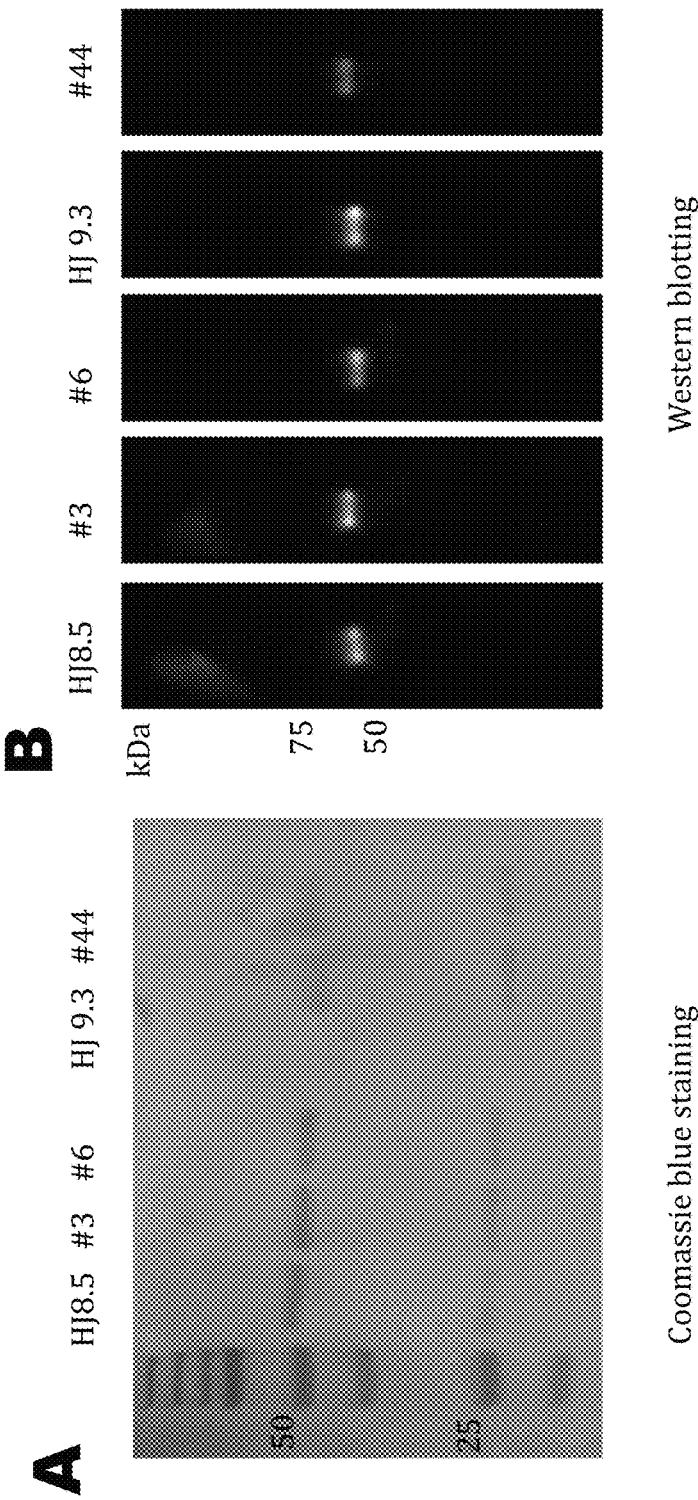
FIG. 24 depicts images of the anti-tau antibodies after 6 weeks infusion in P301S tg mice by (A) Coomassie blue staining and (B) immunoblotting against recombinant longest human tau isoform hTau40 using antibodies taken from the pump before and after 6 weeks infusion.
Figure 25:
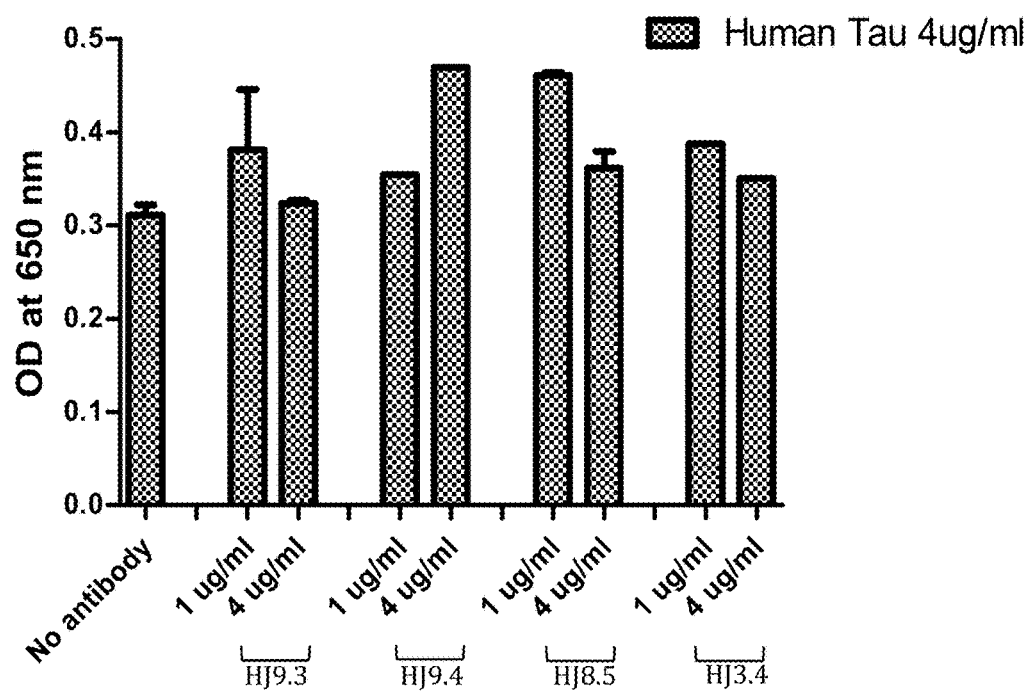
FIG. 25 depicts a graph showing lack of interference of infused tau antibodies in HJ8.7-BT2B ELISA for total tau. Indicated concentrations of antibodies were pre-incubated with recombinant human tau protein before applying to ELISA.

To confirm that the experimental design did not result in antibody degradation and/or inactivity, antibodies were collected from the Alzet pump after 6 weeks of infusion into mouse brain and loaded onto an SDS-PAGE gel. The gel was first stained by Coomassie blue dye (FIG. 24A) and then analyzed by western blotting using antibodies taken from the pump before and after the 6 week infusion (FIG. 24B). All the antibodies were stable and active after 6 weeks in the Alzet pump at physiological temperature in vivo. It was further confirmed that spiking of recombinant human tau protein with different infusion antibodies did not interfere with HJ8.7-BT2B ELISA assay for measuring total tau (FIG. 25).

Figure 26:
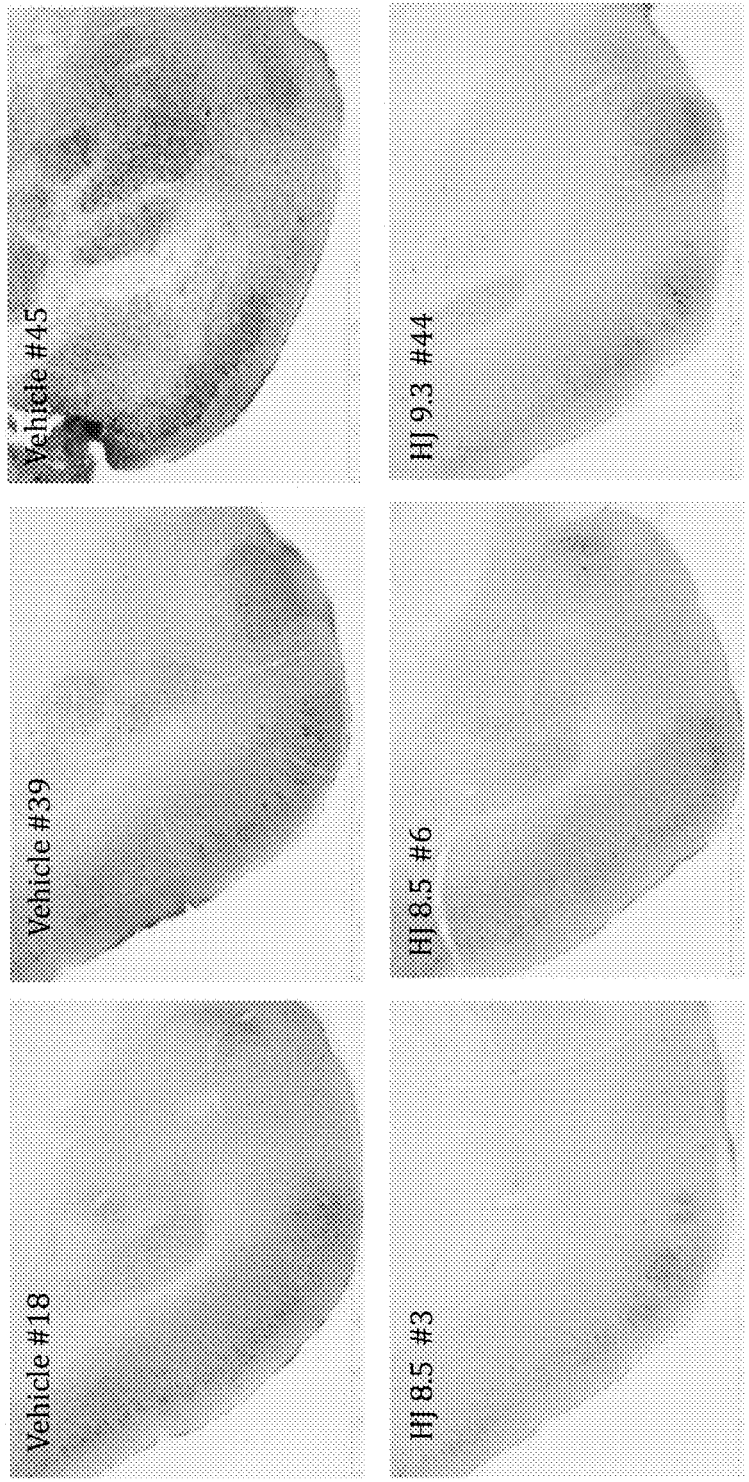
FIG. 26 depicts images of coronal sections of piriform cortex of treated 9 month old P301S tg mice treated with vehicle/PBS (top panels) or different anti-tau monoclonal antibodies (HJ8.5, HJ9.3 as labeled in bottom panels). Sections were stained with biotinylated AT8 antibody, which recognizes an abnormally phosphorylated form of tau.
Figure 27:
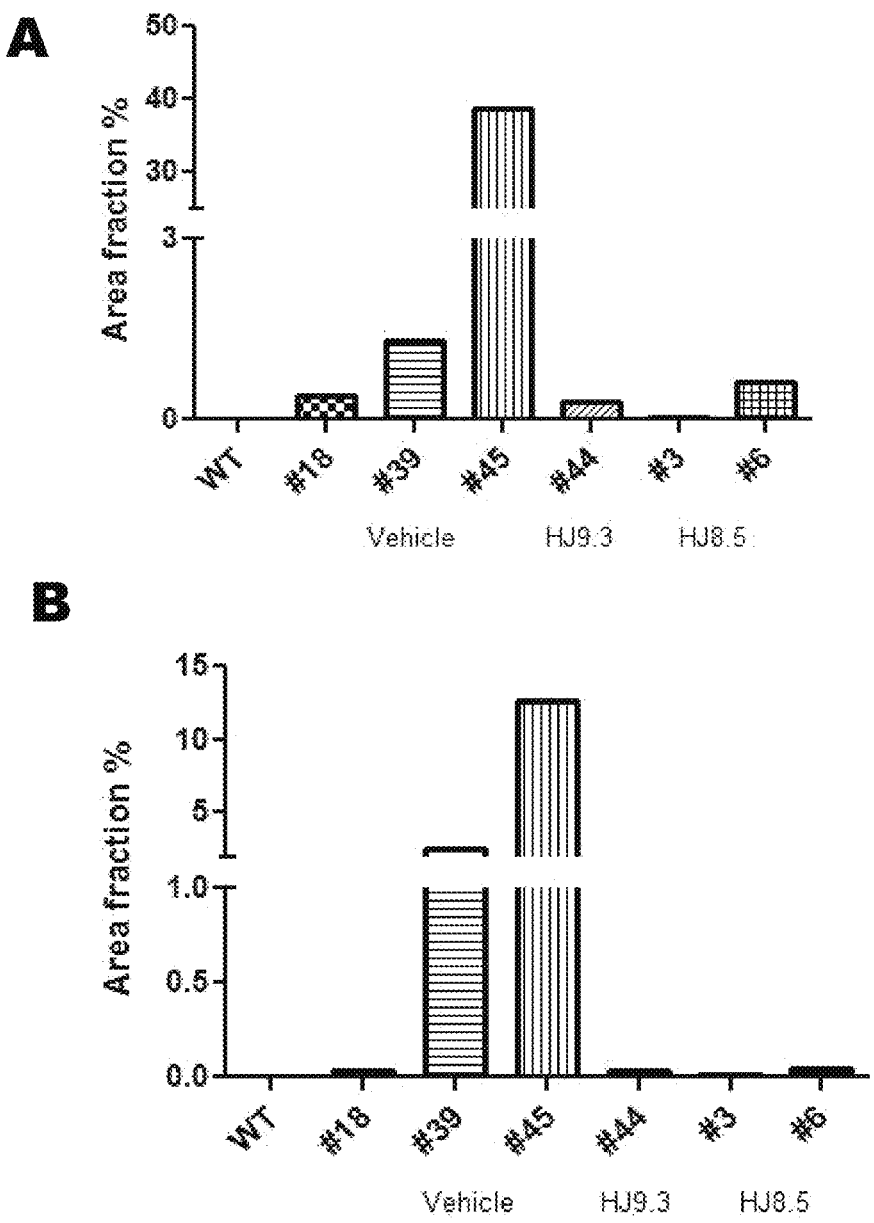
FIG. 27 depicts graphs showing the percent of area covered by AT8 staining of neurofibrillary tangles in the (A) hippocampus CA2 and CA3, (B) amygdala, (C) piriform cortex, and (D) entorhinal cortex.
Figure 27:
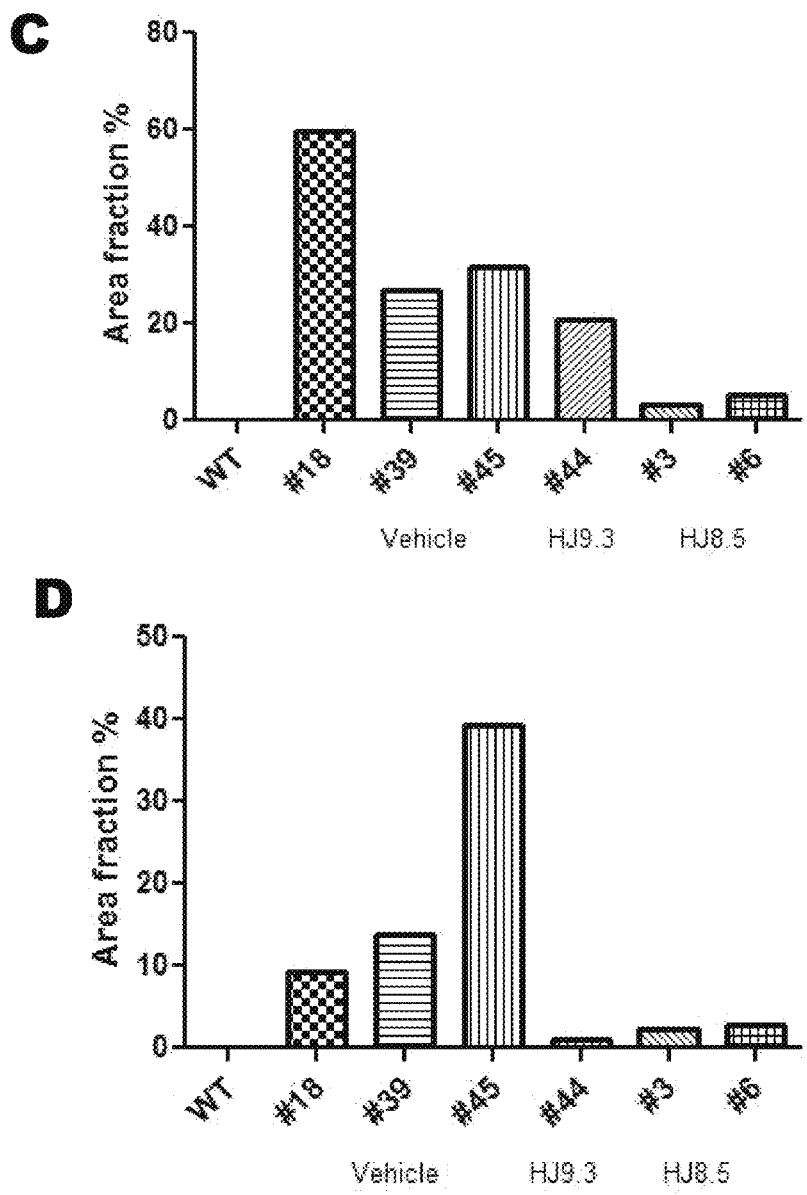
Figure 28:
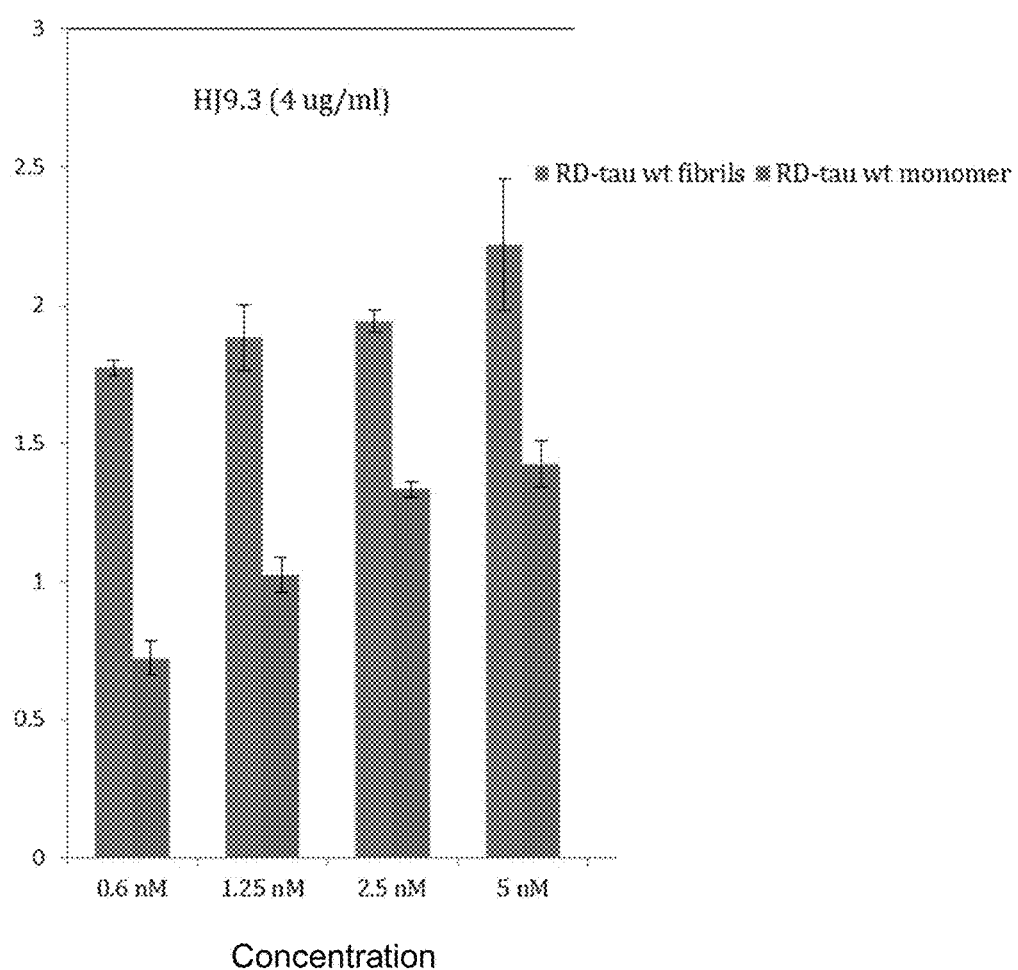
FIG. 28 graphs showing HJ9.3 antibody detection of tau fibrils and RD-tau monomer by ELISA. Different concentrations of RD-wt tau monomers and fibrils were coated on ELISA plate. HJ9.3 was used as the primary antibody. For the detection anti-mouse HRP linked antibody was used.

To determine whether antibody treatment reduced pathological tau staining, tau staining was assessed in tissue sections of the 9-month old, P301S tg mice treated with Vehicle/PBS or the anti-tau monoclonal antibodies. Coronal sections of the piriform cortex were stained with biotinylated AT8 antibody, which recognizes an abnormally phosphorylated form of tau. Quantitative analyses of preliminary immunohistochemistry data showed that abnormally phosphorylated tau load was remarkably reduced after infusion of HJ8.5 and HJ9.3 in mouse brain (FIGS. 26 and 27). Biochemical analysis of these effects are underway. If successful, passive immunization against tau propagation and pathology could become a therapeutic approach to treat Alzheimer's Disease, fronto-temporal dementia or other tauopathies.

Discussion for Examples 3-7

Figure 29:
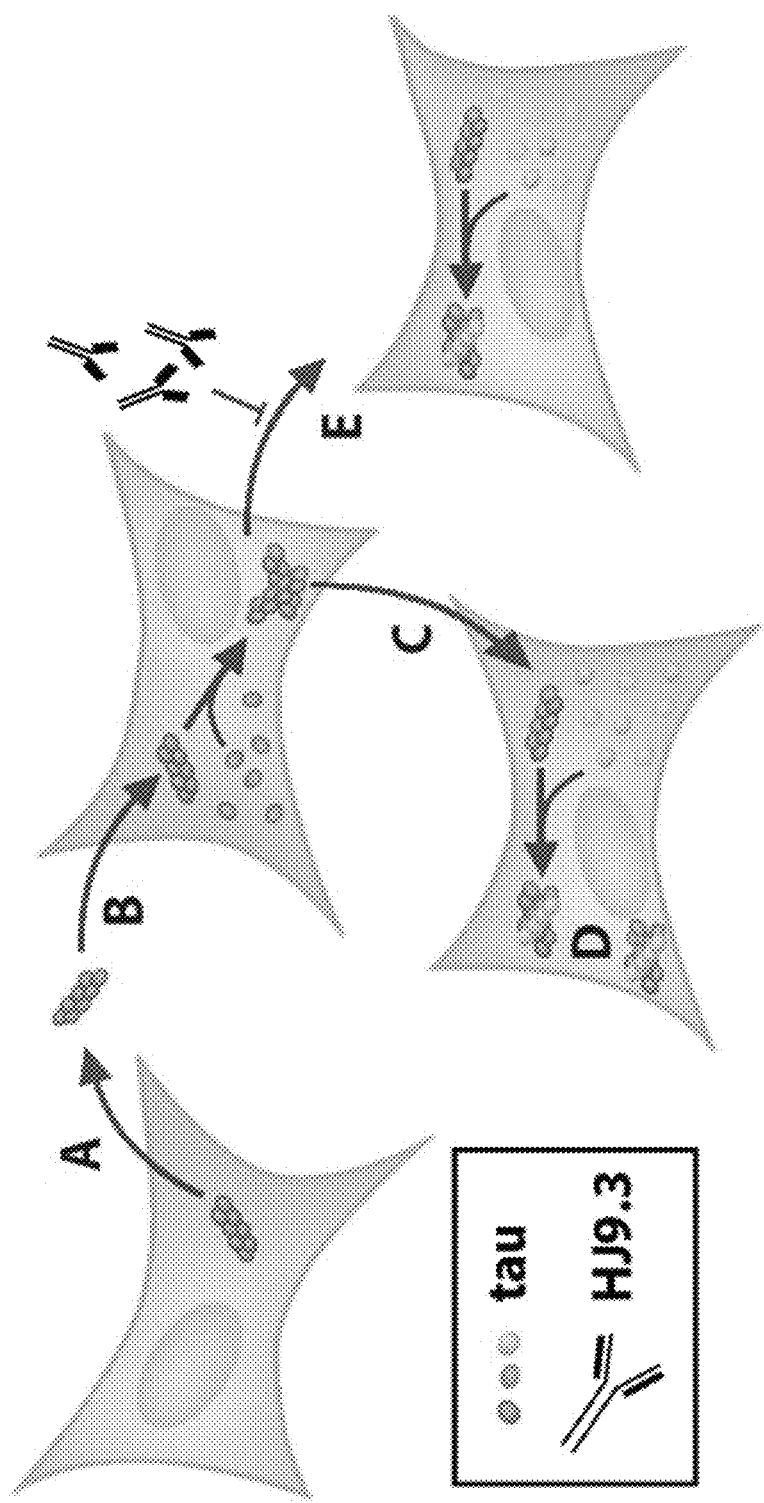
FIG. 29 depicts a schematic illustrating trans-cellular propagation of tau aggregation occurring via transfer of fibrils within the cell medium. Protein aggregate in a donor cell escapes the cell (A), enters a recipient cell (B), and directly contacts natively folded protein (C) to amplify the misfolded state (D). This cell-cell movement is mediated by fibrils that are released directly into the medium. These fibrils can be trapped within the extracellular space by an anti-tau antibody (HJ9.3) that interferes with cell-cell propagation (E).

It has been previously proposed that prion-like mechanisms involving templated conformational change and transcellular propagation of aggregation could explain the relentless progression of tauopathies and other neurodegenerative diseases. This would consist of the release of a protein aggregate from a donor cell, entry into a recipient cell, and direct contact with natively folded protein to amplify the misfolded state. However, mechanistic evidence to support this model of tauopathy has been incomplete, and transcellular propagation of tau misfolding in this manner has not previously been demonstrated. Examples 3-7 now describe transcellular propagation of tau aggregation in cultured cells via secreted tau aggregates, and propose a likely mechanism. First documented was spontaneous formation of RD tau fibrils in transfected cells using X-34 staining and AFM of extracted material. Then observed was the coincidence of tau derived from two separate cells in intracellular inclusions using confocal microscopy. This was associated with increased detergent insolubility of tau RD(ΔK)-YFP upon co-culture with cells expressing an aggregation-prone form of the protein, RD(LM)-HA. Also documented was this increase in aggregation using FRET between RD(LM)-CFP/YFP that were co-expressed within the same cells. This was detected by acceptor photobleaching (microscopy), and spectral methods (FPR). Next used was FRET between RD(LM)-CFP and RD(LM)-YFP expressed in separate cell populations to document that propagation occurred by direct protein contact. This method was then extended to document amplification of tau protein misfolding within the cell populations in successive culture conditions. Transcellular propagation of tau aggregation is mediated by fibrils that are released directly into the extracellular space, because transfer is sensitive to extracellular volume, conditioned medium can increase intracellular aggregation, and an anti-tau antibody (HJ9.3) interfered with cell propagation, and trapped extracellular tau fibrils. Using a variety of techniques, the applicants have thus documented the trans-cellular aggregate propagation via templated conformational change and propose a simple model to explain these phenomena (FIG. 29).

Trans-Cellular Propagation—

Although spontaneous movement of aggregated tau between cells has been previously described, it was unknown whether tau protein aggregates could propagate a misfolded state between cells by direct contact of the proteins, as opposed to indirect effects on the cell. Cell culture studies of α-synuclein have also suggested propagation, but it is unclear what is the nature of the species (e.g. aggregates vs. dimers vs. monomer) derived from donor cells and those formed in recipient cells. Likewise, SOD1 aggregates can transfer between cells via the medium to induce further aggregation, but the precise nature of the responsible protein conformers, and whether direct protein-protein contact occurs is unclear. Injection of purified Aβ42 and tau fibrils into transgenic mouse brain induces aggregation of endogenous tau, with nearby development of tau fibrils, but it is difficult to rule out seeding by injected protein. Work from the Applicants' lab, and subsequently from others has documented movement of tau aggregates and induction of aggregation by recombinant protein from the outside to the inside of the cell. But no prior study of the tau protein has demonstrated bona fide propagation: aggregate movement from one cell to another, direct contact with the native protein, conversion of the protein in the recipient cell to a fibrillar state, and amplification of the misfolded species.

This work demonstrated these phenomena in several ways. First, it was found that co-culture of an aggregation-prone form of tau RD(LM)-HA with cells expressing RD(ΔK)-YFP leads to co-localization in β-sheet positive inclusions. Next, it was observed that co-culture of cells expressing RD(LM)-HA with another population expressing both RD(ΔK)-CFP and RD(ΔK)-YFP led to an increase of FRET signal, suggesting that movement of RD(LM)-HA into cells expressing the FRET pair was inducing their aggregation. To demonstrate direct contact and coaggregation of tau aggregates moving between cells, RD(ΔK)-CFP and RD(ΔK)-YFP were expressed in separate populations. This led to a FRET signal derived from trans-cellular movement and co-aggregation that disappeared if either one of the constructs contained a double proline mutation to block β-sheet formation. Induction of full-length tau-YFP aggregation by transfer of RD-CFP aggregates was also observed, but the efficiency is reduced (data not shown). Finally, the efficiency of FRET induced by trans-cellular movement of protein aggregates increased significantly by preliminary co-culture of RD(LM)-HA expressing cells with those expressing RD(ΔK)-CFP, demonstrating that an aggregated state can be amplified within a population of cells.

Antibody Modulation of Tau Aggregate Propagation—

Antibodies against Aβ peptide, which is predominantly extracellular, can prevent Aβ aggregation in the brain and remove existing aggregates. While there are potential side effects, such antibodies hold promise as treatments. However, the success of vaccination in mouse models of tauopathy and synucleinopathy has been puzzling in light of the fact that the target proteins are predominantly intracellular. It was observed that HJ9.3, a mouse monoclonal antibody against tau-RD, inhibited the trans-cellular propagation of tau aggregation. However, this antibody had no effect on intracellular aggregation of tau. Chronic exposure of the cell medium to this antibody strongly increased the steady state tau levels in the media. This was corroborated by flow cytometry studies which indicated that HJ9.3 blocks transfer of aggregates from one cell to another. Finally, HJ9.3/tau complexes trapped at the cell surface were observed. The effect of this antibody suggested strongly that tau fibrils are released into the extracellular space, and are not propagating misfolding primarily via cell-cell transfer in exosomes or tunneling nanotubes, as has been proposed for prions. Further, aggregates present outside the cell, if not trapped by HJ9.3, are likely taken up again into cells. Multiple modes of inhibition are conceivable for therapeutic antibodies, including disaggregation of protein fibrils, blockade of conversion within cells, and promotion of intracellular degradation. Our results with HJ9.3 are most consistent with interference with cell uptake as one mechanism that could be used to block tauopathy, and suggest new ways to consider development and optimization of therapeutic antibodies for neurodegenerative diseases.

Trans-Cellular Propagation Via Fibrillar Tau—

The effectiveness of HJ9.3 in blocking propagation of tau aggregation allowed use of this antibody to trap the responsible species. Immuno-affinity purification of tau from conditioned medium revealed fibrillar tau. No tau fibrils in medium from control cells were observed, or from those expressing the β-sheet-resistant RD(PP)-HA, which produced amorphous aggregates. RD(ΔK)-HA and RD(LM)-HA expression each caused fibril secretion into the extracellular space. It has been unclear how protein aggregation in one cell might influence the aggregation in a neighboring cell, and it was formally possible that cytokines, exosomes, or direct connections between cells might facilitate this process. These possibilities cannot be completely excluded. However, these results are most consistent with free fibrillar species as mediators of propagation through the extracellular space. This work suggests answers to several important questions about the mechanisms by which protein aggregates propagate from one cell to another in culture, and thus how they might do so in vivo. In conjunction with the methods described here to monitor trans-cellular propagation, it may be possible to target this process with pharmacological and biological agents for more effective treatment of tauopathies and other neurodegenerative diseases.

Methods for Examples 1-8

Antibodies

The longest mouse recombinant tau isoform mTau40 (432 aa) and the longest human tau isoform hTau40 (441 aa) were produced in the laboratory of Eva Mandelkow and used as standards in the tau ELISA. The mouse monoclonal antibody Tau-5, which recognizes both human and mouse tau (epitope at residues 218-225), was from the laboratory of L. Binder (LoPresti et al., 1995; Porzig et al., 2007). Monoclonal antibodies HJ8.1 and HJ9.3 are mouse monoclonal antibodies raised by immunizing against human tau and mouse tau, respectively, in tau knock-out mice (The Jackson Laboratory). Both antibodies recognize mouse and human tau on Western blots, by immunoprecipitation, and in ELISA assays. HJ9.3 recognizes the microtubule binding region (MTBR) of tau. Mouse monoclonal antibody BT-2, which also recognizes human and mouse tau (epitope at residues 194-198), was obtained from Pierce. Rabbit polyclonal antibody directed against Tau (ab64193, epitope located in the repeat domain region) was purchased from Abcam, Cambridge, Mass. Mouse monoclonal antibody directed against hemagglutinin HA (HA.11 Clone 16B12) was purchased from Covance, Emeryville, Calif. Rabbit polyclonal GFP antibody (sc-8334) was purchased from Santa Cruz Biotechnology.

Plasmids

Sequences encoding the four repeat domain (RD) of the microtubule associated protein tau were used for protein expression. In addition to the wild-type form, various tau mutants were created: ΔK280 Δ(K); P301L/V337M (LM); ΔK280/I277P/I308P (PP). These sequences were either subcloned into pcDNA3.1 (Invitrogen) with a C-terminal hemagglutinin (HA) tag, or into pEYFP-N1 or pECFP-N1 (Clontech) to create Cterminal fluorescent protein fusions.

Animals

P301S tg mice (line PS19), which overexpress P301S human T34 isoform tau (1N4R), have been generated and characterized previously and are on a B6C3 background. P301S tg mice were obtained from the Jackson Laboratory. Tau knock-out mice were obtained from The Jackson Laboratory. Age and genetic background matched nontransgenic mice littermates were used as wildtype mice. In all experiments, both male and female were used in this study.

Immunoprecipitation and Immunoblot Analysis

Immunoprecipitation and immunoblot analysis. Hippocampal microdialysis samples were collected at 1.0 l/min for 15 h from P301S tau transgenic mouse and wild-type mice. ISF was immunoprecipitated by Dynabeads (Invitrogen) coated with HJ8.1 or HJ9.3 tau antibody according to the manufacturer's instructions. Precipitated fractions were loaded on a reducing 4-12% Bis-Tris mini-gel (Invitrogen) and transferred to nitrocellulose membrane. Biotinylated BT-2 antibody (Pierce) and Poly-HRP-conjugated streptavidin (Thermo Scientific) were used to eliminate the interference of precipitated antibodies. HEK293 cells were cultured in Dulbecco's Modified Eagle Medium (DMEM) supplemented with 10% fetal bovine serum, 100 µg/mL penicillin and 100 µg/mL streptomycin. Cultures were maintained in a humidified atmosphere of 5% CO2 at 37° C. For transient transfections, cells plated in Optimem medium were transfected using Lipofectamine/Plus reagent and 600 ng of appropriate DNA constructs (Invitrogen, Carlsbad, Calif., USA) according to manufacturer's recommendations, and harvested 24 h or 48 h later for further analyses.

Detergent Fractionation and Western Blot Analyses

HEK293 cells were plated at 400,000 cells/well in a 12-well plate. The following day cells were transfected with 600 ng of plasmid. After 48 h, cells were harvested with 0.05% trypsin for 3 minutes at 37° C., pelleted briefly at 7000×g and lysed in 100 µl of 1% Triton in PBS containing protease inhibitors. Soluble cytosolic proteins were then collected by centrifugation at 14,000×g for 10 minutes. Insoluble proteins were obtained by resuspending the pellet in RIPA/SDS buffer and centrifugation at 20,000×g for 15 minutes following benzonase nuclease digestion of nucleic acids. For co-culture experiments, equal numbers of cells transfected with RD(LM)-HA and RD(ΔK)-YFP were co-cultured together for 48 h before harvesting and Western blotting. Equivalent amounts of HEK293 cell protein extract from each fraction were analyzed using 4%-20% polyacrylamide gels (Biorad); antibody directed against tau RD (which recognizes an epitope in the RD region) at a 1:2000 dilution (ab64193, Abcam, Cambridge, Mass.) and/or antibody directed against GFP at 1:1000 dilution (sc-8334, Santa Cruz Biotechnology, Inc.). A chemiluminescence-based peroxidase-conjugated secondary antibody reaction was performed and detected by X-ray film. Quantification was performed using Image J analysis software.

Co-Culture Experiments: Measuring RD-CFP/YFP Co-Aggregation by FRET

HEK293 cells were plated at 300,000 cells/well in a 12-well plate. The following day, cells were transfected with 600 ng of plasmid as described above. Co-transfected cells received a combination of 150 ng of RD-CFP constructs and 450 ng of RD-YFP constructs. 15 h later, cells were harvested with 0.05% trypsin for 3 minutes at 37° C., and a fraction of cells were re-plated in a 96-well plate in quadruplicate, or on ibidi µ-slides (ibidi GmbH, Germany) for imaging by microscopy. Cells were then cultured an additional 48 h before fixation with 4% paraformaldehyde and analysis.

Co-Culture Experiments: Measuring Induction of RD-YFP Aggregation by RD-HA

HEK293 cells were transfected with either RD(ΔK)-YFP or RD(LM)-HA in 12-well plates. After 15 h the cells were replated together onto ibidi μ-slides and cocultured an additional 48 h. They were then fixed and stained with anti-HA antibody and X-34 for analysis by microscopy.

Co-Culture Experiments: Propagation Assays in Co-Culture

Two populations of HEK293 cells in a 12-well plate were co-transfected with 300 ng RD(LM)-HA and 300 ng RD(ΔK)-CFP together, or with RDΔ(K)-YFP. After 15 h, equal percentages of the two populations were co-cultured for 48 h in a 96-well plate format. Cells were then fixed with 4% paraformaldehyde and FRET analysis was performed using the Fluorescent Plate Reader (FPR). For FRET microscopy analysis, two populations of HEK293 cells in a 12-well plate were transfected with 600 ng RD(LM)-CFP or with RD(LM)-YFP. After 15 h, equal percentages of the two populations were co-cultured for 48 h on ibidi μ-slides. Cells were then fixed with 4% paraformaldehyde and FRET acceptor photobleaching was conducted.

Co-Culture Experiments: Amplification of Tau Aggregation in Serial Culture

HEK293 cells were transfected in a 12-well plate with 600 ng of various forms of nonfluorescent RD-HA and cultured for 24 h. A second group of cells were transfected with CFP or RD(ΔK)-CFP. Equal percentages of the first and second populations were then co-cultured for 48 h. At this point, 50% of this population was plated with a population of cells transfected with RD(ΔK)-YFP in a 96-well plate for 48 h. Cells were then fixed with 4% paraformaldehyde for FRET analyses using the FPR.

Media Transfer and Conditioned Media Experiments

HEK293 cells were transfected in a 12-well plate with either 600 ng of RD(LM)-HA or co-transfected with a combination of 150 ng of RD(ΔK)-CFP construct and 450 ng of RD(ΔK)-YFP construct. 15 h later, cells were harvested with 0.05% trypsin for 3 minutes at 37° C. An equivalent number of cells expressing RD(ΔK)-YFP/CFP and RD(LM)-HA were co-cultured for 48 h in varying amounts of cell culture medium. Cells were then fixed with 4% paraformaldehyde and FRET analysis was performed. For the conditioned media experiments, 15 h after transfection, media from RD(LM)-HA cells containing transfection complexes was replaced with fresh media. Cells expressing RD(ΔK)-YFP/CFP were harvested with 0.05% trypsin for 3 minutes at 37° C. and replated in 96-well plate. 24 h later, conditioned media from cells transfected with RD(LM)-HA was collected and added to cells expressing RD(ΔK)-YFP/CFP. 48 h later cells were fixed with 4% paraformaldehyde and FRET analysis was performed.

Fluorescence Resonance Energy Transfer (FRET) Assays: FRET Measurements by Microscopy with Photobleaching HEK293 cells transfected for cotransfection and co-culture experiments as described earlier were prepared for FRET acceptor photobleaching microscopy. All images were obtained using a C-Apochromat 40×1.2 NA lens (Carl Zeiss Advanced Imaging Microscopy, 07740 Jena, Germany 100× (CFP). Digital images were acquired using a Zeiss LSM510 Meta NLO Multiphoton/Confocal laser scanning microscope system on the Zeiss Axiovert 200M. Channels used for imaging were as follows: the donor CFP was stimulated using a 458 nm argon laser and fluorescence collected with a 480-520 nm bandpass filter; the acceptor YFP was stimulated using a 514 nm argon laser and fluorescence collected with a long-pass 560 nm filter. To create an image in which the intensity reflected an estimate of FRET efficiency, the value of the initial CFP image was subtracted from the final CFP image obtained after photobleaching on a pixel-by-pixel basis, and this difference was multiplied by 100 and divided by the final CFP image intensity: 100× ($CFP_{final}$–$CFP_{initial}$)/$CFP_{final}$. Proper adjustments were made for partial acceptor photobleaching. Image arithmetic and grayscale to-color image conversion were done using NIH ImageJ 1.44 software.

FRET Assays: Fluorescence Plate Reader

Spectral FRET measurements (FRET/donor) were obtained using a TecanM1000 fluorescence plate reader according to methods previously described. When donor and acceptor are not fused to the same protein, spectral FRET measurements depend on careful control for the relative amount of donor and acceptor proteins expressed within the cell. All values on the plate reader were first background subtracted against mock-transfected cells. The YFP signal in each well ($Smpl485ex/528em$ FRET) was used to estimate RD-YFP expression levels, and it was likewise assumed that under experimental conditions that RD-CFP/YFP do not vary independently. This helps eliminate the possibility that changes in apparent FRET are due simply to variations in RD expression levels. Relative contribution of acceptor activation (528 nm) by donor excitation signal (435 nm) to the overall FRET measurement was corrected by determining the "crossover activation" fraction for acceptor, X, where X=RD-YFP signal measured at 435ex/528em divided by the signal measured at 485ex/528em. This "crossover activation" is essentially constant across different expression levels of RD-YFP encountered in the experiments. The "measured" FRET value in each sample is recorded at 435ex/528em, the "donor" value (CFP) is recorded at 435ex/485em. The "actual" FRET/donor value for each well is then reflected as:

$$FRET_{actual}=(Smpl_{435ex/528em}-X*(Smpl_{435ex/528em}))/Smpl_{435ex/528em}$$

This method of measuring protein aggregation by FRET has reliably allowed detection of subtle changes in response to pharmacologic as well as genetic manipulations of androgen receptor and huntingtin protein aggregation that were corroborated by visual and biochemical analyses. Since the relative amount of spectral FRET measured depends on the ratio of acceptor:donor, a constant ratio of 3:1 was used when RD-CFP and RD-YFP are co-expressed within the same cell. This provides close to maximal FRET efficiency while allowing for acceptable signal:noise in the measurement of donor signal.

Atomic Force Microscopy (AFM)

RIPA-insoluble proteins were extracted from transfected HEK293 cells and incubated on mica chips (Ted Pella, Inc) for 10 minutes. Samples were then rinsed twice with 100 μl ddH2O and left at RT to dry. The following day, atomic force microscopy was performed using a MFP-3D atomic force microscope (Asylum Research).

Immunofluorescence and Confocal Microscopy

HEK293 cells transfected for co-culture experiments as described earlier were prepared for immunofluorescence and X-34 staining. After fixation in 4% paraformaldehyde for 15 min at RT, cells were washed twice in PBS at room temperature (RT) for 5 min, and permeabilized in 0.25% Triton X-100 in PBS at RT for 10 minutes. Cells were blocked with a blocking solution containing 1% normal goat serum, 20 mg/ml BSA, 0.25% Triton X-100 in PBS for 3 h at RT. Primary mouse monoclonal antibody against HA (Covance, Emeryville, Calif.) was diluted 1:2000 in blocking solution and applied to cells overnight at 4° C. Cells were then washed with PBS containing 0.1% Triton X-100 3 times for 5 minutes each and incubated with anti-mouse Alexa546-conjugated secondary antibody (Invitrogen) diluted at 1:400 in blocking solution. Cells were then washed with PBS containing 0.1% Triton X-100 3 times for 5 min each, and exposed to 1 μM X-34 prepared in a solution of 40% ethanol, 60% PBS, and 20 mM NaOH for 10 min at RT. Cells were then washed 3 times for 2 min each in 40% EtOH, 60% PBS and rinsed twice in 1×PBS for 5 min each. Images were captured using confocal microscopy (405 Confocal Microscope-Zeiss). For the characterization of the mechanism of HJ9.3 antibody blockade of propagation, HEK293 cells were transfected with RD(ΔK)-YFP or mock transfected. Following culture of RD(ΔK)-YFP cells or mock-transfected cells in the presence of HJ9.3 for 48 hrs, cells were fixed with 4% PFA, permeabilized with 0.25% TritonX-100 and then exposed to goat anti-mouse Alexa 546 labeled secondary antibody. Images were captured using confocal microscopy (Confocal Microscope-Zeiss).

Propidium Iodide (PI) Cell Death Assay

HEK293 cells were plated at 75,000 cells/well in a 96-well plate. The following day, cells were transfected in quadruplicate with 100 ng of various forms of non-fluorescent RD-HA plasmids or exposed to transfection complexes without DNA. The next day, media containing transfection complexes were removed, and replaced with fresh media. Non-transfected cells were treated with varying concentrations of staurosporine (1, 2, 4, 20 μM) for 30 minutes at 37° C. as a positive control for cell death. Staurosporine solution was then removed and all cells were exposed to 5 μg/ml of propidium iodide for 10 minutes at 37° C. Propidium iodide solution was then replaced with phenol-free media and fluorescence was read on the plate reader at 535 nm excitation and 617 nm emission.

Immunoprecipitation

Transfected cell populations were co-cultured either alone or in the presence of mouse monoclonal antibody HJ9.3 (1:1000 which is equivalent to 2.5 ng/μl of antibody) or pooled mouse IgG antibody for 3 h, 6 h, 9 h, 12 h, 24 h or 48 h. Conditioned media were collected and protein-G-agarose beads (100 μl of 50% slurry beads from Pierce) were added to the media and incubated overnight at 4° C. with rotation. 18 h later, 500 μl of binding buffer (Pierce) was added to samples and centrifuged at 2000×g for 3 minutes. Supernatant was discarded, and this wash step was repeated three times. Proteins bound to beads were then eluted using a high salt elution buffer (50 μl) with incubation at room temperature for 5 minutes. Samples were then centrifuged at 2000×g for three minutes and supernatant collected. This elution step was repeated once for a total of 100 μl eluate. Another sample of conditioned media not initially exposed to HJ9.3 or IgG was incubated with the HJ9.3 (1:1000) or IgG antibodies overnight at 4° C. with rotation, followed by the same immunoprecipitation protocol as described above. Samples from all conditions were analyzed on 4-20% polyacrylamide gels (BioRad) and detected with rabbit polyclonal antibody directed against tau RD at 1:2000 dilution in 5% dry milk in TBS/Tween (ab64193, Abcam, Cambridge, Mass.). A chemiluminescence-based peroxidase conjugated secondary antibody reaction was performed and detected by X-ray film.

Flow Cytometry

HEK293 cells were plated in a 10-cm plate at ~80% confluency. Cells were then transfected with 24 μg of RD(LM)-YFP construct or transduced with mCherry lentivirus. The following day, cells were harvested by treating with 0.05% trypsin for 3 minutes at 37° C., pelleted and resuspended in fresh media. The two cell populations were co-cultured either alone or in the presence of mouse monoclonal antibody HJ9.3 directed against Tau-RD at 1:1000 or 1:10,000 dilutions for 48 h (1:1000 is equivalent to 2.5 ng/μl of antibody). After this time, cells were harvested and resuspended in Hanks balanced medium containing 1% FBS and 1 mM of EDTA. Cells premixed just prior to cytometry were used as negative controls. Cells were counted using the MoFlo high speed cell sorter (Beckman Coulter) and the percentage of dual positive cells was analyzed for each of the conditions. Each condition had three biological replicates, with 50,000 cells analyzed in each experimental condition.

Intracerebroventricular (ICV) Injection of Anti-Tau Monoclonal Antibodies

P301S tau transgenic mice which express P301S human T34 isoform (1N4R) were used in this study. At 6 months age these mice develop tau pathology. Therefore, antibodies were infused into the left lateral ventricle by cerebroventricular injection at 6 months of age and these infusions were carried for 12 weeks. After treatment, mice brains were processed for immunohistochemistry and biochemical analysis by ELISA and immunoblotting.

Intracerebroventricular injections were performed by using Alzet osmotic pumps, 2006 model. Brain cannula attached to an Alzet pump assembly were surgically implanted into the left lateral ventricle of each mouse at the position 0.4 mm anteroposterior to bregma, 1.0 mm lateral to midline and 2.5 mm dorsoventral. After treatment, placement of the cannula was verified by cresyl violet staining.

Introduction for Examples 9-15

Tau is a microtubule-associated protein that forms intracellular aggregates in several neurodegenerative diseases collectively termed tauopathies. These include Alzheimer's disease (AD), progressive supranuclear palsy (PSP), corticobasal degeneration (CBD), and frontotemporal dementia (FTD). Tau is a highly soluble and natively unfolded protein which binds and promotes the assembly of microtubules. In tauopathies, tau accumulates in hyperphosphorylated neurofibrillary tangles (NFTs) that are visualized within dystrophic neurites and cell bodies upon appropriate staining. The amount of tau pathology correlates with progressive neuronal dysfunction and synaptic loss, and functional decline in humans and transgenic mouse models.

In human tauopathies, pathology progresses from one brain region to another in disease-specific patterns, although the underlying mechanism is not yet clear. The prion hypothesis holds that tau aggregates escape cells of origin to enter adjacent cells, where they seed further tau aggregation and propagate pathology. The inventors have previously observed that recombinant tau fibrils will induce aggregation of full-length intracellular tau in cultured cells, and that aggregated forms of tau transfer between cells (Frost et al., 2009; Nat Rev Neurosci 11, 155-159). Further, the inventors found that intracellular tau fibrils are released free into the media, where they propagate aggregation by direct interaction with native tau in recipient cells. An anti-tau antibody (HJ9.3) blocks this process by preventing tau aggregate uptake into recipient cells (Kfoury et al., 2012; J Biol Chem 287, 19440-19451). In addition to similar experiments with recombinant tau, it has been shown that paired helical filaments from AD brain induce cytoplasmic tau aggregation. Injection of brain extract from human P301S tau transgenic mice into the brains of mice expressing wild-type human tau induces assembly of wild-type human tau into filaments and spreading of pathology. Similar effects occurred after injection of recombinant full-length or truncated tau fibrils, which caused rapid induction of NFT-like inclusions that propagated from injected sites to connected brain regions in a time-dependent manner. Finally, selective tau expression in the entorhinal cortex caused late pathology in the axonal terminal zones in cells in the dentate gyrus and hippocampus, consistent with trans-synaptic movement of aggregates. A growing body of work thus supports the idea that tau aggregates transfer between cells, and might be targeted with therapeutic antibodies.

In mouse models that mimic aspects of AD and Parkinson's disease (PD), passive immunization using antibodies against Aβ and alpha synuclein can reduce Aβ and alpha-synuclein deposition in brain, and improve behavioral deficits. Active immunization in tauopathy mouse models using tau phospho peptides reduced tau pathology and in some studies improved behavior deficits. However, in one study active immunization of C57BL/6 wild type mice with full length recombinant tau induced tau pathology and neurologic deficits. In two passive vaccination studies, there was reduced tau pathology and improved motor function when the antibody was given prior to the onset of pathology. While several of the tau immunization studies appear to have some beneficial effects, the maximal expected efficacy of anti-tau antibodies administered after the onset of pathology, the optimal tau species to target, and the mechanism of the therapeutic effect have remained unknown.

Example 9

Characterization of Anti-Tau Antibodies

The inventors have previously observed that tau aggregates, but not monomer, are up taken by cultured cells, and that internalized tau aggregates trigger intracellular tau aggregation in recipient cells (Frost et al., 2009; Nat Rev Neurosci 11, 155-159; Kfoury et al., 2012; J Biol Chem 287, 19440-19451). The HJ8 series of 8 mouse monoclonal antibodies (raised against full-length human tau) and HJ9 series of 5 antibodies (raised against full-length mouse tau) were characterized in an adapted cellular biosensor system previously described in Kfoury et al. (2012; J Biol Chem 287, 19440-19451) that measures cellular tau aggregation induced by the addition of brain lysates containing tau aggregates. The antibodies had variable effects in blocking seeding, despite the fact that all antibodies efficiently bind tau monomer and stain neurofibrillary tangles. Three antibodies were selected with different potencies in blocking seeding for the studies presented herein.

Figure 30:
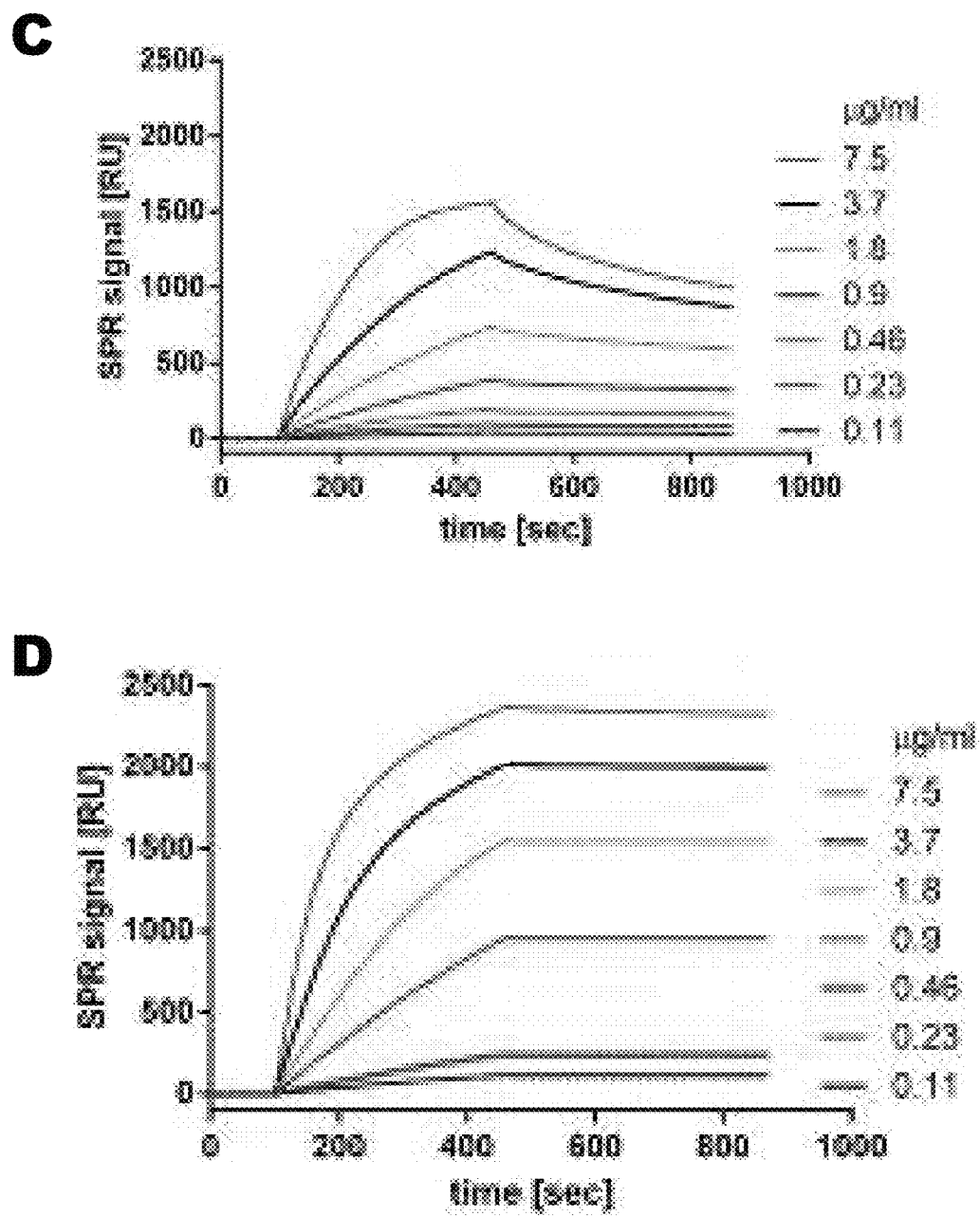
FIG. 30. Characterization of anti-tau antibodies by surface plasmon resonance (SPR) and Immunoblotting. The figure depicts SPR sensorgrams showing the binding of each anti-tau antibody towards immobilized recombinant human tau (longest isoforms hTau40, 441 aa) and immobilized mouse tau (longest isoforms mTau40, 432 aa). Each antibody was run with various concentrations (0.11, 0.23, 0.46, 0.90, 1.8, 3.7, 7.5 µg/ml) and plots are shown in the corresponding color. (A) SPR sensorgrams of HJ9.3 antibody binding to immobilized human tau and immobilized mouse tau (B). (C) SPR sensorgrams of HJ9.4 antibody binding to immobilized human tau and immobilized mouse tau (D). SPR sensorgrams of HJ8.5 antibody binding to immobilized (E) human and (F) mouse tau. (G) RAB soluble fractions of 3 month old tau knockout (KO), 3 month old wild-type (WT), 3 month old P301S (3 mo) and 9 month old P301S (9 mo) mice were analyzed by immunoblot by using the indicated anti-tau antibodies.
Figure 30G:
Figure 31:
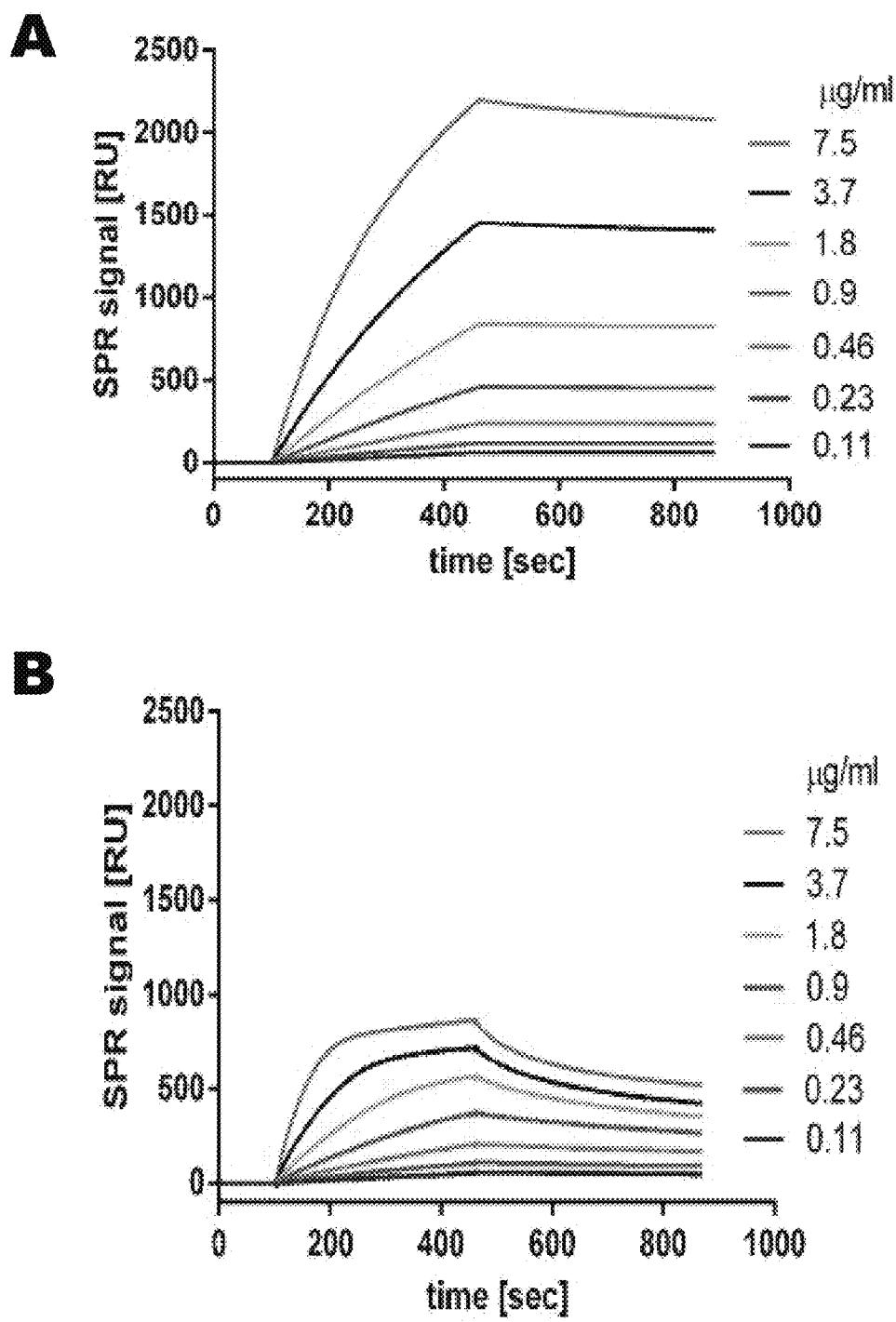
FIG. 31. SPR sensorgram of the interaction between anti-tau antibodies towards immobilized human tau fibrils. SPR sensorgrams of HJ9.3 (A), HJ9.4 (B) and HJ8.5 (C) anti tau antibodies run with various concentrations towards immobilized human tau fibrils.
Figure 31C:
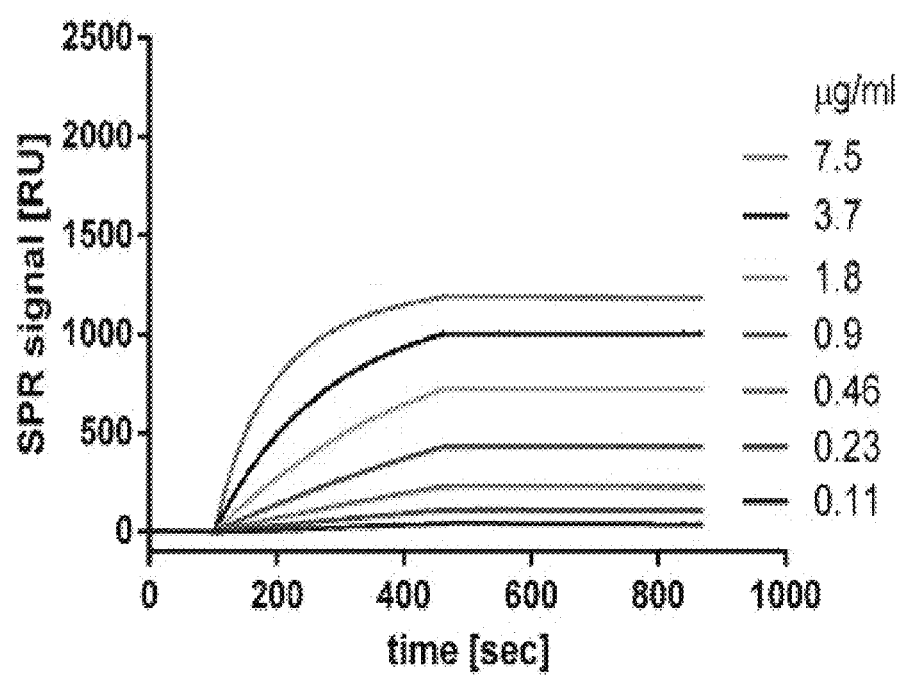

Prior to testing in vivo, the binding affinities and epitopes of the antibodies, which are all IgG2b isotype, were determined. Human and mouse tau was immobilized on a sensor chip CM5 for surface plasmon resonance (SPR) (FIG. 30). The HJ9.3 antibody, raised against mouse tau, recognizes both human (FIG. 30A) and mouse (FIG. 30B) tau with the same binding constant ($K_D=K_d/K_a=100$ pM) (FIG. 30G). The association ($K_a$) and dissociation ($K_d$) was calculated by using BIAevaluation software (Biacore AB) selecting Fit kinetics simultaneous $K_a/K_d$ (Global fitting) with 1:1 (Langmuir) interaction model. The $K_a$ and $K_d$ of HJ9.3 towards human ($K_a=7.5\times10^4$ Ms$^{-1}$, $K_d=7.5\times10$-6 s$^{-1}$) and mouse tau ($K_a=8.6\times10^4$ Ms$^{-1}$, $K_d=9.1\times10$-6 s$^{-1}$) indicate strong binding to both. The epitope of HJ9.3 was mapped to the repeat domain (RD) region, between amino acids 306-320. HJ9.4, raised against mouse tau, had high affinity $K_D$ (2.2 pM) towards mouse tau with a high association rate constant ($K_a=2.28\times105$ Ms$^{-1}$) and very low dissociation constant ($K_d=5.1\times10$-7 s$^{-1}$) (FIG. 30D and Table 4. However, the same antibody had a much lower affinity ($K_D=6.9$ nM) toward human tau (FIG. 30C and Table 4) with a similar association rate constant ($K_a=1.5\times105$ Ms$^{-1}$) as with mouse tau but with much faster dissociation ($K_d=1.07\times10$-3 s$^{-1}$). Thus, the HJ9.4 interaction with human tau is less stable than with mouse tau. The epitope for this antibody is amino acids 7-13. HJ8.5 was raised against human tau. It binds to human tau (FIG. 30E) but not to mouse tau (FIG. 30F). The $K_D$ (0.3 pM) (FIG. 30E and Table 4) and low dissociation rate ($K_d=4.38\times10^{-8}$ s$^{-1}$), indicate that HJ8.5 binds human tau with very high affinity. The epitope of HJ8.5 was mapped to amino acids 25-30. All 3 anti-tau antibodies strongly recognized human tau fibrils on SPR (FIG. 31). Because the fibrils have multiple identical epitopes, the association and dissociation rates could not be directly calculate.

TABLE 4

Association rate constant ($K_a$), dissociation rate constant ($K_d$) and binding constant ($K_D$) of each antibody towards human and mouse tau. BIAevaluation software (Biacore AB) was used to calculate $K_a$ and $K_d$ by selecting Fit kinetics simultaneous $K_a/K_d$ (Global fitting) with 1:1 (Langmuir) interaction model. Ms$^{-1}$ = millisecond, M = molar, s = second

|  |  | HJ9.3 | HJ9.4 | HJ8.5 |
|---|---|---|---|---|
| Humuan tau | $K_a$ (Ms$^{-1}$) | 7.55 × 10$^4$ | 1.53 × 10$^5$ | 1.3 × 10$^5$ |
|  | $K_d$ (s$^{-1}$) | 7.51 × 10$^{-6}$ | 1.07 × 10$^{-3}$ | 4.34 × 10$^{-8}$ |
|  | $K_D$ (M) | 99 pM | 6.9 nM | 0.336 pM |
| Mouse tau | $K_a$ (Ms$^{-1}$) | 8.61 × 10$^4$ | 2.28 × 10$^5$ | — |
|  | $K_d$ (s$^{-1}$) | 9.16 × 10$^{-6}$ | 5.1 × 10$^{-7}$ | — |
|  | $K_D$ (M) | 100 pM | 2.24 pM | — |

Figure 32:
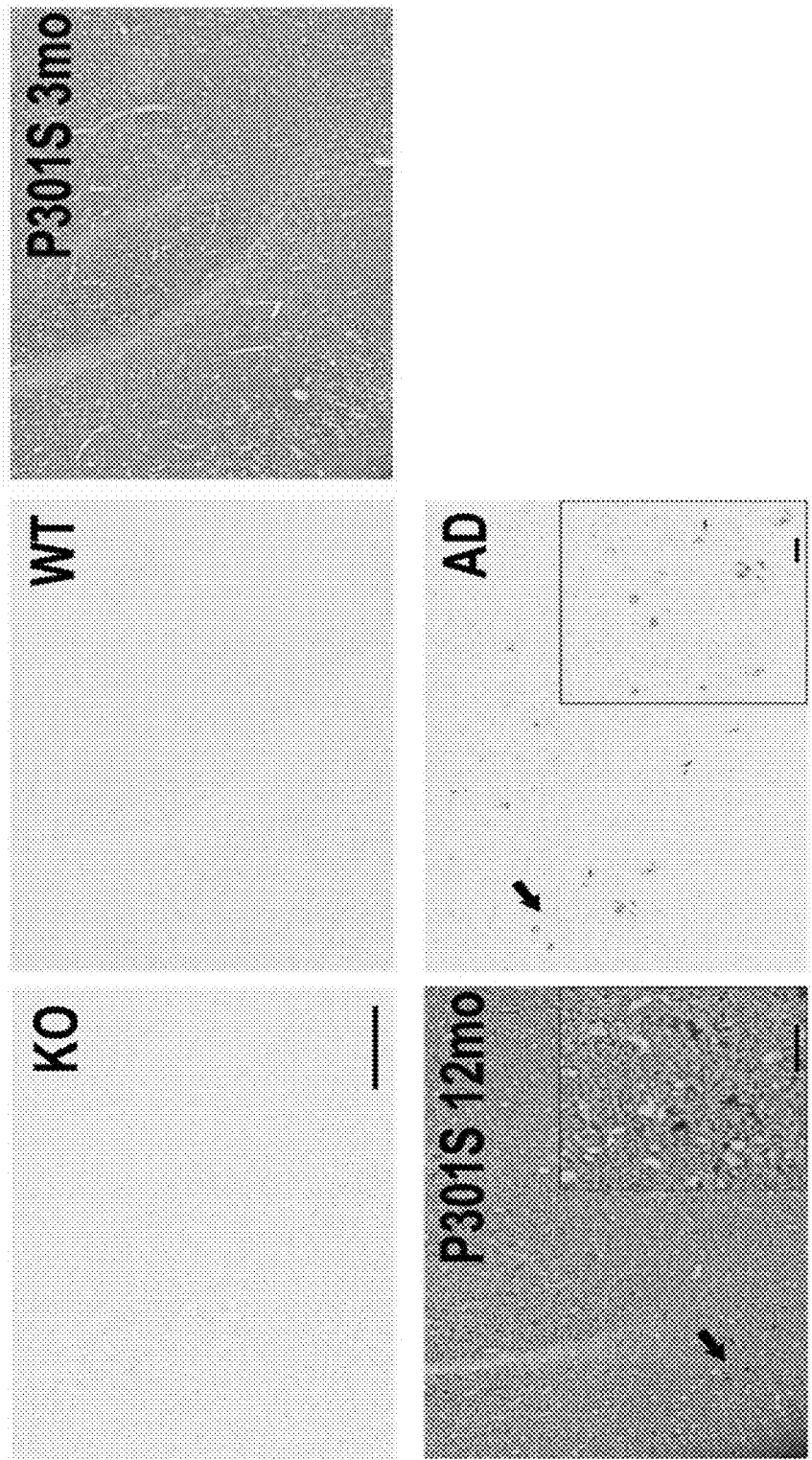
FIG. 32. Characterization of anti-tau antibodies in different assays. Immunostaining of brain sections from 3 month old tau knockout (KO), 3 month old wild type (WT), 3 month old P301S (3 mo), 12 month old P301S (12 mo) mice from the region of the piriform cortex and from the frontal cortex of Alzheimer's disease (AD) tissue were stained with biotinylated HJ8.5 antibody. Insert in 12 month old P301S micrograph shows cell body staining in addition to diffuse neuropil staining. Black arrow indicates the area magnified. Insert in human AD brain cortex micrograph shows the staining of neurofibrillary tangles (NFT) in higher magnification. Black arrow indicates the area magnified. Scale bar is 250 µm in panel with tau KO, same magnification images. Scale bar 50 µm in inserts of P301S 12 mo and AD.

The antibodies were also assessed by immunoblotting and immunostaining. On Western blots, all 3 antibodies bound to human tau (FIG. 30H). HJ9.3 and HJ9.4 bound to mouse tau while HJ8.5 did not (FIG. 30H). Consistent with our prior findings of the inventors (Yamada et al., 2011; J Neurosci 31, 13110-13117), there appeared to be less reassembly buffer (RAB) soluble tau in 9 month old compared to 3 month old P301S mice. It was also found that HJ8.5 stained human tau in 3 month and 9-12 month old transgenic P301S mouse brains. Tau immunoreactivity was present throughout the cell bodies and processes (FIG. 32). In 9-12 month old P301S mice with tau aggregates, HJ8.5 detected tau aggregates in cell bodies (FIG. 32A). Other antibodies produced similar results (Table 5). All antibodies bound to neurofibrillary tangles and neuropil threads in AD brain (FIG. 32).

TABLE 5

Relative efficacy of anti-tau antibodies in different assays.

|  | HJ8.5 | | HJ9.3 | | HJ9.4 | |
|---|---|---|---|---|---|---|
| Method | Human tau | Mouse tau | Human tau | Mouse tau | Human tau | Mouse tau |
| Western blot | ++ | − | +++ | +++ | ++ | ++ |
| Immunostaining | +++ | − | + | + | ++ | +++ |
| Human AD brain NFT's | +++ | N/A | + | N/A | + | N/A |

Example 10

Tau-Antibodies Block the Uptake and Seeding Activity of P301S Tau Aggregates

Figure 33:
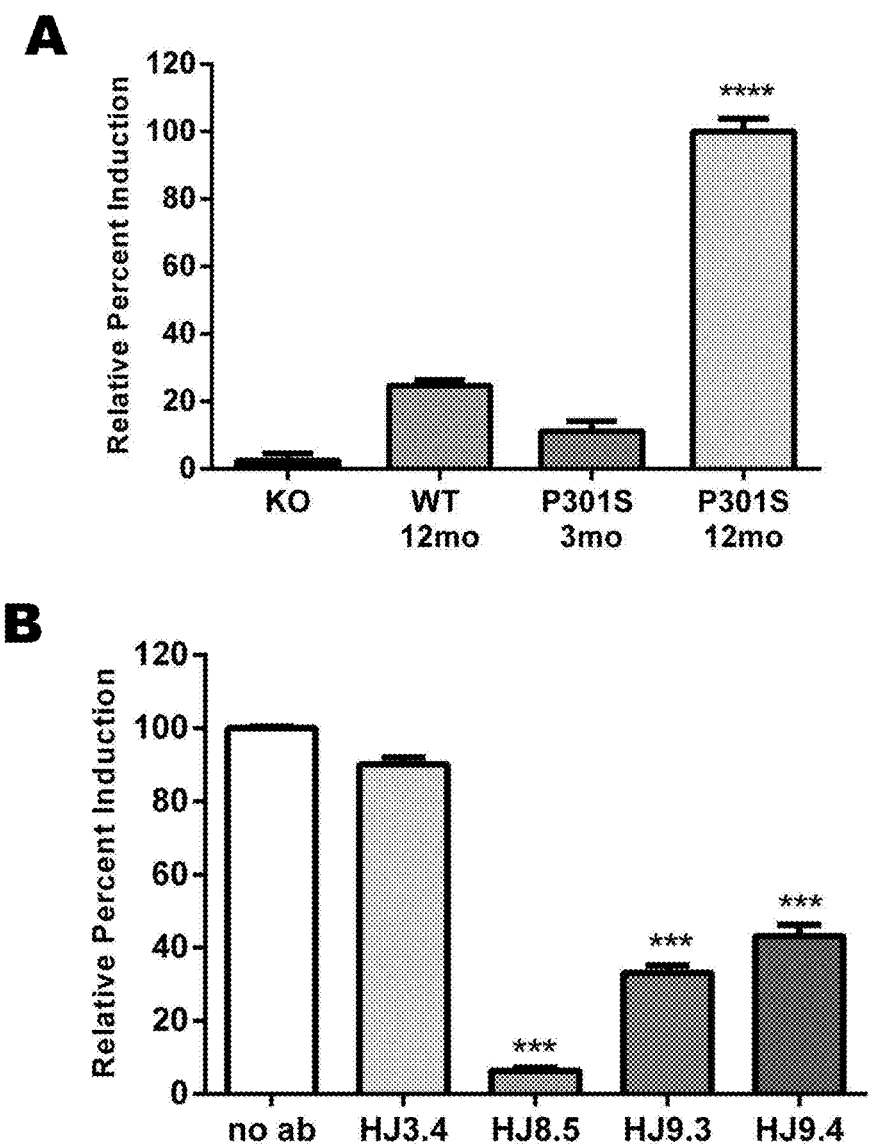
FIG. 33. Tau-antibodies block the uptake and seeding activity of P301S tau aggregates as detected by a FRET assay. HEK293 cells expressing RD($\Delta$K280)-CFP/YFP were exposed to 2.5 µg of total protein of 1×TBS brain lysates for 24 h. (A) Brain lysates collected from 12 mo old P301S mice induced much greater seeding activity (n=5) as compared to lysates from knockout (KO) mice (n=7), wild type (WT) mice (n=6) or young 3-mo old P301S mice (n=2) (**$p<0.0001$). (B) HEK293 cells were co-transfected with RD ($\Delta$K280)-CFP and RD ($\Delta$K280)-YFP. 18 hrs later, pre-incubated P301S brain lysates with or without incubation of anti-tau antibodies (HJ8.5, HJ9.3 and HJ9.4) or control antibody (HJ3.4, anti A$\beta$ antibody) were added to cells. All the tau antibodies incubated with P301S brain lysates significantly blocked seeding activity. Statistical significance was determined by one-way ANOVA followed by Dunnett's post hoc test for multiple comparisons by using GraphPad Prism 5.0 software (*$p>0.001$). (C) Titration of these antibodies with various concentrations (0.125 µg/ml, 0.25 µg/ml, 0.5 µg/ml, 1 µg/ml and 2 µg/ml) was performed with a fixed amount of P301S brain lysates. 24 hrs later, FRET analysis was performed. Out of all tau-antibodies we used, HJ8.5 was the most potent in blocking the uptake and seeding activity of P301S brain lysates. Statistical significance was determined by two-way ANOVA followed by Bonferroni post hoc test for multiple comparisons. (** $p<0.0001$, * $p<0.01$, Values represent mean±SEM).

To evaluate seeding activity present in P301S brain lysates, a cellular biosensor system previously described by the inventors (Kfoury et al., 2012) was adapted. This is based on expression of the repeat domain of tau (aa 243-375) containing the ΔK280 mutation fused either to cyan or yellow fluorescent protein (RD(ΔK)-CFP/YFP). Uptake of exogenous aggregates into these cells triggers intracellular aggregation of RD(ΔK)-CFP/YFP that is detected by fluorescence resonance energy transfer (FRET) recorded on a fluorescence plate reader. Clarified brain lysates from 12 month old P301S mice added to the biosensor cell system induced strong aggregation of the RD(ΔK)-CFP/YFP reporter, indicating the presence of tau seeding activity (FIG. 33A). The seeding activity from 12-mo P301S brain homogenate mice roughly corresponds to 50 nM (monomer equivalent) of recombinant full length fibrils (data not shown).

Figure 33C:
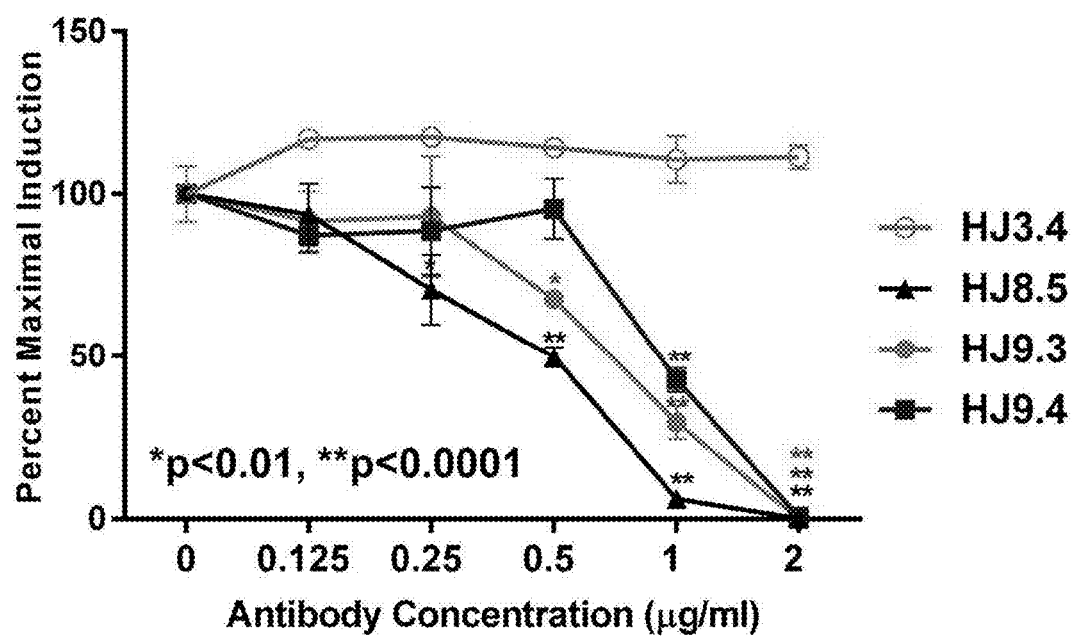
Figure 34:
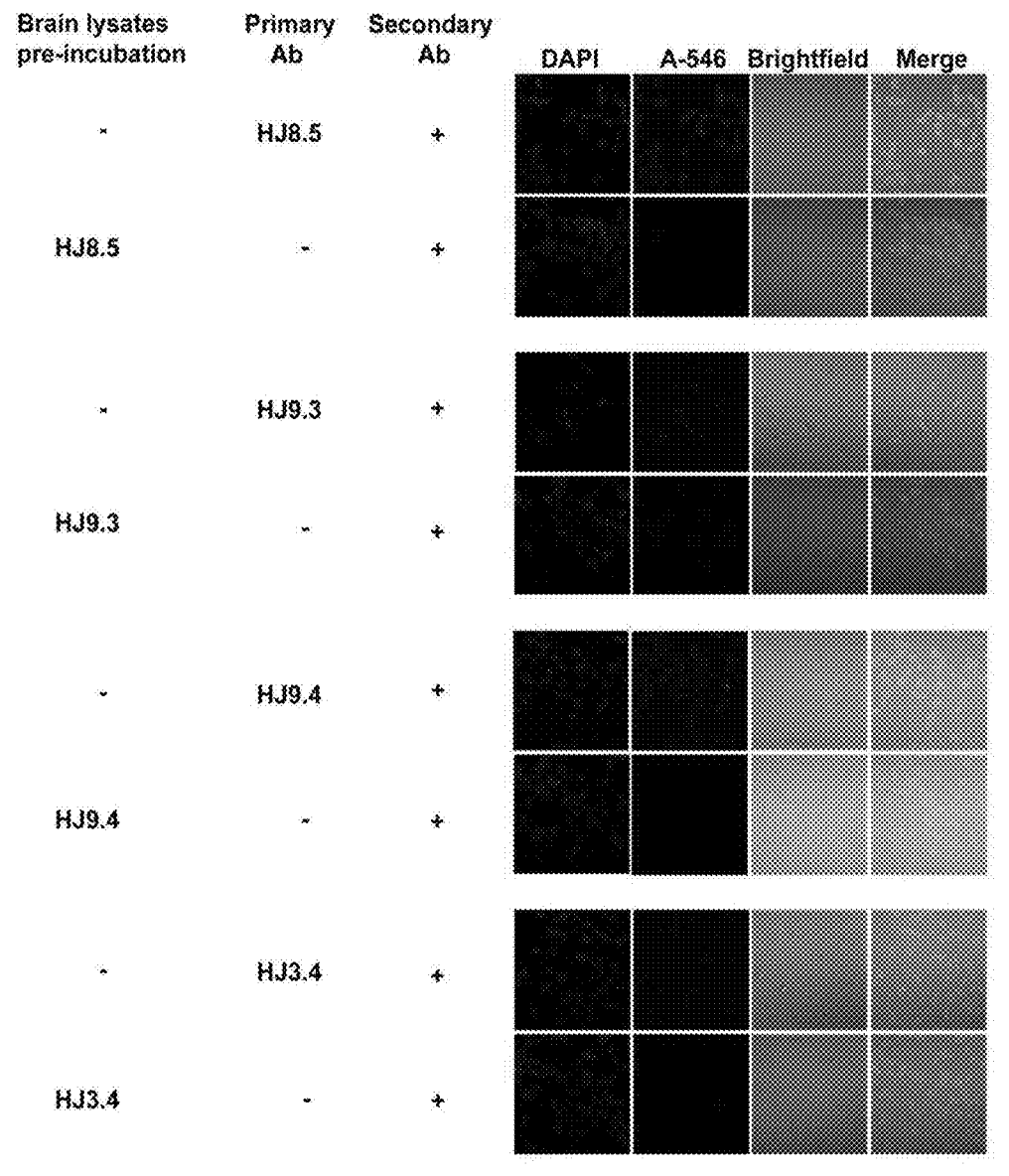

There was little to no aggregation induced by lysates from tau knockout mice, wild-type mice, or 3 month old P301S mice lacking tau pathology (FIG. 33A). The anti-tau antibodies (HJ8.5, HJ9.3 and HJ9.4) were assessed for their ability to block the uptake, and seeding activity of these lysates. HJ3.4 (mouse monoclonal anti-Aβ antibody) was a negative control. The anti-tau antibodies effectively blocked seeding activity (FIG. 33B). To determine their relative efficacy, the antibodies (0.125, 0.25, 0.5, 1, 2 µg/ml) were titrated against a fixed amount of P301S brain lysate (FIG. 33C). The HJ8.5 antibody blocked seeding activity at concentrations as low as 0.25 µg/ml compared to controls. At 0.5 µg/ml, both HJ8.5 and HJ9.3 antibody significantly blocked uptake and seeding activity compared to control. HJ9.4 was least potent in blocking the uptake and seeding activity, consistent with its higher affinity for mouse tau. All 3 anti-tau antibodies detected tau aggregates internalized following uptake by HEK293 cells, as detected by post-hoc cellular permeabilization and staining. However, when these antibodies were pre-incubated with and without P301S brain lysates, none of these antibodies were detected inside cells upon staining with anti-mouse secondary antibody (FIG. 34). While other modes of inhibition are possible, these data are consistent with a mechanism based on blocking cellular uptake of tau aggregates.

Example 11

Intracerebroventricular Infusion of Anti-Tau Antibodies

In the mouse colonies, P301S mice first develop intracellular tau pathology beginning at 5 months of age. To test the efficacy of the 3 antibodies by chronic intracerebroventricular (ICV) administration, a catheter was surgically implanted into the left lateral ventricle of each mouse at 6 months of age and continuously infused anti-tau antibodies for 3 months via Alzet subcutaneous osmotic mini-pump (FIG. 35A). Anti-Aβ antibody HJ3.4 and phosphate buffered saline (PBS) were used as negative controls. After 6 weeks, each pump was replaced with one filled with fresh antibody solution or PBS. At the time of brain dissection, catheter placement in the left lateral ventricle of each mouse was verified by cresyl violet staining (FIG. 35B). Only mice with correctly placed catheters were included in the analyses. To test the stability of the antibodies after 6 weeks in vivo (FIG. 35A), residual pump contents were collected upon removal from the animals, and the antibodies were assessed using SDS-PAGE and Coomassie blue staining. Light and heavy chains were intact, with no fragmentation, and retained tau binding activity on western blot (data not shown). To estimate the concentration of anti-tau antibodies in CSF and serum during the infusion, biotinylated HJ8.5 (HJ8.5B) was administered for 48 hours (~7.2 µg/day) (FIG. 35A). The concentration of free HJ8.5B was 7.3 µg/ml in the CSF and 6.2 µg/ml in the serum, indicating significant clearance of the antibody from the CNS to the periphery (Table 6). HJ8.5B bound to human tau was also detected in both CSF and serum, though the concentration was lower than that of free antibody (Table 6).

TABLE 6

Levels of biotinylated HJ8.5 antibody that is free (not bound to tau) and HJ8.5 antibody bound to tau in serum and cerebrospinal fluid (CSF) 48 hrs after IP or ICV administration.

| Treatment | CSF | Serum | CSF Conc. As % Serum Conc. |
|---|---|---|---|
| | Conc. Of free HJ8.5B (µg/ml) | | |
| HJ8.5B injected IP (50 mg/kg/48 hrs) | 0.9 ± 0.1 | 552 ± 38.6 | 0.16 ± 0.02 |
| HJ8.5B injected ICV (ca. 14 µg/48 hrs) | 7.3 ± 1.6 | 6.2 ± 0.5 | 95.4 ± 19.4 |
| | Conc. Of HJ8.5B bound to tau (µg/ml) | | |
| HJ8.5B injected ICV (ca. 14 µg/48 hrs) | 0.10 ± 0.02 | 0.04 ± 0.03 | 53 ± 4.6 |

Example 12

Anti-Tau Antibody Treatment Reduces Abnormally Phosphorylated Tau

Figure 36:
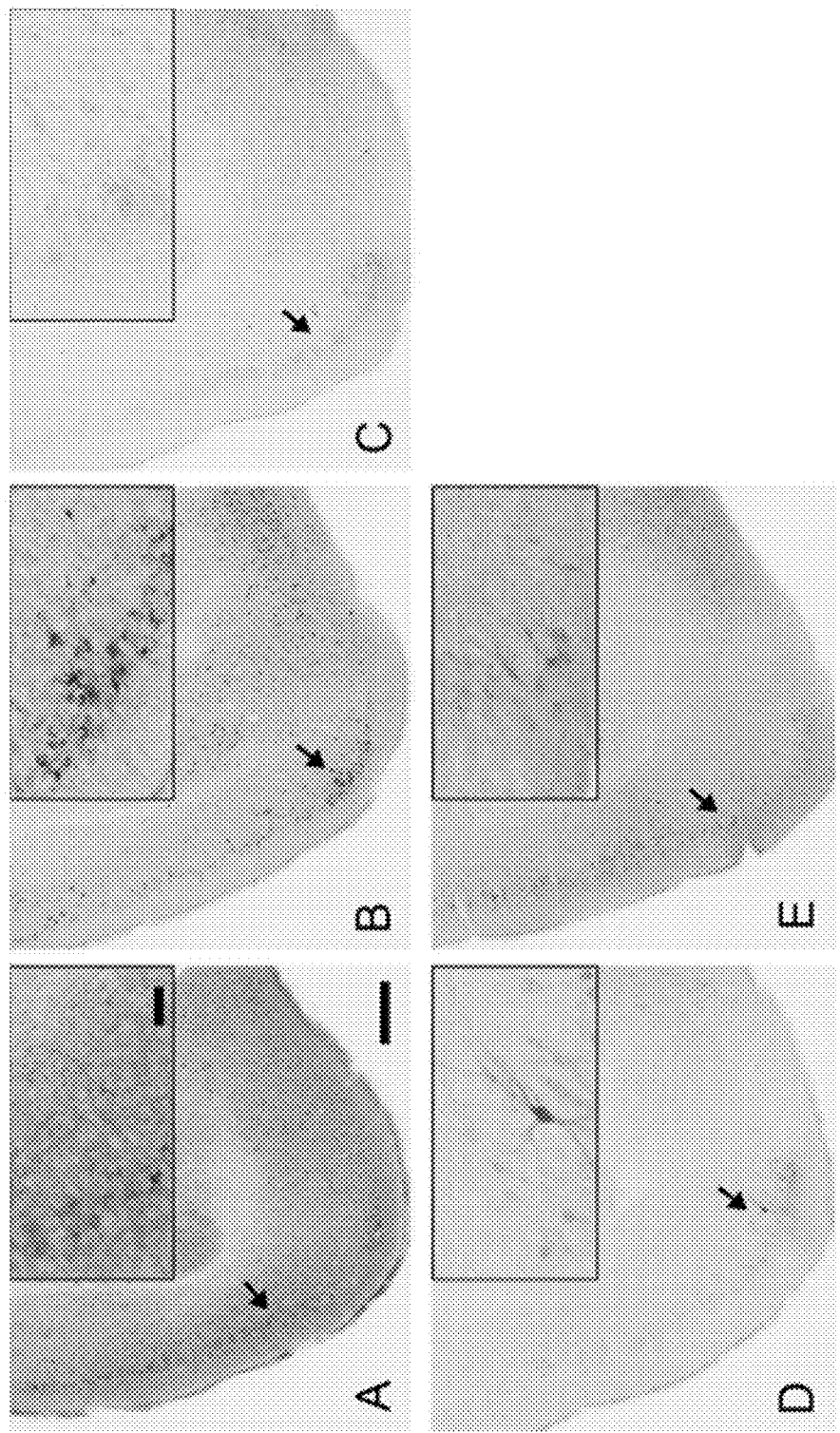
FIG. 36. Anti-tau antibodies strongly decreased AT8 staining in P301S mouse brain. Representative coronal sections of PBS (A), HJ3.4 antibody (B), HJ8.5 antibody (C), HJ9.3 antibody (D) and HJ9.4 antibody (E) treated 9 month old P301S mice stained with biotinylated AT8 antibody in regions including the piriform cortex and amygdala. Scale bar is 250 μm. Inserts in A to E show the higher magnification of biotinylated AT8 antibody staining of phosphorylated tau, scale bar is 50 μm.
Figure 37:
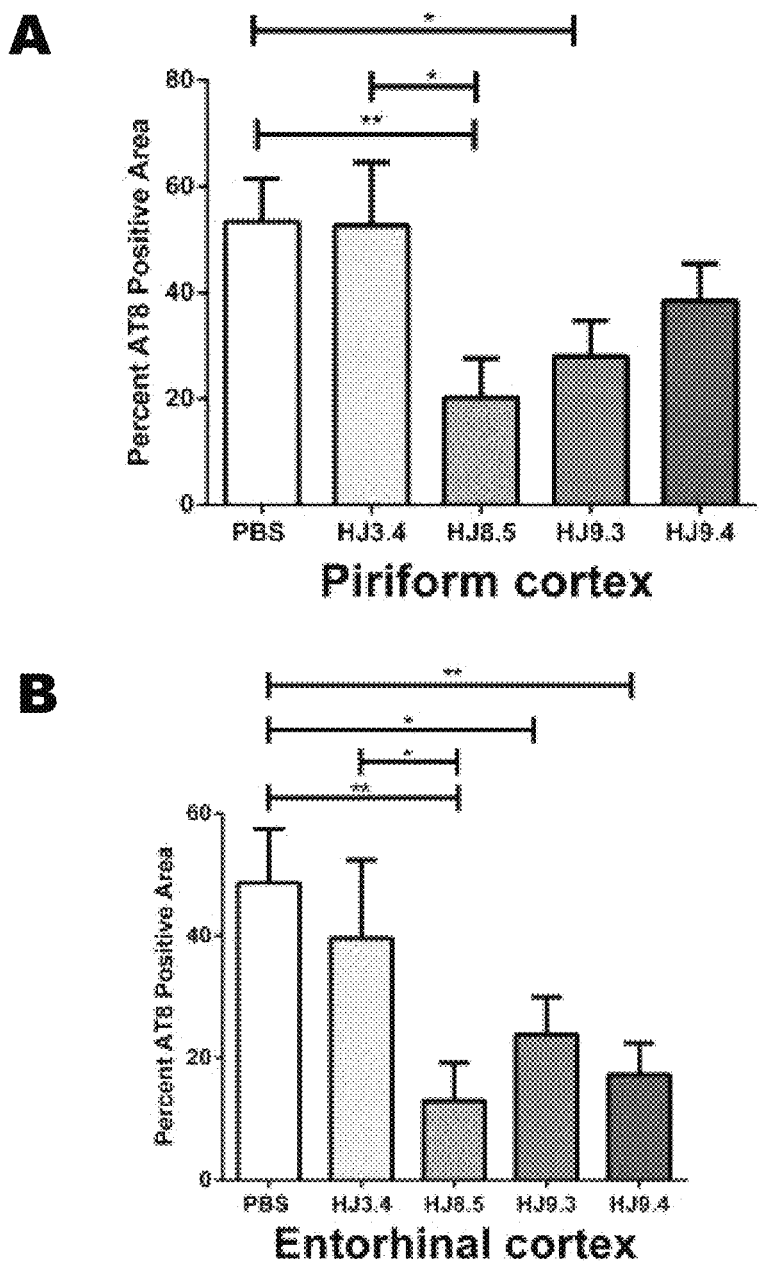
FIG. 37. Certain anti-tau antibodies strongly decrease AT8 staining in P301S mouse brain. Percent of the area covered by biotinylated AT8 staining of abnormally phosphorylated tau in piriform cortex (A), entorhinal cortex (B), amygdala (C) and hippocampus CA1 region (D) in mice treated with the anti-tau antibodies HJ8.5 (N=13), HJ9.3 (N=15), HJ9.4 (N=13), the anti-Aβ antibody, HJ3.4 (N=8), or PBS (N=16) in 9 month old P301S mice. There was reduced AT8 staining in several different brain regions in the anti-tau antibody treated mice compared to PBS or HJ3.4 antibody treated mice. HJ8.5 had the largest effects. ** $p<0.01$, * $p<0.05$, values represent mean±SEM.
Figure 37:
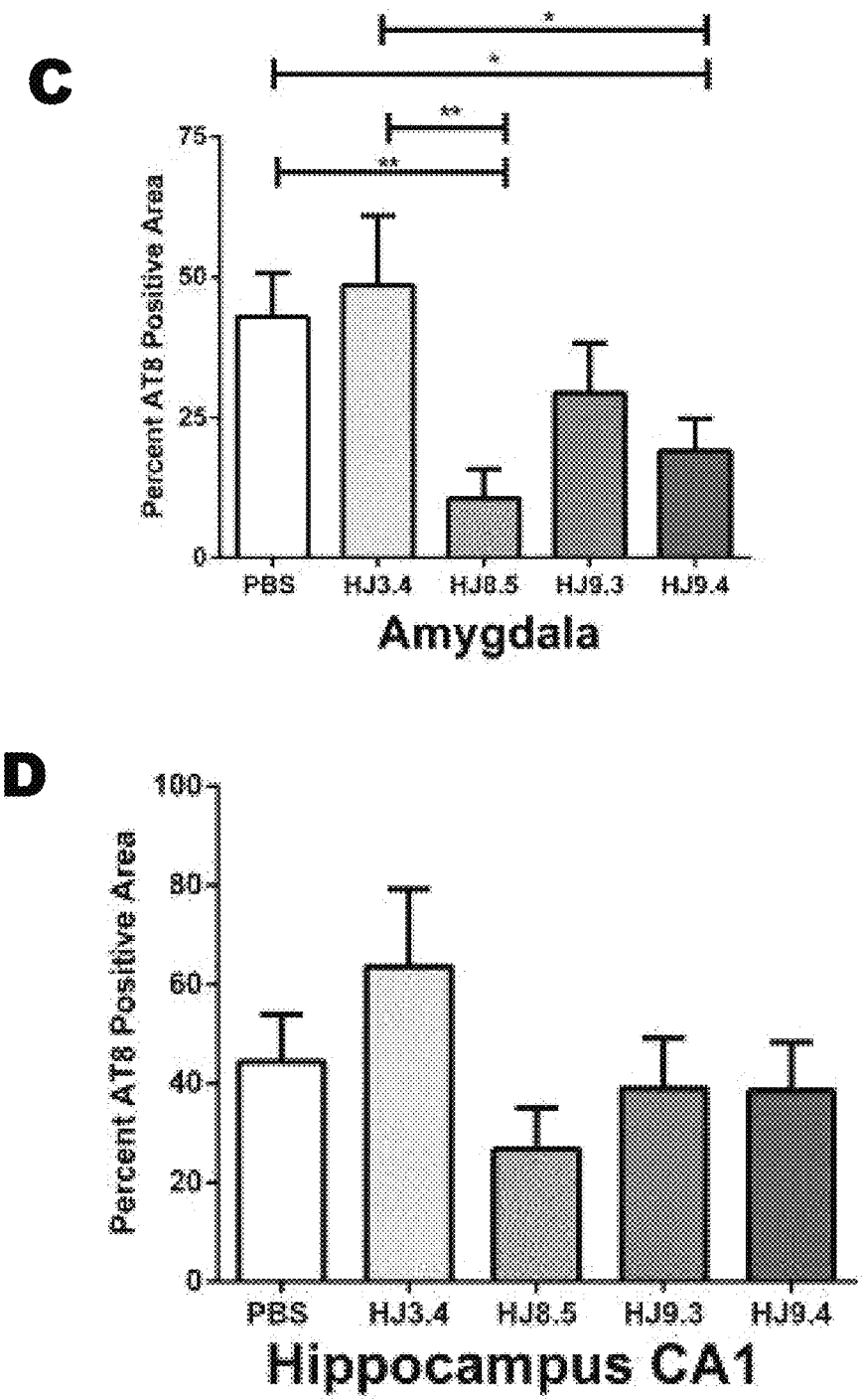
Figure 38:
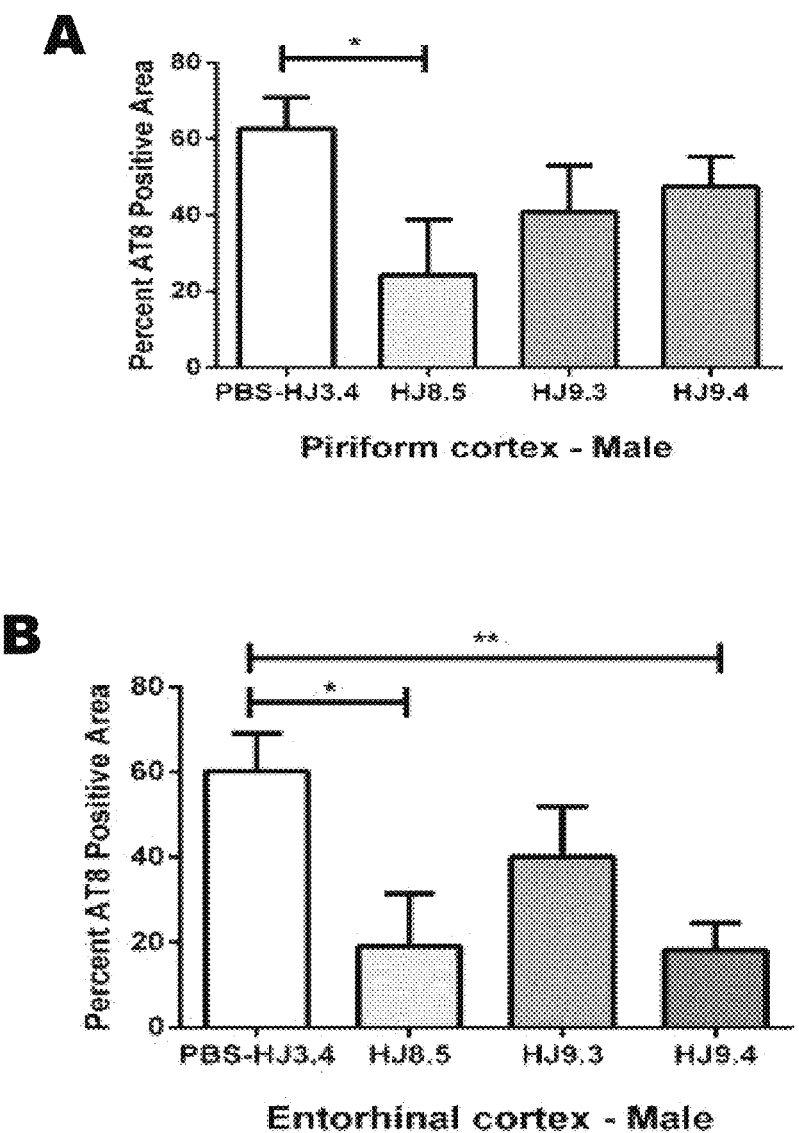
FIG. 38. Quantification of biotinylated AT8 antibody staining in male and female P301S mice. Percent of area covered by biotinylated AT8 staining of abnormally phosphorylated tau in male (A) and female P301S mice (B) in piriform cortex (A and E), entorhinal cortex (B and F), amygdala (C and G) and hippocampal CA1 regions (D and H) in anti-tau antibody (HJ8.5, HJ9.3 and HJ9.4), control antibody (HJ3.4) plus PBS treated mice.

To determine the extent of tau pathology in P301S mice after 3 months of treatment, multiple stains for tau pathology were carried out. Brain sections were first assessed by immunostaining with the anti-phospho tau antibody AT8 (FIG. 36). AT8 binds phosphorylated residues Ser202 and Thr205 of both mouse and human tau (FIG. 36). In mice treated with PBS and HJ3.4, AT8 strongly stained neuronal cell bodies and the neuropil in multiple brain regions, particularly in the piriform cortex, entorhinal cortex, amygdala, and hippocampus (FIGS. 36A and 36B). HJ8.5 treatment strongly reduced AT8 staining (FIG. 36C), especially in the neuropil. HJ9.3 and HJ9.4 also decreased AT8 staining but the effects were slightly less (FIGS. 36D and 36E). Quantitative analysis of AT8 staining in piriform cortex (FIG. 37A), entorhinal cortex (FIG. 37B), and amygdala (FIG. 37C) demonstrated a strong but variable reduction in phospho-tau in all anti-tau antibody treated mice. HJ8.5 antibody markedly reduced AT8 staining in piriform cortex, entorhinal cortex, and amygdala. HJ9.3 had slightly decreased effects compared to HJ8.5, and HJ9.4 had significant effects in both entorhinal cortex and amygdala but not in the piriform cortex (FIG. 37). The hippocampus exhibited much more variable AT8 staining vs. other brain regions, predominantly in cell bodies, and thus was not statistically different in treatment vs. control groups (FIG. 37D). Because it has been reported that male P301S mice have greater tau pathology than females, the effect of both gender and treatment were also assessed (FIG. 38). In addition to an effect of treatment, there was significantly more AT8 staining in all brain regions analyzed in male mice (Table 7). However, the effects of the antibodies were still highly significant and virtually identical after adjusting for gender (Table 8). The treatment groups versus controls in males and females were also compared separately, and the effects of antibody HJ8.5 remained most significant (FIGS. 38A and 38B).

TABLE 7 p Values of Treatment/Gender

|  | Amygdala | Entorhinal cortex | Hippocampus | Piriform cortex |
|---|---|---|---|---|
| Treatment | 0.0107 | 0.0053 | 0.2917 | 0.0147 |
| Gender | 0.0026 | 0.0027 | 0.0244 | 0.0067 | p values determined by two-way ANOVA considering treatment and gender as factors. For amygdala, entorhinal cortex, and piriform cortex regions, treatment and gender are both significant factors with p values <0.05, but for hippocampus CA1 region, treatment is not a significant factor with p value = 0.2917 while gender is a significant factor with p value = 0.0244.

TABLE 8

|  | Amygdala | | Entorhinal cortex | | Hippocampus CA1 | | Piriform cortex | |
|---|---|---|---|---|---|---|---|---|
|  | p value-1 | p value-2 | p value-1 | p value-2 | p value-1 | p value-2 | p value-1 | p value-2 |
| Control vs. HJ8.5 | 0.0009 | 0.0009 | 0.0022 | 0.0022 | 0.0421 | 0.0526 | 0.011 | 0.0113 |
| Control vs. HJ9.3 | 0.0956 | 0.1605 | 0.0335 | 0.0576 | 0.2486 | 0.3889 | 0.0566 | 0.0982 |
| Control vs. HJ9.4 | 0.0106 | 0.0072 | 0.0077 | 0.005 | 0.2427 | 0.2427 | 0.1787 | 0.1569 | p values were calculated before and after adjustment of gender. p value-1: not adjusted by gender; p value-2: adjusted by gender. p value-1 was determined by one-way ANOVA, treatment is the independent variable, p value-2 was determined by two-way ANOVA. treatment and gender are independent variables.

Example 13

Correlation of Multiple Staining Modalities

Figure 39A:
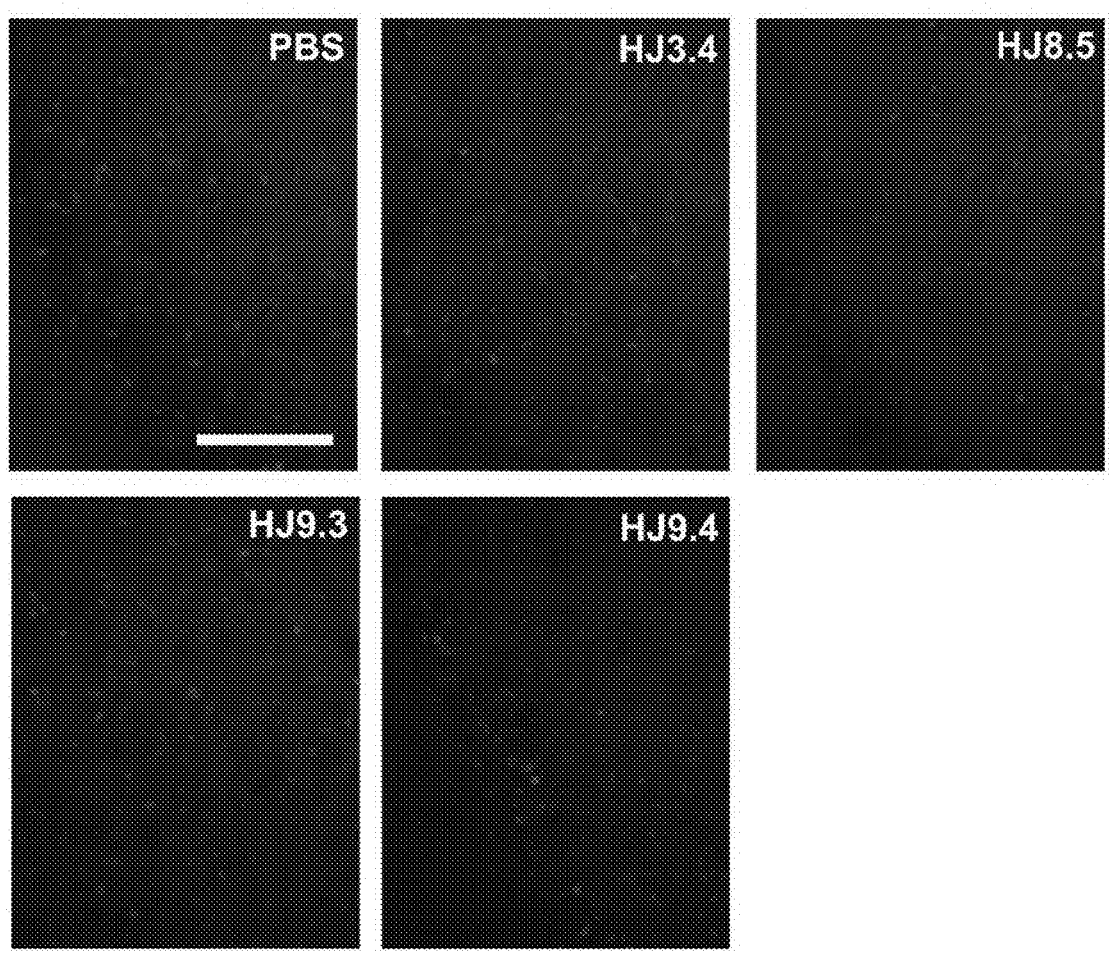
FIG. 39. Some anti-tau antibodies strongly decrease ThioS staining of neurofibrillary tangles in P301S mouse brain. (A) Representative images of ThioS staining of neurofibrillary tangles in the piriform cortex of 9 month old P301S mice treated for 3 months with PBS, HJ3.4, HJ8.5, HJ9.3 and HJ9.4 antibodies. ThioS staining of neurofibrillary tangles was reduced in HJ8.5 antibody treated mice compared to the PBS or HJ3.4 antibody treated mice. Scale bar represents 100 μm. (B) Semi quantitative assessment of ThioS staining by scoring from 1 (no staining) to 5 (maximum staining) in all anti-tau antibody and control treated mice. HJ8.5 antibody treated mice had significantly less ThioS staining compared to PBS or HJ3.4 antibody treated mice. *$p<0.05$, **$p<0.01$.
Figure 39B:
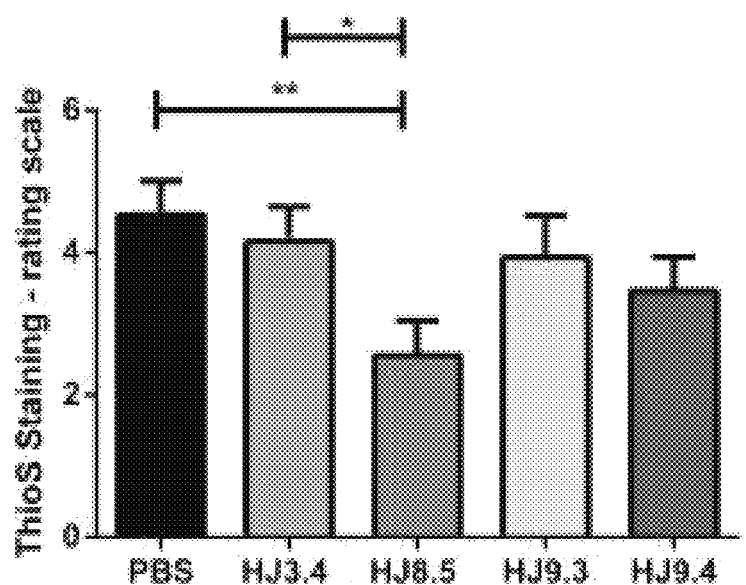

To test for tau amyloid deposition, thioflavin S (ThioS) was used to stain brain sections (FIG. 39). ThioS staining was semi-quantitatively assessed using a blinded rater who gave a score from 1 (no staining) to 5 (maximum staining) in all control and anti-tau antibody treated mice. By semi-quantitative assessment, HJ8.5 treatment significantly reduced ThioS staining compared to PBS and HJ3.4 (FIGS. 39A and 39B). Mice treated with PBS, HJ8.5, and HJ9.3 (n=6 from each group) were also stained with PHF1 monoclonal antibody, which recognizes tau phospho-residues Ser396 and Ser404. AT8 and PHF1 staining significantly correlated (r=0.630, p=0.005) (FIG. 40A) showing that 2 anti-phospho tau antibodies to different tau epitopes give similar results.

Figure 40:
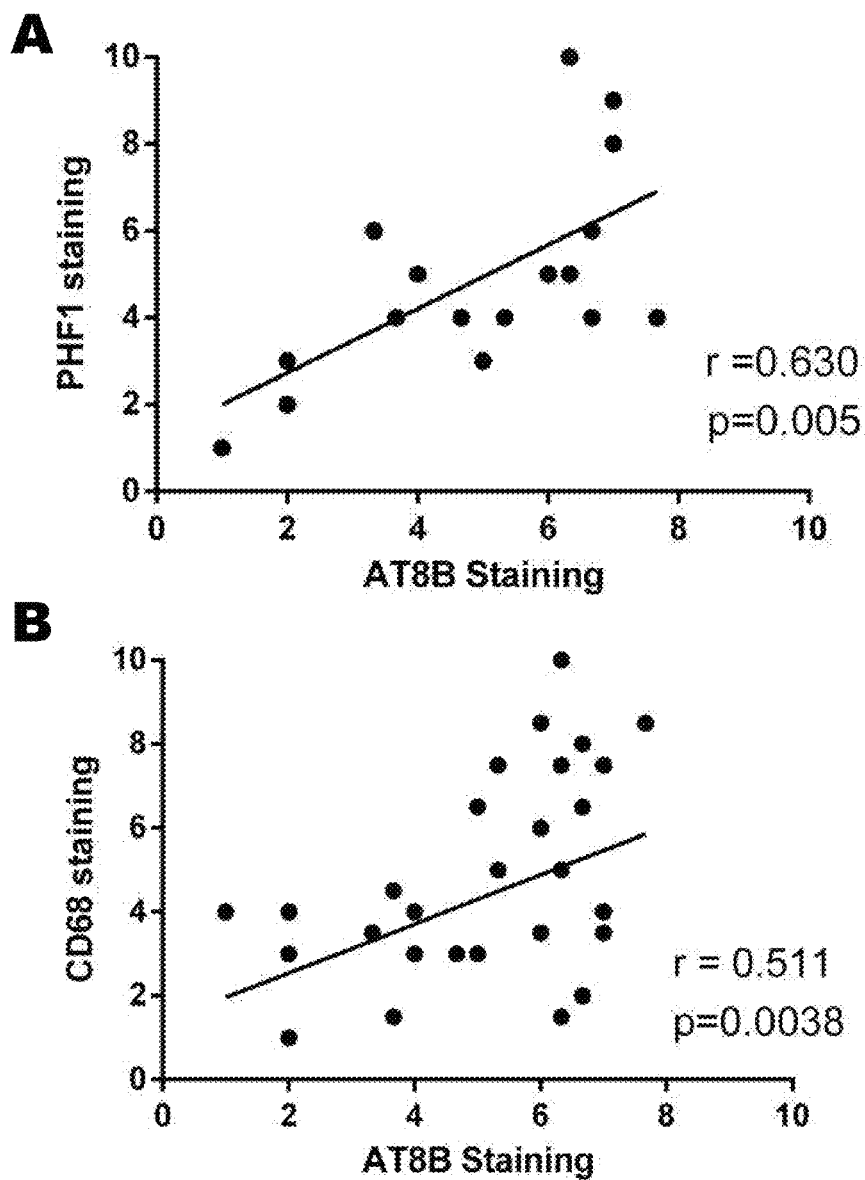
FIG. 40. Correlations between phospho-tau staining, and activated microglial staining. (A) Biotinylated AT8 staining of phospho-tau in HJ8.5 (N=6), HJ9.3 (N=6) and PBS treated 9 month old P301S mice (N=6 per each group) showed strong correlation with PHF1 staining, another phospho-tau antibody. (B) Strong correlation was observed between CD68 staining of activated microglia and biotinylated AT8 staining of phospho-tau in all groups (N=6 per each group) (C) Immunoblotting of representative 70% FA fraction samples (N=4) were analyzed with polyclonal mouse anti-tau antibodies (Abcam).
Figure 41:
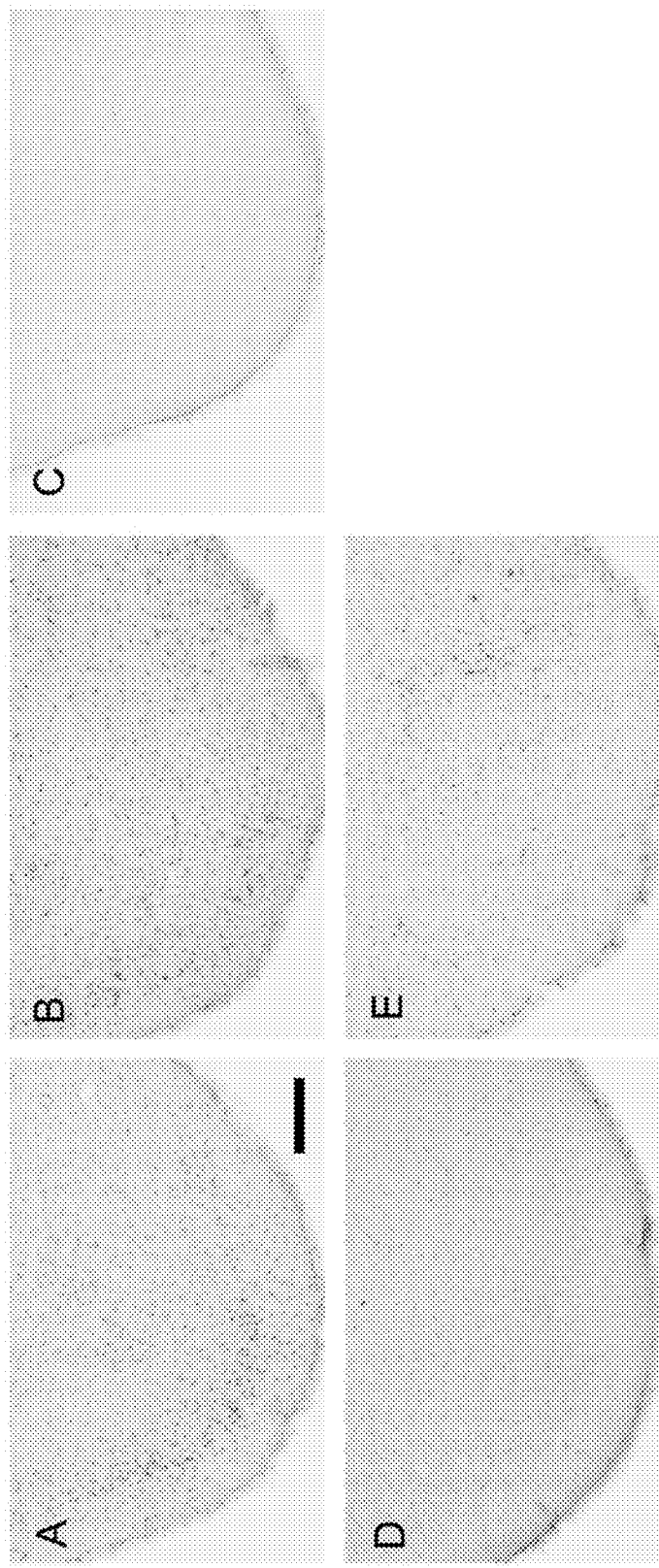
FIG. 41. CD68 staining of activated microglia. Mice were assessed for microglial activation in P301S mice. Representative images of CD68 staining of activated microglia in the piriform cortex of 9 month old P301S mice treated with PBS (A), HJ3.4 antibody (B), HJ8.5 antibody (C), HJ9.3 antibody (D) and HJ9.4 antibody (E).

Many neurodegenerative diseases, including tauopathies, exhibit microglial activation in areas of the brain surrounding protein aggregation and cell injury. Microglial activation was assessed in the treatment groups using anti-CD68 antibody (FIG. 41). HJ8.5 and HJ9.3 treatment reduced microglial activation in piriform cortex, entorhinal cortex, and amygdala compared to controls (FIG. 41A-41D). HJ9.4 had a weaker effect in the piriform cortex compared to HJ8.5 and HJ9.3 (FIG. 41C-41E), consistent with the AT8 staining results (FIG. 37A). Microglial activation strongly correlated with AT8 staining in all samples (r=0.511, p=0.0038) (FIG. 40B).

Example 14

Anti-Tau Antibodies Reduce Detergent-Insoluble Tau and Seeding Activity

Figure 40C:
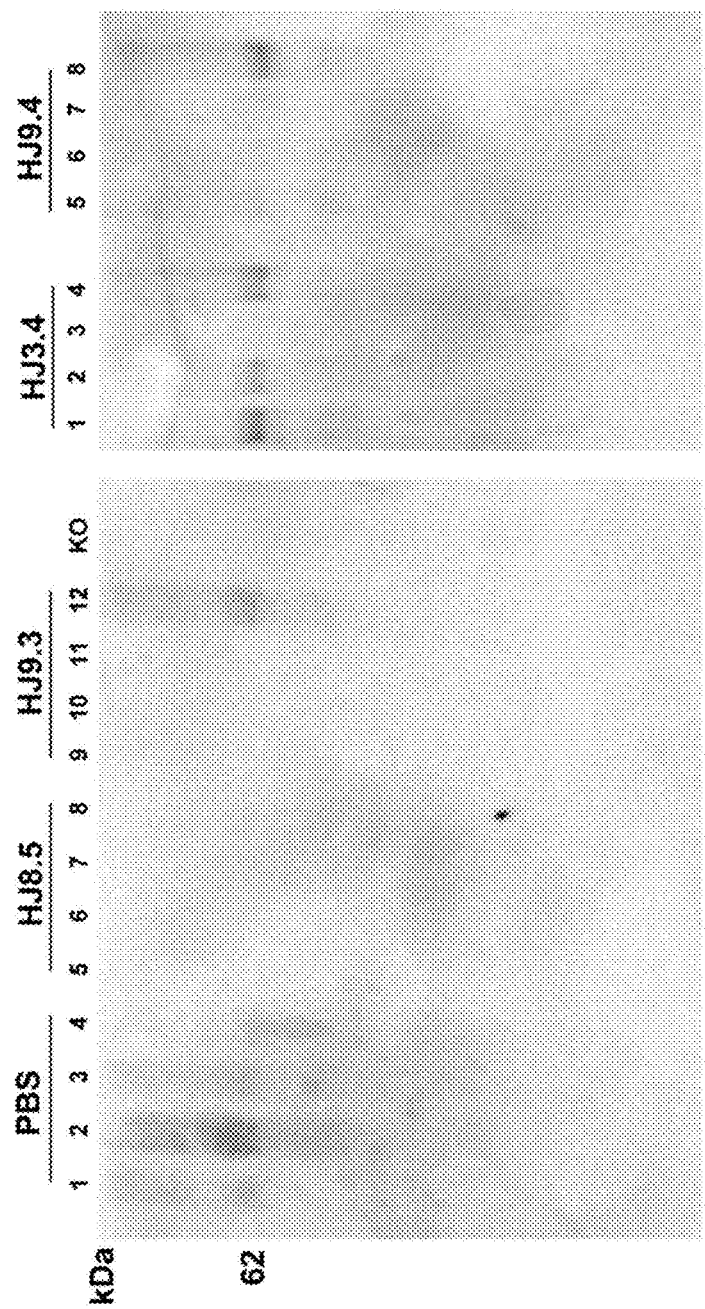
Figure 42:
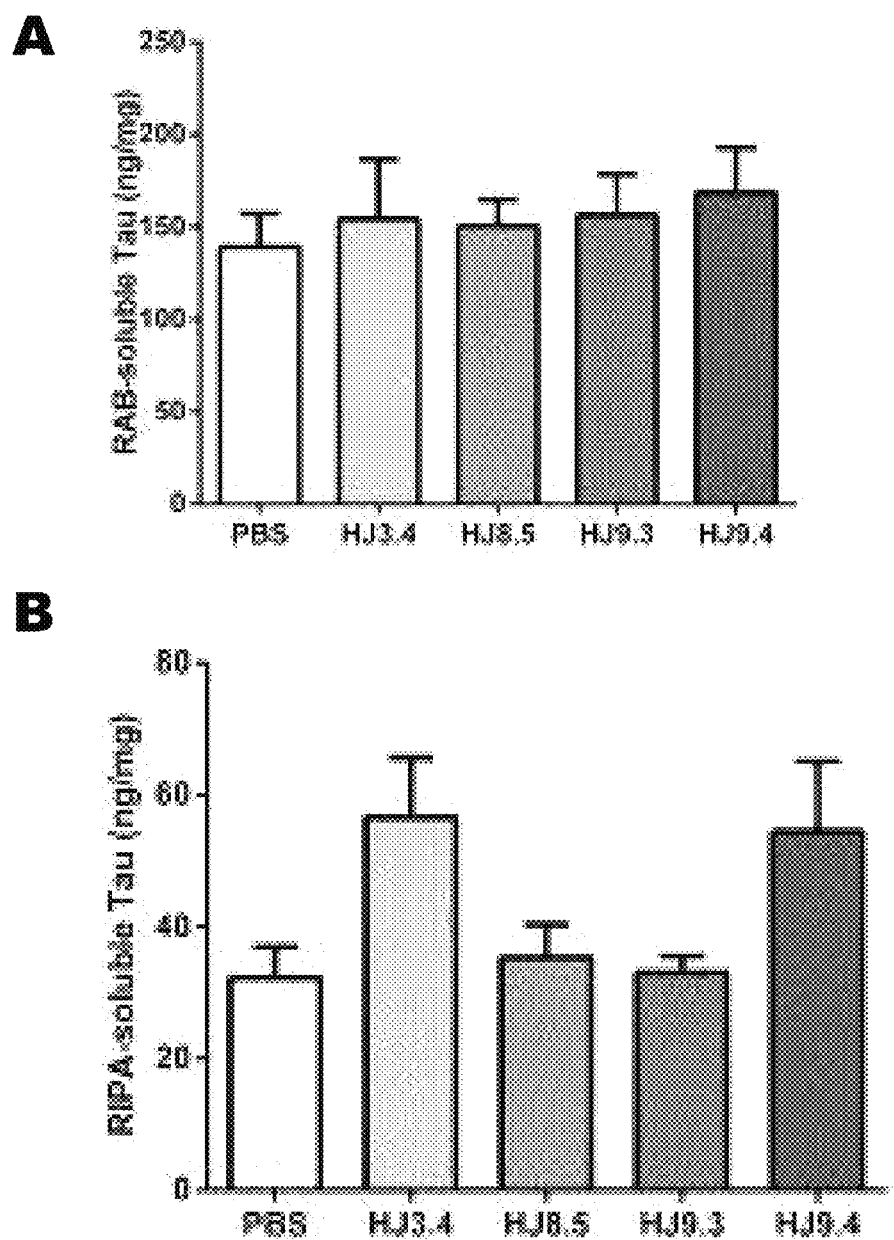
FIG. 42. Insoluble tau levels are reduced by antibodies HJ8.5 and HJ9.3 in P301S mice. The cortex of all the treated mice [PBS (N=16), HJ3.4 antibody (N=8) HJ8.5 (N=13), HJ9.3 (N=15), HJ9.4 (N=13)] were sequentially extracted by RAB (A), RIPA (B) and 70% FA (C) and their tau levels were quantified by ELISA. There were no statistical differences in soluble tau levels in RAB and RIPA fractions between the groups. However, there was a significant decrease of insoluble tau levels in 70% FA fractions in the HJ8.5 and HJ9.3 anti-tau antibodies treated mice compared to the PBS or HJ3.4 antibody treated groups. Insoluble tau levels in the HJ9.4 antibody treated mice were not different from the control groups (**$p<0.01$). Levels of human tau (D), mouse tau (E) and phospho tau at Ser202 and Thr205 (F) levels were assessed in 70% FA fractions by specific anti-human, anti-mouse, or anti-phospho tau antibodies by ELISA (n=6 mice per treatment group). There was a decrease in human tau levels in all groups of anti-tau antibody treated mice and no change in mouse tau levels. In 70% FA fractions, we also found that phospho tau at Ser202 and Thr205 as detected by AT8 reactivity was reduced in anti-tau antibody treated mice compared to controls, similar to total human tau.
Figure 42:
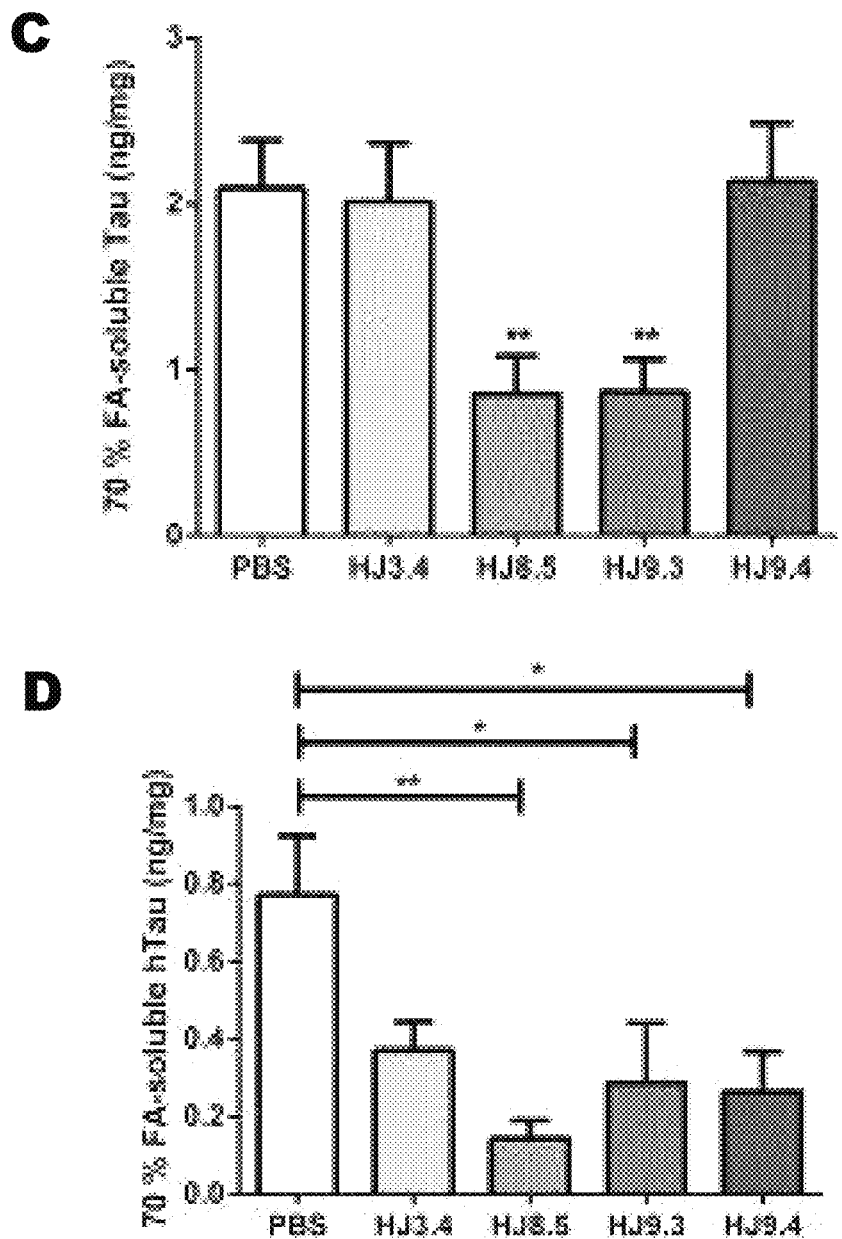
Figure 42:
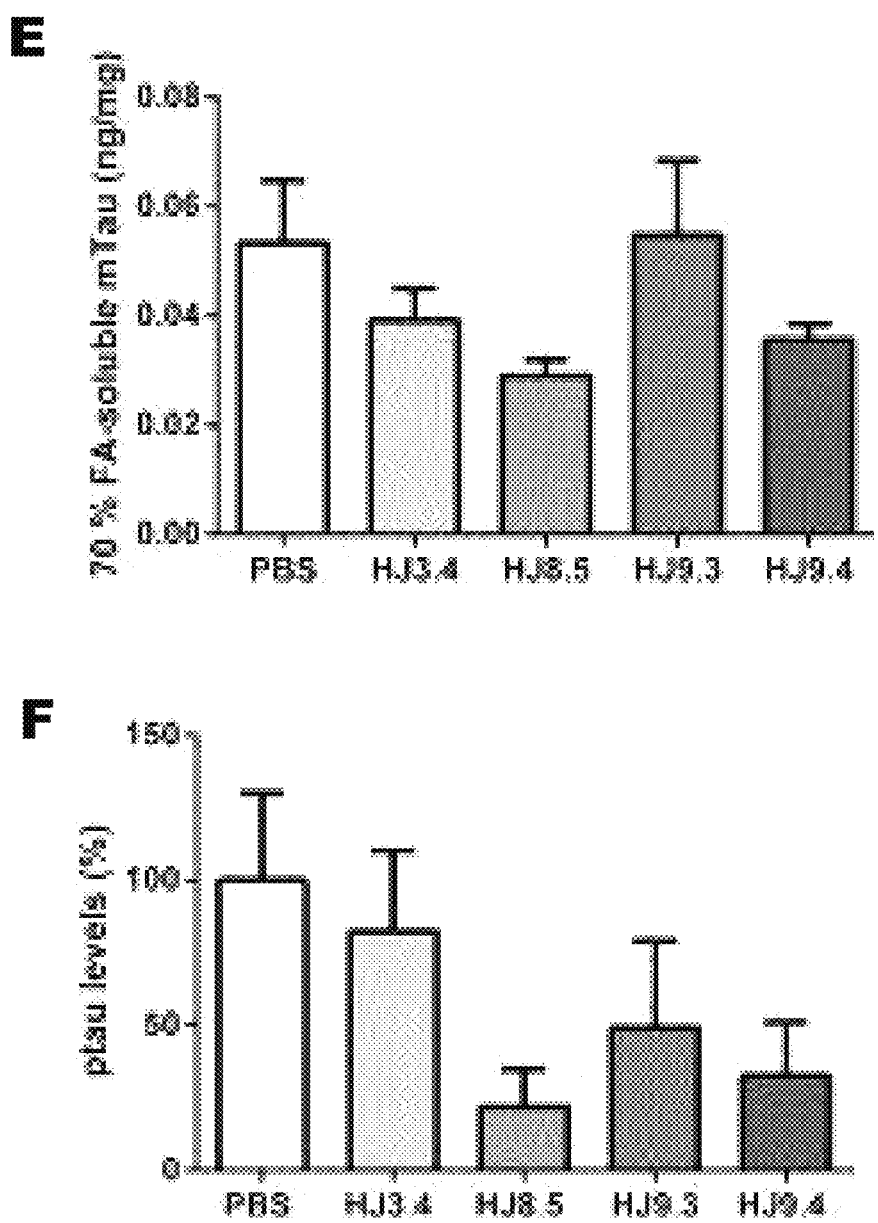

To determine the level of soluble and insoluble tau in the cortex, sequential biochemical extraction with RAB (aqueous buffer), radio immunoprecipitation assay (RIPA)(detergent buffer), and 70% formic acid (FA) were performed to solubilize the final pellet. Total tau was quantified by ELISA with anti-tau antibody HJ8.7, which detects both human and mouse tau with the same $K_D$ (0.34 pM). The possibility that the treatment antibodies would interfere with the ELISA was excluded by spiking positive control samples with these antibodies prior to analysis and observing no interference (data not shown). All mice that were assessed by pathological analysis in FIG. 37 were analyzed. Total tau levels in the RAB (FIG. 42A) or RIPA (FIG. 42B) soluble fractions were similar among all groups. The detergent-insoluble/70% FA soluble fractions were analyzed by neutralizing the samples prior to ELISA and western blot. Every animal studied was analyzed, and it was found that HJ8.5 and HJ9.3 decreased detergent-insoluble tau by >50% vs. controls (FIG. 42C). Representative samples (n=4 from each group) illustrate by western blot decreased levels of insoluble tau in mice treated with HJ8.5 and HJ9.3 (FIG. 40C). Insoluble tau levels were no different in HJ9.4-treated groups versus PBS or HJ3.4. Human and mouse tau were also assessed specifically in the detergent-insoluble/70% FA soluble fractions in N=6 mice per group in which the mean AT8 staining reflected the mean values of results in FIG. 37. There was significantly more human tau than mouse tau in the 70% FA soluble fraction, and the antibodies significantly lowered human but not mouse tau in this fraction (FIGS. 42D and 42E). In these same samples, levels of AT8 immunoreactive signal were assessed by ELISA. The AT8 signal was lower in the antibody treated samples (FIG. 42F), similar to what was seen for total tau in this fraction.

Figure 43:
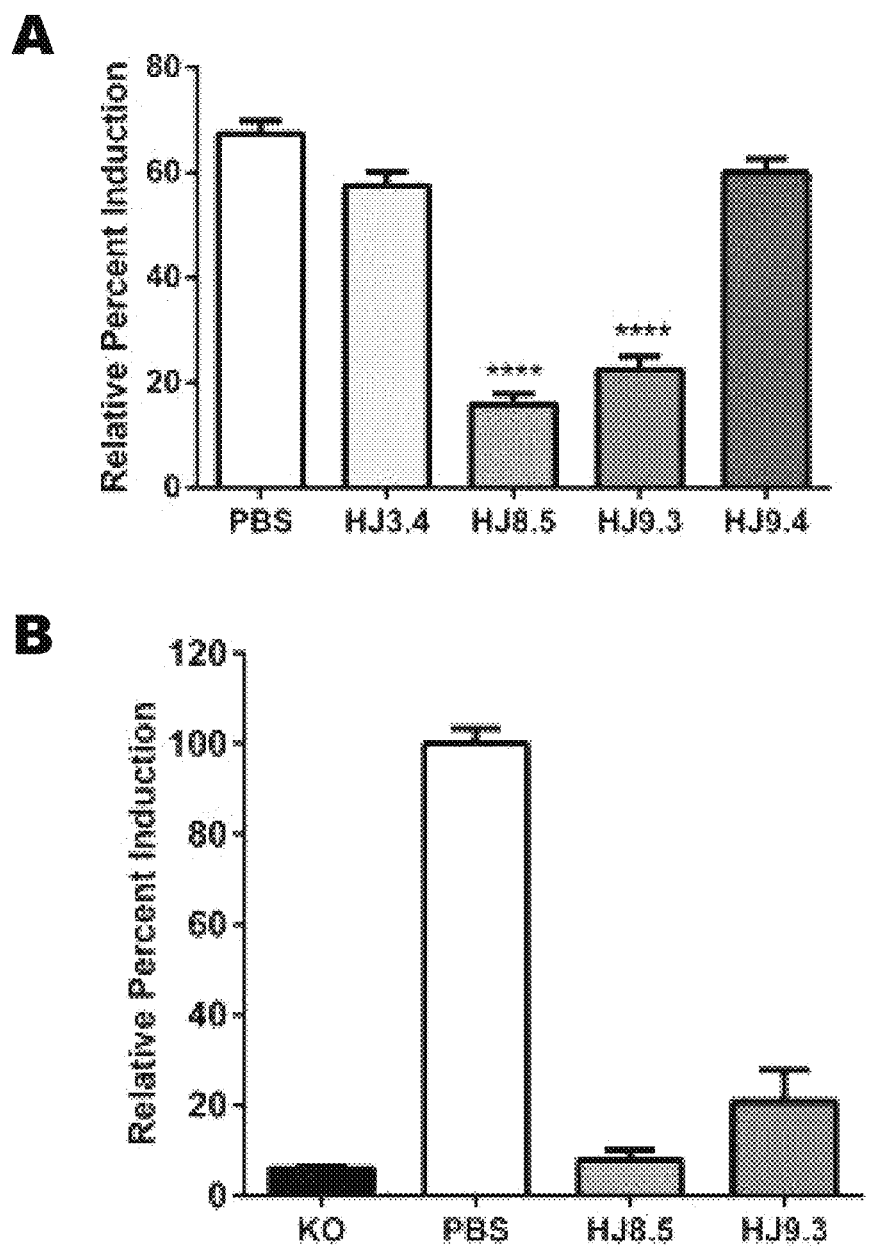
FIG. 43. Anti-tau antibody treated P301S mice have decreased tau seeding activity in cortical extracts as detected by FRET assay. (A) Tau seeding activity was measured with RAB soluble fractions of all PBS (N=16), HJ3.4 (N=8), HJ8.5 (N=13), HJ9.3 (N=15), and HJ9.4 (N=13) treated mice on HEK293 cells by FRET assay. HEK293 cells were co-transfected with RD (ΔK280)-CFP and RD (ΔK280)-YFP. 18 hrs later, RAB soluble fractions were added to cells. Seeding activity was significantly reduced in HJ8.5, and HJ9.3 antibody treated mice compared to the PBS or HJ3.4 antibody treated mice. RAB soluble fractions from HJ9.4 antibody treated mice did not have decreased seeding activity compared to the PBS or HJ3.4 antibody RAB soluble fractions (*$p<0.001$, Values represent mean±SEM). (B) RAB soluble fractions were immunoprecipitated from tau knockout, PBS, or anti-tau antibody treated mice. Elution of any seeding activity from the antibody/bead complexes was measured by FRET assay. There was significantly less seeding activity observed in HJ8.5 and HJ9.3 antibody treated mice versus PBS-treated mice (**$p<0.0001$, values represent mean±SEM). (C) 70% FA fractions of 9 month old P301S brain cortex region of all treated groups analyzed by ELISA showed a strong correlation with FRET analysis performed with the RAB soluble fractions. (D) Comparison between tau levels (X-axis) and seeding activity (Y-axis) present in RAB soluble fractions of 9 month old P301S brain cortex of all treated mice assessed. There was no significant correlation between these 2 measures. (E) Tau species in the RAB soluble fractions of 3 month old knockout (KO), 3 month old wild type (WT), 3 month old P301S, and 9 month old PBS-treated P301S mice were separated on SDD-AGE, followed by western blotting. Polyclonal mouse anti-tau antibody was used for detecting tau species. High molecular weight tau species present in the RAB soluble fraction in both 3 month old P301S mice and larger amounts present in 9 month old P301S mice.
Figure 43:
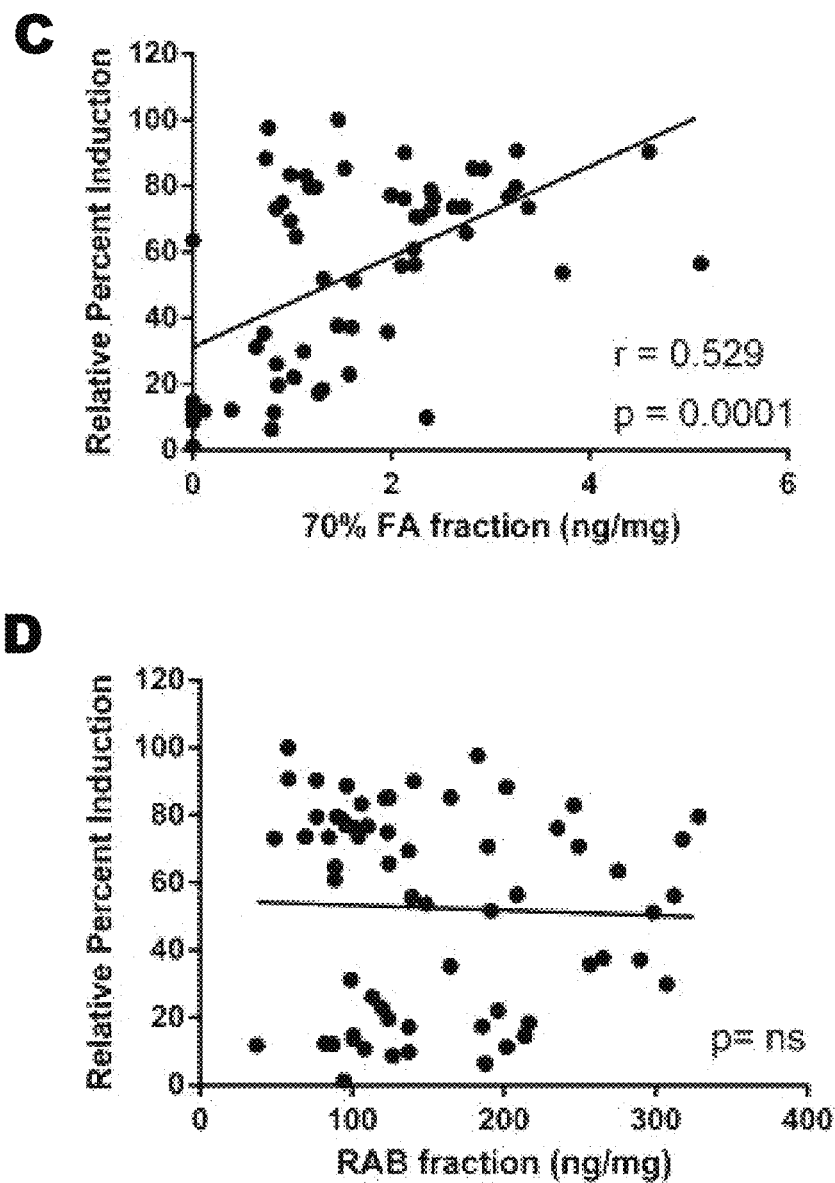

It was hypothesized that a reduction of tau aggregation in brain would correlate with a reduction in seeding activity. Thus, the cellular biosensor assay was used to test for P301S brain seeding activity in the cortical RAB soluble fractions from the different treatment groups. Prior data by the inventors assessing ISF tau in P301S mice suggested the possible presence of extracellular tau aggregates in equilibrium with both the biochemically soluble and insoluble pools of tau (Yamada et al., 2011; J Neurosci 31, 13110-13117). First, intracellular aggregation of RD(ΔK)-CFP/YFP was assessed after treating the cells with lysates from mice treated with PBS or HJ3.4. Lysates from these groups strongly induced FRET signal (FIG. 43A). Markedly less seeding activity was observed in lysates from the cortical tissue of mice treated with HJ8.5 and HJ9.3 (FIG. 43A). This was not due to residual antibody in the brain lysates, because immunoprecipitation of the brain lysates followed by elution of seeding activity from the antibody/bead complexes produced the same pattern (FIG. 43B). Thus HJ8.5 and HJ9.3 reduce seeding activity in the P301S tau transgenic mouse brain. HJ9.4 did not significantly reduce seeding activity (FIG.

Figure 43E:

43A). Seeding activity strongly correlated with the amount of detergent-insoluble/formic acid-soluble tau detected by ELISA (Pearson's r=0.529, p=0.0001) (FIG. 43C), but did not correlate with total tau in RAB fractions (FIG. 43D). It was hypothesized that seeding activity is due to tau aggregates present in the RAB soluble fraction. To test for this, Semi-Denaturing Detergent-Agarose Gel Electrophoresis (SDD-AGE) was performed followed by Western blot. In addition to tau monomer, higher molecular weight tau species present in 3 month old P301S mice and a larger amount present in 9 month old P301S mice was observed (FIG. 43E). A component of these higher molecular weight species likely constitutes the seeding activity detected in the FRET assay and may be in equilibrium with the tau present in the detergent-insoluble/formic acid-soluble fraction.

Example 15

Anti-Tau Antibodies Rescue Contextual Fear Deficits

Figure 44:
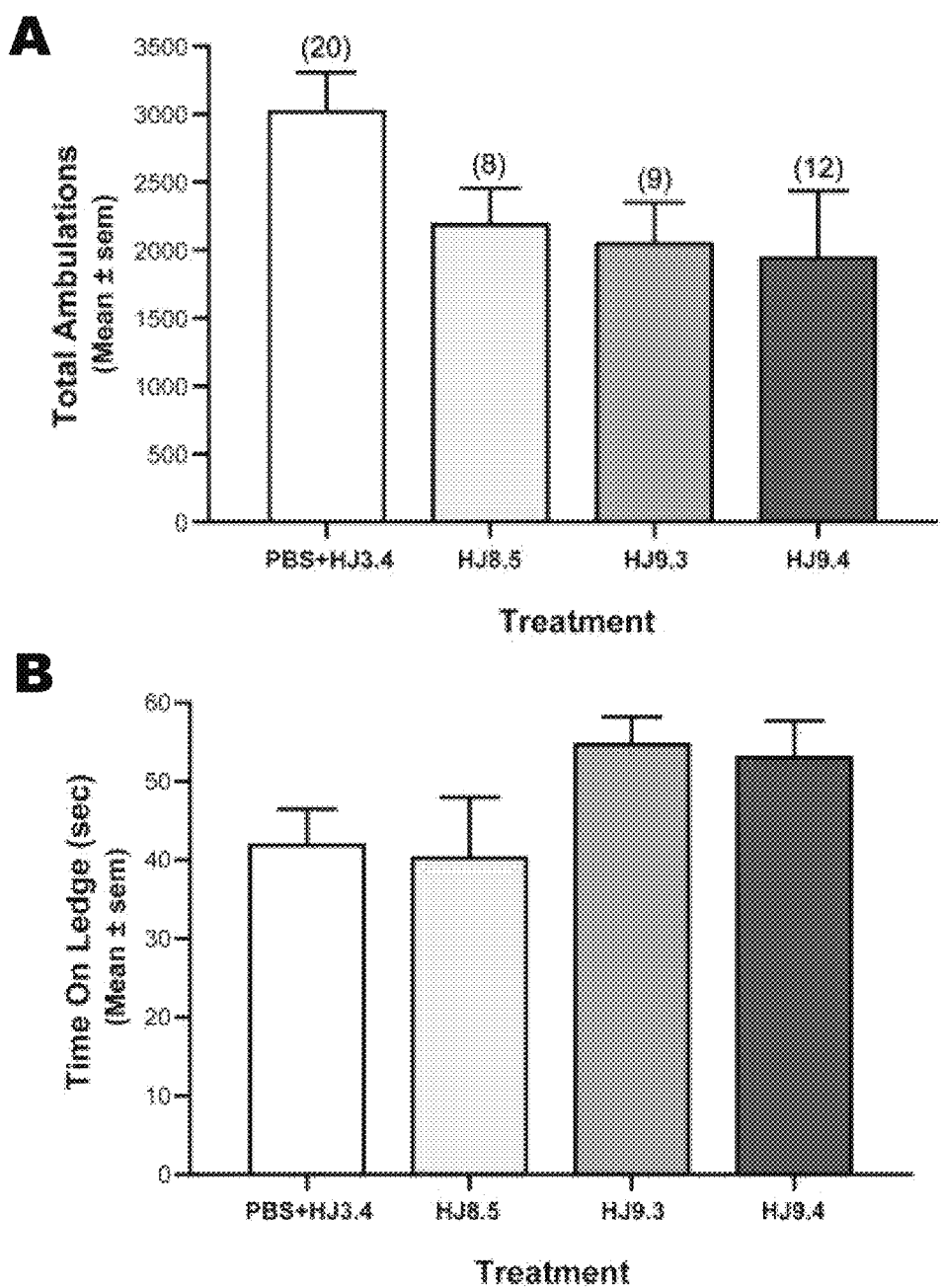
FIG. 44. Groups did not differ significantly in terms of locomotor activity, sensorimotor function or on the auditory cue component of the conditioned fear test. The results of rmANOVAs failed to reveal significant main or interaction effects involving Treatment for total ambulations in the holeboard test (A), for the ledge test (B) or any other of the sensorimotor measures (not shown), or on the accelerating rotarod (C). Data from the altered context baseline on day 3 of conditioned fear testing yielded a significant effect of Treatment (*$p=0.027$) and subsequent comparisons showed that a large portion of this effect was due to significant differences between the HJ9.4 mice and the PBS+HJ3.4 control group ($p=0.0007$). (D). However, no significant main or interaction effects of Treatment were found following an rmANOVA on the auditory cue data (min 3-10) suggesting that the freezing levels were not significantly different among the groups during this time (E). To assess whether activity levels may have had an effect on freezing during the contextual fear test on day 2, we computed Pearson's correlation coefficient (r) between total ambulations measured during the holeboard test versus % time spent freezing during the contextual fear test and found that they were not significantly correlated (p=0.39) (F).
Figure 44:
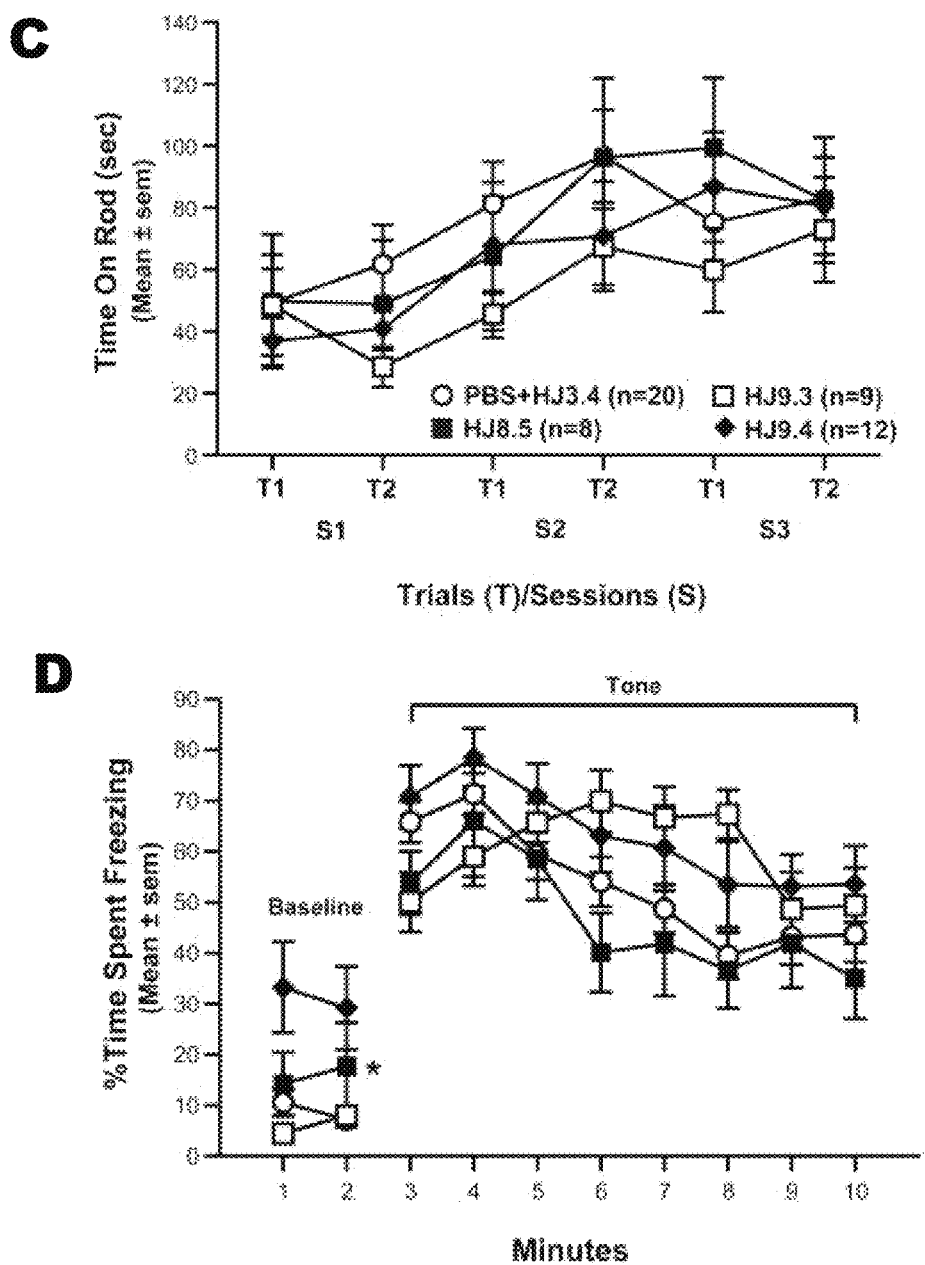
Figure 44:
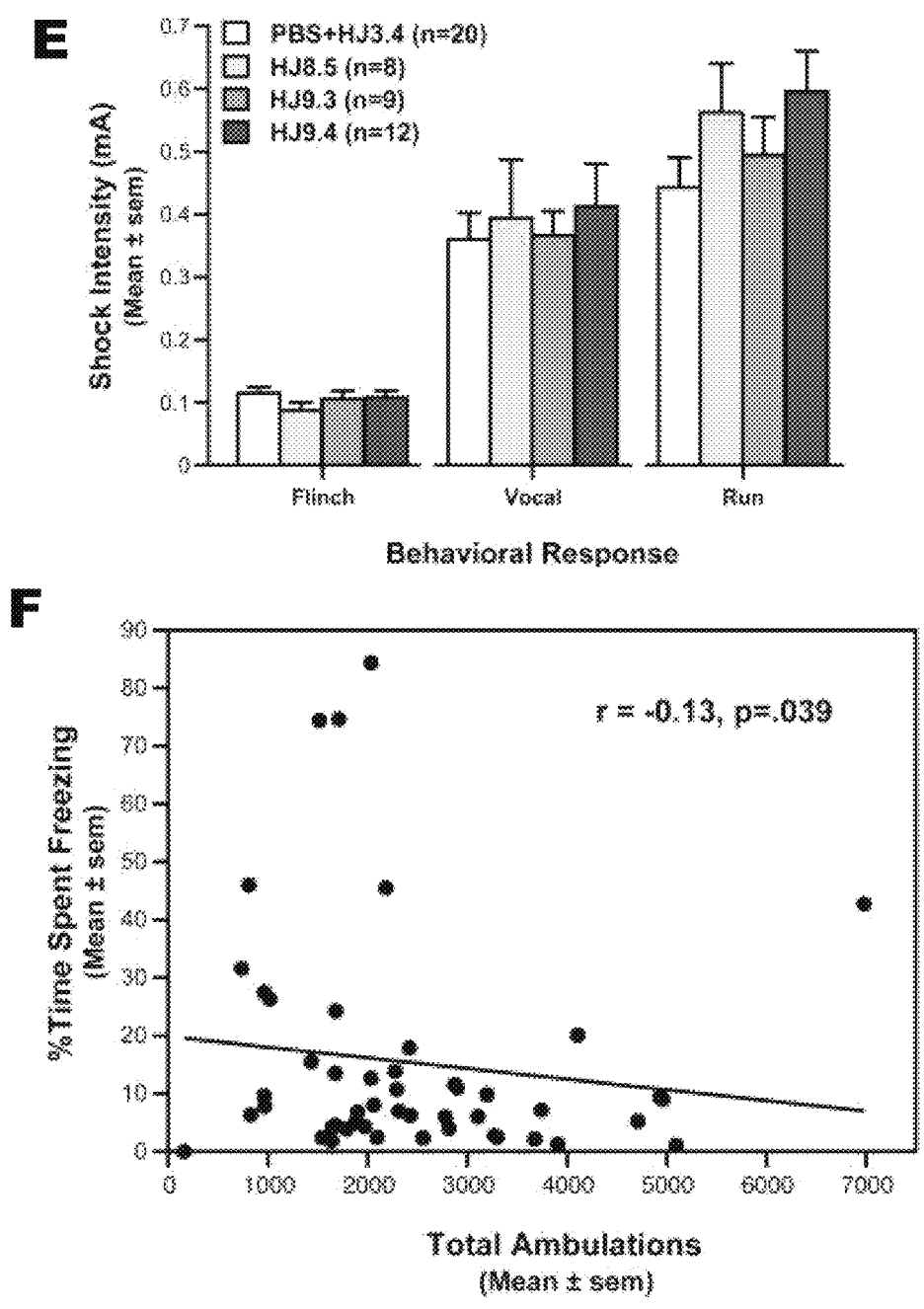

In studies of P301S Tau transgenic mice at 9 months of age, the control and anti-tau antibody treated groups were compared in a variety of behaviors. The groups did not differ in locomotor activity, exploration, or measures of sensorimotor function (FIG. 44). The ability of the anti-tau antibody treatments to rescue cognitive deficits in P301S mice was evaluated by assessing the performance of the mice on the conditioned fear procedure. On day 1, all four treatment groups of mice exhibited similar levels of baseline freezing during the first two minutes in the training chamber. This was confirmed by rmANOVA, which failed to reveal any significant overall main effects or interactions involving treatment (FIG. 45A). In addition, all four groups showed similar levels of freezing during the tone-shock (T/S) conditioned stimulus-unconditioned stimulus (CS-US) pairings (FIG. 45A). The general lack of differences in freezing levels between groups across the three T/S pairings was documented by a non-significant effect of Treatment and a non-significant Genotype by Minutes interaction.

In contrast to the absence of differences among groups during testing on day 1, there were robust differences in freezing levels from the contextual fear test (form of associative learning) conducted on day 2 between two of the anti-tau antibody groups and the PBS+HJ3.4 control mice (FIG. 45B). Subsequent planned comparisons indicated that the HJ8.5 mice showed significantly elevated freezing levels averaged across the 8-minute test session (FIG. 45C) compared to the PBS+HJ3.4 control group, [F(1,45)=8.30, p=0.006], as did to a lesser extent the HJ9.4 mice, [F(1,45)=5.60, p=0.022]. Thus, HJ8.5 appeared to have a stronger effect overall in preserving associative learning.

Discussion for Examples 9-15

One model for the pathogenesis of the tauopathies holds that aggregates produced in one cell escape or are released into the extracellular space to promote aggregation in neighboring or connected cells. It was observed that selection of therapeutic antibodies that specifically block tau seeding activity from brain lysates predicts potent in vivo responses at least as strong if not stronger than prior reports of active or passive tau vaccination. Experiments were began with a cellular biosensor assay that is sensitive to the presence of extracellular tau aggregates. It was found that brain lysates from P301S transgenic mice contained seeding activity that could induce further intracellular aggregation. After screening a panel of anti-tau antibodies, three were selected with variable activities in blocking tau seeding activity. These antibodies were infused ICV over three months into P301S tauopathy mice, beginning at a time when pathology had initiated (6 months). Infusion of the antibodies resulted in appreciable concentrations of antibody present in both CSF and serum, consistent with previous reports of efflux of antibodies from the CNS to the periphery. Treatment with HJ8.5, the most potent antibody in vitro, profoundly reduced tau pathology, strongly decreasing it from the neuropil. This effect was detected with multiple independent stains, biochemical analyses of insoluble tau, and by analysis of residual tau seeding activity present in brain lysates. Further, this treatment improved the one behavioral deficit detected in this model. All antibodies block tau aggregate uptake into cells, and none is observed within cells in the presence or absence of extracellular aggregates in the assays. The efficacy of these antibodies implies a clear role for extracellular tau in the pathogenesis of neuropathology that was previously thought to be cell-autonomous. Further, this work extends prior findings by the inventors, which suggest that aggregate flux may occur in the setting of intracellular pathology, raising the possibility of therapies that can assist in aggregate clearance by targeting extracellular species. Finally, this work has important implications for the design of therapeutic antibodies, and suggests that targeting seeding activity in particular may produce the most effective agents.

Mechanism-Based Antibody Therapy

Several prior active and passive peripheral immunotherapy approaches against tau have also reduced tau pathology and improved behavioral deficits, but the underlying rationale for antibody choice was based either on a phospho-epitope, reactivity with neurofibrillary tangles, or was not stated. One tau immunization study, performed by vaccinating mice with full length tau, induced pathology in wild type mice. However, subsequent active immunization approaches with phospho-tau peptides in tau transgenic models reduced tau pathology and showed behavioral improvement. In a passive immunization study, JNPL3 tau transgenic mice were administered the PHF1 antibody intraperitoneally at 2-3 months of age, prior to the onset of tauopathy. PHF-1 targets a pathological form of abnormally phosphorylated tau. Treatment reduced tau pathology and improved behavior. However, while it decreased insoluble phosphorylated tau, total insoluble tau did not change. In another passive immunization study, JNPL3 and P301S mice (at age 2-3 months, prior to the onset of tauopathy) were peripherally administered the PHF1 or MC1 antibody, which targets an aggregate-associated epitope. Both treatments improved tau pathology and delayed the onset of motor dysfunction. In these prior studies, the mechanism of action of the antibodies was not clear, and none was explicitly tested. Indeed, some proposed an intracellular mechanism. Moreover, no study appears to have produced the magnitude of reduction in tau pathology described in the examples provided herein, with the caveats that antibodies were infused into the CNS while the other studies utilized peripheral infusion; and different animal models were utilized.

This study was explicitly designed to test a prediction that extracellular tau seeds are a key component of pathogenesis. The study began with a selection process to pick antibodies capable of blocking tau seeding in vitro, purposely testing agents with a range of predicted activities. All antibodies tested in vivo effectively block aggregate uptake and seeding, providing a basis for their observed activity. In addition, correlation of antibody affinity, epitope, isotype, glycosylation, and ability to bind phosphorylated forms of tau may be important to assess in future studies. This is also the first study to report the effects of direct, intra-CNS infusion of anti-tau antibodies. Despite the fact that the antibodies utilized each target different tau epitopes and none targets phospho-tau, 2 of 3 strongly reduced abnormal tau load both immunohistologically and biochemically, and two significantly improved memory, one to a greater extent than the other. Effects on tau pathology also correlated very well with a reduction in intrinsic seeding activity.

HJ8.5 and HJ9.3 strongly decreased pathological tau seeds in vivo. A strong reduction in tau pathology might occur by preventing induction of tau aggregation in neighboring cells. While HJ9.4 did not decrease pathology as potently, it did decrease tau pathology in the amygdala. The variation in effectiveness in different brain regions among the antibodies may be due to the formation of region-specific aggregate conformers for which the antibodies have subtle differences in binding affinity.

Once extracellular tau aggregates are sequestered by anti-tau antibodies in vivo, their metabolic fate is not yet clear. After 3 months of antibody administration, reduced microglial activation were found, presumably due to less tau-related pathology and neurodegeneration. However, this could be due to more efficient clearance of extracellular aggregates, with a reduction in related microglial activation. Several months of passive immunization with anti-Aβ antibodies has also been noted to reduce microgliosis. The mechanism by which antibody/tau complexes are cleared in vivo, and the mechanism via which they decrease tau pathology, remains to be definitively clarified. It has been suggested that immunization with anti-α-synuclein antibodies clears α-synuclein aggregates by promoting lysosomal degradation. A recent study with anti-α-synuclein antibodies showed that the antibodies targeted α-synuclein clearance mainly via microglia, presumably through Fc receptors. Neurons express Fcγ receptors, and may be able to internalize IgG complexed with antigen by high affinity FcγRI receptor. Internalized tau antibodies may also contact tau in endosomes and eventually induce clearance of intracellular tau aggregates by the endosomal/autophagy-lysosomal system. Though the anti-tau antibodies used in the study described herein can bind extracellular tau assemblies, no evidence of significant localization within cells was found. That does not, however, rule out the possibility that cells in vivo take up antibody/tau complexes to influence tau aggregate clearance as well as inflammation. For example, it has recently been shown that antibodies complexed with viruses can bind to the cytosolic IgG receptor TRIM21, targeting the antibody/virus complex to the proteasome. In addition, antibodies bound to TRIM21 were shown to activate immune signaling. While interaction with antibodies/noninfectious antigen complexes with TRIM21 has not yet been shown, it may be interesting to determine if such a mechanism is relevant to the anti-tau antibodies. Interestingly, there is also evidence in the P301S model of tauopathy that the innate immune system is activated prior to the development of significant tau pathology, and that early immunsuppresion attenuates tau pathology. It may be possible that antibodies capture tau aggregates induced by inflammation, reducing subsequent aggregate-induced inflammation and disease progression.

Extracellular Tau and Spreading of Tau Pathology

The work presented herein implicitly tests the role of extracellular tau in pathogenesis. It is now abundantly clear that extracellular tau aggregates can trigger fibril formation of native tau inside cells, whether their source is recombinant protein or tau extracted from mammalian cells. A role for free tau aggregates was originally hypothesized (i.e. not membrane-enclosed) as mediators of trans-cellular propagation based on our prior work, in which HJ9.3 added to the cell media blocked internalization, and immunoprecipitated free fibrils (Kfoury et al., 2012; J Biol Chem 287, 19440-19451).

In animal models, tau aggregates can apparently spread from one region to another (e.g. entorhinal cortex to neurons downstream in the dentate gyrus and hippocampus). The inventors have found that monomeric tau is constantly released in vivo into the brain interstitial fluid even under non-pathological conditions (Yamada et al., 2011; J Neurosci 31, 13110-13117). The inventors also found that exogenous aggregates would reduce levels of soluble ISF tau, suggesting that seeding and/or sequestration phenomena can occur in this space (Yamada et al., 2011; J Neurosci 31, 13110-13117). Taken together, abundant evidence supports the concept that extracellular tau aggregates form, and can be taken up by adjacent cells, connected cells, or possibly back into the same cell, thereby increasing the burden of protein misfolding. This evidence makes a clear prediction: therapy that captures extracellular seeding activity should ameliorate disease. The findings described in the examples presented herein are consistent with this idea.

The Role of Tau Flux in Pathogenesis

It would not be predicted a priori that a mouse model such as P301S, which drives mutant tau expression via the prion promoter in virtually all neurons, should benefit from antibody treatments that block trans-cellular propagation of aggregation. In theory, pathology could occur independently in all neurons that express this aggregation-prone protein. However, prior work by the inventors in tissue culture suggested a role for flux of tau aggregates, since HJ9.3 added to the cell media increased the steady state level of aggregates over time. While the model of aggregate flux requires further testing, the results presented herein are consistent with this idea, since antibody treatment profoundly reduced intracellular tau pathology. It is predicted that antibodies that block tau uptake may create a "sink" in the extracellular space that may promote clearance by another mechanism, possibly involving microglia.

Therapeutic Antibodies and Targeting Seeding Activity

The pharmaceutical industry is devoting increasing efforts to develop therapeutic antibodies that target aggregation-prone proteins that accumulate within cells. The principal criteria have been that the antibodies will bind epitopes known to accumulate in diseased brain. This approach may or may not lead to antibodies with optimal activity in vivo. The examples herein supports a new model of therapeutic antibody development that emphasizes efficacy in blocking the seeding activity present in the brain. Using this approach, antibodies with higher apparent efficacy than has previously been reported were identified. In an extension of the prion hypothesis, it is further proposed that distinct tau aggregate "strains" may predominate in patients with different types of tauopathy, and these may have unique sensitivities to different antibodies. In any case, the use of sensitive in vitro assays of antibody efficacy as described here may allow much more efficient development and optimization of antibody-based therapies.

The strong protective effect of the anti-tau antibodies, particularly with the HJ8.5 antibody, suggests that this type of approach should be considered as a treatment strategy for human tauopathies. While chronic administration of antibodies via an ICV approach may be possible, in future studies, it may be important to determine the PK/PD response with peripheral administration of these antibodies when given in both a prevention and treatment mode. In addition, the tau seeding assay may be useful to monitor target engagement by the antibodies.

Experimental Procedures for Examples 9-15

Antibodies

HJ9.3 and HJ9.4 mouse monoclonal antibodies were raised by immunizing tau knockout mice (The Jackson laboratory) against mouse tau, and HJ8.5 and HJ8.7 monoclonal antibodies were raised by immunizing tau knockout mice against human tau. HJ9.3, HJ9.4 and HJ8.7 monoclonal antibodies recognize both mouse and human tau. However, HJ8.5 monoclonal antibody binds only to human tau (epitope is at residues 25-30 [NCBI reference sequence: NP_005901]). HJ9.3 antibody recognizes the RD region of tau (epitope at residues 306-320). HJ9.4 antibody recognizes the N-terminal region of tau (epitope is at residues 7-13). As a control antibody, HJ3.4 mouse monoclonal antibody was used, which recognizes the N-terminal region of the human Aβ sequence (epitope at residues 1-16). HJ8.5, 9.3, and 9.4 monoclonal antibodies are of the IgG2b isotype. Rabbit polyclonal tau antibody (ab64193, epitope located at repeat domain region) was purchased from Abcam. Mouse monoclonal biotinylated BT-2 antibody, recognizes human and mouse tau (epitope at residues 194-198) and was purchased from Pierce. Rat anti-mouse monoclonal CD68 antibody was purchased from AbD SeroTec. Biotinylated AT8 antibody was purchased from Thermo scientific.

Surface Plasmon Resonance

Surface plasmon resonance experiments were performed on BIAcore 2000 surface plasmon resonance instrument (GE Healthcare-BIAcore). Biacore sensor chip CM-5 was activated by using EDC (1-ethyl-3-(3-dimethylaminopropyl)-carbodiimide) and NHS (N-hydroxysuccinimide) in a 1:1 ratio for 7 minutes. The sensor chip surface was saturated by immobilizing 5 µg/ml of recombinant human or mouse tau or human tau fibrils in 10 mM Sodium acetate pH 3.5 with a flow rate of 5 µl/min. The remaining unbound area was blocked by 1 M Ethanolamine pH 8.5. For reference, one flow cell is activated with NHS and EDS, followed by blocking with 1M ethanolamine. Then all the anti-tau antibodies were injected at different concentrations (0.11, 0.23, 0.46, 0.9, 1.8, 3.7, 7.5 µg/ml) in filtered, degassed 0.01 M Hepes buffer, 0.15 M NaCl, 0.005% surfactant P20, pH 7.4 at a flow rate of 10 µl/min. All samples were run in duplicate. After each run with a single antibody concentration, the surface of the chip was totally regenerated by using 10 mM Glycine pH 1.7, to remove the bound antibody to tau, without disturbing the immobilized tau on the chip. Data analysis was performs by using BIAevaluation software (GE healthcare-BIAcore).

Tau Fibrilization

8 µM recombinant full length human tau was pre-incubated with 2 mM dithiothreitol for 45 min at room temperature then 10 mM HEPES and 100 mM NaCl and 8 µM heparin were added for a total volume of 200 µl followed by incubation for 7 day at 37° C. to form fibrils. After fibril formation, the remaining monomers of tau in the sample were separated by using 100 kDa Microcon centrifugal filters according to manufacturer's instructions (Millipore).

IP and ICV Administration of Biotinylated HJ8.5 Antibody

Mouse monoclonal HJ8.5 antibody was biotinylated according to the manufacturer's instructions (Sulfo-NHS-LC-Biotin kit, Pierce). Biotinylated HJ8.5 (HJ8.5B) was administered by interperitoneal injection (IP) at 50 mg/kg in 5-6 month old P301S mice (n=3). After 48 hrs, mice were sacrificed. Serum and CSF was collected and stored at −80° C. until use. HJ8.5B was also administered by intracerebroventricular injection (ICV) by surgically implanted osmotic pumps into the left lateral ventricle of 5-6 month old P301S mice (n=3). This antibody was continuously infused for 48 hrs. After 48 hrs, mice were sacrificed. Serum and CSF was collected and stored at −80° C. until use.

Intracerebroventricular (ICV) Injection Procedure

ICV infusions were performed by Alzet osmotic pumps, 2006 model (Durect). The age of the mice was 6 months at the time of surgery. Before the surgery, an L-shaped cannula was attached to tubing (3 cm, long), which was then attached to Alzet pumps carrying antibody or vehicle (phosphate buffer saline—PBS, pH 7.4). This assembly was pre-incubated in PBS for 60 hrs at 37° C. to activate the pump prior to placement into the lateral ventricle. The assembly was surgically implanted with the use of a stereotactic apparatus (David Kopf Instruments) into the left lateral ventricle of each mouse at 0.4 mm anteroposteriorly to bregma, 1.0 mm lateral to midline, and 2.5 mm dorsoventral to the surface of the brain under isoflurane anesthesia. Alzet osmotic pumps were placed under the skin by making a subcutaneous pocket with a curved, blunt ended scissors. Each implanted cannula was secured with dental cement along with small anchor stainless steel screws. After the cement dried, the skin was sutured. The antibody (2 mg/ml) or PBS in the pump was continually infused into the left lateral ventricle of the brain. These osmotic pumps carry a maximum of 200 µl of volume, and they pump with a flow rate of 3.6 µl/day resulting in an infusion of 7.2 µg of antibody per day. In each mouse, osmotic pumps were changed once after 6 weeks of infusion. The solution remaining in the Alzet pump was collected after its removal from each mouse and stored at −80° C. At the age of 9 months, all mice were sacrificed. All surgically implanted mice were housed singly.

Histology

After 12 weeks of the treatment, P301S mice were anesthetized intraperitoneally with pentobarbital 200 mg/kg), followed by perfusion with 3 U/ml heparin in cold Dulbecco's PBS. The brain was removed and cut into two hemispheres. The left side of the brain was fixed for 24 hrs in 4% paraformaldehyde and transferred to 30% sucrose in PBS and stored at 4° C. prior to freezing in powdered dry ice and stored at −80° C. Half brains were cut coronally into 50 µm sections with a freezing sliding microtome and all sections were stored in 24 well plates with cryoprotectant solution (0.2M phosphate buffered saline, 30% sucrose, 30% ethylene glycol) at −20° C. until use. The hippocampus and cortex were dissected from the freshly perfused right hemisphere of each brain for biochemical analysis. All the dissected tissues were stored at −80° C. until analyzed. The placement of the cannula into the left lateral ventricle was verified by mounting brain sections 300 µm apart and stained by cresyl violet as previously described (Holtzman et al., 1996; Ann Neurol 39, 114-122). The stained tissues were scanned using a NanoZoomer digital pathology system (Hamamatsu Photonics).

Cell Culture/Seeding Assay: P301S Brain Lysates and Antibody Treatment

HEK293 cells were cultured in Dulbecco's Modified Eagle Medium (DMEM) supplemented with 10% fetal bovine serum, 100 µg/mL penicillin and 100 µg/mL streptomycin. Cultures were maintained in a humidified atmosphere of 5% CO2 at 37° C. For transient transfections, HEK293 cells were plated at 250,000 cells/well in a 12-well plate in optimem medium and transfected using Lipofectamine 2000 reagent and 600 ng of appropriate DNA constructs (Invitrogen) according to manufacturer's recommendations. Co-transfected cells received a combination of 150 ng of RD(ΔK280)-CFP constructs and 450 ng of RD(ΔK280)-YFP constructs. 15 h later, cells were harvested with 0.05% trypsin for 3 minutes at 37° C. and then re-plated in a 96-well plate in quadruplicate for 15 hrs. Then, P301S brain lysates [prepared in 1×TBS with protease (Roche) and phosphatase inhibitors (Roche)] that were pre-incubated with all anti-tau monoclonal antibodies (HJ8.5, 9.3 and 9.4) or HJ3.4 antibody (monoclonal anti-Aβ antibody) were added at various concentrations (0.125 µg/ml, 0.25 µg/ml, 0.5 µg/ml, 1 µg/ml and 2 µg/ml) for 16 hrs at 4° C. with rotation. To determine the seeding activity in the P301S mice treated for 3 months with different antibodies, RAB soluble fractions of all treated mice were also added to cells at various concentrations. Cells were cultured an additional 24 h before fixation with 4% paraformaldehyde, and FRET analysis was performed.

Immunoprecipitation

RAB soluble fractions from PBS or antibody-treated mice were incubated in the presence of mouse monoclonal anti-tau antibodies HJ9.3 and HJ8.5 cross-linked to protein-G-agarose beads (per kit recommendation-Pierce Crosslink Immunoprecipitation kit) at 4° C. with end-over-end rotation for 24 hours. In addition, RAB soluble fractions from antibody treated mice were incubated in the presence of un-conjugated protein-G-agarose beads at 4° C. with end-over-end rotation for 24 hours. 18 h later, 500 µl of binding/wash buffer (Pierce) was added to samples and centrifuged at 2000×g for 3 minutes. Supernatant was discarded, and this wash step was repeated three times. Proteins bound to beads were then eluted using a low pH elution buffer (25 µl) with incubation at room temperature for 5 minutes. Samples were then centrifuged at 2000×g for three minutes and supernatant collected. This elution step was repeated once for a total of 50 µl eluates. Tau-immunoprecipitates (IP) containing tau aggregates were reapplied to co-transfected RD(ΔK)-CFP/YFP cells at equivalent amounts to initial brain lysates experiments for further analysis with the seeding assay.

Brain Tissue Extraction

The cortex of each brain was homogenized in 30 µl/mg of RAB buffer [100 mM MES, 1 mM EDTA, 0.5 mM MgSO4, 750 mM NaCl, 20 mM NaF, 1 mM Na3VO4, supplemented by protease inhibitor (Roche) and phosphatase inhibitor (Roche)]. In brief, the samples were centrifuged at 50,000 g for 20 min at 4° C. using an Optima MAX-TL Ultracentrifuge (Beckman). The supernatants were collected as RAB soluble fractions and pellets were resuspended in RIPA buffer [150 mM NaCl, 50 mM Tris, 0.5% deoxycholic acid, 1% Triton X-100, 0.5% SDS-25 mM EDTA, pH 8.0, supplemented by protease inhibitor (Roche) and phosphatase inhibitor (Roche)], 30 µl/mg and centrifuged at 50,000 g for 20 min at 4° C. The supernatants were collected as RIPA soluble fractions. The pellets were further resuspended in 70% formic acid, 10 µl/mg and centrifuged at 50,000 g for 20 min at 4° C. The supernatants were collected as 70% formic acid fractions. All fractions were stored in −80° C. until analyzed.

Electrophoresis and Immunoblotting

Gel electrophoresis was performed under reducing conditions by 4-12% NuPAGE Bis-Tris gels (Invitrogen) followed by transfer to PVDF membrane by using IBlot apparatus (Invitrogen). 70% formic acid fractions were neutralized before loading and subjecting to gel electrophoresis by diluting 1:3 with 1:1 mixture of 10N NaOH and neutralization buffer (1 mol/L Tris base; 0.5 mol/L NaH4PO4). Pre-stained molecular weight standards "See-Blue" (Invitrogen) were included in each run. Membranes were blocked with 5% milk in Tris buffered saline (TBS) containing 0.1% of Tween 20. Then, membranes were washed 3 times for 5 minutes each. Rabbit polyclonal tau antibodies (Abcam, 1:2000) were used as primary antibodies for the detection tau in formic acid fractions. Treated mouse anti-tau antibodies collected before and after its infusion from osmotic pumps were also used as primary antibodies. The membranes were subsequently incubated with Goat anti-rabbit or Goat anti mouse secondary antibody (GE Healthcare, 1:2000). All the membranes were developed with ECL prime substrate (GE Healthcare). Bands were visualized with G:Box Chemiluminescent Imager (Syngene).

To determine the immunoreactivity of anti-tau antibodies to tau from brain homogenates, RAB soluble fractions of 9 month old P301S and 3 month old P301S mice, 3 month old wild type mice and 3 month old tau knockout mice samples were separated by SDS-PAGE followed by western blotting. Total protein of 1 µg from each RAB soluble fraction was loaded onto 4-12% NuPAGE Bis-Tris gels (Invitrogen) under reducing conditions followed by transfer to nitrocellulose membrane by using IBlot apparatus (Invitrogen). The membranes were blocked with 5% milk in TBS with 0.05% tween 20 (TBST) followed by incubation with primary antibodies (HJ8.5, HJ9.3 and HJ9.4). HRP-conjugated donkey anti-mouse IgG (1:2000, Santa cruz) was used as secondary antibody and membranes were developed using Lumigen TMA6 (GE Healthcare).

ELISA to Detect Free HJ8.5B and HJ8.5B Bound to Tau

The concentration of free HJ8.5B was determined in serum and CSF of mice 48 hrs after IP or ICV administration. Ninety-six well ELISA plates were coated with 50 ng/ml of recombinant human tau at 4° C. ELISA plates were blocked with 4% BSA at 37° C. for 1 hr. Plates were then washed 5 times followed by incubating with serum and CSF samples diluted in sample buffer (0.25% BSA in PBS, 300 nM Tris pH 7.4 supplemented with protease inhibitors) and incubated at 4° C. overnight. The next day, plates were washed 8 times with PBS followed by the addition of streptavidin-poly-horseradish peroxidase-40 (1:6000, Fitzgerald), for 1.5 hr, in the dark, at room temperature. Plates were then washed 8 times with PBS and developed with Super Slow ELISA TMB (Sigma) and read at 650 nm. Different concentration of HJ8.5B was used to create a standard curve that was run in each plate in addition to serum and CSF samples.

The concentration of HJ8.5B bound to tau was measured by coating 96 well ELISA plates with 20 µg/ml of HJ8.7 antibody at 4° C. ELISA plates were blocked with 4% BSA at 37° C. for 1 hr. Plates were then washed 5 times followed by incubating with serum and CSF samples diluted in sample buffer and incubated at 4° C. overnight. The next day, plates were washed 8 times with PBS and plates were incubated with streptavidin-poly-horseradish peroxidase-40 (1:6000, Fitzgerald), for 1.5 hr, in the dark, at room temperature. Plates were then washed 8 times with PBS and developed with Super Slow ELISA TMB (Sigma) and read at 650 nm. Different dilutions of purified HJ8.5B complexed with recombinant tau were used to create a standard curve in each plate.

Tau Sandwich ELISA Assay

To determine total tau levels, ELISA half 96 well plates (Costar) were coated with HJ8.7 antibody (20 µg/ml) in carbonate buffer pH 9.6 and incubated at 4° C., overnight on a shaker. ELISA plates were washed 5 times with PBS with a BioTek EL×405 plate washer and blocked with 4% BSA in PBS for 1 hr at 37° C. Plates were then washed 5 times followed by incubating wells with RAB, RIPA, or 70% FA biochemically extracted soluble brain tissue fractions diluted in sample buffer (0.25% BSA in PBS, 300 nM Tris pH 7.4 supplemented by protease inhibitor) and incubated at 4° C. 70% FA fractions were neutralized by diluting 1:20 with 1M Tris pH 11 followed by diluting with sample buffer. The next day, plates were washed 8 times with PBS followed by the addition of the biotinylated mouse monoclonal anti-tau antibody BT-2 antibody (0.3 µg/ml, Pierce) in 0.5% BSA in PBS for 1.5 hr at 37° C. Plates were then washed 8 times in PBS followed by addition of streptavidin-poly-horseradish peroxidase-40 (1:4000), for 1.5 hr, in the dark, at room temperature. Plates were then washed 8 times with PBS, developed with Super Slow ELISA TMB (Sigma) and absorbance read at 650 nm on BioTek Synergy 2 plate reader. Recombinant human tau was used to create a standard in each plate. Negative control wells included omission of primary antibody in each plate. The longest recombinant human (hTau40, 441aa) and mouse tau (mTau40, 432aa) isoforms produced in the laboratory of Eva-Maria Mandelkow were used as standards in the ELISA assays.

To determine the levels of human tau in 70% FA fractions, ELISA 96 well plates were coated with mouse monoclonal antibody Tau5 (20 µg/ml) and mouse monoclonal anti-human tau specific biotinylated HT7 antibody (0.2 ug/ml, Thermo Scientific) for detection. For mouse tau levels in the 70% FA fraction, ELISA 96 well plates were coat with monoclonal anti-mouse tau specific HJ9.2 antibody (20 µg/ml) and monoclonal biotinylated HJ8.7 was used for detection. Recombinant human and mouse tau were used for standards on each plate. To determine phospho tau levels at positions Ser202 and Thr205, ELISA half 96 well plates were coated with mouse monoclonal HJ8.7 antibody (20 µg/ml) and biotinylated AT8 antibody (0.2 ug/ml, Thermo Scientific) was used as detection antibody.

Immunohistochemistry

To detect the presence of abnormally phosphorylated tau in the brain, three 50 µm coronal brain sections spaced 300 µm apart from all treated mice were assessed. The brain sections were blocked with 3% milk in Tris-buffered saline (TBS) and 0.25% (vol/vol) Triton-X followed by incubation at 4° C. overnight with the biotinylated AT8 antibody (Thermo Scientific, 1:500) which recognizes tau phosphorylated at ser202 and thr205. Biotinylated PHF1 antibody (1:200) which recognizes abnormally phosphorylated tau at residues ser396 and ser404 was also used to determine the correlation between AT8 and PHF1 antibody staining. For correlation studies, mice (N=6) were randomly selected from the HJ8.5, HJ9.3, and PBS-treated groups. The stained tissues were scanned using the NanoZoomer digital pathology system. To determine the correlation between the AT8 staining and activated microglial staining, brain sections from selected mice of all the treated groups (N=6), were blocked with 10% normal goat serum in TBS with 0.25% (vol/vol) Triton-X was incubated with a rat anti-mouse CD68 antibody (AbD SeroTec, 1:500) at 4° C. overnight. The sections were then incubated with biotinylated goat anti-rat IgG antibody, mouse adsorbed (Vector, 1:2000). All sections were scanned with a NanoZoomer slide scanner (Hamamatsu Photonics). All images were exported by using NDP viewer software and quantified by using ImageJ software (National Institutes of Health). For AT8 staining, 3 brain sections from each mouse separated by 300 µm, corresponding approximately to sections at Bregma coordinates −1.4, −1.7, and −2.0 mm in the mouse brain atlas were used. These sections were used to determine the percentage of area occupied by abnormally phosphorylated biotinylated AT8 antibody staining. All converted images were uniformly thresholded to quantify AT8 staining and the average of all three sections was used to determine the percentage of area covered by abnormally phosphorylated tau staining for each mouse. For PHF-1 and CD68 staining, two brain sections from each mouse were used, separated by 300 µm and correspond to bregma coordinates −2.3 and −2.6 mm in the mouse brain atlas. To determine ThioS staining, brain sections from randomly selected mice from all the treated groups (N=6) were stained in ThioS in 50% ethanol (0.25 mg/ml) for 3 min, followed by washing in 50% ethanol and distilled water. Slices were then mounted, dried and images were assessed by microscopy with the Nanozoomer. Two brain sections from each mouse were used as described adjacent to those used for PHF-1 and CD68 staining.

Semi-Denaturing-Agarose Gel Electrophoresis (SDD-AGE)

For separation of tau species present in the different RAB soluble fractions of 3 month old tau knockout (KO), 3 months old wild type (WT), 3 months old P301S and 9 month old PBS-treated P301S mice, the previously described Semi-Denaturing Detergent-Agarose Gel Electrophoresis (SDD-AGE) method was employed with minor modifications. Samples were run on horizontal 1.5% agarose gels in Buffer G (20 mM Tris, 200 mM Glycine) with 0.2% SDS. Samples were incubated in the sample buffer (60 mM Tris-HCl pH 6.8, 0.2% SDS, 5% glycerol, and 0.05% bromphenol blue) for 7 min at RT. After the electrophoresis, proteins were transferred from gels to Immobilon-P PVDF sheets (Millipore) at 4° C. in Laemmli Buffer (Buffer G/0.1% SDS). Membranes were blotted using an anti-tau specific rabbit polyclonal antibody (Abcam) at 1:2000. Blots were developed using the GE ECL Plus system.

Immunofluorescence

HEK293 cells were plated at 75,000 cells/well in 24 well plates coated with poly D-lysine. To determine whether anti-tau antibodies used can detect tau species taken up by the HEK293 cells, the cells were treated with P301S brain lysates for 2 hrs, followed by washing 3× with PBS, fixed with 4% paraformaldehyde for 15 min at room temperature followed by washing 3 times with PBS at room temperature. Cells were permeabilized with 0.1% Triton X-100 for 10 min, washed 3 times with PBS, then blocked with 0.25% Triton X-100 in PBS containing 10% normal goat serum and 20 mg/ml BSA. Then cells were incubated with anti-mouse secondary antibody conjugated with Alexa-fluor 546. To determine whether antibody can enter the cells, P301S brain lysates were pre-incubated with and without the different anti-tau antibodies HJ8.5, HJ9.3, and HJ9.4 or the HJ3.4 antibody to Aβ. The lysates were then added to HEK293 cells for 2 hrs, fixed and permeabilized. Secondary antibody conjugated with Alexa-fluor 546 was used to identify the antibodies. 4',6'-diamidino-2-phenylindole (DAPI; shown in blue) was used for nuclear stain. All the images were captured by using a Zeiss LSM5 confocal microscope (Zeiss).

Statistical Analysis of Pathological and Biochemical Data

All data are presented as mean±SEM, and different conditions were compared using one-way ANOVA followed by Dunnett's post hoc test to compare controls with treatment groups. Statistical significance was set at $P<0.05$. Statistics were performed using GraphPad Prism 5.04 for Windows (Graph Pad Software Inc.). For quantitative assessment of AT8 staining, gender is a significant factor so results were adjusted by gender using SAS version 9.2 software.

Statistical Analysis Applying Treatment and Gender as Factors

The control group (PBS and HJ3.4) mean was compared with each treatment group. (mean of PBS+mean of HJ3.4)/2 VS mean of treatment). Two-way ANOVA was used to test whether gender and treatment are significant factors, which is achieved by PROC GLM in SAS Version 9.2 and their p Values are shown in Table 7. A contrast statement was used in PROC GLM of SAS Version 9.2 to access all comparisons. Gender as an adjustment factor in the two-way ANOVA was applied and p Values before/after the adjustment are shown in FIG. 38D.

Behavioral Tests

Mice were assessed on locomotor activity and exploratory behaviors and on a battery of sensorimotor measures and the rotarod to provide additional control data for interpreting the results of the conditional fear test, which was used to evaluate cognitive function. The conditioned fear test was conducted last in the series of tests to preclude effects of brief footshocks on other behavioral indices.

Holeboard Exploration, Sensorimotor Battery and Rotarod.

All mice were evaluated on the holeboard exploration test where total ambulations (whole body movements) and hole pokes were quantified over a 30-min period and provided indices of locomotor activity and exploration. The protocol involved the use of a computerized holeboard apparatus (41×41×38.5 cm high) containing 4 corner and 4 side holes, with a side hole being equidistant between the corner holes (Learning Holeboard; MotorMonitor, Kinder Scientific, LLC, Poway, Calif.). Photobeam instrumentation was used to quantify total ambulations and exploratory hole pokes during the test session. This procedure has served as the habituation component of our general holeboard exploration/olfactory preference test. The mice were also tested on a battery of seven sensorimotor measures that were used to assess balance (ledge, platform), coordination (pole, 60° and 90° inclined screens), strength (inverted screen), and initiation of movement out of a small circumscribed area (walking initiation). This battery was used in previous publications and greater procedural details may be found in (Wozniak et al. (2004; Neurobiol Dis 17, 403-414). The rotarod test was similar to previously-published methods and included three types of trials: 1) stationary rod (60 s maximum; 2) constant speed rotarod (2.5 rpm for 60 s maximum; and 3) accelerating rotarod (2.5-10.5 rpm over 0-180 s). Our protocol consisted of testing each mouse on one stationary rod trial, two constant speed rotarod trials, and two accelerating rotarod trials for each of three test sessions that were separated by 3 days to limit motor learning.

Conditioned Fear.

Mice were evaluated on the conditioned fear test, which was the last behavioral measure conducted. Briefly, the mice were trained and tested in two Plexiglas conditioning chambers (26 cm×18 cm, and 18 cm high) (Med-Associates, St. Albans, Vt.) with each chamber containing distinct and different visual, odor, and tactile cues. Each mouse was placed into the conditioning chamber for a 5-min trial and freezing behavior was quantified during a 2-min baseline period. Beginning at 3 min and at 60-s intervals thereafter, the mice were exposed to 3 tone-shock pairings where each pairing included a 20-s presentation of an 80 dB tone (conditioned stimulus; CS) consisting of broadband white noise followed by a 1.0 mA continuous footshock (unconditioned stimulus; CS) presented during the last second of the tone. Broadband white noise was used instead of a frequency-specific tone in an effort to avoid possible auditory deficits that might occur with age. The mice were placed back into the conditioning chamber the following day and freezing behavior was quantified over an 8-min period to evaluate contextual fear conditioning. Twenty four hours later, the mice were placed into the other chamber containing different cues and freezing behavior was quantified during a 2-min "altered context" baseline and over the subsequent 8 min, during which time the auditory cue (tone; CS) was presented. Freezing was quantified using FreezeFrame image analysis software (Actimetrics, Evanston, Ill.), which allowed for simultaneous visualization of behavior while adjusting a "freezing threshold," which categorized behavior as freezing or not freezing during 0.75 s intervals. Freezing was defined as no movement except for that associated with normal respiration, and the data were presented as percent of time spent freezing. To assess the extent of contextual fear conditioning, we conducted analyses within each treatment group which involved comparing the percent time spent freezing averaged over the 2-min baseline on day 1 with the averaged percent time spent freezing during the first 2 min of the contextual fear test on day 2, as well as with freezing levels averaged across the entire 8-min session. Shock sensitivity was evaluated following completion of the conditioned fear testing, according to previously described procedures in Khuchua et al. (2003; Neuroscience 119, 101-111).

Statistical Analyses of Behavioral Data

Analysis of variance (ANOVA) models were typically used to analyze the behavioral data (Systat 12, Systat Software, Chicago, Ill.). The conditioned fear data were analyzed using repeated measures (rm) ANOVA models containing one between-subjects variable (Treatment) and one within-subjects (repeated measures) variable (Minutes). The Huynh-Feldt adjustment of alpha levels was utilized for all within-subjects effects containing more than two levels to protect against violations of sphericity/compound symmetry assumptions underlying rmANOVA models. Planned comparisons between the PBS+HJ3.4 control group and each of the three other antibody treatment groups (i.e., HJ8.5, HJ9.3, HJ9.4) were conducted within ANOVA models for testing certain key hypotheses. In other instances, pair-wise comparisons were conducted following relevant, significant overall ANOVA effects, which were subjected to Bonferroni correction when appropriate. Pearson's correlation coefficient (r) was also calculated between the total ambulations recorded during the holeboard test and the percent time spent freezing during the contextual fear test on day 2.

Example 16

Tau ELISA Assay

An ELISA assay was developed in order to detect the presence of pathological tau aggregates in plasma samples of patients. Antibodies used in this assay include mouse monoclonal anti-tau HJ9.3 and HJ9.2. HJ9.3 is biotinylated using One-step Antibody Biotinylation Kit (HJ9.3-Bio). This sandwich ELISA utilizes HJ9.3 and HJ9.2, at equivalent concentration, as capture antibodies. 96-well half area plates (Costar 3690) are coated with 20 µg/ml of HJ9.2/HJ9.3 prepared in bicarbonate buffer pH 9.6 (50 µl/well) and incubated at 4° C. overnight. Following a blocking step using 4% BSA/PBS, plasma samples (diluted 1:4 in sample buffer: 0.25% BSA/PBS, 300 nM Tris PH 7.4~8.0, 1× protease inhibitors) are applied in triplicates to wells (50 µl/well). Plates are then incubated at 4° C. overnight. For detection, HJ9.3-Bio prepared in 0.5% BSA/PBS at 0.3 µg/ml was added to wells for 1.5 hr at 37° C. A secondary streptavidin-polyHRP40 antibody at 1:4,000 dilution in 0.5% BSA/PBS (50 µl/well and 1.5 hr in dark on a shaker at RT) is used for final detection through an enzymatic reaction using TMB super slow substrate. The ELISA has been designed to optimize detection of rare species in plasma. Initial embodiments included coating the surface of the ELISA plate with antibody pairs to optimize trapping of aggregates. However it would be equally plausible to use antibody coated beads from larger volumes of fluid samples to increase the sensitivity of the assay. Negative plasma collected from healthy young participants was used to calculate the background signal of the assay. Tau seeds presence in the experimental samples is reported as fold induction over signal from negative plasma.

A set of plasma samples from pre-clinical and Alzheimer's Disease (AD) patients previously tested with the disclosed seeding assay were used to validate the sandwich tau ELISA assay. 12 control patients (CDR 0) with no seeding activity (Negative) and 12 patients (CDR >0) with seeding activity (Positive) were tested using the newly developed ELISA assay. These patients were previously determined to have seeding activity or not in CSF and plasma based on a biosensor cellular assay. In this cellular assay, RD fragments of the tau protein containing the ΔK280 mutation are fused to cyan or yellow fluorescent protein. This enables detection of aggregation by measuring fluorescence resonance energy transfer via FRET. Extracellular aggregates are brought into the cell and trigger intracellular aggregation of the tau FRET reporter proteins.

Figure 45:
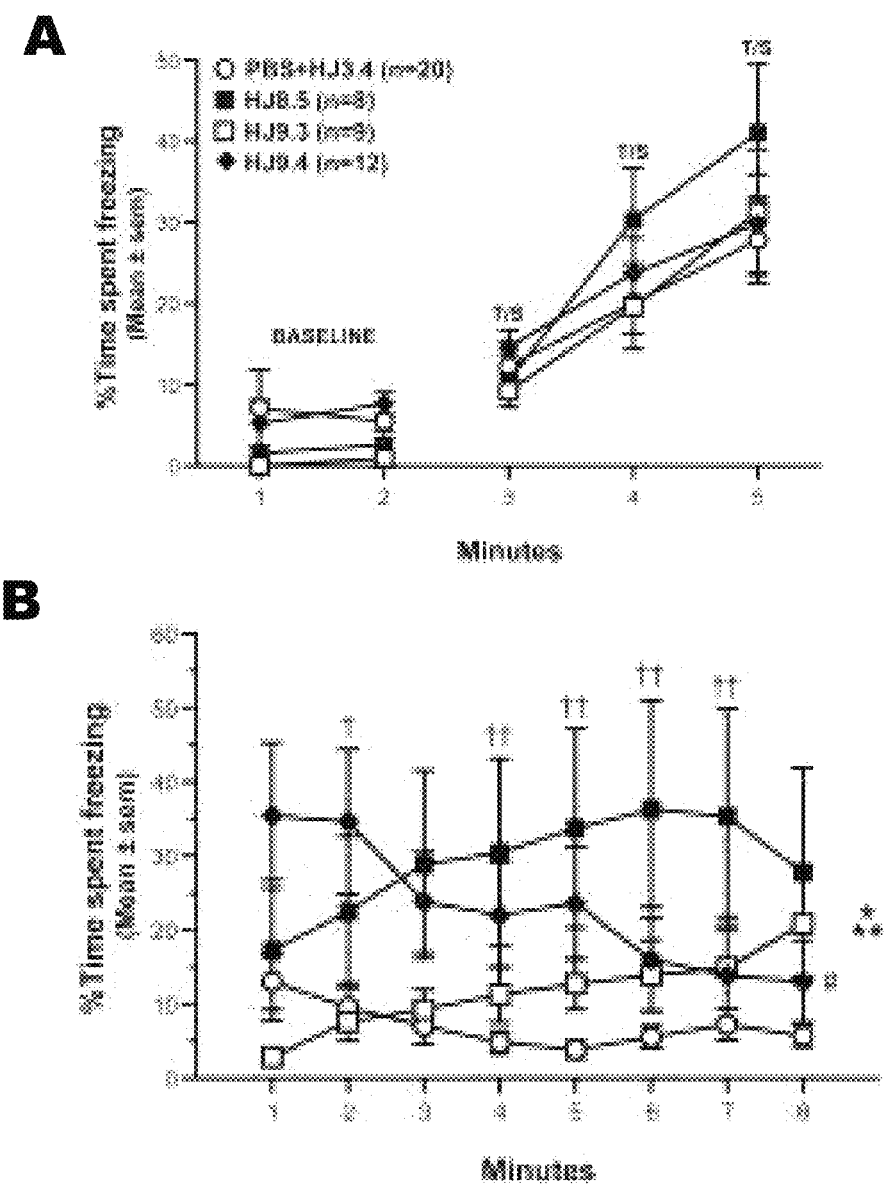
FIG. 45. Contextual fear conditioning deficits in P301S tau transgenic mice are rescued by HJ8.5 and HJ9.4 antibody treatments. (A) On day 1 of conditioned fear testing, no differences were observed among groups in freezing levels during either the 2-min baseline condition or the tone/shock (T/S) training as indicated by the lack of a significant main or interaction effects involving Treatment following rmANOVAs on these data. (B) In contrast, a significant effect of Treatment (*p=0.019) and a significant Treatment by Minutes interaction (p=0.0001) were observed following an rmANOVA on freezing levels during the contextual fear testing on day 2. Only the HJ9.4 group showed significant habituation from minute 1 versus minute 8, (#p=0.002). (C) Subsequent planned comparisons showed that freezing in the HJ8.5 and HJ9.4 tau antibody groups was significantly increased relative to the PBS+HJ3.4 control group when averaged across the 8-min session (p=0.006 and *p=0.022, respectively). However, further analyses of the data showed that the largest differences between the HJ9.4 group and the PBS+HJ3.4 controls occurred during minute 2 (†p=0.004), while the largest differences between the HJ8.5 treated mice and the control group were found during minutes 4-7 (††p<0.004) as depicted in "B".
Figure 45C:
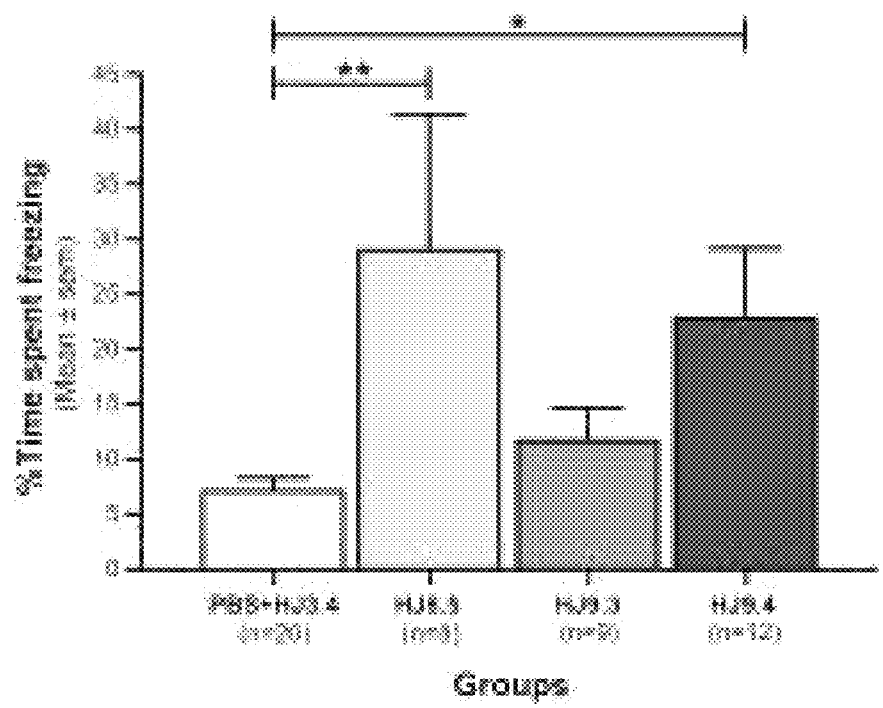
Figure 46:
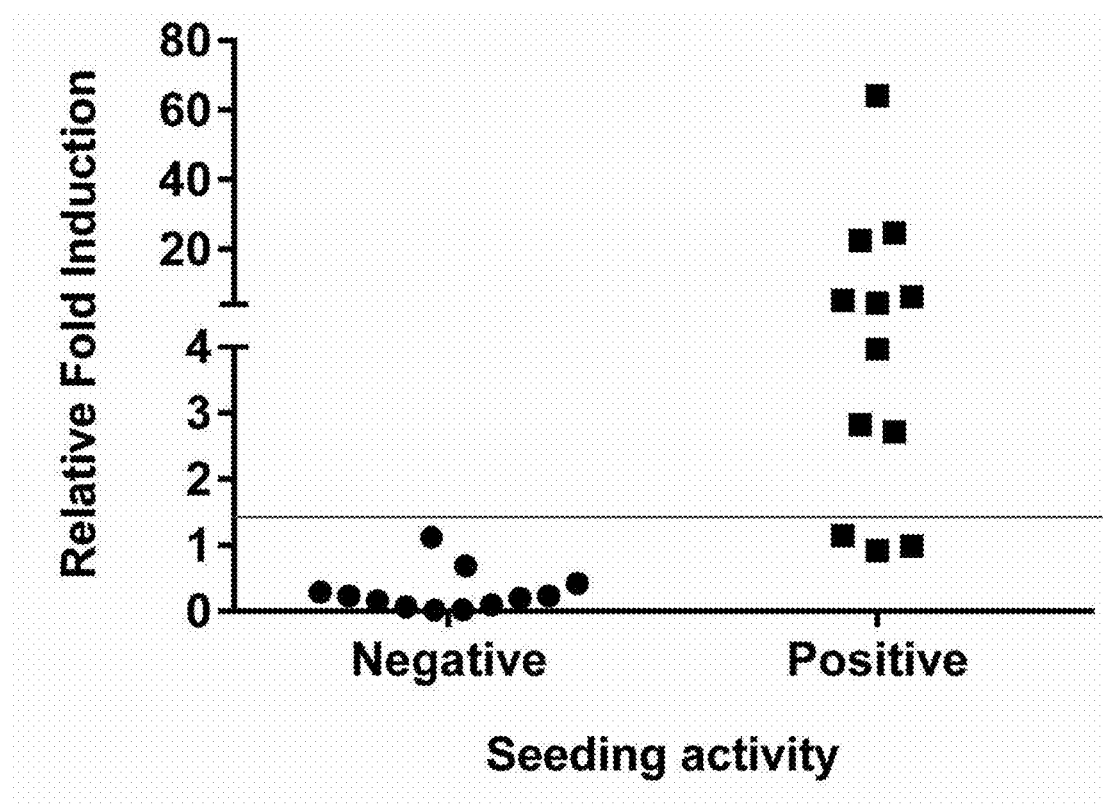
FIG. 46 depicts a graph showing a sandwich Tau ELISA assay can be used to discriminate between plasma samples that are positive for seeding activity and plasma samples that are negative for seeding activity. Seeding activity was determined as described in Kfoury et al 2012 J Biol Chem 287(23). Amount of tau aggregate is reported as relative fold-change induction over signal from plasma collected from healthy young humans (i.e. background signal of the assay).

As shown in FIG. 45, no tau aggregates were detected in the plasma of patients with negative seeding activity compared to the clear tau presence of seeds in the plasma of AD patients with positive seeding activity. This cell-free based assay could be used in a more clinical setting as a non-invasive diagnostic tool for many tauopathies including Alzheimer's Disease. Further, it could allow detection of those with incipient pathology who are destined to develop dementia, facilitating clinical trial design by enriching a sample population. Finally, it could be used to monitor efficacy of anti-tau or other anti-dementia therapies.

Example 17

Figure 47:
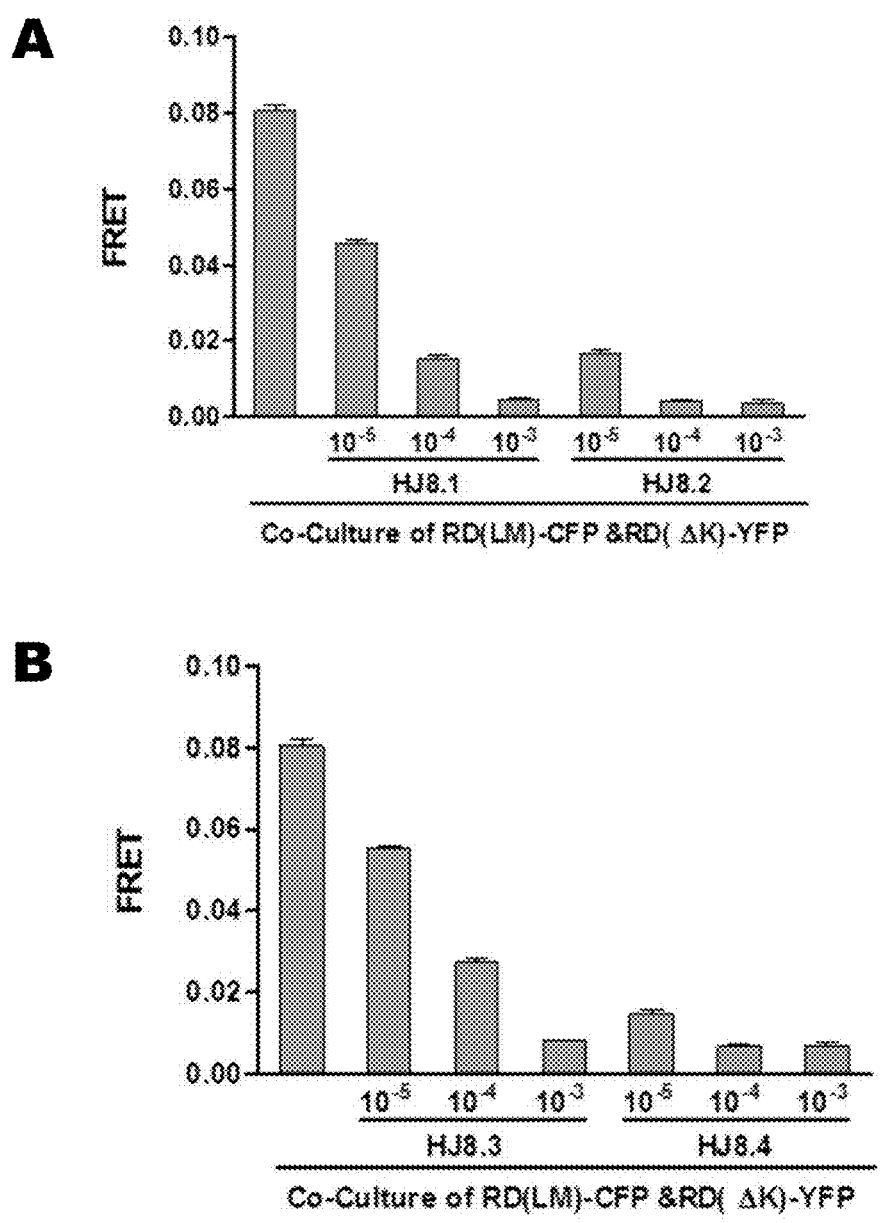
FIG. 47 depicts graphs showing the effect of anti-tau antibodies of the invention on a tau cellular propagation assay. In each graph, the first bar represents medium without added antibody, representing baseline efficiency of propagation. (A) HJ8.1 and HJ8.2; (B) HJ8.3 and HJ8.4; (C) HJ8.5 and HJ8.7; (D) HJ8.8 and HJ9.1; (E) HJ9.2 and HJ9.3; (F) HJ9.4 and HJ9.5.

A cellular propagation assay was set up to measure the propagation of tau aggregates from one population to another. A fragment of tau comprised of the repeat domain (RD) was used either as an untagged form with two disease-associated mutations (LM: P301L/V337M) to promote aggregation of the CFP-tagged form, or one disease-associated mutation (ΔK: ΔK280). One group of cells was transfected with RD(LM) and RD(ΔK280)-CFP, and another was transfected with RD(ΔK280)-YFP. FRET was recorded on a fluorescence plate reader from cells grown in quadruplicate in a 96-well format. FRET signal derives from RD-CFP aggregates transferring to cells containing RD-YFP, and vice-versa. Multiple antibodies were added to the medium at various dilutions indicated. The starting concentration of antibody was ~1 mg/ml. For example, a $10^{-3}$ dilution indicates a final concentration of ~1 µg/ml. After 24 h the cells were fixed and FRET measurements recorded. Data for individual antibodies are presented in FIG. 47. Some antibodies were very potent at preventing trans-cellular propagation of aggregation (e.g. HJ8.2, HJ9.1). Others were effective in a more intermediate fashion (e.g. HJ9.3), and some were essentially not effective (HJ8.7). In each graph, the first bar represents medium without added antibody, representing baseline efficiency of propagation.

Figure 48:
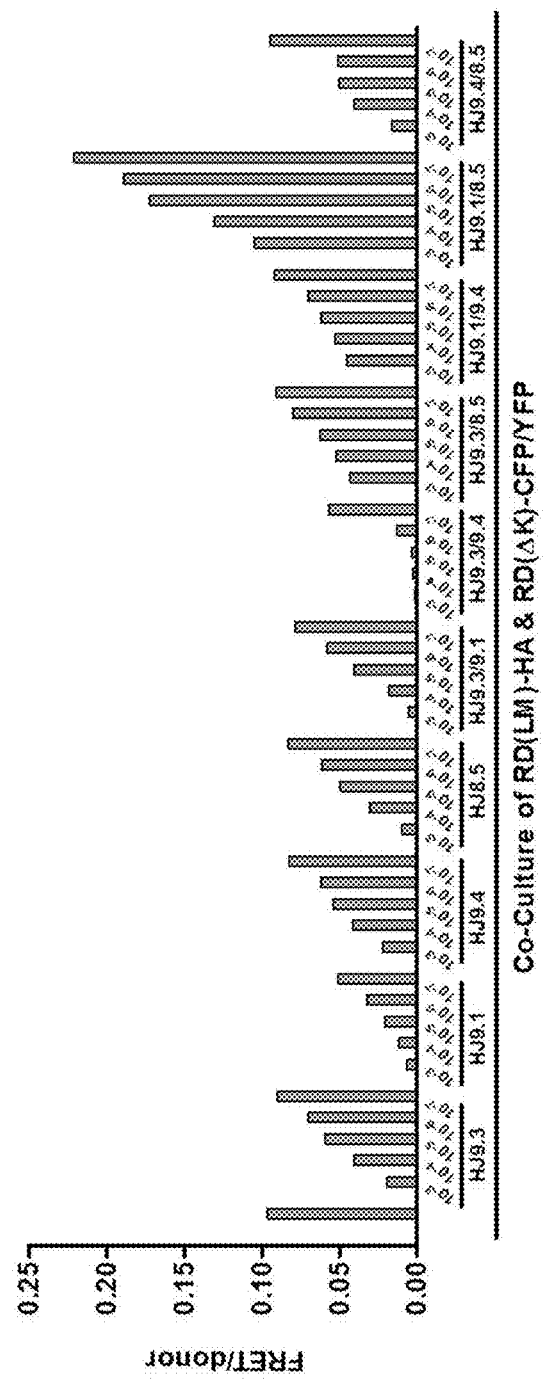
FIG. 48 depicts a graph showing the effect on tau propagation of individual anti-tau antibodies or equimolar mixtures of anti-tau antibodies in a cell-based assay.
Figure 49:
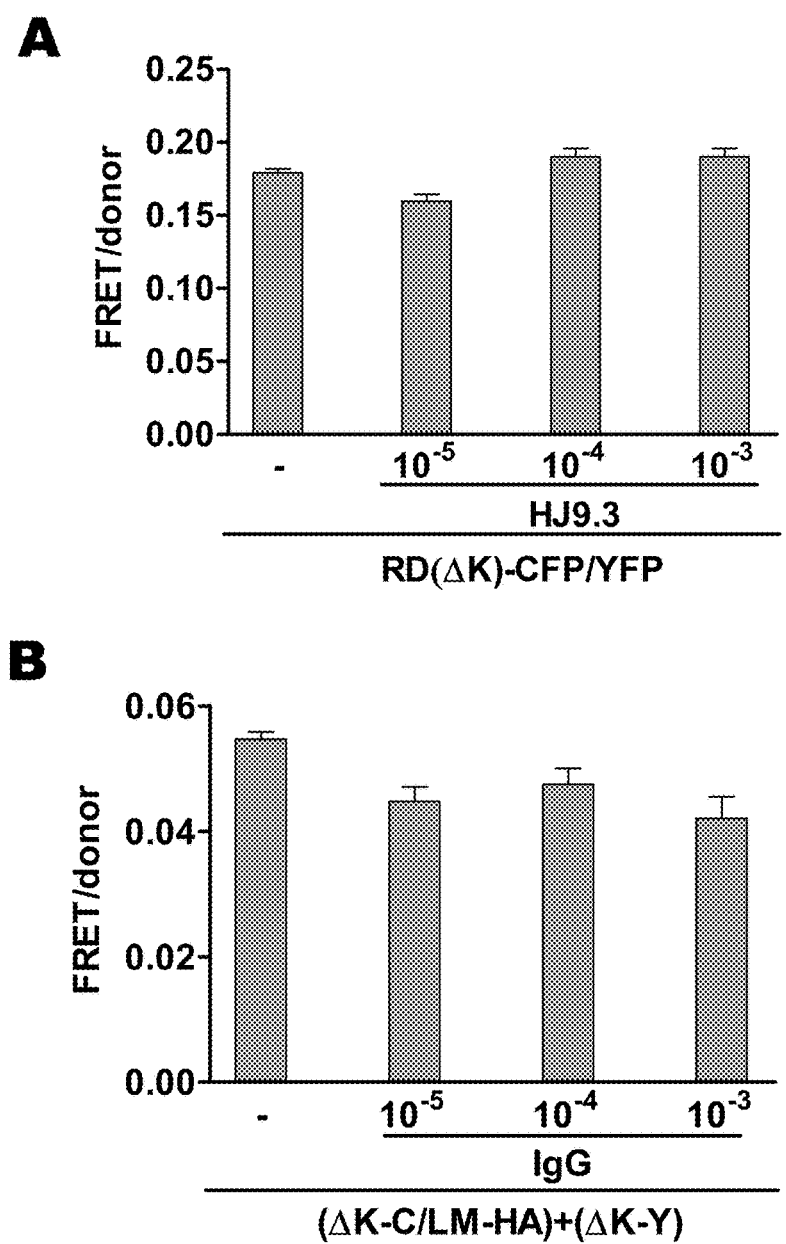
FIG. 49 depicts in (A) a graph showing HJ9.3 antibody has no effect on intracellular tau aggregation when RD(ΔK)-CFP/YFP are co-expressed within the same cell, and in (B) a graph showing that nonspecific IgG has no effect on trans-cellular propagation of tau aggregation.

To test for synergy of antibodies, effects on propagation were determined in the setting of individual antibodies diluted over an indicated concentration range, or antibodies were mixed at an equimolar ratio and then titrated over the same range. Some pairs were strongly synergistic (e.g. HJ9.3/9.4), while others interfered with one another (HJ8.5/9.1) (FIG. 48).

Figure 50:
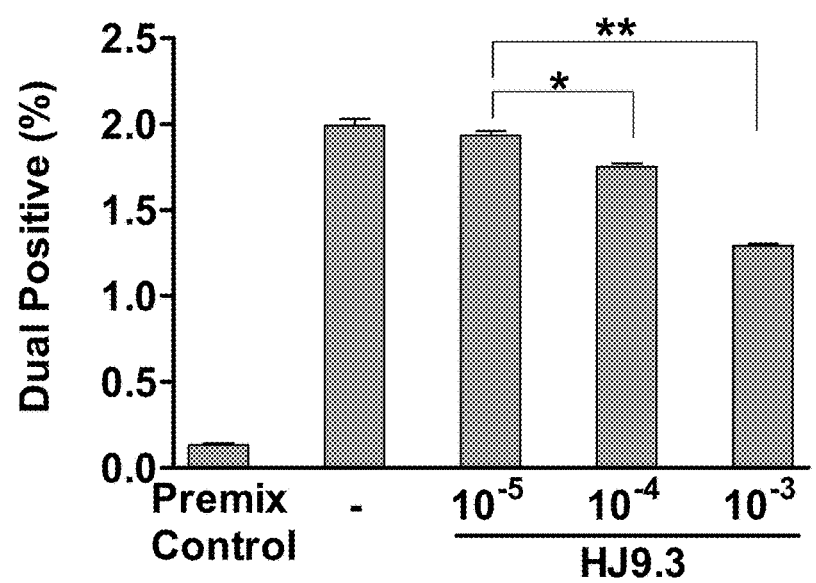
FIG. 50 depicts a graph showing HJ9.3 inhibits tau aggregate uptake, as measured by flow cytometry. Cells were exposed to recombinant RD fibrils that were chemically labeled with a fluorescent dye. After trypsinization and dispersion, the cells were counted using a flow cytometer. HJ9.3 dose-dependently reduces the number of fluorescently labeled cells, indicating inhibition of aggregate uptake.

The effect of an antibody on tau aggregate uptake may also be measured by flow cytometry. Cells were exposed to recombinant RD fibrils that were chemically labeled with a fluorescent dye. After trypsinization and dispersion, the cells were counted using a flow cytometer. HJ9.3 dose-dependently reduces the number of fluorescently labeled cells, indicating inhibition of aggregate uptake (FIG. 50).

What is claimed is:

1. An isolated monoclonal anti-tau antibody, wherein the antibody comprises:

a light chain variable region comprising a CDR1 of amino acid sequence SEQ ID NO: 16, a CDR2 of amino acid sequence SEQ ID NO: 17, and a CDR3 of amino acid sequence SEQ ID NO: 18, and a heavy chain variable region comprising a CDR1 of amino acid sequence SEQ ID NO: 19, a CDR2 of amino acid sequence SEQ ID NO: 20, and a CDR3 of amino acid sequence SEQ ID NO: 21.

2. The isolated monoclonal anti-tau antibody of claim 1, wherein the antibody specifically binds human tau with an Affinity of Interaction (KD) of 0.1 pM to 10 nM.

3. The isolated monoclonal anti-tau antibody of claim 1, wherein the antibody specifically binds human tau with an Affinity of Interaction (KD) of 0.1 pM to 1 nM.

4. The isolated monoclonal anti-tau antibody of claim 1, wherein the antibody specifically binds human tau and does not bind mouse tau.

5. The isolated monoclonal anti-tau antibody of claim 1, wherein the antibody is a humanized antibody.

6. The isolated monoclonal anti-tau antibody of claim 1, wherein the antibody is specifically able to block tau seeding activity in a cellular tau aggregation assay.

7. The isolated monoclonal anti-tau antibody of claim 1, wherein the antibody is a chimeric antibody.

8. The isolated monoclonal anti-tau antibody of claim 1, wherein the light chain variable region and the heavy chain variable region comprise framework regions.

9. The isolated monoclonal anti-tau antibody of claim 8, wherein the antibody is an IgG isotype.

10. The isolated monoclonal anti-tau antibody of claim 9, wherein the antibody is a chimeric antibody.

11. The isolated monoclonal anti-tau antibody of claim 9, wherein the antibody is a humanized antibody.

12. The isolated monoclonal anti-tau antibody of claim 9, wherein the antibody is an IgG4 isotype.

13. The isolated monoclonal anti-tau antibody of claim 12, wherein the antibody is a chimeric antibody.

14. The isolated monoclonal anti-tau antibody of claim 12, wherein the antibody is a humanized antibody.

* * * * *

UNITED STATES PATENT AND TRADEMARK OFFICE
CERTIFICATE OF CORRECTION

PATENT NO. : 9,834,596 B2
APPLICATION NO. : 14/412309
DATED : December 5, 2017
INVENTOR(S) : David Holtzman et al.

Page 1 of 1

It is certified that error appears in the above-identified patent and that said Letters Patent is hereby corrected as shown below:

In the Specification

Corrected Government Support Paragraph at Column 1, Lines 5-7:
This invention was made with government support under W81XWH-13-2-0017 awarded by the ARMY/MRMC and NS071835 awarded by the National Institutes of Health. The government has certain rights in the invention.

Signed and Sealed this
Sixteenth Day of July, 2019

Andrei Iancu
*Director of the United States Patent and Trademark Office*

SEQUENCE LISTING

```
<160> NUMBER OF SEQ ID NOS: 21

<210> SEQ ID NO 1
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 1

Asp Arg Lys Asp Gln Gly Gly Tyr Thr Met His Gln Asp
1               5                   10

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Lys Thr Asp His Gly Ala Glu
```

```
<210> SEQ ID NO 3
<211> LENGTH: 7
<212> TYPE: PRT
<213> ORGANISM: Artificial Sequence
<220> FEATURE:
<223> OTHER INFORMATION: SYTHENSIZED

<400> SEQUENCE: 3

Pro Arg His Leu Ser Asn Val
1               5

<210> SEQ ID NO 4
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 4

Glu Pro Arg Gln
1

<210> SEQ ID NO 5
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 5

Ala Ala Gly His Val
1               5

<210> SEQ ID NO 6
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 6

Thr Asp His Gly Ala Glu Ile Val Tyr Lys Ser Pro Val Val Ser Gly
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 7

Glu Phe Glu Val Met Glu Asp
1               5

<210> SEQ ID NO 8
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 8

Gly Gly Lys Val Gln Ile Ile Asn Lys Lys
1               5                   10
```

<210> SEQ ID NO 9
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 9

Ser Lys Ile Gly Ser Thr Glu Asn Leu Lys His
1               5                   10

<210> SEQ ID NO 10
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 10

Thr Asp His Gly Ala Glu
1               5

<210> SEQ ID NO 11
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 11

Lys Thr Asp His Gly Ala
1               5

<210> SEQ ID NO 12
<211> LENGTH: 333
<212> TYPE: DNA
<213> ORGANISM: Artificial Sequence
<220> FEATURE:
<223> OTHER INFORMATION: SYNTHESIZED

<400> SEQUENCE: 12
gacattgtgc tgacacagtc tcctgcttcc ttagctgtat ctctgggaca gagggccacc      60
atctcatgca gggccagcca agtgtcagt acatctagat atagttatat acactggtac     120
caacagaaac caggacagcc acccaaactc ctcatcaagt atgcatccaa cctagaatct     180
ggggtccctg ccaggttcag tggcagtggg tctgggacag acttcaccct caacatccat     240
cctctggagg aggaggatgc tgcaacatat tactgtcacc acagttggga gattccgctc     300
acgttcggtg ctgggaccaa gctggagctg aaa                                  333

<210> SEQ ID NO 13
<211> LENGTH: 345
<212> TYPE: DNA
<213> ORGANISM: Artificial Sequence
<220> FEATURE:
<223> OTHER INFORMATION: SYNTHESIZED

<400> SEQUENCE: 13
gaagtgaagg ttgaggagtc tggaggaggc ttggtgcaac ctggaggatc catgaaactc      60
tcctgtgttg tctctggatt cactttcagt aactactggg tgaactgggt ccgccagtct     120
ccagagaagg ggcttgagtg ggttgctcaa attagattga atctgataa ttatgcaaca      180 cattatgagg agtctgtgaa agggaggttc accatctcaa gagatgattc caaaagtagt     240

```
gtctatctgc aaatgaacaa cctaagggct gaagacagtg gaatttatta ctgcactaac    300
tgggaagact actggggcca aggcaccact ctcacagtct cctca                    345
```

<210> SEQ ID NO 14
<211> LENGTH: 111
<212> TYPE: PRT
<213> ORGANISM: Artificial Sequence
<220> FEATURE:
<223> OTHER INFORMATION: SYNTHESIZED

<400> SEQUENCE: 14

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Leu Glu Glu Glu Asp Ala Ala Thr Tyr Tyr Cys His His Ser Trp
                85                  90                  95

Glu Ile Pro Leu Thr Phe Gly Ala Gly Thr Lys Leu Glu Leu Lys
            100                 105                 110
```

<210> SEQ ID NO 15
<211> LENGTH: 115
<212> TYPE: PRT
<213> ORGANISM: Artificial Sequence
<220> FEATURE:
<223> OTHER INFORMATION: SYNTHESIZED

<400> SEQUENCE: 15

```
Glu Val Lys Val Glu Glu Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Val Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Glu Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Ser Gly Ile Tyr
                85                  90                  95

Tyr Cys Thr Asn Trp Glu Asp Tyr Trp Gly Gln Gly Thr Thr Leu Thr
            100                 105                 110

Val Ser Ser
        115
```

<210> SEQ ID NO 16
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 16

```
Arg Ala Ser Gln Ser Val Ser Thr Ser Arg Tyr Ser Tyr Ile His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 17

Tyr Ala Ser Asn Leu Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 18

His His Ser Trp Glu Ile Pro Leu Thr
1               5

<210> SEQ ID NO 19
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 19

Asn Tyr Trp Val Asn
1               5

<210> SEQ ID NO 20
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 20

Gln Ile Arg Leu Lys Ser Asp Asn Tyr Ala Thr His Tyr Glu Glu Ser
1               5                   10                  15

Val Lys Gly

<210> SEQ ID NO 21
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 21

Trp Glu Asp Tyr
1
```